US008273544B2

(12) United States Patent
Fantl et al.

(10) Patent No.: US 8,273,544 B2
(45) Date of Patent: *Sep. 25, 2012

(54) METHODS FOR DIAGNOSIS, PROGNOSIS AND METHODS OF TREATMENT

(75) Inventors: Wendy J. Fantl, San Francisco, CA (US); David B. Rosen, Mountain View, CA (US); Alessandra Cesano, Redwood City, CA (US); Santosh K. Putta, Foster City, CA (US); James R. Hackett, San Jose, CA (US); Michael Walker, Mountain View, CA (US); Jing Shi, Mountain View, CA (US)

(73) Assignee: Nodality, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/083,156

(22) Filed: Apr. 8, 2011

(65) Prior Publication Data

US 2011/0269154 A1    Nov. 3, 2011

Related U.S. Application Data

(63) Continuation of application No. 12/910,769, filed on Oct. 22, 2010, and a continuation-in-part of application No. 12/460,029, filed on Jul. 10, 2009, now Pat. No. 8,227,202.

(60) Provisional application No. 61/382,793, filed on Sep. 14, 2010, provisional application No. 61/373,199, filed on Aug. 12, 2010, provisional application No. 61/350,864, filed on Jun. 2, 2010, provisional application No. 61/265,743, filed on Dec. 1, 2009, provisional application No. 61/265,585, filed on Dec. 1, 2009, provisional application No. 61/254,131, filed on Oct. 22, 2009, provisional application No. 61/079,766, filed on Jul. 10, 2008, provisional application No. 61/085,789, filed on Aug. 1, 2008, provisional application No. 61/120,320, filed on Dec. 5, 2008.

(51) Int. Cl.
*G01N 33/53* (2006.01)
*G01N 33/567* (2006.01)
*G01N 33/00* (2006.01)

(52) U.S. Cl. .................. 435/7.21; 435/7.23; 435/7.24; 435/6.14

(58) Field of Classification Search .................. None
See application file for complete search history.

(56) References Cited

U.S. PATENT DOCUMENTS

| 4,979,824 A | 12/1990 | Mathies et al. |
|---|---|---|
| 5,137,809 A | 8/1992 | Loken et al. |
| 5,234,816 A | 8/1993 | Terstappen |
| 5,599,681 A | 2/1997 | Epstein et al. |
| 5,605,805 A | 2/1997 | Verwer et al. |
| 5,919,646 A | 7/1999 | Okun et al. |
| 5,968,738 A | 10/1999 | Anderson et al. |
| 6,232,299 B1 | 5/2001 | Jirousek et al. |
| 6,280,967 B1 | 8/2001 | Ransom et al. |
| 6,379,917 B1 | 4/2002 | Okun et al. |
| 6,495,333 B1 | 12/2002 | Willmann et al. |
| 6,506,551 B1 | 1/2003 | Chiorazzi et al. |
| 6,558,916 B2 | 5/2003 | Veerapandian et al. |
| 6,592,822 B1 | 7/2003 | Chandler |
| 6,673,554 B1 | 1/2004 | Kauvar |
| 6,733,743 B2 | 5/2004 | Jordan |
| 6,821,740 B2 | 11/2004 | Darzynkiewicz et al. |
| 6,872,574 B2 | 3/2005 | Cravatt et al. |
| 6,958,221 B2 | 10/2005 | Veerapandian et al. |
| 6,972,198 B2 | 12/2005 | Craig et al. |
| 7,001,725 B2 | 2/2006 | Singh et al. |
| 7,070,943 B2 | 7/2006 | Darzynkiewicz et al. |
| 7,102,005 B2 | 9/2006 | Agnew et al. |
| 7,183,385 B2 | 2/2007 | Comb et al. |
| 7,236,888 B2 | 6/2007 | Allbritton et al. |
| 7,316,906 B2 | 1/2008 | Chiorazzi et al. |
| 7,326,577 B2 | 2/2008 | Shults et al. |
| 7,329,502 B2 | 2/2008 | Staudt et al. |
| 7,381,535 B2 | 6/2008 | Perez et al. |
| 7,392,199 B2 | 6/2008 | Karlov et al. |
| 7,393,656 B2 | 7/2008 | Perez et al. |
| 7,419,777 B2 | 9/2008 | Bacus |
| 7,563,584 B2 | 7/2009 | Perez et al. |
| 7,695,924 B2 | 4/2010 | Perez et al. |
| 7,695,926 B2 | 4/2010 | Perez et al. |
| 7,939,278 B2 | 5/2011 | Perez et al. |
| 2002/0127604 A1 | 9/2002 | Allbritton et al. |

(Continued)

FOREIGN PATENT DOCUMENTS

WO    WO 99/44067 A1    9/1999

(Continued)

OTHER PUBLICATIONS

U.S. Appl. No. 61/048,657, filed Apr. 29, 2008, Covey et al. U.S. Appl. No. 61/087,555, filed Apr. 8, 2008, Covey et al.
Alvarez, et al. Signal Transducer and Activator of Transcription 3 Is Required for the Oncogenic Effects of Non—Small-Cell Lung Cancer—Associated Mutations of the Epidermal Growth Factor Receptor. Cancer Research. 2006;66:3162-3168.
Benekli, et al. Signal transducer and activator of transcription proteins in leukemias. Blood. Apr. 15, 2003;101(8):2940-54.

(Continued)

*Primary Examiner* — Daniel C Gamett
(74) *Attorney, Agent, or Firm* — Wilson Sonsini Goodrich & Rosati

(57) ABSTRACT

The present invention provides an approach for the determination of the activation states of a plurality of proteins in single cells. This approach permits the rapid detection of heterogeneity in a complex cell population based on activation states, expression markers and other criteria, and the identification of cellular subsets that exhibit correlated changes in activation within the cell population. Moreover, this approach allows the correlation of cellular activities or properties. In addition, the use of modulators of cellular activation allows for characterization of pathways and cell populations. Several exemplary diseases that can be analyzed using the invention include AML, MDS, and MPN.

36 Claims, 49 Drawing Sheets

U.S. PATENT DOCUMENTS

| | | |
|---|---|---|
| 2002/0177179 A1 | 11/2002 | Glickman et al. |
| 2002/0197658 A1 | 12/2002 | Delaney et al. |
| 2003/0148321 A1 | 8/2003 | Pecker et al. |
| 2003/0190688 A1 | 10/2003 | Crosby et al. |
| 2003/0190689 A1 | 10/2003 | Crosby et al. |
| 2003/0203416 A1 | 10/2003 | Staudt et al. |
| 2003/0219827 A1 | 11/2003 | Comb et al. |
| 2003/0232364 A1 | 12/2003 | Shaughnessy et al. |
| 2004/0063088 A1 | 4/2004 | Berg et al. |
| 2004/0072184 A1 | 4/2004 | Yoganathan et al. |
| 2004/0076984 A1 | 4/2004 | Eils |
| 2004/0106156 A1 | 6/2004 | Perez et al. |
| 2004/0126784 A1 | 7/2004 | Hitoshi et al. |
| 2004/0137539 A1 | 7/2004 | Bradford |
| 2004/0170995 A1 | 9/2004 | Lograsso et al. |
| 2004/0180380 A1 | 9/2004 | Lee et al. |
| 2004/0219592 A1 | 11/2004 | Berg et al. |
| 2004/0224371 A1 | 11/2004 | De Matos et al. |
| 2004/0229284 A1 | 11/2004 | Luciw et al. |
| 2004/0241636 A1 | 12/2004 | Michnick et al. |
| 2004/0248151 A1 | 12/2004 | Bacus et al. |
| 2005/0009112 A1 | 1/2005 | Edgar et al. |
| 2005/0042694 A1 | 2/2005 | Darzynkiewicz et al. |
| 2005/0074834 A1 | 4/2005 | Chaplen et al. |
| 2005/0084924 A1 | 4/2005 | Shults et al. |
| 2005/0112700 A1 | 5/2005 | Perez et al. |
| 2005/0126961 A1 | 6/2005 | Bissler et al. |
| 2005/0131006 A1 | 6/2005 | Mukherjee et al. |
| 2005/0216961 A1 | 9/2005 | Delaney |
| 2005/0250127 A1 | 11/2005 | Fisher et al. |
| 2005/0281743 A1 | 12/2005 | Delaney |
| 2006/0029944 A1 | 2/2006 | Huang et al. |
| 2006/0035211 A1 | 2/2006 | Levinson et al. |
| 2006/0040338 A1 | 2/2006 | Westwick et al. |
| 2006/0046249 A1 | 3/2006 | Huang et al. |
| 2006/0046272 A1 | 3/2006 | Chow et al. |
| 2006/0073474 A1 | 4/2006 | Perez et al. |
| 2007/0009923 A1 | 1/2007 | Nolan et al. |
| 2007/0105165 A1 | 5/2007 | Goolsby et al. |
| 2007/0172847 A1 | 7/2007 | Bonavida et al. |
| 2007/0196868 A1 | 8/2007 | Perez et al. |
| 2007/0196869 A1 | 8/2007 | Perez et al. |
| 2007/0196870 A1 | 8/2007 | Perez et al. |
| 2008/0026383 A1 | 1/2008 | Pepper et al. |
| 2008/0182262 A1 | 7/2008 | Perez et al. |
| 2008/0254489 A1 | 10/2008 | Perez et al. |
| 2008/0260754 A1 | 10/2008 | Li et al. |
| 2009/0068681 A1 | 3/2009 | Perez et al. |
| 2009/0081699 A1 | 3/2009 | Perez et al. |
| 2009/0098594 A1 | 4/2009 | Fantl et al. |
| 2009/0269773 A1 | 10/2009 | Fantl et al. |
| 2009/0269800 A1 | 10/2009 | Covey et al. |
| 2009/0291458 A1 | 11/2009 | Cohen et al. |
| 2009/0307248 A1 | 12/2009 | Moser et al. |
| 2010/0009364 A1 | 1/2010 | Fantl et al. |
| 2010/0014741 A1 | 1/2010 | Banville et al. |
| 2010/0030719 A1 | 2/2010 | Covey et al. |
| 2010/0042351 A1 | 2/2010 | Covey et al. |
| 2010/0086951 A1 | 4/2010 | Hedley et al. |
| 2010/0099109 A1 | 4/2010 | Fantl et al. |
| 2010/0105074 A1 | 4/2010 | Covey et al. |
| 2010/0151472 A1 | 6/2010 | Nolan et al. |
| 2010/0184092 A1 | 7/2010 | Perez et al. |
| 2010/0204973 A1 | 8/2010 | Parkinson et al. |
| 2010/0209929 A1 | 8/2010 | Fantl et al. |
| 2010/0215644 A1 | 8/2010 | Fantl et al. |
| 2010/0233733 A1 | 9/2010 | Fantl |
| 2010/0240542 A1 | 9/2010 | Soper et al. |
| 2010/0285594 A1 | 11/2010 | Purvis, Jr. |
| 2010/0297676 A1 | 11/2010 | Fantl et al. |
| 2011/0020839 A1 | 1/2011 | Perez et al. |
| 2011/0059861 A1 | 3/2011 | Nolan et al. |
| 2011/0104717 A1 | 5/2011 | Fantl et al. |
| 2011/0262468 A1 | 10/2011 | Fantl et al. |

FOREIGN PATENT DOCUMENTS

| | | |
|---|---|---|
| WO | WO 03/067210 A2 | 8/2003 |
| WO | WO 03/067210 A3 | 12/2003 |
| WO | WO 2006/012507 A2 | 2/2006 |
| WO | WO 2006/050333 A2 | 5/2006 |
| WO | WO 2006/086111 A2 | 8/2006 |
| WO | WO 2006/012507 A3 | 10/2006 |
| WO | WO 2006/050333 A3 | 10/2006 |
| WO | WO 2007/015886 A2 | 2/2007 |
| WO | WO 2007/027906 A2 | 3/2007 |
| WO | WO 2007/027957 A2 | 3/2007 |
| WO | WO 2007/056192 A2 | 5/2007 |
| WO | WO 2007/056192 A3 | 7/2007 |
| WO | WO 2007/127335 A2 | 11/2007 |
| WO | WO 2007/140316 A1 | 12/2007 |
| WO | WO 2008/009004 A2 | 1/2008 |
| WO | WO 2007/127335 A3 | 6/2008 |
| WO | WO 2007/015886 A3 | 10/2008 |
| WO | WO 2008/009004 A3 | 10/2008 |
| WO | WO 2007/027957 A3 | 1/2009 |
| WO | WO 2009/025847 A2 | 2/2009 |
| WO | WO 2006/086111 A3 | 4/2009 |
| WO | WO 2009/025847 A3 | 6/2009 |
| WO | WO 2009/134944 A2 | 11/2009 |
| WO | WO 2009/134944 A3 | 11/2009 |
| WO | WO 2010/006291 A1 | 1/2010 |
| WO | WO 2010/028277 A1 | 3/2010 |
| WO | WO 2010/045651 A1 | 4/2010 |
| WO | WO 2007/027906 A3 | 11/2010 |
| WO | WO 2010/135608 A1 | 11/2010 |
| WO | WO 2009/134944 A3 | 2/2510 |

OTHER PUBLICATIONS

Collins, et al. Multipotent hematopoietic cell lines derived from C/EBPa (−/−) knockout mice display granulocyte macrophage-colony-stimulating factor, granulocytecolony-stimulating factor and retinoic acid-induced granulocytic differentiation. Blood. 2001;98:2382-8.

De Fougerolles, et al. Characterization of ICAM-2 and evidence for a third counter-receptor for LFA-1. J Exp Med. 1991; 174: 253-67.

Figueiredo-Pontes, et al. Determination of P-glycoprotein, MDR-related protein 1, breast cancer resistance protein, and lung-resistance protein expression in leukemic stem cells of acute myeloid leukemia. Clinical Cytometry. 2008;74B(3):163-168.

Gert-Jan, et al. G-CSF receptor truncations found in SCN/AML relieve SOCS3- controlled inhibition of STAT5 but leave suppression of STAT3 intact. Blood. 2004;104:667-74.

Ikezoe, et al. The antitumor effects of sunitinib (formerly SU11248) against a variety of human hematologic malignancies. enhancement of growth inhibition via inhibition of mammalian target of rapamycin signaling. Mol Cancer Ther. Oct. 2006;5(10):2522-30.

Kikukawa, et al. Study of p53 in elderly patients with myelodysplastic syndromes by immunohistochemistry and DNA analysis. American Journal of Pathology 1999;155:717-721.

Kornblau, et al. Dynamic single-cell network profiles in acute myelogenous leukemia are associated with patient response to standard induction therapy. Clin Cancer Res. Jul. 15, 2010;16(14):3721-33. (abstract).

Krutzik, et al. Coordinate analysis of murine immune cell surface markers and intracellular phosphoproteins by flow cytometry. J Immunol. 2005. 175(4):2357-65.

Marvin et al. Normal bone marrow signal transduction profiles: a requisite for enhanced detection of signaling dysregulations in AML. Blood. Jan. 13, 2011. doi:10.1182/blood-2010-10-316026 [Epub ahead of print].

Matsumoto, et al. Adhesion mediated by LFA-1 is required for efficienct IL-12- induced NK and NKT cell cytotoxicity. Eur J Immunol. 2000; 30: 3723-31.

Moser, et al. Improved outcome of chronic Pseudomonas aeruginosa lung infection associated with induction of a Thl-dominated cytokine response. Clin Exp Immunol. 2002; 127: 206-13.

Mukai, et al. Critical role of CD11a (LFA-1) in therapeutic efficacy of systemically transferred antitumor effector T cells. Cell Immunol. 1999; 192: 122-32.

Padua, et al. RAS, FMS and p53 mutations and poor clinical outcome in myelodysplasias: a 10-year follow-up. Leukemia. 1998;12:887-892.
Sakatsume, et al. The Jak Kinases Differentially Associate with the α and β (Accessory Factor) Chains of the Interferon γ Receptor to Form a Functional Receptor Unit Capable of Activating STAT Transcription Factors. J. Biol. Chem. 1995;270:17528-17534.
Seita, et al. Lnk negatively regulates self-renewal of hematopoietic stem cells by modifying thrombopoietin-mediated signal transduction. Proc Natl Acad Sci U S A. Feb. 13, 2007;104(7):2349-54.
Shankaran, et al. IFNgamma and lymphocytes prevent primary tumour development and shape tumour immunogenicity. Nature. Apr. 26, 2001;410(6832):1107-11.
Uesugi, et al. Inhibition of ATRA-induced myeloid differentiation in acute promyelocytic leukemia by a new protein tyrosine phosphatase inhibitor, 3,4-dephostatin. J Exp Clin Cancer Res. Sep. 2000;19(3):363-6.
Weber, et al. Cytohesin-1 is a dynamic regulator of distinct LFA-1 functions in leukocyte arrest and transmigration triggered by chemokines. Curr Biol. 2001; 11:1969-74.
Zheng, et al. Regulation of STAT3 and STAT5 in the differentiation of FLT3/ITD expressing 32Dcl3 cells induced by G-CSF and CEP-701. Abstract 2935.Blood. 2002; 100(11) and 44th Annual Meeting of the American Society of Hematology. Philadelphia, PA, USA. Dec. 6-10, 2002.
Bartram, et al. Translocation of c-ab 1 oncogene correlates with the presence of a Philadelphia chromosome in chronic myelocytic leukaemia. Nature. Nov. 17-23, 1983;306(5940):277-80.
Czech, M. PIP3 and PIP2: Complex Roles at the Cell Surface. Cell, 2000; 100:603-606.
Perfetto, et al. Seventeen-colour flow cytometry: unravelling the immune system. Nat Rev Immunol. Aug. 2004;4(8):648-55.
Sachs, et al. Bayesian network approach to cell signaling pathway modeling. Sci STKE Sep. 3, 2002;2002(148):PE38.
Chow, et al. Constitutive phosphorylation of the S6 ribosomal protein via mTOR and ERK signaling in the peripheral blasts of acute leukemia patients. Experimental hematology. 2006; 34(9):1182-1190.
UK office action and search report dated Nov. 18, 2011 for GB Application No. 1017857.2.
U.S. Appl. No. 13/384,181, filed Jan. 13, 2012, Cesano et al.
Cesano, et al. Single-cell network profiling as tool to identify AML chemotherapy resistant cell phenotypes under in vivo therapeutic pressure. Blood. Nov. 2009; 114(22):165. abstract #397.
Covey, et al. Modulated multiparametric phosphoflow cytometry in hematological malignancies: technologies and clinical applications. Best Pract Res Clin Haematol. Sep. 2010;23(2):319-31. Epub Nov. 10, 2010.
Diaz-Flores, et al. Intracellular signals as molecular biomarkers for therapeutic responses in Kras mutant myeloid cells. Blood. Nov. 2007; 110(11)part1;635a abstract #2196.
Perl, et al. Single-cell pharmacodynamic monitoring of S6 ribosomal protein in AML blasts during a clinical trial combining the mTOR inhibitor sirolimus with mitoxantrone, etoposide, and cytarabine chemotherapy. Blood. Nov. 2009; 114(22):172. abstract #413.
UK search report Apr. 23, 2012 for GB Application No. 1017857.2.
Amico, et al. Differential response of human acute myeloid leukemia cells to gemtuzumab ozogamicin in vitro: role of Chkl and Chik2 phosphorylation and caspase 3. Blood. Jun. 1, 2003;101(11):4589-97.
Bai, et al. Dimerization of the extracellular calcium-sensing receptor (CaR) on the cell surface of CaR-transfected HEK293 cells. J Biol Chem. Sep. 4, 1998; 273(36):23605-10.
Bindoli, et al.Thiol chemistry in peroxidase catalysis and redox signaling. Antioxid Redox Signal. 2008. 10(9):1549-64.
Kumar, et al. 2-methoxyestradiol blocks cell-cycle progression at G(2)/M phase and inhibits growth of human prostate cancer cells. Mol Carcinog. Jul. 2001;31(3):111-24.
Walter, et al. ITIM-dependant endocytosis of CD33-related Siglecs: role of intracellular domain, tyrosine phosphorylation, and the tyrosine phosphatases, Shp1 and Shp, Journal. Leuk. Bio., 83:Jan. 2008, p. 200-211.
U.S. Appl. No. 60/304,434, filed Jul. 10, 2001, Perez et al.
U.S. Appl. No. 60/310,141, filed Aug. 2, 2001, Nolan et al.
U.S. Appl. No. 61,048,657, filed Apr. 29, 2008, Covey et al.
U.S. Appl. No. 61/048,886, filed Apr. 29, 2008, Fantl et al.
U.S. Appl. No. 61/048,920, filed Apr. 29, 2008, Fantl et al.
U.S. Appl. No. 61/055,362, filed May 22, 2008, Cohen et al.
U.S. Appl. No. 61/079,537, filed Jul. 10, 2008, Putta.
U.S. Appl. No. 61/079,551, filed Jul. 10, 2008, Putta.
U.S. Appl. No. 61/079,579, filed Jul. 10, 2008, Banville et al.
U.S. Appl. No. 61/079,766, filed Jul. 10, 2008, Fantl et al.
U.S. Appl. No. 61/085,789, filed Apr. 1, 2008, Fantl et al.
U.S. Appl. No. 61/087,55, filed Apr. 8, 2008, Covey et al.
Allende, et al. A novel CD18 genomic deletion in a patient with severe leucocyte adhesion deficiency: a possible CD2/lymphocyte function-associated antigen-1 functional association in humans. Immunology. 2000; 99: 440-50.
Alvarez, et al. Signal Transducer and Activator of Transcription 3 Is Required for the Oncogenic Effects of Non-Small-Cell Lung Cancer-Associated Mutations of the Epidermal Growth Factor Receptor. Cancer Research. 2006;66:3162-3168.
Anderson, et al. Simultaneous fluorescence-activated cell sorter analysis of two distinct transcriptional elements within a single cell using engineered green fluorescent proteins. Proc Natl Acad Sci USA. 1996; 93: 8508-11.
Aul, et al. Evaluating the prognosis of patients with myelodysplastic syndromes. Ann Hematol. 2002;81(9):485-97.
Bacon, et al. Interleukin 12 induces tyrosine phosphorylation and activation of STAT4 in human lymphocytes. Proc. Natl. Acad. Sci. USA. 1995;92:7307-7311.
Baldus, et al. Clinical outcome of de novo acute myeloid leukemia patients with normal cytogenetics is affected by molecular genetic alterations: a concise review. British J. Haematology. 2007;137:387-400.
Baldus, et al. BAALC expression predicts clinical outcome of de novo acute myeloid leukemia patients with normal cytogenetics: a Cancer and Leukemia Group B study. Blood. 2003;102:1613-18.
Bardet, et al. Single cell analysis of phosphoinositide 3-kinase/Akt and ERK activation in acute myeloid leukemia by flow cytometry. Haematologica. Jun. 2006;91(6):757-64.
Barrow, et al. You say ITAM and I say ITIM, let's call the whole thing off: the ambiguity of immunoreceptor signalling. Eur J Immunol. 2006;36(7):1646-53.
Baxter, et al. Acquired mutation of the tyrosine kinase JAK2 in human myeloproliferative disorders. The Lancet. 2005;365(9464):1054-1061.
Baxter, et al. Acquired mutation of the tyrosine kinase JAK2 in human myeloproliferative neoplasms. Lancet. 2005;365(9464):1054-1061.
Belloc, et al. Flow cytometry detection of caspase 3 activation in preapoptotic leukemic cells. Cytometry. Jun. 1, 2000;40(2):151-60.
Bene, et al. Detection of receptor clustering by flow cytometric fluorescence anisotropy measurements. Cytometry. 2000; 40: 292-306.
Benekli, et al. Signal transducer and activator of transcription proteins in leukemias. Blood. Apr. 15, 2000;101(8):2940-54.
Bienz. APC: the plot thickens. Curr Opin Genet Dev. 1999; 9(5): 595-603.
Birkenkamp, et al. Regulation of constitutive STAT5 phosphorylation in acute myeloid leukemia blasts. Leukemia. 2001; 15(12):1923-31.
Bleijs, et al. A single amino acid in the cytoplasmic domain of the beta 2 integrin lymphocyte function-associated antigen-1 regulates avidity-dependent inside-out signaling. J Biol Chem. 2001; 276: 10338-46.
Boissel, et al. Incidence and prognostic impact of c-Kit, FLT3 LIGAND, and Ras gene mutations in core binding factor acute myeloid leukemia (CBF-AML). Leukemia. 2006;20(6):965-970.
Broxmeyer, et al. The suppressive influences of human tumor necrosis factors on bone marrow hematopoietic progenitor cells from normal donors and patients with leukemia: synergism of tumor necrosis factor and interferon-gamma. Journal of Immunology. 1986;36:4487-4495.
Calo, et al. STAT proteins: from normal control of cellular events to tumorigenesis. J Cell Physiol. Nov. 2003;197(2):157-68.

Castillo, et al. Proliferative response of mantle cell lymphoma cells stimulated by CD40 ligation and IL-4. Leukemia. Feb. 2000;14(2):292-8.
Choudhary, et al. Activation mechanisms of STAT5 by oncogenic FLt3 ligand-ITD. Blood. 2007;110(1):370-4.
Choudhary, et al. AML-associated Flt3 kinase domain mutations show signal transduction differences compared with Flt3-ITD mutations. Blood. 2005;106:265-73.
Chow, et al. Measurement of MAP kinase activation by flow cytometry using phospho-specific antibodies to MEK and ERK: potential for pharmacodynamic monitoring of signal transduction inhibitors. Cytometry. Apr. 15, 2001;46(2):72-8.
Collins, et al. Multipotent hematopoietic cell lines derived from C/EBPa (-/-) knockout mice display granulocyte macrophage-colony-stimulating factor, granulocyte-colony-stimulating factor and retinoic acid-induced granulocytic differentiation. Blood. 2001;98:2382-8.
Colucci, et al. Redundant role of the Syk protein tyrosine kinase in muse NK cell differentiation. J Immunol. 1999; 163: 1769-74.
Craig, et al. Flow cytometric immunophenotyping for hematologic neoplasms. Blood. Apr. 15, 2008;111(8):3941-67.
Crans-Vargas, et al. CREB as a prognostic marker in acute leukemia. Abstract. Blood. 2001; 98(11), part 1, p. 316a.
Damle, et al. Differential regulatory effects of intercellular adhesion molecule-1 on costimulation by CD28 counter-receptor B7. J Immunol. 1992; 149: 2541-8.
Danna, et al. Transcending the biomarker mindset: deciphering disease mechanisms at the single cell level. Curr Opin Chem Biol. Feb. 2006;10(1):20-7.
Dantuma, et al. Short-lived green fluorescent proteins for quantifying ubiquitin/proteasome-dependent proteolysis in living cells. Nat Biotechnol. 2000; 18: 538-43.
Davis, et al. Determination of CD4 antigen density on cells: role of antibody valency, avidity, clones, and conjugation. Cytometry. 1998; 33: 197-205.
De Fougerolles, et al. Characterization of ICAM-2 and evidence for a third counter-receptor for LFA-1. J Exp Med. 1991; 174: 253-27.
De Fougerolles, et al. Heterogenous glycosylation of ICAM-3 and lack of interaction with Mac-1 and p150,95. Eur J Immunol 1995; 25: 1008-12.
De Rosa, et al. 11-color, 13-parameter flow cytometry: Identification of human naive T cells by phenotype, function, and T-cell receptor diversity. Nat Med. 2001; 7: 245-8.
Deeths, et al. ICAM-1 and B7-1 provide similar but distinct costimulation for CD8+ T cells, while CD4+ T cells are poorly costimulated by ICAM-1. Eur J Immunol. 1999; 29: 45-53.
Devine, et al. Role of LFA-1, ICAM-1, VLA4 and VCAM-1 in lymphocyte migration across retinal pigment epithelial monolayers in vitro. Immunology. 1996; 88: 456-62.
Diacovo, et al. A functional integrin ligand on the surface of platelets: intercellular adhesion molecule-2. J Clin Invest. 1994; 94: 1243-51.
Dikic, et al. A role for Pyk2 and Src in linking G-protein-coupled receptors with MAP kinase activation. Nature. 1996; 383: 547-50.
Doepfner, et al. Targeting receptor tyrosine kinase signaling in acute myeloid leukemia. Crit Rev Oncol Hematol. Sep. 2007;63(3):215-30.
Donskov, et al. Expression and function of LFA-1 on A-NK and T-LAK cells: role in tumor target killing and migration into tumor tissue. Nat Immun. 1996; 15: 134-46.
Ebert, et al. An Erythroid Differentiation Signature Predicts Response to Lenalidomide in Myelodysplastic Syndrome. PLoS Medicine. 2008;5(2):312-322.
Erlanson, et al. Flow cytometric quantification of cyclin E in human cell lines and hematopoietic malignancies. Cytometry. Jul. 1, 1998;32(3):214-22.
European search report and search opinion dated Feb. 22, 2011 for Application No. 10180167.8.
Fiering, et al. Improved FAGS-Gal: flow cytometric analysis and sorting of viable eukaryotic cells expressing reporter gene constructs. Cytometry. 1991; 12: 291-301.
Figueiredo-Pontes, et al. Determination of P-glycoprotein, MDR-related protein 1, breast cancer resistance protein, and lung-resistance protein expression in leukemic stem cells of acute myeloid leukemia. Clincal Cytometry. 2008;74B(3): 163-168.
Fine, et al. The role of LFA-1/ICAM-1 interactions during murine T lymphocyte development. J Immunol. 1991; 147: 2852-9.
Frank, et al. Interleukin 2 signaling involves the phosphorylation of Stat proteins. Proc. Natl. Acad. Sci. USA. 1995;92:7779-7783.
Frohling, et al. Prognostic significance of activating FLT3 mutations in younger adults (16 to 60 years) with acute myeloid leukemia and normal cytogenetics: a study of the AML Study Group Ulm. Blood. 2002;100:4372-80.
Fujii, et al. Activation of Stat5 by interleukin 2 requires a carboxyl-terminal region of the interleukin 2 receptor beta chain but is not essential for the proliferative signal transmission. Proc. Natl. Acad. Sci USA. 1995;92:5482-5486.
Galaris, et al. Redox signaling and cancer: The role of "labile" iron. Cancer Letters. 2008;266(1):21-29.
Geiger, et al. Cytohesion-1 regulates beta-2 integrin-mediated adhesion through both ARF-GEF function and interaction with LFA-1. Embo J. 2000; 19: 2525-36.
Georgiou, et al. Serial determination of FLT3 mutations in myelodysplastic syndrome patients at diagnosis, follow up or acute myeloid leukaemia transformation: incidence and their prognostic significance. Br J Haematol. 2006;134(3):302-6.
Gert-Jan, et al. G-CSF receptor truncations found in SCN/AML relieve SOCS3-controlled inhibition of STAT5 but leave suppression of STAT3 intact. Blood. 2004;104:667-74.
Gery, et al. Adaptor protein Lnk negatively regulates the mutant MPL, MPLW515L associated with myeloproliferative neoplasms. Blood. 2007;110(9):3360-3364.
Gilliand, et al. The roles of FLT3 in hematopoiesis and leukemia. Blood. 2002;100:1532-1542.
Griffioen, et al. Endothelial intercellular adhesion molecule-1 expression is suppressed in human malignancies: the role of angiogenic factors. Cancer Res. 1996; 56: 1111-7.
Griffioen, et al. Tumor angiogenesis is accompanied by a decreased inflammatory response of tumor-associated endothelium. Blood. 1996; 88: 667-73.
Gueller, et al. Adaptor protein Lnk associates with Tyr(568) in c-Kit. Biochem J. 2008;415(2):241-5.
Hanahan, et al. The Hallmarks of Cancer. Cell. 2000;100(1):57-70.
Hayakawa, et al. SFK-STAT pathway: an alternative and important way to malignancies. Annals of the New York Academy of Sciences. 2006;1086:213-22.
Helander, et al. ICAM-2 redistributed by ezrin as a target for killer cells. Nature. 1996; 382: 265-8.
Ho, et al. MDR1 and BCRP1 expression in leukemic progenitors correlates with chemotherapy response in acute myeloid leukemia. Experimental Hematology. 2008;36:433-442.
Hofmann, et al. Mutation analysis of the DNA-damage checkpoint gene CHK2 in myelodysplastic syndromes and acute myeloid leukemias. Leukemia Research. 2001;25:333-338.
Hogg, et al. A novel leukocyte adhesion deficiency caused by expressed by nonfunctional beta2 integrins Mac-1 and LFA-1. J Clin Invest. 1999; 103: 97-106.
Igietseme, et al. The intercellular adhesion molecule type-1 is required for rapid activation of T helped type 1 lymphocytes that control early acute phase of genital chlamydial infection of mice. Immunology. 1999; 98: 510-8.
Ikezoe, et al. The antitumor effects of sunitinib (formerly SU11248) against a variety of human hematologic malignancies: enhancement of growth inhibition via inhibition of mammalian target of rapamycin signaling. Mol Cancer Ther. Oct. 2006; 5(10):2522-30.
International search report dated Nov. 24, 2009 for PCT/US2009/050295.
Irish, et al. Mapping normal and cancer cell signalling networks: towards single-cell proteomics. Nat. Rev. Cancer. 2006. 6:146-155.
Irish, et al. Altered B-cell receptor signaling kinetics distinguish human follicular lymphoma B cells from tumor-infiltrating nonmalignant B cells. Blood. Nov. 1, 2006;108(9):3135-42.
Irish, et al. Flt3 Y591 duplication and Bcl-2 overexpression are detected in acute myeloid leukemia cells with high levels of phosphorylated wild-type p53. Blood. 2007. 109(6):2589-96.

Irish, et al. Kinetics of B cell receptor signaling in human B cell subsets mapped by phosphospecific flow cytometry. J Immunol. Aug. 1, 2006;177(3):1581-9.

Irish, et al. Single cell profiling of potentiated phospho-protein networks in cancer cells. Cell. Jul. 23, 2004;118(2):217-28.

Iyer, et al. Quantitation of CD38 expression using QuantiBRITE™ beads. Cytometry. 1998; 33: 206-12.

James, et al. A unique clonal JAK2 mutation leading to constitutive signalling causes polycythaemia vera. Nature. 2005;434:1144-1148.

Jiang, et al. Pivotal role of phosphoinositide-3 kinase in regulation of cytotoxicity in natural killer cells. Nat Immunol. 2000; 1: 419-25.

Johnson, et al. Effector caspases are dispensable for the early nuclear morphological changes during chemical-induced apoptosis. J Cell Sci. 2000; 113: 2941-53.

Karp, et al. Targeting Vascular Endothelial Growth Factor for Relapsed and Refractory Adult Acute Myelogenous Leukemias. Clinical Cancer Res. 2004;10:3577-85.

Kennedy, et al. Akt/Protein kinase B inhibits cell death by preventing the release of cytochrome c from mitochondria. Mol Cell Biol. 1999; 19: 5800-10.

Kikukawa, et al. Study of p53 in elderly patients with myelodysplastic syndromes by immunohistochemistry and DNA analysis. American Journal of Pathology. 1999;155:717-721.

Kindler, et al. Indentification of a novel activating mutation (Y842C) within the activation loop of FLT3 in a patient with AML. Abstract 4681. Blood. 2003; 102(11):239B-240B and 45th Annual Meeting of the American Society of Hematology. San Diego, CA, USA. Dec. 6-9, 2003.

Kishimoto, T. Signal transduction through homo- or heterodimers of gp130. Stem Cells. 1994;12(Suppl 1):37-44;discussion 44-5.

Kliche, et al. Signaling by human herpesvirus 8 kaposin A through direct membrane recruitment of cytohesin-1. Mol Cell. 2001; 7: 833-43.

Koretzky, et al. SLP76 and SLP65: complex regulation of signalling in lymphocytes and beyond. Nature Reviews Immunology. 2006;6:67-78.

Kornblau, et al. Dynamic single-cell network profiles in acute myelogenous leukemia are associated with patient response to standard induction therapy. Clin Cancer Res. 2010 Jul 15;16(14):3721-33. (abstract).

Kralovics, et al. A Gain-of-Function Mutation of JAK2 in Myeloproliferative Disorders. N Engl J Med. 2005;352:1779.

Kralovics, et al. Altered gene expression in myeloproliferative neoplasms correlates with the activation of signaling by the V617F mutation of JAK2. Blood. 2005;106(10):3374-3376.

Krutzik, et al. High-content single-cell drug screening with phosphospecific flow cytometry. Natural Chemical Biology. 2008. 4(2):132-42.

Krutzik, et al. Intracellular phospho-protein staining techniques for flow cytometry: monitoring single cell signaling events. Cytometry A. 2003; 55(2): 61-70.

Krutzik, et al. Analysis of protein phosphorylation and cellular signaling events by flow cytometry: techniques and clinical applications. Clinical Immunology. 2004; 110: 206-21.

Krutzik, et al. Coordinate analysis of murine immune cell surface markers and intracellular phosphoproteins by flow cytemetry. J Immunol. 2005. 175(4):2357-65.

Krutzik, et al. Intracellular phospho-protein staining techniques for flow cytometry: monitoring single cell singaling events. Cytometry Part A. 2003; 55A:61-70.

Krutzik. Characterization of the murine immunological signaling network with phosphospecific flow cytometry. J Immunol. 2005. 175(4): 2366-73.

Kulik, et al. Antiapoptotic signaling by the insulin-like growth factor I receptor, phosphatidylinositol 3-kinase, and Akt. Mol Cell Biol. 1997; 17: 1595-606.

Kurotaki, et al. Apoptosis, bcl-2 expression and p53 accumulation in MDS, MDS derived acute myeloid leukemia and de novo acute myeloid leukemia. Acta Haematologica. 2000;102:115-123.

Lecoeur, et al. A novel flow cytometric assay for quantitation and multiparametric characterization of cell-mediated cytotoxicity. J Immunol Methods. 2001; 253: 177-87.

Legrand, et al. Pgp and MRP Activities Using Calcein-AM Are Prognostic Factors in Adult Acute Myeloid Leukemia Patients. Blood. 1998;91:4480-4488.

Leith, et al. Acute Myeloid Leukemia in the Elderly: Assessment of Multidrug Resistance (MDR1) and Cytogenetics Distinguishes Biologic Subgroups With Remarkably Distinct Responses to Standard Chemotherapy. A Southwest Oncology Group Study. Blood. 1997;89:3323-3329.

Leith, et al. Frequency and Clinical Significance of the Expression of the Multidrug Resistance Proteins MDR1/P-Glycoprotein, MRP1, and LRP in Acute Myeloid Leukemia. A Southwest Oncology Group Study. Blood. 1999;94:1086-1099.

Lenkei, et al. Performance of calibration standards for antigen quantitation with flow cytometry. Cytometry. 1998; 33: 188-96.

Levine, et al. Activating mutation in the tyrosine kinase JAK2 in polycythemia vera, essential thrombocythemia, and myeloid metaplasia with myelofibrosis. Cancer Cell. 2005;7(4):387-397.

Lub, et al. Dual role of the actin cytoskeleton in regulating cell adhesion mediated by the integrin lymphocyte function-associated molecule-1. Mol Biol Cell. 1997; 8: 341-51.

Marcucci, et al. Overexpression of the ETS-related gene, ERG, predicts a worse outcome in acute myeloid leukemia with normal karyotype: a Cancer and Leukemia Goruop B study. J. Clinical Oncology. 2005;23:9234-42.

Marone, et al. Targeting phosphoinositide 3-kinase—Moving towards therapy. Biochimica et Biophysica Acta (BBA)—Proteins & Proteomics. 2008;1784:159-185.

Marvin et al. Normal bone marrow signal transduction profiles: a requisite for enhanced detection of signaling dysregulations in AML. Blood. Jan 13, 2011. doi:10.1182/blood-2010-10-316026 [Epub ahead of print].

Mates, et al. Intracellular redox status and oxidative stress: implications for cell proliferation, apoptosis, and carcinogenesis. Arch Toxicol. May 2008;82(5):273-99.

Matsumoto, et al. Adhesion mediated by LFA-1 is required for efficient IL-12-induced NK and NKT cell cytotoxicity. Eur J Immunol. 2000; 30: 3723-31.

McDowall, et al. The I domain of integrin leukocyte function-associated antigen-1 is involved in a conformational change leading to high affinity binding to ligand intercellular adhesion molecule 1 (ICAM-1). J Biol Chem. 1998; 273: 27396-403.

Melchert, et al. The role of lenalidomide in the treatment of patients with chromosome 5q deletion and other myelodysplastic syndromes. Current Opinion in Haematology. 2007;14:123-129.

Menard, et al. Biologic and therapeutic role of HER2 in cancer. Oncogene. 2003. 22(42): 6570-8.

Meshinchi et al. Structural and functional Alterations of FLT3 in Acute Myeloid Leukemia. Clin Cancer Res. 2009;15(13):4263-4269.

Miller, et al. Intercellular adhesion molecule-1 dimerization and its consequences for adhesion mediated by lymphocyte function associated-1. J Exp Med. 1995; 182: 1231-41.

Moon, et al. Molecular mechanisms of ZD1839 (Iressa)-induced apoptosis in human leukemic U937 cells. Acta Pharmacol Sin. Aug. 2007;28(8):1205-14.

Morgan, et al. Cell-cycle-dependent activation of mitogen-activated protein kinase kinase (MEK-1/2) in myeloid leukemia cell lines and induction of growth inhibition and apoptosis by inhibitors of Ras signaling. Blood. Mar. 15, 2001;97(6):1823-34.

Morgan, et al. Superantigen-induced T cell:B cell conjugation is mediated by LFA-1 and required signaling though Lck, but not ZAP-70. J Immunol. 2001; 167: 5708-18.

Morkve, et al. Quantitation of biological tumor markers (p53, c-myc, Ki-67 and DNA ploidy) by multiparameter flow cytometry in non-small-cell lung cancer. Int J Cancer. Dec. 2, 1992;52(6):851-5.

Moser, et al. Improved outcome of chronic Pseudomonas aeruginosa lung infection associated with induction of a Th1-dominated cytokine response. Clin Exp Immunol. 2002; 127: 206-13.

Mukai, et al. Critical role of CD11 a (LFA-1) in therapeutic efficacy of systemically transferred antitumor effector T cells. Cell Immunol. 1999; 192: 122-32.

Musso, et al. Regulation of JAK3 expression in human monocytes: phosphorylation in response to interleukins 2, 4, and 7. J. Exp. Med. 1995;181:1425-1431.

Nam, et al. The PI3K-Akt mediates oncogenic Met-induced centrosome amplification and chromosome instability. Carcinogenesis. Sep. 2010;31(9):1531-40. Abstract only.

Neeson, et al. Characterization of activated lymphocyte-tumor cell adhesion. J Leukoc Biol. 2000; 67: 847-55.

Neubauer, et al. Mutations in the ras proto-oncogenes in patients with myelodysplastic syndromes. Leukemia. 1994;8:638-641.

Nielson, et al. Expression of the activation antigen CD69 predicts functionality of in vitro expanded peripheral blood mononuclear cells (PBMC) from healthy donors and HIV-infected patients. Clin Exp Immunol 1998; 114: 66-72.

Nishimura, et al. Distinct role of antigen-specific T helper type 1 (Th1) and Th2 cells in tumor eradication in vivo. J Exp Med. 1999; 190: 617-27.

Nolan, et al. Fluorescence activated cell analysis and sorting of viable mammalian cells based on beta-D-galactosidase activity after transduction of *Escherichia coli* lacZ. Proc Natl Acad Sci USA. 1988; 85: 2603-7.

Okuda, et al. AML1, the target of multiple chromosomal translocations in human leukemia, is essential for normal fetal liver hematopoiesis. Cell. 1996;84:321-30.

Olsen, et al. Function-based isolation of novel enzymes from a large library. Nat Biotechnol. 2000; 18: 1071-4.

Onishi, et al. Applications of retrovirus-mediated expression cloning. Exp Hematol. 1996; 24: 324-9.

Padro, et al. Overexpression of vascular endothelial growth factor (VEGF) and its cellular receptor KDR (VEGFR-2) in the bone marrow of patients with acute myeloid leukemia. Leukemia. 2002;16:1302-1310.

Padua, et al. RAS, FMS and p53 mutations and poor clinical outcome in U myelodysplasias: a 10-year follow-up. Leukemia. 1998;12:887-892.

Papa, et al. Proapoptotic activity and chemosensitizing effect of the novel Akt inhibitor perifosine in acute myelogenous leukemia cells. Leukemia. Jan. 2008;22(1):147-60.

Pardanani, et al. MPL515 mutations in myeloproliferative and other myeloid disorders: a study of 1182 patients. Blood. 2006.108:3472-3476.

Paul, et al. Myeloid specific human CD33 is an inhibitory receptor with differential ITIM function in recruiting the phosphatases SHP-1 and SHP-2. Blood. 2000;96:483-490.

Perez, et al. Activation of the PKB/AKT pathway by ICAM-2. Immunity. 2002; 16: 51-65.

Perez, et al. Flow cytometric analysis of kinase signaling cascades. Methods Mol Biol. 2004;263:67-94.

Perez, et al. Leukocyte functional antigen 1 lowers T cell activation thresholds and signaling through cytohesin-1 and Jun-activating binding protein 1. Nat Immunol. Nov. 2003;4(11):1083-92.

Perez, et al. LFA-1 signaling through p44/42 is coupled to perforin degranulation in CD56+CD8+ natural killer cells. Blood. Aug. 15, 2004;104(4):1083-93.

Perez, et al. Phospho-proteomic immune analysis by flow cytometry: from mechanism to translational medicine at the single-cell level. Immunol Rev. Apr. 2006;210:208-28.

Perez, et al. Simultaneous measurement of multiple active kinase states using polychromatic flow cytometry. Nat Biotechnol. 2002; 20: 155-62.

Peterson, et al. Coupling of the TCR to integrin activation by Slap-130/Fyb. Science. 2001; 293: 2263-5.

Pikman, et al. MPLW515L Is a Novel Somatic Activating Mutation in Myelofibrosis with Myeloid Metaplasia. PLoS Med. 2006;3(7):e270.

Plasilova, et al. TRAIL (Apo2L) suppresses growth of primary human leukemia and myelodysplasia progenitors. Leukemia. 2002;16:67-73.

Poppe, et al. Expression analyses identify MEL as a prominent target of 11q23 amplification and support an etiologic role for MLL gain of function in myeloid malignancies. Blood. 2004;103:229-235.

Pruneri, et al. Angiogenesis in myelodysplastic syndromes. British Journal of Cancer. 1999;81:1398-1401.

Raaijmakers. ATP-binding-cassette transporters in hematopoietic stem cells and their utility as therapeutical targets in acute and chronic myeloid leukemia. Leukemia. 2007;21:2094-2102.

Radoja, et al. CD8+ tumor-infiltrating T cells are deficient in perforin-mediated cytolytic activity due to defective microtubule-organizing center mobilization and lytic granule exocytosis. J Immunol. 2001; 167: 5042-51.

Renneville et al, Cooperating gene mutations in acute myeloid leukemia: a review of the literature. Leukemia. 2008;22:915-31.

Rice, et al. HOX deregulation in acute myeloid leukemia. Journal of Clinical Investigation. 2007;117(4):865-868.

Risso, et al. CD69 in resting and activated T lymphocytes. Its association with a GTP binding protein and biochemical requirements for its expression. J Immunol. 1991; 146: 4105-14.

Rosen, et al. Functional characterization of FLT3 receptor signaling deregulation in acute myeloid leukemia by single cell network profiling (SCNP). PLoS One. Oct. 27, 2010;5(10):e13543.

Sakatsume, et al. The Jak Kinases Differentially Associate with the $\alpha$ and $\beta$ (Accessory Factor) Chains of the Interferon 7 Receptor to Form a Functional Receptor Unit Capable of Activating STAT Transcription Factors. J. Biol. Chem. 1995;270:17528-17534.

Salomon, et al. LFA-1 interaction with ICAM-1 and ICAM-2 regulates Th2 cytokine production. J Immunol 1998; 161: 5138-42.

Sawanobori, et al. Expression of TNF receptors and related signaling molecules in the bone marrow from patients with myelodysplastic syndromes. Leukemia Research. 2003;27:583-591.

Schaefer, et al. IGF-I and Prostate Cancer. Science. 1998; 282:199a.

Scharfe, et al. JAK3 protein tyrosine kinase mediates interleukin-7-induced activation of phosphatidylinositol-3' kinase. Blood. 1995;86:2077-2085.

Scharffetter-Kochanek, et al. Spontaneous skin ulceration and defective T cell function in CD18 null mice. J Exp Med. 1998; 188: 119-31.

Schepers, et al. STAT5 is required for long-term maintenance of normal and leukemic human stem/progenitor cells. Blood. 2007;110(8):2880-2888.

Schittenheim, et al. FLT3 K663Q is a novel AML-associated oncogenic kinase: determination of biochemical properties and sensitivity to sunitnib. Leukemia. 2006;20:2008-14.

Seita, et al. Lnk negatively regulates self-renewal of hematopoietic stem cells by modifying thrombopoietin-mediated signal transduction. Proc Natl Acad Sci USA. Feb. 13, 2007;104(7):2349-54.

Shankar, et al. CREB is amplified in AML blasts and is associated with an increased risk of relapse and decreased event-free survival. Abstract. Blood. 2004; 104(11), Part 1, p. 166A.

Shankar, et al. Role of cyclic AMP response element binding protein in human leukemias. Cancer. Nov. 1, 2005;104(9):1819-24.

Shankar, et al. The role of CREB as a proto-oncogene in hematopoiesis and in acute myeloid leukemia. Cancer Cell. Apr. 2005;7(4):351-62.

Shankaran, et al. IFNgamma and lymphocytes prevent primary tumour development and shape tumour immunogenicity. Nature. Apr. 26, 2001;410(6832):110711.

Shaw, R. Ras, PI(3)K and mTOR signaling controls tumor cell growth. Nature. 2006;441:424-430.

Shibuya, et al. Physical and functional association of LFA-1 with DNAM-1 adhesion molecule. Immunity. 1999; 11: 615-23.

Shier, et al. Defective CD8+ T cell activation and cytolytic function in the absence of LFA-1 cannot be restored by increased TCR signaling. J Immunol. 1999; 163: 4826-32.

Shulz, et al. Single-Cell Phospho-Protein Analysis by Flow Cytometry. Current Protocols in Immunology. 2007;78:8.17.1-20.

Soede, et al. LFA-1 to LFA-1 signals invole zeta-associated protein-70 (ZAP-70) tyrosine kinase: relevance for invasion and migration of a T cell hybridoma. J Immunol. 1999; 163: 4253-61.

Somersalo, et al. Activation of natural killer cell migration by leukocyte integrin-binding peptide from intracellular adhesion molcule-2 (ICAM-2). J Biol Chem. 1995; 270: 8629-36.

Song, et al. Flow cytometry based biosensor for detection of multivalent proteins. Anal Biochem. 2000; 284: 35-41.

Spiekermann, et al. Overexpression and constitutive activation of FLT3 induces STAT5 activation in primary acute myeloid leukemia blast cells. Clinical Cancer Research. Jun. 2003; 9:2140-2150.

Staquet, et al. Expression of ICAM-3 on human epidermal dendritic cells. Immunobiology. 1995; 192: 249-61.

Starling, et al. Intercellular adhesion molecule-3 is the predominant co-stimulatory ligand for leukocyte function antigen-1 on human blood dendritic cells. Eur J Immunol. 1995; 25: 2528-32.

Steffen, et al. The molecular pathogenesis of acute myeloid leukemia. Critical Reviews in Oncology/Hematology. 2005;56:195-221.

Stelzer, et al. Use of Multiparameter Flow Cytometry and Immunophenotyping for the Diagnosis and Classfication of Acute Myeloid Leukemia. In Immunophenotyping. New York, NY: Wiley-Liss, 2000.

Stephenson, et al. Possible co-existence of RAS activation and monosomy 7 in the leukemic transformation of myelodysplastic syndromes. Leukemia Research. 1995;19:741-8.

Stirewalt, et al. Novel FLT3 point mutations within exon 14 found in patients with acute myeloid leukemia. Br. J. Haematol. 2004;124:481-84.

Sugai, et al. Allelic losses of 17p, 5q, and 18q loci in diploid and aneuploid populations of multiploid colorectal carcinomas. Hum Pathol. 2000; 31: 925-30.

Sugimoto, et al. Mutations of the p53 gene in MDS and MDS-derived leukemia. Blood. 1993;81:3022-6.

Tanaka, et al. Intercellular adhesion molecule 1 underlies the functional heterogeneity of synovial cells in patients with rheumatoid arthritis: involvement of cell cycle machinery. Arthritis Rheum. 2000; 43(11): 2513-22.

Tefferi. JAK and MPL mutations in myeloid malignancies. Leukemia and Lymphoma. 2008;49(3):388-397.

Thomas, et al. Spontaneous activation and signaling by overexpressed epidermal growth factor receptors in glioblastoma cells. Int J Cancer. 2003; 104(1): 19-27.

Tobal, et al. Mutation of the human FMS gene (M-CSF receptor) in myelodysplastic syndromes and acute myeloid leukemia. Leukemia. 1990;4:486-489.

Touw, et al. Granulocyte colony-stimulating factor: key factor or innocent bystander in the development of secondary myeloid malignancy? J. Natl. Cancer. Inst. 2007;99:183-186.

Uesugi, et al Inhibition of ATRA-induced myeloid differentiation in acute promyelocytic leukemia by a new protein tyrosine phosphatase inhibitor, 3,4-dephostatin. J Exp Clin Cancer Res. Sep. 2000;19(3):363-6.

UK office action and search report dated Feb. 22, 2011 for GB Application No. 1017857.2.

Van Meter, et al. K-RasG12D expression induces hyperproliferation and aberrant signaling in primary hematopoietic stem/progenitor cells. Blood. May 1, 2007;109(9):3945-52.

Vivanco, I. The Phosphatidylinositol 3-Kinase-AKT Pathway in Human Cancer. Nature Reviews: Cancer. 2002;2:489-501.

Wang, et al. Decreased production of reactive oxygen intermediates is an early event during in vitro apoptosis of rat thymocytes. Free Radic Biol Med. 1996;20:533-42.

Wang, et al. The TEL/ETV6 gene is required specifically for hematopoiesis in the bone marrow. Genes and Development. 1998;12:2392-402.

Weber, et al. Cytohesin-1 is a dynamic regulator of distinct LFA-1 functions in leukocyte arrest and transmigration triggered by chemokines. Curr Biol. 2001; 11: 1967-74.

Whang, et al. Inactivation of the tumor suppressor PTEN/MMAC1 in advanced human prostate cancer through loss of expression. Proc Natl Acad Sci USA. 1998; 95(9): 5246-50.

Yamamoto, et al. Activating mutation of D835 within the activation loop of FLT3 in human hematologic malignancies. Blood. 2001;97:2434-39.

Yu, et al. IL-2 activation of NK cells: involvement of MKK1/2/ERK. but not p38 kinase pathway. J Immunol 2000; 164: 6244-51.

Yunis, et al. Mechanisms of ras mutation in myelodysplastic syndrome. Oncogene. 1989;4:609-614.

Zhao, et al. Interferon-α-induced Expression of Phospholipid Scramblase 1 through STAT1 Requires the Sequential Activation of Protein Kinase Cδ and Jnk. J. Biol. Chem. 2005;280:42707-42714.

Zheng, et al. Regulation of STAT3 and STAT5 in the differentiation of FLT3/ITD expressing 32Dcl3 cells induced by G-CSF and CEP-701. Abstract 2935.Blood. 2002; 100(11) and 44th Annual Meeting of the American Society of Hematology. Philadelphia, PA, USA. Dec. 6-10, 2002.

Zhou, et al. The ABC transporter Bcrp1/ABCG2 is expressed in a wide variety of stem cells and is a molecular determinant of the side-population phenotype. Nature Medicine. 2001;7:1028-1034.

Zwaan, et al. FLT3 internal tandem duplication in 234 children with acute myeloid leukemia (AML): prognostic significance and relation to cellular drug resistance. Blood. 2003;102:2387-94.

Apperley, et al. Bone marrow transplantation for chronic myeloid leukaemia in first chronic phase: importance of a graft-versus-leukaemia effect. Br J Haematol. Jun. 1988;69(2):239-45.

Bagrintseva, et al. FLT3-ITD-TKD dual mutants associated with AML confer resistance to FLT3 PTK inhibitors and cytotoxic agents by overexpression of Bcl-x(L). Blood. May 1, 2005;105(9):3679-85.

Bartram, et al. Translocation of c-ab1 oncogene correlates with the presence of a Philadelphia chromosome in chronic myelocytic leukaemia. Nature. Nov. 17-23, 1983;306(5940):277-80.

Cairo, et al. Contol of multivalent interactions by binding epitope density. J Am Chem Soc. 2002; 124(8): 1615-9.

Caligaris-Cappio, et al. Infrequent normal B lymphocytes express features of B-chronic lymphocytic leukemia. J Exp Med. Feb. 1, 1982;155(2):623-8.

Cantley, et al. Oncogenes and signal transduction. Cell. Jan. 25, 1991;64(2):281-302.

Chen, et al. Down-regulation of the c-Jun N-terminal kinase (JNK) phosphatase M3/6 and activation of JNK by hydrogen peroxide and pyrrolidine dithiocarbamate. Oncogene. 2001. 20(3):367-74.

Chung, et al. The biology of Abl during hemopoietic stem cell differentiation and development. Oncogene. Apr. 6, 1995;10(7):1261-8.

Clark, et al. Regulation of human B-cell activation and adhesion. Annu Rev Immunol. 1991;9:97-127.

Cochran, et al. Receptor clustering and transmembrane signaling in T cells. Trends in Biochemical Sciences. 2001; 26(5): 304-10.

Countouriotis, et al. Cell surface antigen and molecular targeting in the treatment of hematologic malignancies. Stem Cells. 2002;20(3):215-29.

Czech, M. PIP3 and PIP2: Complex Roles at the Cell Surface. Cell, 2000; 100:603606.

Di Bacco, et al. Molecular abnormalities in chronic myeloid leukemia: deregulation of cell growth and apoptosis. Oncologist. 2000;5(5):405-15.

European search report Jul. 10, 2006 for Application No. 02805693.5.

European Search Report dated Nov. 2, 2010 for EP Application No. EP08795509.

Fantl, et al. High Level phosphatas activity revealed in chronic lymphocytic leukemia cells that use mutated ommunoglobulin heavy chain variable region genes and lack high-level expression of the zeta-assocaited protein(ZAP-70). Blood. 2007. 110(11): Part 1 pp. 228A-229A (Abstracts).

Friedman, et al. Bayesian network classifiers. Machine Learning. 1997; 29:131-163.

Friedman, et al. Inferring cellular networks using probabilistic graphical models. Science. Feb. 6, 2004;303(5659):799-805.

Friedman, et al. Using Bayesian networks to analyze expression data. J Comput Biol. 2000;7(3-4):601-20.

Garrido, et al. Three-color versus four-color multiparameter cell cycle analyses of primary acute myeloid leukemia samples. Cytometry. Apr. 15, 2000;42(2):83-94.

Hamblin, et al. Unmutated Ig V(H) genes are associated with a more aggressive form of chronic lymphocytic leukemia. Blood. Sep. 15, 1999;94(6):1848-54.

Hartemink, et al. Using graphical models and genomic expression data to statistically validate models of genetic regulatory networks. Pac Symp Biocomput. 2001;:422-33.

Haswell, et al. Analysis of the oligomeric requirements for signaling by CD40 using soluble multimeric forms of its ligands, CD154. Eur J Immunol 2001; 31(10): 3094-100.

Hunter. Cooperation between oncogenes. Cell. Jan. 25, 1991;64(2):249-70.

International preliminary report on patentability dated Mar. 4, 2010 for PCT/US2008/009975.

International preliminary report on patentability dated May 5, 2008 for PCT/US2006/043050.
International search report and written opinion dated Mar. 20, 2009 for PCT/US2008/009975.
International search report and written opinion dated May 2, 2007 for PCT/US2006/043050.
International search report dated Jul. 10, 2006 for PCT/US2005/026026.
International search report dated Sep. 21, 2010 for PCT/US2010/035690.
International search report dated Oct. 5, 2006 for PCT/US2006/002583.
International search report dated Oct. 15, 2003 for PCT/US2002/022328.
International search report dated Oct. 15, 2009 for PCT/US2008/000655.
Khalidi, et al. The immunophenotype of adult acute myeloid leukemia: high frequency of lymphoid antigen expression and comparison of immunophenotype, French-American-British classification, and karyotypic abnormalities. Am J Clin Pathol. Feb. 1998;109(2):211-20.
Koester, et al. Intracellular markers. J Immunol Methods. Sep. 21, 2000;243(1-2):99-106.
Liu, et al. Overexpression of cyclin D1 in accelerated-phase chronic myeloid leukemia. Leuk Lymphoma. Dec. 2004;45(12):2419-25.
Mahmoud, et al. Induction of CD45 expression and proliferation in U-266 myeloma cell line by interleukin-6. Blood. 1998. 92(10):3887-97.
Neben, et al. Gene expression patterns in acute myeloid leukemia correlate with centrosome aberrations and numerical chromosome changes. Oncogene. Mar. 25, 2004;23(13):2379-84.
Norris. Multivariate analysis and reverse engineering of signal transduction pathways. Masters thesis. The University of British Columbia. Apr. 2002; pp. 152.
Nurse. Universal control mechanism regulating onset of M-phase. Nature. 1990; 344:503-508.
Pallis, et al. Flow cytometric measurement of phosphorylated STAT5 in AML: lack of specific association with FLT3 internal tandem duplications. Leuk Res. Sep. 2003;27(9):803-5.
Pascual, et al. Analysis of somatic mutation in five B cell subsets of human tonsil. J Exp Med. Jul. 1, 1994;180(1):329-39.
Pe'er, et al. Inferring subnetworks from perturbed expression profiles. Bioinformatics. 2001;17 Suppl 1:S215-24.
Perfetto, et al. Seventeen-colour flow cytometry: unravelling the immune system. Nat Rev Immunol Aug. 2004;4(8):648-55.
Pettersen, et al. CD47 signals T cell death. The American Association of Immunologists. 1999; 162: 7031-40.
Rezaei, et al. Leukemia markers expression of peripheral blood vs bone marrow blasts using flow cytometry. Med Sci Monit. Aug. 2003;9(8):CR359-62.
Sachs, et al. Analysis of signaling pathways in human T-cells using bayesian network modeling of single cell data. Proceedings of the 2004 IEEE computational systems bioinformatics conferences. 2004; p. 644.
Sachs, et al. Bayesian network approach to cell signaling pathway modeling. Sci STKE. Sep. 3, 2002;2002(148):PE38.
Sachs, et al. Causal protein-signaling networks derived from multiparameter single-cell data. Science. Apr. 22, 2005;308(5721):523-9.
Salomon, et al. LFA-1 interaction with ICAM-1 and ICAM-2 regulates Th2 cytokine production. J Immunol. 1998; 161: 5138-42.
Schlessinger, et al. Growth factor signaling by receptor tyrosine kinases. Neuron. Sep. 1992;9(3):383-91.
Schulz. Single-cell phospho-protein analysis by flow cytometry. Curr Protoc Immunol. 2007; Chapter 8:Unit 8.17.
Solling, et al. Free light chains of immunoglobulins in serum from patients with leukaemias and multiple myeloma. Scand J Haematol. Apr. 1982;28(4):309-18.
Stelzer, et al. Immunophenotyping. New York, NY: Wiley-Liss, 2000.
Szegedi, et al. A new method to localize acid phosphatase using the confocal laser-scanning microscope. Pathol Oncol Res. 1998;4(3):217-23.

Taylor, et al. Complement-opsonized IgG antibody/dsDNA immune complexes bind to CR1 clusters on isolated human erythrocytes. Clinical Immunology and Immunopathology. 1991; 61: 143-60.
Trinchieri. Biology of natural killer cells. Adv Immunol. 1989;47:187-376.
Walter, et al. Tyrosine phosphorylation enhances ITIM-dependent internalization of CD33, the target for the anti-AML imunnoconjugate, gentuzumab ozogamicin. Part 1 2006. 108(11):Abstract 729A.
Woolf, et al. Bayesian analysis of signaling networks governing embryonic stem cell fate decisions. Bioinformatics. Mar. 2005;21(6):741-53.
Zupo, et al. CD38 expression distinguishes two groups of B-cell chronic lymphocytic leukemias with different responses to anti-IgM antibodies and propensity to apoptosis. Blood. Aug. 15, 1996;88(4):1365-74.
Amendment, Request for continued examination (RCE), and response to notice to file corrected application papers dated Jan. 18, 2012 for U.S. Appl. No. 12/460,029.
Amico, et al. Differential response of human acute myeloid leukemia cells to gemtuzumab ozogamicin in vitro: role of Chk1 and Chk2 phosphorylation and caspase 3. Blood. Jun. 1, 2003;101(11):4589-97.
Bat, et al. Dimerization of the extracellular calcium-sensing receptor (CaR) on the cell surface of CaR-transfected HEK293 cells. J Biol Chem. Sep. 4, 1998;273(36):2
Bernstein, et al. DNA repair/pro-apoptotic dual-role proteins in five major DNA repair pathways: fail-safe protection against carcinogenesis. Mutat Res. Jun. 2002;511(2):145-78.
Bindoli, et al. Thiol chemistry in peroxidase catalysis and redox signaling. Antioxid Redox Signal. 2008. 10(9):1549-64.
Burks, et al. IRS proteins and beta-cell function. Diabetes. 2001. S140-S145, Suppl 1:S140-5.
Chang, et al., Lymphocyte proliferation modulated by glutamine: involved in the endogenous redox reaction; Clin Exp Immunol. Sep. 1999; 117(3): 482-488.
Chou, et al. Acute promyelocytic leukemia: recent advances in therapy and molecular basis of response to arsenic therapies. Curr Opin Hematol. 2005. 12(1):1-6.
Corcoran, et al. Characterization of ligand binding by the human p55 tumour-necrosis-factor receptor. Involvement of individual cysteine-rich repeats. Eur J Biochem. 1994. 223(3):831-40.
D'Ambrosio, et al. Chemokine receptors in inflammation: an overview J Immunol Methods. 2003. 273(1-2):3-13.
DiJoseph, et al. Antitumor efficacy of a combination of CMC-544 (inotuzumab ozogamicin), a CD22-targeted cytotoxic immunoconjugate of calicheamicin, and rituximab against non-Hodgkin's B-cell lymphoma. Clin Cancer Res. 2006. 12(1):242-9.
DiJoseph, et al. Potent and specific antitumour efficacy of CMC-544, a CD22-targeted immunoconjugate of calicheamicin, against systemically disseminated B cell lymphoma. Clin Cancer Res. 2004;10:8620-8629.
Egger, et al. Epigenetics in human disease and prospects for epigenetic therapy. Nature. 2004. 429(6990):457-63.
Green. Apoptotic pathways: the roads to ruin. Cell. 1998. 94(6):695-8.
Grell, et al. The transmembrane form of tumor necrosis factor is the prime activating ligand of the 80 kDa tumor necrosis factor receptor. Cell. 1995. 83(5):793-802.
Hirai, et al. A novel putative tyrosine kinase receptor encoded by the eph gene. Science. 1987. 238(4834):1717-20.
Hunter. Signaling—2000 and beyond. Cell. 2000. 100(1):113-27.
International search report dated Mar. 9, 2010 for PCT Application No. US2009/61195.
Karihtala, et al. Reactive oxygen species and antioxidant mechanisms in human tissues and their relation to malignancies. APMIS. 2007. 115(2):81-103.
Kim, et al. Constitutively activated FLT3 phosphorylates Bad partially through pim-1. Br J Haematol. Sep. 2006;134(5):500-9.
Kovtun, et al. Antibody-Drug Conjugates Designed to Eradicate Tumors with Homogeneous and Heterogeneous Expression of the Target Antigen, *Cancer Research* 66, 3214-3221, Mar. 15, 2006.

Kroeger, et al. Constitutive and agonist-dependent homo-oligomerization of the thyrotropin-releasing hormone receptor. Detection in living cells using bioluminescence resonance energy transfer. J Biol Chem. 2001. 276(16):12736-43.

Kumar, et al. 2-methoxyestradiol blocks cell-cycle progression at G(2)/M phase and inhibits growth of human prostate cancer cells. Mol Carcinog. 2001 Jul;31(3):111-24.

Leyval, et al., Flow cytometry for the intracellular pH measurement of glutamate producing Corynebacterium glutamicum, Journal of Microbiological Methods, vol. 29, Issue 2, May 1, 1997, pp. 121-127.

Lindberg, et al. cDNA cloning and characterization of eck, an epithelial cell receptor protein-tyrosine kinase in the eph/elk family of protein kinases. Mol Cell Biol. 1990. 10(12):6316-24.

Linenberger, et al. Multidrug-resistance phenotype and clinical responses to gemtuzumab ozogamicin. Blood. Aug. 15, 2001;98(4):988-94.

Mack, et al. Detection of caspase-activation in intact lymphoid cells using standard caspase substrates and inhibitors. J Immunol Methods. Jul. 31, 2000;241(1-2):19-31.

Malhotra, et al. Molecular biology of protein kinase C signaling in cardiac myocytes. Mol Cell Biochem. 2001. 225(1-):97-107.

Mandler, et al. Herceptin-geldanamycin immunoconjugates: pharmacokinetics, biodistribution, and enhanced antitumor activity. *Cancer Res.* 2004;64:1460-1467.

Minami, et al. Different antiapoptotic pathways between wild-type and mutated FLT3: insights into therapeutic targets in leukemia. Blood. Oct. 15, 2003;102(8):2969-75.

Neote, et al. Molecular cloning, functional expression, and signaling characteristics of a C-C chemokine receptor. Cell. 1993. 72(3):415-25.

Notice of Allowance dated Nov. 1, 2011 for U.S. Appl. No. 12/460,029.

Parsons, et al. An integrated genomic analysis of human glioblastoma multiforme. Science. 2008. 321(5897):1807-12.

Pawson. Regulation and targets of receptor tyrosine kinases. Eur J Cancer. 2002. 38 Suppl 5:S3-10.

Rocheville, et al. Subtypes of the somatostatin receptor assemble as functional homo- and heterodimers. J Biol Chem. 2000. 275(11):7862-9.

Sanderson, et al. In vivo drug-linker stability of an anti-CD30 dipeptide-linked auristatin immunoconjugate. Clin Cancer Res. 2005;11:843-852.

Setsukinai, et al. Development of novel fluorescence probes that can reliably detect reactive oxygen species and distinguish specific species. J Biol Chem. 2003. 278(5):3170-5.

Shankar, et al. ABT-869, a multitargeted receptor tyrosine kinase inhibitor: inhibition of FLT3 phosphorylation and signaling in acute myeloid leukemia. Blood. Apr. 15, 2007;109(8):3400-8. Epub Jan. 5, 2007.

Singh, et al. Recent trends in targeted anticancer prodrug and conjugate design. Curr Med Chem. 2008. 15(18):1802-26.

Tockman, et al. Considerations in bringing a cancer biomarker to clinical application. Cancer Res. May 1, 1992;52(9 Suppl):2711s-2718s.

Ushio-Fukai, et al. Reactive oxygen species and angiogenesis: NADPH oxidase as target for cancer therapy. Cancer Lett. 2008. 266(1):37-52.

Valli, et al., Intracellular pH Distribution in Saccharomyces cerevisiae Cell Populations, Analyzed by Flow Cytometry, Applied and Environmental Microbiology, Mar. 2005, p. 1515-1521, vol. 71, No. 3.

Walter, et al. ITIM-dependant endocytosis of CD33-related Siglecs: role of intracellular domain, tyrosine phosphorylation, and the tyrosine phosphatases, Shp 1 and Shp, Journal. Leuk. Bio., 83:Jan. 2008, p. 200-211.

Walter, et al., Influence of CD33 expression levels and ITIM-dependent internalization on gemtuzumab ozogamicin-induced cytotoxicity, Blood 2005: 105: 1295-1302.

Walter, et al., Phosphorylated ITIMs enable ubiquitylation of an inhibitory cell surface receptor, Traffice 2008:9: 267-279.

Watanabe, et al. Poly(ADP-ribose) polymerase-1 inhibits ATM kinase activity in DNA damage response. Biochem Biophys Res Commun. Jun. 25, 2004;319(2):596-602.

Weider, et al., Measurement of intracellular pH using flow cytometry with carboxy-SNARF-1. Cytometry, Nov. 1993;14(8):916-21.

Yang, et al. Hydroxyl radicals as an early signal involved in phorbol ester-induced monocyte differentiation of HL60 cells. Biochem Biophys Res Commun. 1994;200:1650-7.

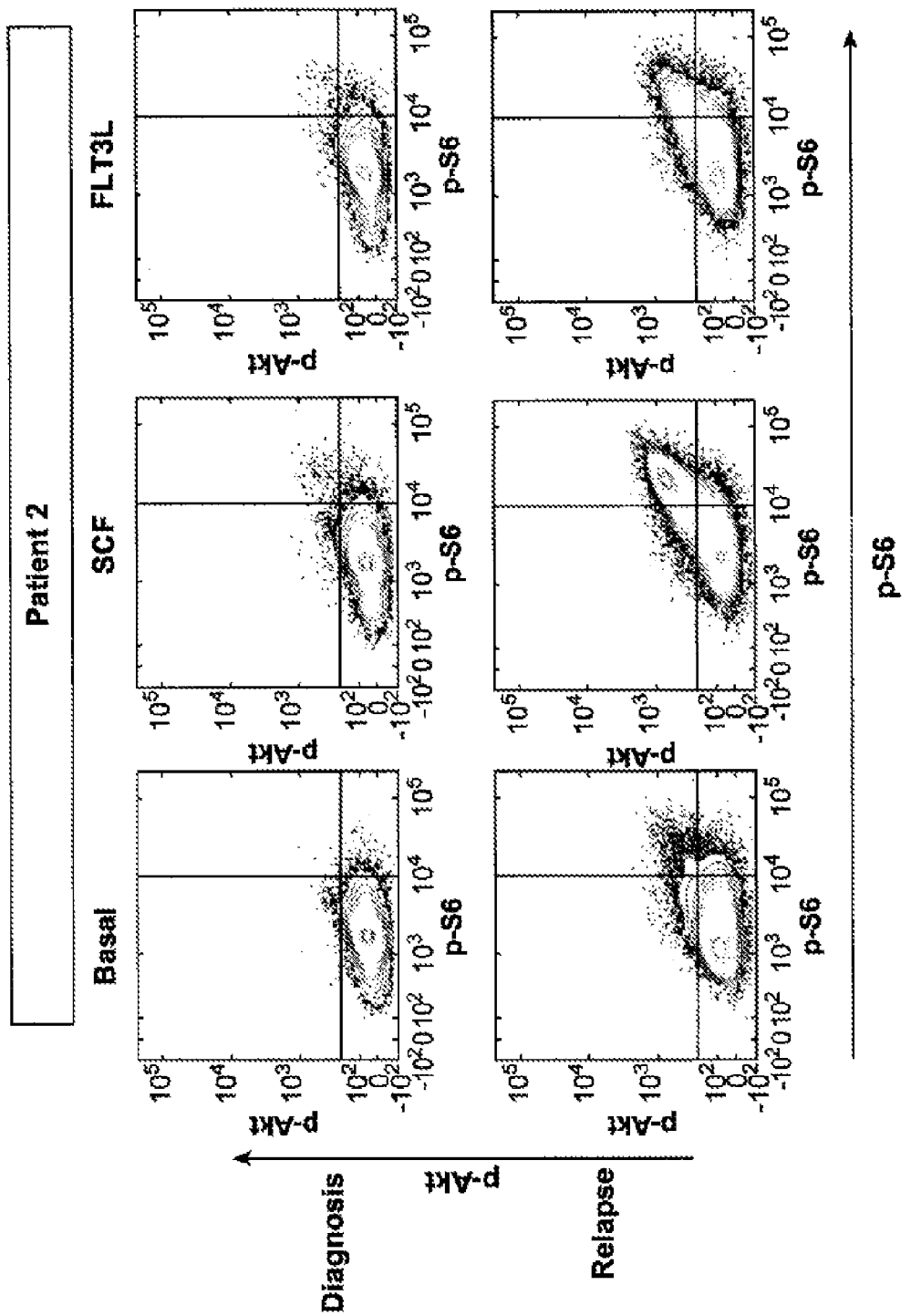
FIG. 6 (Cont. 1)

| Modulator: | %TotalBlastsPositiveforBothp-Aktandp-S6 | | | | | |
|---|---|---|---|---|---|---|
| | None(Basal) | | SCF | | Flt3L | |
| | Diagnosis | Relapse | Diagnosis | Relapse | Diagnosis | Relapse |
| Patient 1 | 0.15% | 0.21% | 1.00% | 3.20% | 0.40% | 0.45% |
| Patient 2 | 0.16% | 7.91% | 1.24% | 31.70% | 1.07% | 18.10% | b

FIG. 6 (Cont. 2)

*Note: Absolute values are not directly comparable between studies

Summary table comparing FLT3 Receptor & FLT3L induced signaling between normal BM Myeloblasts (BMMb) and FLT3-WT AML

| Node | Metric | Study 1 | | | | Study 2 | | | |
|---|---|---|---|---|---|---|---|---|---|
| | | Healthy BMMb | FLT3-WT AML | | | Healthy BMMb | FLT3-WT AML | | |
| | | Ave | Ave | Min | Max | Ave | Ave | Min | Max |
| Surface Markers: | | | | | | | | | |
| FLT3 Receptor ↓ Relative Expression | | 2.30 | 1.97 | 0.79 | 4.33 | 1.20 | 1.27 | 0.94 | 2.04 |
| FLT3L induced signaling:* | | | | | | | | | |
| FLT3L → p-S6 | | 0.51 | 0.96 | -0.22 | 2.91 | 0.62 | 1.03 | -0.47 | 3.54 |
| FLT3L → p-Akt | | 0.50 | 0.63 | -0.13 | 2.31 | 0.43 | 0.50 | -0.47 | 1.66 |
| FLT3L → p-Erk | | 0.19 | 0.33 | -0.18 | 0.98 | 0.41 | 0.25 | -0.27 | 0.95 |
| FLT3L → p-CREB | | -0.11 | 0.37 | -0.20 | 1.29 | 0.18 | 0.12 | -0.17 | 0.40 |
| FLT3L → p-Stat5 | | -0.06 | 0.08 | -0.47 | 2.57 | 0.41 | 0.35 | -0.01 | 0.55 |
| FLT3L → p-PLCγ2 | | -0.21 | -0.11 | -0.53 | 0.21 | 0.01 | 0.04 | -0.04 | 0.09 |

* Signaling assessed at 15'

Note: Mean values are not directly comparable between Study 1 and Study 2 due to experimental configuration and methodological improvements between studies.

No statistics were applied for the Healthy BMMb comparison within Study1 or Study2 alone due to the low number of healthy donors.

FIG. 13

Variance in signaling between FLT3-WT samples, FLT3-ITD samples, and Healthy BMMb.

| Node | Metric | Standard Deviation | | | Levene's test p-value | |
|---|---|---|---|---|---|
| | | Healthy BMMb | FLT3-ITD AML | FLT3-WT AML | FLT3-WT vs Healthy BMMb | FLT3-ITD vs Healthy BMMb | FLT3-WT vs FLT3-ITD |
| FLT3L→p-S6 | Fold | 0.179 | 0.343 | 0.921 | 0.0030 | 0.0004 | 0.6499 |

Levene's test assesses the equality of variances in different samples.
A significant p value in a Levene's test infers unequal variance between groups.
Variance of signaling was compared between AML samples from Study 1 and Healthy BMMb from a separate study.

Variance in signaling between FLT3 NPM1 molecular subgroups.

Node | Metric: FLT3L→p-S6 | Fold

| Molecular Subgroup: | Levene's test p-value | | | |
|---|---|---|---|---|
| | FLT3-ITD NPM1-Mut | FLT3-ITD NPM1-WT | FLT3-WT NPM1-Mut | FLT3-WT NPM1-WT |
| FLT3-ITD NPM1-Mut | 1 | 0.267 | 0.08 | 0.007 |
| FLT3-ITD NPM1-WT | | 1 | 0.64 | 0.024 |
| FLT3-WT NPM1-Mut | | | 1 | 0.1 |
| FLT3-WT NPM1-WT | | | | 1 |

| Node | Metric | Standard Deviation | | | |
|---|---|---|---|---|---|
| | | FLT3-ITD NPM1-Mut | FLT3-ITD NPM1-WT | FLT3-WT NPM1-Mut | FLT3-WT NPM1-WT |
| FLT3L→p-S6 | Fold | 0.111 | 0.419 | 0.452 | 0.530 |

Levene's test assesses the equality of variances in different samples
A significant p value in a Levene's test infers unequal variance between groups Node | Metric: IL-27→p-Stat3 | Fold

| Molecular Subgroup: | Levene's test p-value | | | |
|---|---|---|---|---|
| | FLT3-ITD NPM1-Mut | FLT3-ITD NPM1-WT | FLT3-WT NPM1-Mut | FLT3-WT NPM1-WT |
| FLT3-ITD NPM1-Mut | 1 | 0.137 | 0.216 | 0.036 |
| FLT3-ITD NPM1-WT | | 1 | 0.753 | 0.064 |
| FLT3-WT NPM1-Mut | | | 1 | 0.189 |
| FLT3-WT NPM1-WT | | | | 1 |

| Node | Metric | Standard Deviation | | | |
|---|---|---|---|---|---|
| | | FLT3-ITD NPM1-Mut | FLT3-ITD NPM1-WT | FLT3-WT NPM1-Mut | FLT3-WT NPM1-WT |
| IL-27→p-Stat3 | Fold | 0.135 | 0.279 | 0.340 | 0.683 |

FIG. 14

| | Stauro→cPARP \| Fold | Etoposide→cPARP \| Total | Stauro+ZVAD→cPARP \| Total | FLT3L→p-S6 \| Total | p-Slp76 \| Basal | FLT3L→p-S6 \| Fold | IL-27→p-Stat3 \| Fold | IL-27→p-Stat5 \| Fold |
|---|---|---|---|---|---|---|---|---|
| Stauro→cPARP \| Fold | 1.00 | | | | | | | |
| Etoposide→cPARP \| Total | 0.54 | 1.00 | | | | | | |
| Stauro+ZVAD→cPARP \| Total | 0.98 | 0.61 | 1.00 | | | | | |
| FLT3L→p-S6 \| Total | -0.46 | -0.42 | -0.47 | 1.00 | | | | |
| p-Slp76 \| Basal | -0.30 | -0.52 | -0.38 | 0.39 | 1.00 | | | |
| FLT3L→p-S6 \| Fold | -0.42 | -0.38 | -0.46 | 0.88 | 0.35 | 1.00 | | |
| IL-27→p-Stat3 \| Fold | -0.42 | -0.14 | -0.48 | 0.29 | 0.29 | 0.46 | 1.00 | |
| IL-27→p-Stat5 \| Fold | -0.28 | -0.06 | -0.33 | 0.12 | 0.23 | 0.25 | 0.85 | 1.00 |

FIG. 18

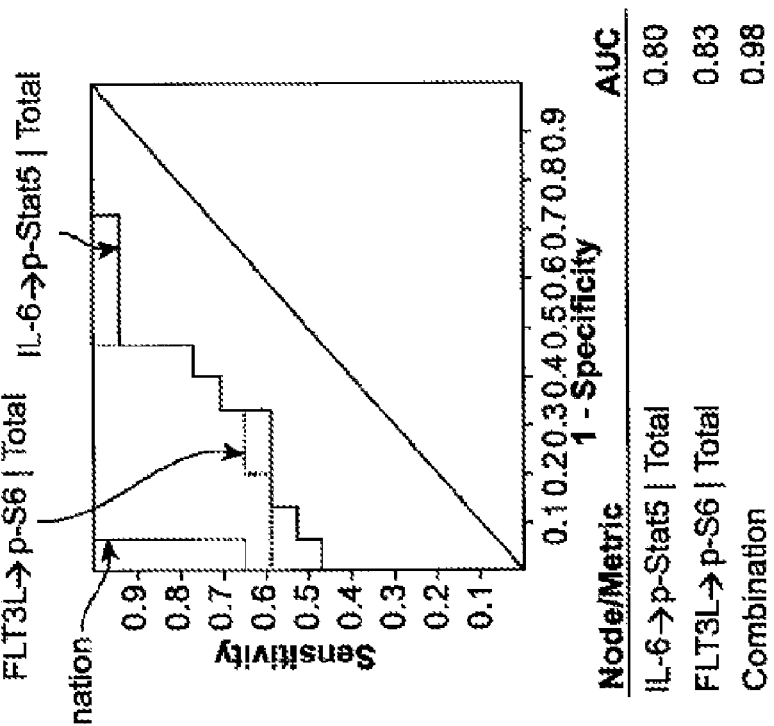
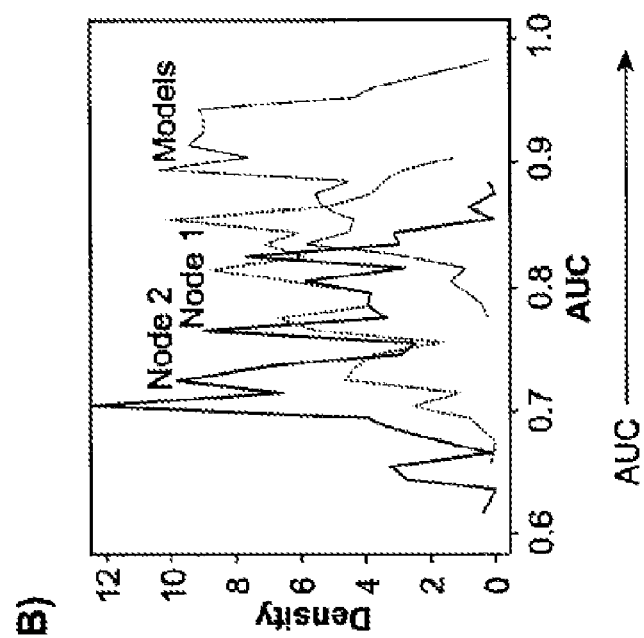
FIG. 19

|  | Staurosporine & ZVAD→c-PARP \| Fold | H₂O₂ & SCF→p-Erk \| Fold | Staurosporine & ZVAD→c-Caspase-8 \| Fold | Staurosporine→c-PARP \| Fold | Staurosporine & ZVAD→c-Caspase-3 \| Fold | Staurosporine→c-Caspase-8 \| Fold | Staurosporine→c-Caspase-3 \| Fold | H₂O₂→p-Stat5 \| Fold | Etoposide→c-PARP \| Fold |
|---|---|---|---|---|---|---|---|---|---|
| Staurosporine & ZVAD→c-PARP \| Fold | 1 | | | | | | | | |
| H₂O₂ & SCF→p-Erk \| Fold | -0.31 | 1 | | | | | | | |
| Staurosporine & ZVAD→c-Caspase-8 \| Fold | 0.83 | -0.1 | 1 | | | | | | |
| Staurosporine→c-PARP \| Fold | 0.77 | -0.15 | 0.68 | 1 | | | | | |
| Staurosporine & ZVAD→c-Caspase-3 \| Fold | 0.8 | -0.26 | 0.89 | 0.61 | 1 | | | | |
| Staurosporine→c-Caspase-8 \| Fold | 0.56 | 0.02 | 0.7 | 0.82 | 0.58 | 1 | | | |
| Staurosporine→c-Caspase-3 \| Fold | 0.71 | -0.14 | 0.68 | 0.88 | 0.68 | 0.84 | 1 | | |
| H₂O₂→p-Stat5 \| Fold | -0.2 | 0.81 | -0.07 | -0.22 | -0.19 | -0.12 | -0.26 | 1 | |
| Etoposide→c-PARP \| Fold | 0.59 | -0.25 | 0.56 | 0.59 | 0.44 | 0.43 | 0.41 | -0.35 | 1 |
| Etoposide & ZVAD→c-PARP \| Fold | 0.57 | -0.28 | 0.54 | 0.6 | 0.46 | 0.42 | 0.49 | -0.26 | 0.67 |
| Etoposide→c-Caspase-3 \| Fold | 0.42 | -0.2 | 0.49 | 0.53 | 0.35 | 0.46 | 0.4 | -0.42 | 0.89 |
| M-CSF→p-S6 \| Fold | 0.24 | -0.16 | 0.29 | 0.21 | 0.23 | 0.31 | 0.17 | -0.04 | 0.32 |
| Etoposide→BCL2 \| Fold | 0.4 | -0.07 | 0.31 | 0.42 | 0.15 | 0.39 | 0.32 | -0.04 | 0.48 |
| Thapsigargin→p-CREB \| Fold | 0.39 | -0.41 | 0.35 | 0.3 | 0.41 | 0.14 | 0.19 | -0.35 | 0.53 |
| PMA→p-CREB \| Fold | 0.37 | -0.27 | 0.34 | 0.38 | 0.38 | 0.16 | 0.21 | -0.37 | 0.61 |
| IFNγ→p-Stat5 \| Fold | -0.32 | 0.18 | -0.1 | -0.36 | -0.09 | -0.06 | -0.08 | 0.18 | 0.5 |
| TNFα→p-NFkB-p65 \| Fold | 0.27 | -0.43 | 0.37 | 0.26 | 0.38 | 0.24 | 0.2 | -0.53 | 0.58 |
| H₂O₂→p-Erk \| Fold | -0.28 | 0.94 | -0.11 | -0.11 | -0.27 | 0.05 | -0.08 | 0.74 | -0.28 |
| IL-6→p-S6 \| Fold | -0.05 | -0.07 | -0.07 | -0.18 | -0.01 | -0.34 | 0.27 | -0.09 | 0.06 |
| IL-6→p-CREB \| Fold | 0.41 | -0.14 | 0.57 | 0.4 | 0.57 | 0.26 | 0.33 | -0.26 | 0.53 |
| G-CSF→p-Erk \| Fold | 0.12 | -0.13 | 0.27 | 0.16 | -0 | 0.09 | 0.04 | -0.38 | 0.51 |
| FLT3L→p-S6 \| Fold | -0.39 | 0.19 | -0.27 | -0.55 | -0.04 | -0.52 | -0.39 | 0.18 | -0.33 |
| Etoposide→p-Chk2 \| Fold | -0.43 | -0.05 | -0.39 | -0.39 | -0.29 | -0.3 | -0.24 | 0.11 | -0.75 |
| IL-27→p-Stat5 \| Fold | -0.24 | 0.39 | -0.13 | -0.45 | -0.2 | -0.43 | -0.47 | 0.39 | -0.09 |
| IL-27→p-Stat3 \| Fold | -0.43 | 0.26 | -0.26 | -0.56 | -0.23 | -0.55 | -0.54 | 0.24 | -0.09 |

Blue = negative correlation, yellow = no relationship, green = positive correlation

FIG. 21

| Etoposide & ZVAD→c-PARP \| Fold | Etoposide→c-Caspase-3 \| Fold | M-CSF→p-S6 \| Fold | Etoposide→BCL2 \| Fold | Thapsigargin→p-CREB \| Fold | PMA→p-CREB \| Fold | IFNγ→p-Stat5 \| Fold | TNFα→p-NFκB-p65 \| Fold | $H_2O_2$→p-Erk \| Fold | IL-6→p-S6 \| Fold | IL-6→p-CREB \| Fold | G-CSF→p-Erk \| Fold | FLT3L→p-S6 \| Fold | Etoposide→p-Chk2 \| Fold | IL-27→p-Stat5 \| Fold | IL-27→p-Stat3 \| Fold |
|---|---|---|---|---|---|---|---|---|---|---|---|---|---|---|---|
| 1 | | | | | | | | | | | | | | | |
| 0.6 | 1 | | | | | | | | | | | | | | |
| 0.29 | 0.21 | 1 | | | | | | | | | | | | | |
| 0.32 | 0.29 | 0.19 | 1 | | | | | | | | | | | | |
| 0.59 | 0.38 | 0.51 | 0.25 | 1 | | | | | | | | | | | |
| 0.56 | 0.42 | 0.41 | 0.11 | 0.87 | 1 | | | | | | | | | | |
| -0.36 | -0.44 | -0.16 | -0.01 | -0.44 | -0.53 | 1 | | | | | | | | | |
| 0.59 | 0.5 | 0.42 | 0.23 | 0.75 | 0.77 | -0.29 | 1 | | | | | | | | |
| -0.28 | -0.22 | -0.36 | 0.06 | -0.48 | -0.39 | 0.32 | -0.52 | 1 | | | | | | | |
| 0.19 | 0.01 | 0.16 | 0.06 | 0.48 | 0.38 | -0.01 | 0.39 | -0.1 | 1 | | | | | | |
| 0.39 | 0.51 | 0.25 | -0.09 | 0.53 | 0.68 | -0.29 | 0.6 | -0.26 | 0.28 | 1 | | | | | |
| 0.3 | 0.63 | 0.21 | 0.12 | 0.29 | 0.45 | -0.31 | 0.48 | -0.19 | 0.14 | 0.51 | 1 | | | | |
| -0.25 | -0.27 | -0.13 | -0.52 | -0.12 | -0.12 | 0.28 | -0.07 | 0.12 | 0.38 | 0.11 | -0.19 | 1 | | | |
| -0.3 | -0.73 | -0.31 | -0.47 | -0.35 | -0.44 | 0.46 | -0.37 | 0.01 | -0.07 | -0.34 | -0.48 | 0.2 | 1 | | |
| -0.11 | -0.26 | 0.14 | 0.03 | 0.04 | 0.11 | 0.3 | -0 | 0.33 | 0.41 | -0.06 | 0.06 | 0.34 | 0 | 1 | |
| -0.16 | -0.17 | 0.21 | -0.32 | 0.12 | 0.22 | 0.24 | 0.11 | 0.11 | 0.4 | 0.17 | 0.11 | 0.57 | 0.1 | 0.81 | 1 |

FIG. 21 (Cont.)

| Biological Category | Node \| Metric | AUC$_{ROC}$ | Num. WTs/ITDs | t-test $P$ | Wilcoxon $P$ | Mean Value of WTs/ITDs |
|---|---|---|---|---|---|---|
| Apoptosis | Etoposide & ZVAD→c-Caspase-3 \| Total | 0.73 | 12 / 14 | 0.027 | 0.053 | 0.58 / 1.19 |
| Apoptosis | Etoposide & ZVAD→c-PARP \| Fold | 0.82 | 14 / 14 | 0.009 | 0.003 | 0.89 / 2.16 |
| Apoptosis | Etoposide & ZVAD→c-PARP \| Total | 0.80 | 14 / 14 | 0.001 | 0.006 | 1.40 / 2.86 |
| Apoptosis | Etoposide & ZVAD→p-Chk2, c-PARP \| Quad | 0.73 | 14 / 14 | 0.094 | 0.035 | 0.10 / 0.16 |
| Apoptosis | Etoposide & ZVAD→p-Chk2+, c-PARP \| Quad | 0.78 | 14 / 14 | 0.012 | 0.012 | 0.46 / 0.25 |
| Apoptosis | Etoposide & ZVAD→p-Chk2+, c-PARP + \| Quad | 0.77 | 14 / 14 | 0.009 | 0.015 | 0.30 / 0.49 |
| Apoptosis | Etoposide→BCL2 \| Fold | 0.75 | 13 / 14 | 0.023 | 0.025 | -0.01 / 0.12 |
| Apoptosis | Etoposide→c-Caspase-3 \| Fold | 0.80 | 12 / 14 | 0.010 | 0.008 | 0.53 / 1.50 |
| Apoptosis | Etoposide→c-Caspase-3 \| Total | 0.82 | 12 / 14 | 0.003 | 0.004 | 0.94 / 2.25 |
| Apoptosis | Etoposide→c-PARP \| Fold | 0.83 | 14 / 14 | 0.001 | 0.002 | 0.55 / 2.08 |
| Apoptosis | Etoposide→c-PARP \| Total | 0.82 | 14 / 14 | 0.001 | 0.003 | 1.06 / 2.79 |
| Apoptosis | Etoposide→p-Chk2 \| Fold | 0.71 | 13 / 14 | 0.039 | 0.068 | 0.27 / -0.31 |
| Apoptosis | Etoposide→p-Chk2-, c-PARP + \| Quad | 0.81 | 14 / 14 | 0.005 | 0.005 | 0.21 / 0.44 |
| Apoptosis | Etoposide→p-Chk2+, c-PARP - \| Quad | 0.71 | 14 / 14 | 0.031 | 0.068 | 0.51 / 0.30 |
| Apoptosis | Staurosporine & ZVAD→c-Caspase-3 \| Fold | 0.86 | 15 / 14 | 0.001 | 0.001 | 0.20 / 0.98 |
| Apoptosis | Staurosporine & ZVAD→c-Caspase-3 \| Total | 0.89 | 15 / 14 | 0.001 | 0.000 | 0.46 / 1.18 |
| Apoptosis | Staurosporine & ZVAD→c-Caspase-8 \| Fold | 0.90 | 15 / 14 | 0.000 | 0.000 | -0.25 / 1.12 |
| Apoptosis | Staurosporine & ZVAD→c-Caspase-8 \| Total | 0.77 | 15 / 14 | 0.009 | 0.014 | 4.92 / 5.96 |
| Apoptosis | Staurosporine & ZVAD→c-PARP \| Fold | 0.93 | 15 / 14 | 0.000 | 0.000 | 0.72 / 4.05 |
| Apoptosis | Staurosporine & ZVAD→c-PARP \| Total | 0.94 | 15 / 14 | 0.000 | 0.000 | 0.85 / 4.20 |
| Apoptosis | Staurosporine→c-Caspase-3 \| Fold | 0.84 | 15 / 14 | 0.001 | 0.001 | 1.26 / 2.55 |
| Apoptosis | Staurosporine→c-Caspase-3 \| Total | 0.82 | 15 / 14 | 0.002 | 0.003 | 1.56 / 2.72 |
| Apoptosis | Staurosporine→c-Caspase-8 \| Fold | 0.85 | 15 / 14 | 0.000 | 0.002 | 1.29 / 3.24 |
| Apoptosis | Staurosporine→c-Caspase-8 \| Total | 0.87 | 15 / 14 | 0.000 | 0.000 | 6.45 / 8.09 |
| Apoptosis | Staurosporine→c-PARP \| Fold | 0.86 | 15 / 14 | 0.000 | 0.001 | 2.43 / 5.30 |
| Apoptosis | Staurosporine→c-PARP \| Total | 0.89 | 15 / 14 | 0.000 | 0.000 | 2.56 / 5.44 |
| CCG | CD40L→p-p38 \| Total | 0.68 | 17 / 15 | 0.032 | 0.089 | 0.48 / 0.19 |

FIG. 22

| | | | | | | |
|---|---|---|---|---|---|---|
| CCG | CD40L→p-S6 \| Total | 0.71 | 17 | 15 | 0.048 | 0.040 | 0.54 / 0.20 |
| CCG | EPO→p-Stat1 \| Total | 0.71 | 17 | 15 | 0.054 | 0.044 | 0.29 / 0.45 |
| CCG | EPO→p-Stat5 \| Total | 0.87 | 17 | 15 | 0.000 | 0.000 | 1.12 / 2.16 |
| CCG | FLT3L→p-CREB \| Total | 0.77 | 17 | 15 | 0.012 | 0.009 | 2.20 / 1.65 |
| CCG | FLT3L→p-S6 \| Fold | 0.72 | 17 | 15 | 0.014 | 0.038 | 0.96 / 0.30 |
| CCG | FLT3L→p-S6 \| Total | 0.80 | 17 | 15 | 0.003 | 0.003 | 1.46 / 0.45 |
| CCG | FLT3K→p-S6 \| Total | 0.81 | 17 | 15 | 0.024 | 0.002 | 1.44 / 2.14 |
| CCG | G-CSF→p-Erk \| Fold | 0.72 | 17 | 15 | 0.053 | 0.033 | 0.04 / 0.22 |
| CCG | G-CSF→p-S6 \| Total | 0.84 | 17 | 15 | 0.034 | 0.176 | 0.54 / 0.23 |
| CCG | G-CSF→p-Stat5 \| Total | 0.75 | 17 | 15 | 0.020 | 0.016 | 2.18 / 3.22 |
| CCG | GM-CSF→p-Stat5 \| Total | 0.78 | 17 | 15 | 0.021 | 0.005 | 2.26 / 3.42 |
| CCG | IFNα→p-Stat1 \| Total | 0.77 | 17 | 15 | 0.010 | 0.008 | 0.86 / 1.27 |
| CCG | IFNα→p-Stat3 \| Total | 0.73 | 17 | 15 | 0.042 | 0.027 | 1.92 / 2.49 |
| CCG | IFNα→p-Stat5 \| Total | 0.80 | 17 | 15 | 0.007 | 0.003 | 2.73 / 3.91 |
| CCG | IFNγ→p-Stat5 \| Fold | 0.75 | 17 | 15 | 0.109 | 0.018 | 0.72 / 0.32 |
| CCG | IFNγ→p-Stat5 \| Total | 0.77 | 17 | 15 | 0.004 | 0.008 | 1.84 / 2.68 |
| CCG | IGF-1→p-Stat5 \| Total | 0.85 | 17 | 15 | 0.000 | 0.000 | 1.18 / 2.16 |
| CCG | IL-10→p-Stat5 \| Total | 0.87 | 17 | 15 | 0.000 | 0.000 | 1.25 / 2.26 |
| CCG | IL-27→p-Erk \| Total | 0.71 | 17 | 15 | 0.024 | 0.049 | 0.38 / 0.81 |
| CCG | IL-27→p-S5 \| Total | 0.72 | 17 | 15 | 0.047 | 0.033 | 0.47 / 0.15 |
| CCG | IL-27→p-Stat3 \| Fold | 0.69 | 17 | 15 | 0.029 | 0.076 | 0.64 / 0.23 |
| CCG | IL-27→p-Stat5 \| Total | 0.70 | 17 | 15 | 0.038 | 0.059 | 0.21 / 0.00 |
| CCG | IL-3→p-S6 \| Total | 0.80 | 17 | 15 | 0.000 | 0.000 | 1.48 / 2.35 |
| CCG | IL-3→p-Stat5 \| Total | 0.71 | 17 | 15 | 0.066 | 0.044 | 0.56 / 0.25 |
| CCG | IL-3→p-Stat5 \| Fold | 0.72 | 17 | 15 | 0.084 | 0.033 | 2.68 / 3.53 |
| CCG | IL-4→p-Stat5 \| Total | 0.81 | 17 | 15 | 0.006 | 0.002 | 2.14 / 3.32 |
| CCG | IL-6→p-CREB \| Fold | 0.73 | 17 | 15 | 0.017 | 0.030 | -0.30 / 0.07 |
| CCG | IL-6→p-S6 \| Fold | 0.73 | 17 | 15 | 0.659 | 0.026 | 0.07 / 0.09 |

FIG. 22 (Cont. 1)

| | | | | | | | |
|---|---|---|---|---|---|---|---|
| CCG | IL-6→p-Stat5 \| Total | 0.84 | 17 / 15 | 0.000 | 0.001 | 1.19 / | 2.18 |
| CCG | M-CSF→p-S6 \| Fold | 0.76 | 17 / 15 | 0.020 | 0.011 | -0.14 / | -0.01 |
| CCG | M-CSF→p-Stat5 \| Total | 0.85 | 17 / 15 | 0.000 | 0.000 | 1.30 / | 2.21 |
| CCG | p-SLP-76 \| Basal | 0.76 | 13 / 14 | 0.022 | 0.019 | 1.16 / | -0.19 |
| CCG | p-Stat1 \| Basal | 0.73 | 17 / 15 | 0.018 | 0.030 | 0.29 / | 0.46 |
| CCG | p-Stat5 \| Basal | 0.85 | 17 / 15 | 0.000 | 0.000 | 1.63 / | 2.62 |
| CCG | PMA→p-CREB \| Fold | 0.75 | 17 / 15 | 0.011 | 0.018 | 1.18 / | 1.95 |
| CCG | SCF→p-CREB \| Total | 0.73 | 17 / 15 | 0.040 | 0.027 | 1.96 / | 1.54 |
| CCG | SCF→p-S6 \| Total | 0.65 | 17 / 15 | 0.043 | 0.153 | 0.95 / | 0.43 |
| CCG | SCF→p-Stat5 \| Total | 0.87 | 17 / 15 | 0.000 | 0.000 | 1.26 / | 2.19 |
| CCG | Thapsigargin→p-CREB \| Fold | 0.75 | 17 / 15 | 0.011 | 0.016 | 0.06 / | 0.74 |
| CCG | Thapsigargin→p-CREB \| Total | 0.66 | 17 / 15 | 0.047 | 0.132 | 2.31 / | 2.95 |
| CCG | TNFα→p-NFkB-p65 \| Fold | 0.73 | 17 / 15 | 0.010 | 0.024 | 1.41 / | 2.22 |
| Phosphatase & ROS | H₂O₂ & IFNα→p-Stat1 \| Total | 0.80 | 14 / 14 | 0.004 | 0.007 | 1.65 / | 2.19 |
| Phosphatase & ROS | H₂O₂ & IFNα→p-Stat5 \| Total | 0.81 | 14 / 14 | 0.010 | 0.005 | 2.22 / | 3.30 |
| Phosphatase & ROS | H₂O₂ & SCF→p-Erk \| Fold | 0.91 | 14 / 14 | 0.006 | 0.000 | 0.49 / | 0.08 |
| Phosphatase & ROS | H₂O₂ & SCF→p-Erk \| Total | 0.72 | 14 / 14 | 0.042 | 0.044 | 2.76 / | 2.28 |
| Phosphatase & ROS | H₂O₂→p-Erk \| Fold | 0.73 | 14 / 14 | 0.029 | 0.043 | 0.45 / | 0.03 |
| Phosphatase & ROS | H₂O₂→p-Stat5 \| Fold | 0.84 | 14 / 14 | 0.008 | 0.002 | 0.18 / | -0.36 |
| Surface Markers | ABCG \| PercentPos | 0.73 | 16 / 14 | 0.052 | 0.031 | 7.14 / | 8.58 |
| Surface Markers | ABCG2 \| Rel. Expression | 0.74 | 16 / 14 | 0.015 | 0.028 | 0.21 / | 0.38 |
| Surface Markers | cKit \| PercentPos | 0.71 | 16 / 14 | 0.032 | 0.047 | 48.39 / | 65.21 |

FIG. 22 (Cont. 2)

Summary table of common stratifying pathways between FLT3-WT and FLT3-ITD signaling in AML samples in both studies

| Node | Metric: | FLT3-WT | FLT3-ITD | Study 1 ||||| Study 2 ||||
|---|---|---|---|---|---|---|---|---|---|---|---|
| | | AML | AML | $AUC_{ROC}$ | t-test $P$ | Wilcox. $P$ | Mean Value of WT / ITD | $AUC_{ROC}$ | t-test $P$ | Wilcox. $P$ | Mean Value of WT / ITD |
| PI3K/S6 induced Signaling | | | | | | | | | | | |
| FLT3L → p-S6 | Fold | | ↑ | 0.72 | 0.014 | 0.038 | 0.96 / 0.30 | 0.68 | 0.028 | 0.036 | 1.03 / 0.43 |
| FLT3L → p-S6 | Total | | ↑ | 0.80 | 0.003 | 0.003 | 1.46 / 0.45 | 0.65 | 0.035 | 0.119 | 4.09 / 3.27 |
| Jak/Stat Signaling: | | | | | | | | | | | |
| IL-27 → p-Stat3 | Fold | | ↑ | 0.69 | 0.029 | 0.076 | 0.64 / 0.23 | 0.73 | 0.002 | 0.022 | 0.37 / 0.04 |
| IL-27 → p-Stat5 | Fold | | ↑ | 0.70 | 0.038 | 0.059 | 0.21 / 0.00 | 0.63 | 0.024 | 0.207 | 0.15 / -0.02 |
| Functional Apoptosis Response: | | | | | | | | | | | |
| Etoposide → c-PARP | Total | | ↑ | 0.82 | 0.001 | 0.003 | 1.06 / 2.79 | 0.73 | 0.005 | 0.013 | 2.81 / 4.45 |

↑ = higher signaling response in indicated molecular group

Note: Mean values are not directly comparable between study 1 and study 2 due to experimental configuration and methodological improvements between studies

FIG. 23

| Biological Category | Node\|Metric |
|---|---|
| Apoptosis | Ara-C & Dauno→c-PARP \| Total |
| Apoptosis | c-PARP \| Basal |
| Apoptosis | Etoposide→ c-PARP \| Total |
| Apoptosis | p-Chk2 \| Basal |
| Apoptosis | Staurosoprine & ZVAD→c-PARP \| Fold |
| Apoptosis | Staurosoprine & ZVAD→c-PARP \| Total |
| CCG | FLT3L→p-Akt \| Fold |
| CCG | FLT3L→p-Erk \| Fold |
| CCG | FLT3L→p-S6 \| Fold |
| CCG | FLT3L→p-S6 \| Total |
| CCG | G-CSF→p-Stat1 \| Fold |
| CCG | G-CSF→p-Stat3 \| Fold |
| CCG | G-CSF→p-Stat3 \| Total |
| CCG | G-CSF→p-Stat5 \| Fold |
| CCG | G-CSF→p-Stat5 \| Total |
| CCG | GM-CSF→p-Stat5 \| Fold |
| CCG | IFNα→p-Stat1 \| Fold |
| CCG | IFNα→p-Stat1 \| Total |
| CCG | IFNα→p-Stat3 \| Fold |
| CCG | IFNα→p-Stat3 \| Total |
| CCG | IFNα→p-Stat5 \| Fold |
| CCG | IFNα→p-Stat5 \| Total |
| CCG | IFNγ→p-Stat1 \| Fold |
| CCG | IFNγ→p-Stat5 \| Fold |
| CCG | IL-27→p-Stat1 \| Fold |
| CCG | IL-27→p-Stat1 \| Total |
| CCG | IL-27→p-Stat3 \| Fold |
| CCG | IL-27→p-Stat3 \| Total |
| CCG | IL-27→p-Stat5 \| Fold |
| CCG | IL-4→p-Stat5 \| Fold |
| CCG | M-CSF→p-Erk \| Total |
| CCG | P-Play2 \| Basal |
| CCG | P-SLP-76 \| Basal |
| CCG | PMA→p-CREB \| Fold |
| CCG | PMA→p-CREB \| Total |
| CCG | PMA→p-Erk \| Fold |
| CCG | PMA→p-Erk \| Total |
| CCG | PMA→p-S6 \| Fold |
| CCG | PMA→p-S6 \| Total |
| CCG | SCF→p-Akt \| Fold |
| CCG | SCF→p-Akt \| Total |
| CCG | SCF→p-CREB \| Total |
| CCG | SCF→p-S6 \| Fold |
| Phosphatase & ROS | $H_2O_2$→p-Akt \| Fold |
| Phosphatase & ROS | $H_2O_2$→p-Akt \| Total |
| Phosphatase & ROS | $H_2O_2$→p-Play2 \| Total |
| Phosphatase & ROS | $H_2O_2$→p-SLP76 \| Fold |
| Phosphatase & ROS | $H_2O_2$→p-SLP76 \| Total |

FIG. 26

| $AUC_{ROC}$ | Num of WTs/ITDs | t-test $P$ | Wilcox. $P$ | Mean Value of WTs/ITDs |
|---|---|---|---|---|
| 0.76 | 35 / 9 | 0.001 | 0.018 | 3.34 / 5.13 |
| 0.72 | 47 / 12 | 0.046 | 0.020 | 2.10 / 3.58 |
| 0.73 | 47 / 12 | 0.005 | 0.013 | 2.81 / 4.45 |
| 0.71 | 47 / 12 | 0.062 | 0.024 | 4.53 / 4.07 |
| 0.82 | 13 / 3 | 0.002 | 0.111 | 1.54 / 4.35 |
| 0.97 | 13 / 3 | 0.000 | 0.007 | 3.16 / 6.22 |
| 0.67 | 58 / 15 | 0.553 | 0.043 | 0.59 / 0.45 |
| 0.77 | 58 / 15 | 0.020 | 0.002 | 0.25 / 0.01 |
| 0.68 | 58 / 15 | 0.028 | 0.036 | 1.03 / 0.43 |
| 0.65 | 48 / 12 | 0.035 | 0.119 | 4.09 / 3.27 |
| 0.68 | 49 / 12 | 0.002 | 0.057 | 0.30 / 0.03 |
| 0.69 | 49 / 12 | 0.003 | 0.050 | 1.01 / 0.29 |
| 0.68 | 48 / 12 | 0.003 | 0.053 | 2.59 / 1.82 |
| 0.71 | 49 / 12 | 0.008 | 0.024 | 1.05 / 0.25 |
| 0.70 | 47 / 12 | 0.016 | 0.038 | 3.76 / 2.86 |
| 0.70 | 11 / 3 | 0.020 | 0.068 | 1.96 / 0.61 |
| 0.78 | 35 / 9 | 0.003 | 0.008 | 2.05 / 0.97 |
| 0.73 | 35 / 9 | 0.029 | 0.035 | 2.97 / 2.09 |
| 0.75 | 35 / 9 | 0.016 | 0.025 | 0.98 / 0.47 |
| 0.73 | 35 / 9 | 0.009 | 0.035 | 2.77 / 2.07 |
| 0.75 | 35 / 9 | 0.031 | 0.020 | 1.58 / 0.78 |
| 0.74 | 35 / 9 | 0.047 | 0.030 | 4.44 / 3.45 |
| 0.79 | 15 / 5 | 0.010 | 0.066 | 1.79 / 0.88 |
| 0.76 | 15 / 5 | 0.022 | 0.098 | 0.71 / 0.32 |
| 0.71 | 44 / 11 | 0.000 | 0.028 | 1.01 / 0.28 |
| 0.68 | 43 / 11 | 0.027 | 0.070 | 1.97 / 1.40 |
| 0.73 | 44 / 11 | 0.002 | 0.022 | 0.37 / 0.04 |
| 0.67 | 43 / 11 | 0.027 | 0.082 | 2.08 / 1.61 |
| 0.63 | 44 / 11 | 0.024 | 0.207 | 0.15 / -0.02 |
| 1.00 | 7 / 2 | 0.037 | 0.056 | 0.36 / -0.09 |
| 1.00 | 7 / 2 | 0.003 | 0.056 | 3.08 / 4.42 |
| 1.93 | 7 / 2 | 0.043 | 0.111 | 1.42 / 2.17 |
| 0.68 | 47 / 12 | 0.042 | 0.061 | 1.73 / 1.27 |
| 0.74 | 35 / 9 | 0.016 | 0.027 | 0.76 / 0.20 |
| 0.72 | 35 / 9 | 0.027 | 0.043 | 3.96 / 2.92 |
| 0.75 | 31 / 9 | 0.080 | 0.026 | 2.91 / 1.55 |
| 0.85 | 35 / 9 | 0.001 | 0.001 | 4.26 / 2.68 |
| 0.72 | 35 / 9 | 0.012 | 0.043 | 1.37 / 0.96 |
| 0.72 | 35 / 9 | 0.023 | 0.046 | 5.15 / 3.87 |
| 0.70 | 58 / 13 | 0.289 | 0.029 | 0.48 / 0.14 |
| 0.69 | 47 / 12 | 0.255 | 0.046 | 1.70 / 1.25 |
| 0.86 | 7 / 2 | 0.021 | 0.222 | 2.51 / 3.14 |
| 0.70 | 58 / 13 | 0.035 | 0.025 | 1.11 / 0.50 |
| 0.79 | 52 / 12 | 0.000 | 0.002 | 1.13 / 0.37 |
| 0.70 | 48 / 12 | 0.003 | 0.031 | 1.19 / 0.83 |
| 0.77 | 48 / 12 | 0.003 | 0.005 | 1.90 / 1.24 |
| 0.60 | 51 / 12 | 0.036 | 0.266 | 0.52 / 0.13 |
| 0.77 | 46 / 12 | 0.001 | 0.004 | 2.21 / 1.40 |

FIG. 26 (Cont.)

| Node1 | Node2 | Num WTs/ITDs | AUC Model | AUC Node1 Alone | AUC Node2 Alone | Node1 p-Value | Node2 p-Value |
|---|---|---|---|---|---|---|---|
| Staurosporine & ZVAD→c-Caspase-8 \| Fold | SCF→p-Stat5 \| Total | 15 / 14 | 0.99 | 0.90 | 0.85 | 0.048 | 0.044 |
| IL-6→p-Stat5 \| Total | FLT3L→p-S6 \| Total | 17 / 15 | 0.98 | 0.84 | 0.80 | 0.028 | 0.024 |
| Staurosporine & ZVAD→c-Caspase-8 \| Fold | M-CSF→p-Stat5 \| Total | 15 / 14 | 0.98 | 0.90 | 0.84 | 0.032 | 0.040 |
| Staurosporine & ZVAD→c-Caspase-8 \| Fold | IGF-1→p-Stat5 \| Total | 15 / 14 | 0.98 | 0.90 | 0.85 | 0.047 | 0.047 |
| Staurosporine & ZVAD→c-Caspase-8 \| Fold | H2O2→p-Stat5 \| Fold | 14 / 14 | 0.97 | 0.89 | 0.84 | 0.032 | 0.046 |
| p-Stat5 \| Basal | FLT3L→p-S6 \| Total | 17 / 15 | 0.97 | 0.85 | 0.80 | 0.029 | 0.030 |
| Staurosporine→c-Caspase-8 \| Total | IL-27→p-Erk \| Total | 15 / 14 | 0.97 | 0.87 | 0.71 | 0.014 | 0.021 |
| Staurosporine & ZVAD→c-Caspase-3 \| Total | FLT3L→p-CREB \| Total | 15 / 14 | 0.97 | 0.89 | 0.81 | 0.039 | 0.021 |
| Staurosporine & ZVAD→c-Caspase-8 \| Fold | p-Stat5 \| Basal | 15 / 14 | 0.97 | 0.90 | 0.83 | 0.040 | 0.044 |
| IL-27→p-S6 \| Total | Staurosporine→c-Caspase-8 \| Fold | 15 / 14 | 0.97 | 0.83 | 0.85 | 0.036 | 0.049 |
| H2O2 & SCF→p-Erk \| Fold | Etoposide & ZVAD→p-ChK2+, c-PARP+ \| Quad | 14 / 14 | 0.97 | 0.91 | 0.77 | 0.035 | 0.044 |
| Staurosporine→c-Caspase-8 \| Total | TNFα→p-NFkB-p65 \| Fold | 15 / 14 | 0.97 | 0.87 | 0.69 | 0.008 | 0.022 |
| SCF→p-Stat5 \| Total | Staurosporine→c-Caspase-8 \| Fold | 15 / 14 | 0.97 | 0.85 | 0.85 | 0.030 | 0.028 |
| M-CSF→p-Stat5 \| Total | Staurosporine→c-Caspase-8 \| Fold | 15 / 14 | 0.97 | 0.84 | 0.85 | 0.033 | 0.030 |
| Staurosporine→c-Caspase-8 \| Total | FLT3L→p-S6 \| Total | 15 / 14 | 0.97 | 0.87 | 0.80 | 0.015 | 0.034 |
| FLT3L→p-S6 \| Total | IFNγ→p-Stat5 \| Total | 17 / 15 | 0.96 | 0.80 | 0.77 | 0.014 | 0.017 |
| IL-27→p-S6 \| Total | FLT3L→p-S6 \| Total | 17 / 15 | 0.96 | 0.85 | 0.80 | 0.014 | 0.024 |
| p-Stat5 \| Basal | FLT3L→p-S6 \| Total | 17 / 15 | 0.96 | 0.89 | 0.80 | 0.026 | 0.045 |
| IL-6→p-Stat5 \| Total | Etoposide & ZVAD→p-ChK2+, c-PARP- \| Quad | 14 / 14 | 0.96 | 0.79 | 0.78 | 0.027 | 0.018 |

FIG. 27

| | | | | | |
|---|---|---|---|---|---|
| Staurosporine & ZVAD→c-Caspase-3 \| Fold | H₂O₂→p-Stat5 \| Fold | 14 / 14 | 0.96 | 0.85 | 0.84 | 0.028 | 0.022 |
| IL-6→p-Stat5 \| Total | Etoposide & ZVAD→c-PARP \| Total | 14 / 14 | 0.96 | 0.79 | 0.80 | 0.028 | 0.013 |
| H₂O₂ & SCF→p-Erk \| Fold | Etoposide & ZVAD→p-Chk2+, c-PARP- \| Quad | 14 / 14 | 0.96 | 0.91 | 0.78 | 0.027 | 0.037 |
| Staurosporine & ZVAD→c-Caspase-8 \| Fold | p-Stat5 \| Total | 15 / 14 | 0.96 | 0.90 | 0.88 | 0.037 | 0.037 |
| Staurosporine & ZVAD→c-Caspase-3 \| Total | TNFα→p-NFkB-p65 \| Fold | 15 / 14 | 0.96 | 0.89 | 0.69 | 0.012 | 0.043 |
| SCF→p-Stat5 \| Total | p-SLP-76 \| Total | 13 / 14 | 0.96 | 0.84 | 0.76 | 0.013 | 0.018 |
| Staurosporine→c-Caspase-8 \| Fold | ABCG2 \| PercentPos | 14 / 13 | 0.96 | 0.85 | 0.71 | 0.043 | 0.032 |
| M-CSF→p-Stat5 \| Total | FLT3L→p-S6 \| Total | 17 / 15 | 0.96 | 0.85 | 0.80 | 0.014 | 0.026 |
| SCF→p-Stat5 \| Total | IL-27→p-Erk \| Total | 17 / 15 | 0.96 | 0.87 | 0.71 | 0.006 | 0.028 |
| IGF-1→p-Stat5 \| Total | FLT3L→p-S6 \| Total | 17 / 15 | 0.96 | 0.85 | 0.80 | 0.017 | 0.034 |
| IL-10→p-Stat5 \| Total | FLT3L→p-S6 \| Fold | 17 / 15 | 0.96 | 0.87 | 0.72 | 0.042 | 0.045 |
| Staurosporine→c-Caspase-8 \| Total | Etoposide & ZVAD→c-PARP \| Total | 14 / 14 | 0.96 | 0.86 | 0.80 | 0.024 | 0.031 |
| Staurosporine→c-Caspase-8 \| Total | Etoposide→c-PARP \| Total | 14 / 14 | 0.96 | 0.86 | 0.82 | 0.025 | 0.037 |
| H₂O₂ & SCF→p-Erk \| Fold | G-CSF→p-S6 \| Total | 14 / 14 | 0.96 | 0.91 | 0.65 | 0.026 | 0.039 |
| EPO→p-Stat5 \| Total | H₂O₂ & SCF→p-Erk \| Total | 14 / 14 | 0.96 | 0.85 | 0.72 | 0.040 | 0.035 |
| H₂O₂ & SCF→p-Erk \| Fold | SCF→p-CREB \| Total | 14 / 14 | 0.96 | 0.91 | 0.77 | 0.032 | 0.042 |
| Staurosporine→c-Caspase-8 \| Total | Etoposide→c-Caspase-3 \| Total | 12 / 14 | 0.96 | 0.86 | 0.82 | 0.036 | 0.049 |
| Staurosporine→c-Caspase-8 \| Total | CD40L→p-p38 \| Total | 15 / 14 | 0.96 | 0.87 | 0.67 | 0.016 | 0.032 |
| Staurosporine→c-Caspase-8 \| Total | IL-6→p-CREB \| Fold | 15 / 14 | 0.96 | 0.87 | 0.73 | 0.010 | 0.035 |
| p-Stat5 \| Basal | Staurosporine→c-Caspase-8 \| Total | 15 / 14 | 0.96 | 0.83 | 0.85 | 0.037 | 0.042 |
| Staurosporine & ZVAD→c-Caspase-8 \| Fold | EPO→p-Stat5 \| Total | 15 / 14 | 0.96 | 0.90 | 0.85 | 0.031 | 0.045 |
| Staurosporine & ZVAD→c-Caspase-8 \| Fold | IL-10→p-Stat5 \| Total | 15 / 14 | 0.96 | 0.90 | 0.86 | 0.022 | 0.047 |

FIG. 27 (Cont. 1)

| | | | | | |
|---|---|---|---|---|---|
| Staurosporine→c-Caspase-8 \| Fold | IFNα→p-Stat5 \| Total | 15 / 14 | 0.96 | 0.85 | 0.78 | 0.032 | 0.050 |
| p-Stat5 \| Basal | M-CSF→p-S6 \| Fold | 17 / 15 | 0.96 | 0.89 | 0.77 | 0.013 | 0.032 |
| M-CSF→p-Stat5 \| Total | p-SLP-76 \| Basal | 13 / 14 | 0.96 | 0.82 | 0.76 | 0.013 | 0.017 |
| IGF-1→p-Stat5 \| Total | p-SLP-76 \| Basal | 13 / 14 | 0.96 | 0.85 | 0.76 | 0.020 | 0.025 |
| IL-10→p-Stat5 \| Total | Etoposide→c-PARP \| Fold | 14 / 14 | 0.95 | 0.86 | 0.83 | 0.022 | 0.019 |
| Staurosporine & ZVAD→c-Caspase-3 \| Total | H₂O₂→p-Stat5 \| Fold | 14 / 14 | 0.95 | 0.88 | 0.84 | 0.014 | 0.023 |
| IL-27→p-Stat5 \| Total | H₂O₂ & SCF→p-Erk \| Total | 14 / 14 | 0.95 | 0.82 | 0.72 | 0.009 | 0.023 |
| IL-10→p-Stat5 \| Total | H₂O₂ & SCF→p-Erk \| Total | 14 / 14 | 0.95 | 0.86 | 0.72 | 0.007 | 0.029 |
| IL-10→p-Stat5 \| Total | Etoposide & ZVAD→c-PARP \| Total | 14 / 14 | 0.95 | 0.86 | 0.80 | 0.029 | 0.034 |
| Staurosporine→c-Caspase-8 \| Total | Etoposide→c-PARP \| Fold | 14 / 14 | 0.95 | 0.86 | 0.83 | 0.019 | 0.040 |
| H₂O₂ & SCF→p-Erk \| Fold | Etoposide & ZVAD→p-Chk2-, c-PARP + \| Quad | 14 / 14 | 0.95 | 0.91 | 0.74 | 0.016 | 0.042 |
| SCF→p-Stat5 \| Total | FLT3L→p-S6 \| Total | 17 / 15 | 0.95 | 0.87 | 0.80 | 0.011 | 0.033 |
| EPO→p-Stat5 \| Total | M-CSF→p-S6 \| Fold | 17 / 15 | 0.95 | 0.87 | 0.77 | 0.012 | 0.036 |
| SCF→p-Stat5 \| Total | Etoposide→c-Caspase-3 \| Total | 12 / 14 | 0.95 | 0.85 | 0.82 | 0.021 | 0.039 |

FIG. 27 (Cont.2)

| Pathway | Modulator | Readout | Metric |
|---|---|---|---|
| Apoptosis | Etoposide | p-Chk2_T68 | Ua |
| Apoptosis | Etoposide | p-Chk2_T68 | Fold |
| Apoptosis | Unstim / No Modulator | Cleaved PARP_D214 | Ua |
| Signaling | FLT-3 Ligand | p-Akt_S473 | Uu |
| Signaling | FLT-3 Ligand | p-Akt_S473 | Ua |
| Signaling | FLT-3 Ligand | p-ERK 1/2 T202/Y204 | Fold |
| Signaling | FLT-3 Ligand | p-S6_S235/236 | TotalPhospho |
| Signaling | G-CSF | p-Stat5_Y694 | Ua |
| Signaling | IL-27 | p-Stat1_Y701 | TotalPhospho |
| Signaling | IL-27 | p-Stat1_Y701 | Fold |
| Signaling | IL-27 | p-Stat3_S727 | TotalPhospho |
| Signaling | IL-27 | p-Stat5_Y694 | Ua |
| Signaling | PMA | p-CREB_S133 | TotalPhospho |
| Signaling | PMA | p-ERK 1/2 T202/Y204 | Fold |
| Signaling | PMA | p-ERK 1/2 T202/Y204 | Ua |
| Signaling | PMA | p-S6_S235/236 | TotalPhospho |
| Signaling | SCF | p-Akt_S473 | Ua |
| Signaling | Unstim / No Modulator | p-Akt_S473 | Ua |
| Signaling | Unstim / No Modulator | p-CREB_S133 | Basal |
| Signaling | Unstim / No Modulator | p-SLP-76_Y128 | Ua |
| Signaling | Unstim / No Modulator | p-Stat3_S727 | Basal |
| Signaling | Unstim / No Modulator | p-Stat5_Y694 | Ua |

FIG. 36

METHODS FOR DIAGNOSIS, PROGNOSIS AND METHODS OF TREATMENT

CROSS-REFERENCE

This application is a continuation application of U.S. application Ser. No. 12/910,769, filed Oct. 22, 2010, which claims priority to U.S. application No. 61/382,793, filed Sep. 14, 2010, U.S. application Ser. No. 61/374,613 filed Aug. 18, 2010, U.S. application No. 61/373,199, filed Aug. 12, 2010, U.S. application No. 61/350,864, filed Jun. 2, 2010, U.S. application No. 61/265,743, filed Dec. 1, 2009, U.S. application No. 61/265,585, filed Dec. 1, 2009, U.S. application No. 61/254,131, filed Oct. 22, 2009. This application is a continuation in part of U.S. application Ser. No. 12/460,029 filed Jul. 10, 2009 which claims priority to U.S. Ser. No. 61/079,766 filed Jul. 10, 2008, U.S. Ser. No. 61/085,789 filed Aug. 1, 2008, U.S. Ser. No. 61/104,666 filed Oct. 10, 2008 and U.S. Ser. No. 61/120,320 filed Dec. 5, 2008. Each of these applications is hereby expressly incorporated by reference in their entirety.

BACKGROUND OF THE INVENTION

Many conditions are characterized by disruptions in cellular pathways that lead, for example, to aberrant control of cellular processes, with uncontrolled growth and increased cell survival. These disruptions are often caused by changes in the activity of molecules participating in cellular pathways. For example, alterations in specific signaling pathways have been described for many cancers. Despite the increasing evidence that disruption in cellular pathways mediate the detrimental transformation, the precise molecular events underlying these transformations in diseases remain unclear. As a result, therapeutics may not be effective in treating conditions involving cellular pathways that are not well understood. Thus, the successful diagnosis of a condition and use of therapies will require knowledge of the cellular events that are responsible for the condition pathology.

Acute myeloid leukemia (AML), myelodysplastic syndrome (MDS), and myeloproliferative neoplasms (MPN) are examples of disorders that arise from defects of hematopoietic cells of myeloid origin. These hematopoietic disorders are recognized as clonal diseases, which are initiated by somatic and/or inherited mutations that cause dysregulated signaling in a progenitor cell. The wide range of possible mutations and accompanying signaling defects accounts for the diversity of disease phenotypes and response to therapy observed within this group of disorders. For example, some leukemia patients respond well to treatment and survive for prolonged periods, while others die rapidly despite aggressive treatment. Some patients with myelodysplastic syndrome suffer only from anemia while others transform to an acute myeloid leukemia that is difficult to treat. Despite the emergence of new therapies to treat these disorders the percentage of patients who do not benefit from current treatment is still high. Patients that are resistant to therapy experience significant toxicity and have very short survival times. While various staging systems have been developed to address this clinical heterogeneity, they cannot accurately predict at diagnosis the prognosis or predict response to a given therapy or the clinical course that a given patient will follow.

Accordingly, there is a need for a biologically based clinically relevant re-classification of these disorders that can inform on disease management at the individual level. This classification, based upon the biologic commonalities of the disorders above, will aid clinicians in both prognosis and therapeutic selection at the individual patient level thus improving patient outcomes e.g. survival and quality of life.

There are also needs for a biologically based clinically relevant re-classification of these disorders to aid in new drug target identification and drug screening for agents that may be active against myeloid malignancies.

SUMMARY OF THE INVENTION

In some embodiments, the invention provides methods of diagnosing, prognosing, or determining progression of acute leukemia, myelodysplastic syndrome or myeloproliferative neoplasms in an individual, the method comprising: A] classifying one or more hematopoietic cells associated with acute leukemia, myelodysplastic syndrome or myeloproliferative neoplasms in the individual by a method comprising: a) subjecting a cell population comprising the one or more hematopoietic cells from the individual to a plurality of modulators in a plurality of cultures, b) characterizing a plurality of pathways in one or more cells from the plurality of cultures by determining an activation level of at least one activatable element within a plurality of pathways, and c) classifying one or more hematopoietic cells based on the pathways characterization; and B] making a decision regarding diagnosis, prognosis or progression of acute leukemia, myelodysplastic syndrome or myeloproliferative neoplasms in the individual, where the decision is based on the classification of the cells. In some embodiments, the acute leukemia is acute myeloid leukemia. In some embodiments, the pathways are selected from the group consisting of apoptosis, cell cycle, signaling, or DNA damage pathways.

In some embodiments, the method provides of diagnosing, prognosing, determining progression, predicting a response to a treatment or choosing a treatment for acute leukemia, myelodysplastic syndrome or myeloproliferative neoplasms in an individual, the method comprising: (1) classifying one or more hematopoietic cells associated with acute leukemia, myelodysplastic syndrome or myeloproliferative neoplasms in the individual by a method comprising: a) subjecting a cell population comprising the one or more hematopoietic cells from the individual to no modulator, CD40L, FLT3L, IGF-1, IL-27, IL-3, IL-6, M-CSF, SCF, Thapsigargin, SDF-1α or PMA, b) determining an activation level of p-CREB in one or more cells from the individual, and c) classifying the one or more hematopoietic cells based on the activation levels of p-CREB; and (2) making a decision regarding a diagnosis, prognosis, progression, response to a treatment or a selection of treatment for acute leukemia, myelodysplastic syndrome or myeloproliferative neoplasms in the individual based on the classification of the one or more hematopoietic cells. In some embodiments, the individual is selected from the group consisting of De Novo patient, intermediate risk cytogenetics and high risk cytogenetics, and the cell population is subjected to SDF-1α. In some embodiments, the individual is an individual with Secondary acute leukemia or less than 60 years old, and the cell population is subjected to PMA. In some embodiments, the individual is less than 60 years old, and the population is subjected to Thapsigargin. In some embodiments, the individual has a FLT3 mutation, and the cell population is subjected to FLT3L or PMA. In some embodiments, classifying further comprises identifying a difference in kinetics of the activation level.

In some embodiments, the invention provides methods of diagnosing, prognosing, determining progression, predicting a response to a treatment or choosing a treatment for acute leukemia, myelodysplastic syndrome or myeloproliferative neoplasms in an individual, the method comprising: (1) classifying one or more hematopoietic cells associated with acute leukemia, myelodysplastic syndrome or myeloproliferative neoplasms in the individual by a method comprising: a) subjecting a cell population comprising the one or more hematopoietic cells from the individual to no modulator, CD40L, H2O2, SCF, SDF-1α, TNFα, LPS, PMA, FLT3L and Thapsigargin, b) determining an activation level of p-Erk in one or more cells from the individual, and c) classifying the one or more hematopoietic cells based on the activation levels of p-Erk; and (2) making a decision regarding a diagnosis, prognosis, progression, response to a treatment or a selection of treatment for acute leukemia, myelodysplastic syndrome or myeloproliferative neoplasms in the individual based on the classification of the one or more hematopoietic cells. In some embodiments, the individual is 60 years old or older, and the cell population is subjected to LPS. In some embodiments, the individual is less than 60 years old; and the cell population is subjected to no modulator, PMA or Thapsigargin. In some embodiments the individual has a FLT3 mutation, and the cell population is subjected to FLT3L. In some embodiments, the classifying further comprises identifying a difference in kinetics of the activation level.

In some embodiments, the invention provides methods of diagnosing, prognosing, determining progression, predicting a response to a treatment or choosing a treatment for acute leukemia, myelodysplastic syndrome or myeloproliferative neoplasms in an individual, the method comprising: (1) classifying one or more hematopoietic cells associated with acute leukemia, myelodysplastic syndrome or myeloproliferative neoplasms in the individual by a method comprising: a) subjecting a cell population comprising the one or more hematopoietic cells from the individual to no modulator; FLT3L, H2O2, SCF, IGF-1, M-CSF, b) determining an activation level of p-plcγ2 in one or more cells from the individual, and c) classifying the one or more hematopoietic cells based on the activation levels of p-plcγ2; and (2) making a decision regarding a diagnosis, prognosis, progression, response to a treatment or a selection of treatment for acute leukemia, myelodysplastic syndrome or myeloproliferative neoplasms in the individual based on the classification of the one or more hematopoietic cells. In some embodiments, the individual is a de Novo patient, and the cell population is subjected to SCF or FLT3L.

In some embodiments, the invention provides methods of diagnosing, prognosing, determining progression, predicting a response to a treatment or choosing a treatment for acute leukemia, myelodysplastic syndrome or myeloproliferative neoplasms in an individual, the method comprising: (1) classifying one or more hematopoietic cells associated with acute leukemia, myelodysplastic syndrome or myeloproliferative neoplasms in the individual by a method comprising: a) subjecting a cell population comprising the one or more hematopoietic cells from the individual to no modulator, FLT3L or SCF, b) determining an activation level of p-S6 in one or more cells from the individual, and c) classifying the one or more hematopoietic cells based on the activation levels of p-S6; and (2) making a decision regarding a diagnosis, prognosis, progression, response to a treatment or a selection of treatment for acute leukemia, myelodysplastic syndrome or myeloproliferative neoplasms in the individual based on the classification of the one or more hematopoietic cells. In some embodiments, the individual is a de Novo patient; and the cell population is subjected to no modulator or SCF. In some embodiments, the individual has a FLT3 mutation. In some embodiments, classifying further comprises identifying a difference in kinetics of the activation level.

In some embodiments, the invention provides methods of diagnosing, prognosing, determining progression, predicting a response to a treatment or choosing a treatment for acute leukemia, myelodysplastic syndrome or myeloproliferative neoplasms in an individual, the method comprising: (1) classifying one or more hematopoietic cells associated with acute leukemia, myelodysplastic syndrome or myeloproliferative neoplasms in the individual by a method comprising: a) subjecting a cell population comprising the one or more hematopoietic cells from the individual to no modulator, G-CSF, IL-27, IL-3, IL-6, IFNα, IFNg, IL-10, or GM-CSF, b) determining an activation level of p-Stat 3 in one or more cells from the individual, and c) classifying the one or more hematopoietic cells based on the activation levels of p-Stat 3; and (2) making a decision regarding a diagnosis, prognosis, progression, response to a treatment or a selection of treatment for acute leukemia, myelodysplastic syndrome or myeloproliferative neoplasms in the individual based on the classification of the one or more hematopoietic cells. In some embodiments, the individual is a de Novo patient, and the cell population is subjected to IL-3. In some embodiments, the individual is an individual with secondary acute leukemia, and the cell population is subjected to IFNα. In some embodiments, the individual is 60 years old or older; and the cell population is subjected IL-27. In some embodiments, the individual is less than 60 years old; and the cell population is subjected to GM-CSF, IFNα, IFNg, IL-10 or IL-6. In some embodiments, the individual is an individual with intermediate or high risk cytogenetics; and the cell population is subjected to IFNα, IFNg, G-CSF, IL-10, IL-27 or IL-6. In some embodiments, the individual has a FLT3 mutation; and the cell population is subjected to IL-27, G-CSF, or IFNα.

In some embodiments, the invention provides methods of diagnosing, prognosing, determining progression, predicting a response to a treatment or choosing a treatment for acute leukemia, myelodysplastic syndrome or myeloproliferative neoplasms in an individual, the method comprising: (1) classifying one or more hematopoietic cells associated with acute leukemia, myelodysplastic syndrome or myeloproliferative neoplasms in the individual by a method comprising: a) subjecting a cell population comprising the one or more hematopoietic cells from the individual to G-CSF, IL-6, IFNα, GM-CSF, IFNg, IL-10, or IL-27, b) determining an activation level of p-Stat 5 in one or more cells from the individual, and c) classifying the one or more hematopoietic cells based on the activation levels of p-Stat 5; and (2) making a decision regarding a diagnosis, prognosis, progression, response to a treatment or a selection of treatment for acute leukemia, myelodysplastic syndrome or myeloproliferative neoplasms in the individual based on the classification of the one or more hematopoietic cells. In some embodiments, the individual is a de Novo patient; and the cell population is subjected to IL-6. In some embodiments, the individual is an individual with secondary acute leukemia; and the cell population is subjected to IFNα. In some embodiments, the individual is less than 60 years old, and the cell population is subjected to GM-CSF, IFNα, IFNg, IL-10 or IL-6. In some embodiments the individual is an individual with intermediate or high risk cytogenetics; and the cell population is subjected to IFNα, IFNg, G-CSF, IL-10, IL-27 or IL-6. In some embodiments, the individual has a FLT3 mutation, and the cell population is subjected to IL-27, IFNα, or G-CSF.

In some embodiments, the invention methods of diagnosing, prognosing, determining progression, predicting a response to a treatment or choosing a treatment for acute leukemia, myelodysplastic syndrome or myeloproliferative neoplasms in an individual, the method comprising: (1) classifying one or more hematopoietic cells associated with acute leukemia, myelodysplastic syndrome or myeloproliferative neoplasms in the individual by a method comprising: a) subjecting a cell population comprising the one or more hematopoietic cells from the individual to H2O2 or SCF, b) determining an activation level of p-SLP 76 in one or more cells from the individual, and c) classifying the one or more hematopoietic cells based on the activation levels of p-SLP 76; and (2) making a decision regarding a diagnosis, prognosis, progression, response to a treatment or a selection of treatment for acute leukemia, myelodysplastic syndrome or myeloproliferative neoplasms in the individual based on the classification of the one or more hematopoietic cells. In some embodiments, the individual is an individual with intermediate or high risk cytogenetics; and the cell population is subjected to H2O2.

In some embodiments, the invention provides methods of diagnosing, prognosing, determining progression, predicting a response to a treatment or choosing a treatment for acute leukemia, myelodysplastic syndrome or myeloproliferative neoplasms in an individual, the method comprising: (1) classifying one or more hematopoietic cells associated with acute leukemia, myelodysplastic syndrome or myeloproliferative neoplasms in the individual by a method comprising: a) subjecting a cell population comprising the one or more hematopoietic cells from the individual to H2O2, b) determining an activation level of p-Lck in one or more cells from the individual, and c) classifying the one or more hematopoietic cells based on the activation levels of p-Lck; and (2) making a decision regarding a diagnosis, prognosis, progression, response to a treatment or a selection of treatment for acute leukemia, myelodysplastic syndrome or myeloproliferative neoplasms in the individual based on the classification of the one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, the method comprising: (1) classifying one or more hematopoietic cells associated with acute leukemia, myelodysplastic syndrome or myeloproliferative neoplasms in the individual by a method comprising: a) subjecting a cell population comprising the one or more hematopoietic cells from the individual to SCF, FLT3L, M-CSF or H2O2, b) determining an activation level of p-Akt in one or more cells from the individual, and c) classifying the one or more hematopoietic cells based on the activation levels of p-Akt; and (2) making a decision regarding a diagnosis, prognosis, progression, response to a treatment or a selection of treatment for acute leukemia, myelodysplastic syndrome or myeloproliferative neoplasms in the individual based on the classification of the one or more hematopoietic cells. In some embodiments, the individual is 60 years old, older than 60 years old, an individual with intermediate risk cytogenetics or an individual with high risk cytogenetics. In some embodiments, the individual has a FLT3 mutation; and the cell population is subjected to FLT3L or SCF. In some embodiments, classifying further comprises identifying a difference in kinetics of the activation level.

In some embodiments, the invention provides methods of diagnosing, prognosing, determining progression, predicting a response to a treatment or choosing a treatment for acute leukemia, myelodysplastic syndrome or myeloproliferative neoplasms in an individual, the method comprising: (1) classifying one or more hematopoietic cells associated with acute leukemia, myelodysplastic syndrome or myeloproliferative neoplasms in the individual by a method comprising: a) subjecting a cell population comprising the one or more hematopoietic cells from the individual to no modulator, b) determining an activation level of p-Stat 6 in one or more cells from the individual, and c) classifying the one or more hematopoietic cells based on the activation levels of p-Stat 6; and (2) making a decision regarding a diagnosis, prognosis, progression, response to a treatment or a selection of treatment for acute leukemia, myelodysplastic syndrome or myeloproliferative neoplasms in the individual based on the classification of the one or more hematopoietic cells. In some embodiments, the individual is a de Novo patient.

In some embodiments, the invention methods of diagnosing, prognosing, determining progression, predicting a response to a treatment or choosing a treatment for acute leukemia, myelodysplastic syndrome or myeloproliferative neoplasms in an individual, the method comprising: (1) classifying one or more hematopoietic cells associated with acute leukemia, myelodysplastic syndrome or myeloproliferative neoplasms in the individual by a method comprising: a) subjecting a cell population comprising the one or more hematopoietic cells from the individual to no modulator, Etoposide, Daunorubicin, AraC, or a combination thereof b) determining an activation level of p-Chk2 in one or more cells from the individual, and c) classifying the one or more hematopoietic cells based on the activation levels of p-Chk2; and (2) making a decision regarding a diagnosis, prognosis, progression, response to a treatment or a selection of treatment for acute leukemia, myelodysplastic syndrome or myeloproliferative neoplasms in the individual based on the classification of the one or more hematopoietic cells. In some embodiments, the individual is a de Novo patient, or an individual with secondary acute leukemia; and the cell population is subjected to etoposide. In some embodiments, the individual is an individual with secondary acute leukemia; and the cell population is subjected to no modulator. In some embodiments, the individual is less than 60 years old; and the cell population is subjected to Daunorubicin, AraC, Etoposide or a combination thereof.

In some embodiments, the invention provides methods of diagnosing, prognosing, determining progression, predicting a response to a treatment or choosing a treatment for acute leukemia, myelodysplastic syndrome or myeloproliferative neoplasms in an individual, the method comprising: (1) classifying one or more hematopoietic cells associated with acute leukemia, myelodysplastic syndrome or myeloproliferative neoplasms in the individual by a method comprising: a) subjecting a cell population comprising the one or more hematopoietic cells from the individual to no modulator, Daunorubicin, AraC, Etoposide Staurosporine, ZVAD or a combination thereof; b) determining an activation level of c-PARP in one or more cells from the individual, and c) classifying the one or more hematopoietic cells based on the activation levels of c-PARP; and (2) making a decision regarding a diagnosis, prognosis, progression, response to a treatment or a selection of treatment for acute leukemia, myelodysplastic syndrome or myeloproliferative neoplasms in the individual based on the classification of the one or more hematopoietic cells. In some embodiments, the individual is an individual with secondary acute leukemia, and the cell population is subjected to no modulator or etoposide. In some embodiments, the individual is less than 60 years old; and the cell population is subjected to no modulator, Daunorubicin, AraC, Etoposide, Staurosporine, ZVAD or a combination thereof. In some embodiments, the individual has a FLT3 mutation, and the cell population is subjected to Etoposide.

In some embodiments, the invention methods of diagnosing, prognosing, determining progression, predicting a response to a treatment or choosing a treatment for acute leukemia, myelodysplastic syndrome or myeloproliferative neoplasms in an individual, the method comprising: (1) classifying one or more hematopoietic cells associated with acute leukemia, myelodysplastic syndrome or myeloproliferative neoplasms in the individual by a method comprising: a) subjecting a cell population comprising the one or more hematopoietic cells from the individual to G-CSF; GM-CSF, IFNα, IFNg, IL-10, IL-27 and IL-6, b) determining an activation level of p-Stat 1 in one or more cells from the individual, and c) classifying the one or more hematopoietic cells based on the activation levels of p-Stat 1; and (2) making a decision regarding a diagnosis, prognosis, progression, response to a treatment or a selection of treatment for acute leukemia, myelodysplastic syndrome or myeloproliferative neoplasms in the individual based on the classification of the one or more hematopoietic cells. In some embodiments, the individual is an individual with secondary acute leukemia; and the cell population is subjected to G-CSF or IFNα. In some embodiments, the individual is less than 60 years old, and the cell population is subjected to GM-CSF, IFNα, IFNg, IL-10 or IL-6. In some embodiments, the individual is an individual with intermediate or high risk cytogenetics, and the cell population is subjected to IFNα, IFNg, IL-10, IL-27 or IL-6.

In some embodiments, the invention provides methods of diagnosing, prognosing, determining progression, predicting a response to a treatment or choosing a treatment for acute leukemia, myelodysplastic syndrome or myeloproliferative neoplasms in an individual, the method comprising: (1) classifying one or more hematopoietic cells associated with acute leukemia, myelodysplastic syndrome or myeloproliferative neoplasms in the individual by a method comprising: a) subjecting a cell population comprising the one or more hematopoietic cells from the individual to Staurosporine, ZVAD or a combination thereof, b) determining an activation level of cytochrome C in one or more cells from the individual, and c) classifying the one or more hematopoietic cells based on the activation levels of cytochrome C; and (2) making a decision regarding a diagnosis, prognosis, progression, response to a treatment or a selection of treatment for acute leukemia, myelodysplastic syndrome or myeloproliferative neoplasms in the individual based on the classification of the one or more hematopoietic cells. In some embodiments, the individual is less than 60 years old.

In some embodiments, the invention methods of diagnosing, prognosing, determining progression, predicting a response to a treatment or choosing a treatment for acute leukemia, myelodysplastic syndrome or myeloproliferative neoplasms in an individual, the method comprising: (1) classifying one or more hematopoietic cells associated with acute leukemia, myelodysplastic syndrome or myeloproliferative neoplasms in the individual by a method comprising: a) determining an activation level of at least three activatable elements in the presence of a modulator as listed in Tables 23, or 24 or FIG. 36, and b) classifying the one or more hematopoietic cells based on the activation levels of the activatable elements; and (2) making a decision regarding a diagnosis, prognosis, progression, response to a treatment or a selection of treatment for acute leukemia, myelodysplastic syndrome or myeloproliferative neoplasms in the individual based on the classification of the one or more hematopoietic cells. In some embodiments, at least one activatable element is from an apoptosis pathway. In some embodiments, at least two activatable elements are from an apoptosis pathway. In some embodiments, the activation level of the at least three activatable elements is selected from the group consisting of (i) p-Akt in the presence of SCF, (ii) p-Akt in the presence of FLT3L, (iii) p-Chk2 in the presence of Etoposide; (iv) c-PARP+ in the presence of no modulator and (v) p-Erk 1/2 in the presence of PMA. In some embodiments, the activation level of the at least three activatable elements is selected from the group consisting of (i) p-Akt in the presence of SCF, (ii) p-Akt in the presence of FLT3L, (iii) p-Chk2 in the presence of Etoposide; (iv) c-PARP+ in the presence of no modulator and (v) p-Erk 1/2 in the presence of PMA; and at least two activatable elements are from an apoptosis pathway.

In some embodiments of the methods, the methods further comprise determining the levels of a drug transporter, growth factor receptor and/or a cytokine receptor. In some embodiments, the cytokine receptor, growth factor receptor or drug transporter are selected from the group consisting of MDR1, ABCG2, MRP, P-Glycoprotein, CXCR4, FLT3, and c-kit.

In some embodiments, the activation level is determined by a process comprising the binding of a binding element which is specific to a particular activation state of the particular activatable element. In some embodiments, the binding element comprises an antibody.

In some embodiments, the step of determining the activation level comprises the use of flow cytometry, immunofluorescence, confocal microscopy, immunohistochemistry, immunoelectronmicroscopy, nucleic acid amplification, gene array, protein array, mass spectrometry, patch clamp, 2-dimensional gel electrophoresis, differential display gel electrophoresis, microsphere-based multiplex protein assays, ELISA, and label-free cellular assays to determine the activation level of one or more intracellular activatable element in single cells.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2B measures the frequency of cells with a described property such as cells positive for cleaved PARP (% PARP+), or cells positive for p-S6 and p-Akt. Similarly, measurements examining the changes in the frequencies of cells may be applied such as the Change in % PARP+ which would measure the % PARP+$_{stimulated\ Stained}$−% PARP+$_{Unstimulated\ Stained}$. The AUC$_{unstim}$ metric also measures changes in population frequencies measuring the frequency of cells to become positive compared to an unstimulated condition.

FIG. 13 depicts a table comparing FLT3 Receptor and FLT3L induced signaling between normal BM Myeloblast and FLT3-WT AML.

FIG. 14 depicts the variance in signaling among different FLT3 subgroups.

FIG. 16(a) illustrates differences in FLT3L-induced Stat signaling. FIG. 16(b) illustrates differences in IL-27-induced Stat signaling. FIG. 16(c) illustrates differences in Etoposide-induced apoptosis.

FIG. 18 tabulates the correlations between nodes that stratify FLT3-ITD from FLT3-WT samples.

FIG. 19 provides a schematic overview of bivariate modeling.

FIG. 20(a) illustrates FLT3L-induced S6 signaling in the clinical outliers relative to FLT3-ITD and FLT3-WT samples. FIG. 20(b) illustrates IL-27-induced Stat signaling in the clinical outliers relative to FLT3-ITD and FLT3-WT samples. FIG. 20(c) illustrates IL-27-induced Stat signaling in the clinical outliers relative to FLT3-ITD and FLT3-WT samples.

FIG. 21 tabulates the correlations between nodes that stratify FLT3-ITD from FLT3-WT samples.

FIG. 22 tabulates results from a univariate analysis of differences between FLT3-ITD and FLT3-WT signaling.

FIG. 23 depicts a summary table of common stratifying pathways between FLT3-WT and FLT3-ID signaling in AML samples.

FIG. 26 tabulates results from a univariate analysis of differences between FLT3-ITD and FLT3-WT signaling.

FIG. 27 list all combinations of nodes for which the bivariate model of the combination had an AUC greater than the best single node/metric within the combination.

FIG. 36 tabulates a list of stratifying nodes.

DETAILED DESCRIPTION OF THE INVENTION

Figure 1:
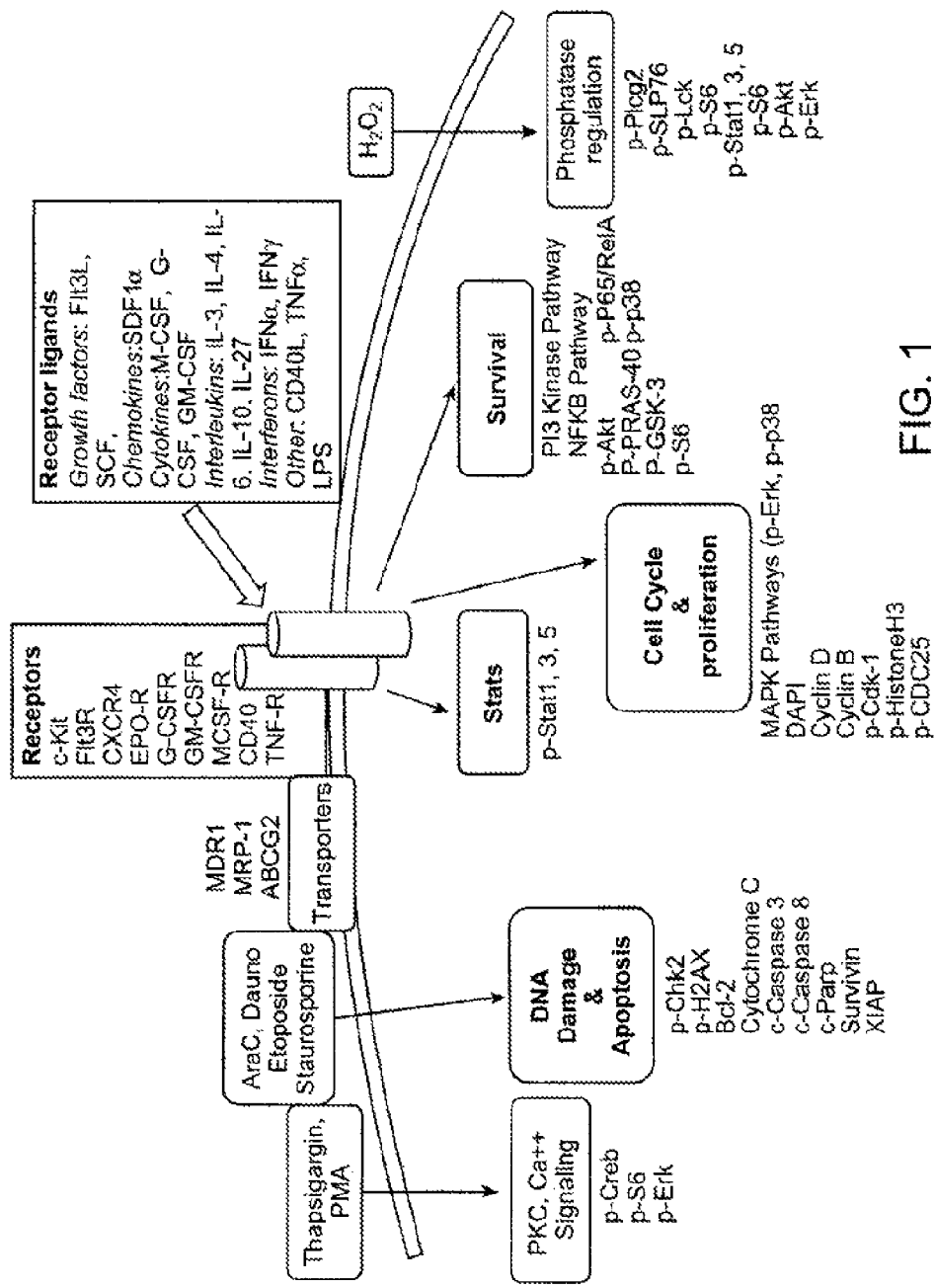
FIG. 1 shows some examples of cellular pathways. For example, cytokines such as G-CSF or growth factors such as FLT-3 Ligand (FLT3L) will activate their receptors resulting in activation of intracellular signaling pathways. Also, chemotherapeutics, such as AraC can be transported inside the cell to cause effects, such as DNA damage, caspase activation, PARP cleavage, etc.

The present invention incorporates information disclosed in other applications and texts. The following patent and other publications are hereby incorporated by reference in their entireties: Haskell et al, Cancer Treatment, 5$^{th}$ Ed., W.B. Saunders and Co., 2001; Alberts et al., The Cell, 4$^{th}$ Ed., Garland Science, 2002; Vogelstein and Kinzler, The Genetic Basis of Human Cancer, 2d Ed., McGraw Hill, 2002; Michael, Biochemical Pathways, John Wiley and Sons, 1999; Weinberg, The Biology of Cancer, 2007; Immunobiology, Janeway et al. 7$^{th}$ Ed., Garland, and Leroith and Bondy, Growth Factors and Cytokines in Health and Disease, A Multi Volume Treatise, Volumes 1A and 1B, Growth Factors, 1996. Other conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, N.Y., Gait, "Oligonucleotide Synthesis: A Practical Approach" 1984, IRL Press, London, Nelson and Cox (2000), Lehninger, Principles of Biochemistry 3rd Ed., W. H. Freeman Pub., New York, N.Y. and Berg et al. (2002) Biochemistry, 5th Ed., W. H. Freeman Pub., New York, N.Y.; and Sambrook, Fritsche and Maniatis. "Molecular Cloning A laboratory Manual" 3rd Ed. Cold Spring Harbor Press (2001), all of which are herein incorporated in their entirety by reference for all purposes.

Patents and applications that are also incorporated by reference include U.S. Pat. Nos. 7,381,535 and 7,393,656 and U.S. Ser. Nos. 10/193,462; 11/655,785; 11/655,789; 11/655,821; 11/338,957, 61/048,886; 61/048,920; 61/048,657; and 61/079,766. Some commercial reagents, protocols, software and instruments that are useful in some embodiments of the present invention are available at the Becton Dickinson Website http://www.bdbiosciences.com/features/products/, and the Beckman Coulter website, http://www.beckmancoulter.com/Default.asp?bhfv=7. Relevant articles include High-content single-cell drug screening with phosphospecific flow cytometry, Krutzik et al., Nature Chemical Biology, 23 Dec. 2007; Irish et al., FLt3 ligand Y591 duplication and Bcl-2 over expression are detected in acute myeloid leukemia cells with high levels of phosphorylated wild-type p53, Neoplasia, 2007, Irish et al. Mapping normal and cancer cell signaling networks: towards single-cell proteomics, Nature, Vol. 6 146-155, 2006; and Irish et al., Single cell profiling of potentiated phospho-protein networks in cancer cells, Cell, Vol. 118, 1-20 Jul. 23, 2004; Schulz, K. R., et al., Single-cell phospho-protein analysis by flow cytometry, Curr Protoc Immunol, 2007, 78:8 8.17.1-20; Krutzik, P. O., et al., Coordinate analysis of murine immune cell surface markers and intracellular phosphoproteins by flow cytometry, J Immunol 2005 Aug. 15; 175(4):2357-65; Krutzik, P. O., et al., Characterization of the murine immunological signaling network with phosphospecific flow cytometry, J Immunol 2005 Aug. 15; 175(4):2366-73; Shulz et al., Current Protocols in Immunology 2007, 78:8.17.1-20; Stelzer et al. Use of Multiparameter Flow Cytometry and Immunophenotyping for the Diagnosis and Classification of Acute Myeloid Leukemia, Immunophenotyping, Wiley, 2000; and Krutzik, P. O. and Nolan, G. P., Intracellular phospho-protein staining techniques for flow cytometry: monitoring single cell signaling events, Cytometry A. 2003 October; 55(2):61-70; Hanahan D., Weinberg, The Hallmarks of Cancer, CELL, 2000 Jan. 7; 100(1) 57-70; Krutzik et al, High content single cell drug screening with phophospecific flow cytometry, Nat Chem Biol. 2008 February; 4(2):132-42. Experimental and process protocols and other helpful information can be found at http://proteomices.stanford.edu. The articles and other references cited below are also incorporated by reference in their entireties for all purposes.

One embodiment of the present invention involves the classification, diagnosis, prognosis of disease or outcome after administering a therapeutic to treat the disease; exemplary diseases include AML, MDS and MPN. Another embodiment of the invention involves monitoring and predicting outcome of disease. Another embodiment is drug screening using some of the methods of the invention, to determine which drugs may be useful in particular diseases. In other embodiments, the invention involves the identification of new druggable targets, that can be used alone or in combination with other treatments. The invention allows the selection of patients for specific target therapies. The invention allows for delineation of subpopulations of cells associated with a disease that are differentially susceptible to drugs or drug combinations. In another embodiment, the invention allows to demarcate subpopulations of cells associated with a disease that have different genetic subclone origins. In another embodiment, the invention provides for the identification of a cell type, that in combination other cell type(s), provide ratiometric or metrics that singly or coordinately allow for surrogate identification of subpopulations of cells associated with a disease, diagnosis, prognosis, disease stage of the individual from which the cells were derived, response to treatment, monitoring and predicting outcome of disease. Another embodiment involves the analysis of apoptosis, drug transport and/or drug metabolism. In performing these processes, one preferred analysis method involves looking at cell signals and/or expression markers. One embodiment of cell signal analysis involves the analysis of phosphorylated proteins and the use of flow cytometers in that analysis. In one embodiment, a signal transduction-based classification of AML, MDS, or MPN can be performed using clustering of phospho-protein patterns or biosignatures. See generally FIG. 1.

In some embodiments, the present invention provides methods for classification, diagnosis, prognosis of disease and outcome after administering a therapeutic to treat the disease by characterizing a plurality of pathways in a population of cells. In some embodiments, a treatment is chosen based on the characterization of plurality of pathways in single cells. In some embodiments, characterizing a plurality of pathways in single cells comprises determining whether apoptosis pathways, cell cycle pathways, signaling pathways, or DNA damage pathways are functional in an individual based on the activation levels of activatable elements within the pathways, where a pathway is functional if it is permissive for a response to a treatment. For example, when the apoptosis, cell cycle, signaling, and DNA damage pathways are functional the individual can respond to treatment, and when at least one of the pathways is not functional the individual can not respond to treatment. In some embodiments, if the apoptosis and DNA damage pathways are functional the individual can respond to treatment.

In some embodiments, the characterization of pathways in conditions such as AML, MDS and MPN shows disruptions in cellular pathways that are reflective of increased proliferation, increased survival, evasion of apoptosis, insensitivity to anti-growth signals and other mechanisms. In some embodiments, the disruption in these pathways can be revealed by exposing a cell to one or more modulators that mimic one or more environmental cue. FIG. 1 shows an example of how biology determines response to therapy. For example, without intending to be limited to any theory, a responsive cells treated with Ara-C will undergo cell death through activation of DNA damage and apoptosis pathways. However, a non-responsive cell might escape apoptosis through disruption in one or more pathways that allows the cell to survive. For instance, a non-responsive cell might have increased concentration of a drug transporter (e.g., MPR-1), which causes Ara-C to be removed from the cells. A non-responsive cell might also have disruptions in one or more pathways involve in proliferation, cell cycle progression and cell survival that allows the cell to survive. A non-responsive cell may have a DNA damage response pathway that fails to communicate with apoptosis pathways. A non-responsive cell might also have disruptions in one or more pathways involve in proliferation, cell cycle progression and cell survival that allows the cell to survive. The disruptions in these pathways can be revealed, for example, by exposing the cell to a growth factor such as FLT3L or G-CSF. In addition, the revealed disruptions in these pathways can allow for identification of target therapies that will be more effective in a particular patient and can allow the identification of new druggable targets, which therapies can be used alone or in combination with other treatments. Expression levels of proteins, such as drug transporters and receptors, may not be as informative by themselves for disease management as analysis of activatable elements, such as phosphorylated proteins. However, expression information may be useful in combination with the analysis of activatable elements, such as phosphorylated proteins.

The discussion below describes some of the preferred embodiments with respect to particular diseases. However, it should be appreciated that the principles may be useful for the analysis of many other diseases as well.

Introduction

Hematopoietic cells are blood-forming cells in the body. Hematopoiesis (development of blood cells) begins in the bone marrow and depending on the cell type, further maturation occurs either in the periphery or in secondary lymphoid organs such as the spleen or lymph nodes. Hematopoietic disorders are recognized as clonal diseases, which are initiated by somatic and/or inherited mutations that cause dysregulated signaling in a progenitor cell. The wide range of possible mutations and accompanying signaling defects accounts for the diversity of disease phenotypes observed within this group of disorders. Hematopoietic disorders fall into three major categories: Myelodysplastic syndromes, myeloproliferative disorders, and acute leukemias. Examples of hematopoietic disorders include non-B lineage derived, such as acute myeloid leukemia (AML), Chronic Myeloid Leukemia (CML), non-B cell acute lymphocytic leukemia (ALL), myelodysplastic disorders, myeloproliferative disorders, polycythemias, thrombocythemias, or non-B atypical immune lymphoproliferations. Examples of B-Cell or B cell lineage derived disorder include Chronic Lymphocytic Leukemia (CLL), B lymphocyte lineage leukemia, Multiple Myeloma, acute lymphoblastic leukemia (ALL), B-cell prolymphocytic leukemia, precursor B lymphoblastic leukemia, hairy cell leukemia or plasma cell disorders, e.g., amyloidosis or Waldenstrom's macroglobulinemia.

Acute myeloid leukemia (AML), myelodysplastic syndrome (MDS), and myeloproliferative neoplasms (MPN) are examples of distinct myeloid hematopoietic disorders. However, it is recognized that these disorders share clinical overlap in that 30% of patients with MDS and 5-10% of patients with MPN will go on to develop AML.

Cell-Signaling Pathways and Differentiating Factors Involved a. AML

Alterations of kinases and phosphatases lead to inappropriate signal transduction, whereas alterations of transcription factors give rise to inappropriate gene expression. Both of these mechanisms contribute to the pathogenesis of AML by the induction of increased proliferation, reduced apoptosis and block of differentiation. The dysregulation of one or more of the key signaling pathways (e.g., RAS/MAPK, PI3K/AKT, and JAK/STAT) is believed to result in growth factor-independent proliferation and clonal expansion of hematopoietic progenitors (HOX deregulation in acute myeloid leukemia. *Journal of Clinical Investigation.* 2007, vol. 117, no. 4, p. 865-868.) See generally Table 1 below which depicts pathways relevant for AML Biology. In some embodiments, the pathways depicted in Table 1 are characterized using the methods described herein by exposing cells to the modulators listed in the table and measuring the readout listed in the table, for each corresponding pathways. Disruption in one or more pathways can be revealed by exposing the cells to the modulators. This can then be used for classification, diagnosis, prognosis of AML, selection of treatment and/or predict outcome after administering a therapeutic.

TABLE 1

| Pathway | Readout | Modulator |
|---|---|---|
| DNA Damage | p-Chk1, p-Chk2, p-ATM, p-ATR, p-H2AX | Etoposide, Ara-C/Daunorubicin, Drug Pump Inhibitors, Mylotarg |
| Drug transporters | MDR-1, ABCG2, MPR | Drug Pump Inhibitors |

TABLE 1-continued

| Pathway | Readout | Modulator |
|---|---|---|
| Apoptosis | Bcl-2, Mcl-1, cytochrome c, survivin, XIAP PARP, Caspses 3, 7 and 8 | Staurosporine, Etoposide, Ara-C/Daunorubicin, Drug Pump Inhibitors, Mylotarg, Zvad, Caspase Inhibitors, |
| Phosphatases | Shp-1, Shp-2,, CD45 | $H_2O_2$ |
| JAK/STAT | p-Stat 1, 3, 4, 5, 6 | Cytokine and Growth Factors |
| Cell Cycle | Myc, Ki-67, Cyclins, DNA stains, p-RB, p16, p21, p27, p15, cyclin D1, cyclin B1, p-Cdk1, p-histoneH3, p-CDC25 | Cytokine and Growth Factors, Mitogens, Apoptosis inducing agents, |
| MAPK | Ras, p-Mek, p-Erk, p-S6, p-38 | Cytokine and Growth Factors, Mitogens, |
| PI3K-AKT | p-Akt, p-S6, p-PRAS40, p-GSK3, p-TSC2, p-p70S6K, 4-EBP1, p-FOXO proteins | Cytokines, Growth Factors, Mitogens, chemokines, Receptor Tyrosine Kinase (RTK) ligands |
| FLT3 and other RTKs | p-PLCg ½, p-CREB, total CREB, p-Akt, p-Erk, p-S6 | Flt3L, Receptor Tyrosine Kinase (RTK) ligands |
| Angiogenesis | PLCγ1, p-Akt, p-Erk | VEGF stim |
| Wnt/b-catenin | Active B-Catenin, Myc, Cyclin D | RTK ligands, growth factors |
| Survival | PI3K, PLCg, Stats | RKT Growth Factors |

There are two main classes of receptors which play an important role in hematopoiesis: Receptors with intrinsic tyrosine kinase activity (RTKs) and those that do not contain their own enzymatic activity and often consist of heterodimers of a ligand-binding alpha subunit and a signal transducing beta subunit, which is frequently shared between a subset of cytokine receptors. Cytoplasmic tyrosine kinases phosphorylate cytokine receptors thereby creating docking sites for signaling molecules resulting in activation of a specific intracellular signaling pathway. Of the first class, Kit and FLt3 receptor have been shown to play an important role in the pathogenesis of AML. Extracellular ligand binding regulates the intracellular substrate specificity, affinity and kinase activity of these proteins. Therefore, the receptor transmits its signal through binding and/or phosphorylation of intracellular signaling intermediates. Despite these differences, the signals transmitted by both classes of receptors ultimately converge on one or more of the key signaling pathways, such as the Ras/Raf/MAPK, PI3K/AKT, and JAK/STAT pathways.

The STAT (signal transducer and activator of transcription) family of proteins, especially STAT3 and STAT5, are emerging as important players in several cancers. (Yu 2004—STATs in cancer. (2008) pp. 9). Of particular relevance to AML, the STATs have been shown to be critical for myeloid differentiation and survival, as well as for long-term maintenance of normal and leukemic stem cells. (Schepers et al. STAT5 is required for long-term maintenance of normal and leukemic human stem/progenitor cells. Blood (2007) vol. 110 (8) pp. 2880-2888) STAT signaling is activated by several cytokine receptors, which are differentially expressed depending on the cell type and the stage of differentiation. Intrinsic or receptor-associated tyrosine kinases phosphorylate STAT proteins, causing them to form a homodimer The activated STAT dimer is able to enter the cell nucleus and activate the transcription of target genes, many of which are involved in the regulation of apoptosis and cell cycle progression. Apart from promoting proliferation and survival, some growth factor receptors and signaling intermediates have been shown to play specific and important roles in myeloid differentiation. For example, G-CSF- or TPO-induced activation of the Ras-Raf-MAP Kinase pathway promotes myeloid or megakaryocytic differentiation in the respective progenitor cells by the activation of c/EBPα (frequently inactivated in myeloid leukemias) and GATA-1, respectively. (B. STEFFEN et al. Critical Reviews in Oncology/Hematology. 2005, vol. 56, p. 195-221.)

Phosphatases: One of the earliest events that occurs after engagement of myeloid receptors is the phosphorylation of cellular proteins on serine, threonine, and tyrosine residues 8, 9, 10. The overall level of phosphorylated tyrosine residues is regulated by the competing activities of protein tyrosine kinases (PTKs) and protein tyrosine phosphatases (PTPs). Decreases in the activity of tyrosine phosphatases may also contribute to an increase in cellular tyrosine phosphorylation following stimulation.

SHP-1 (PTPN6) is a non-receptor protein tyrosine phosphatase that is expressed primarily in hematopoietic cells. The enzyme is composed of two SH2 domains, a tyrosine phosphatase catalytic domain and a carboxy-terminal regulatory domain (Yi, T. L. et al. (1992) Mol Cell Biol 12, 836-46). SHP-1 removes phosphates from target proteins to down regulate several tyrosine kinase regulated pathways. In hematopoietic cells, the N-terminal SH2 domain of SHP-1 binds to tyrosine phosphorylated erythropoietin receptors (EpoR) to negatively regulate hematopoietic growth (Yi, T. et al. (1995) Blood 85, 87-95). Following ligand binding in myeloid cells, SHP-1 associates with IL-3β chain and down regulates IL-3-induced tyrosine phosphorylation and cell proliferation (Yi, T. et al. (1993) Mol Cell Biol 13, 7577-86). Because SHP-1 downregulates signaling pathways emanating from receptor tyrosine kinases, cytokine receptors, multichain recognition receptors and integrins, it is considered a potential tumor suppressor (Wu, C. et al. (2003) Gene 306, 1-12, Bhattacharya, R. et al. (2008) J Mol Signal 3, 8).

SHP-2 (PTPN11) is a ubiquitously expressed, nonreceptor protein tyrosine phosphatase (PTP). It participates in signaling events downstream of receptors for growth factors, cytokines, hormones, antigens and extracellular matrices in the control of cell growth, differentiation, migration and death (Qu, C. K. (2000) Cell Res 10, 279-88). Activation of SHP-2 and its association with Gab1 is critical for sustained Erk activation downstream of several growth factor receptors and cytokines (Maroun, C. R. et al. (2000) Mol Cell Biol 20, 8513-25.).

In AML, when active SHP-1 and SHP-2 dephosphorylates protein kinase (See Koretzky G A et al. Nat Rev Immunol 2006 January; 6(1):67-78. Review). Treatment of cells with a general tyrosine phosphatase inhibitor such as $H_2O_2$ results in an increase in phosphorylation of intracellular signalling molecules. In this experiment, AML patients that were complete responders (CR) to one cycle of standard 7+3 induction therapy showed higher levels of phosphorylated PLCγ2 and SLP-76 upon $H_2O_2$ treatment when compared with non-responders (NR).

FLt3 ligand mutations: During normal hematopoietic development, the FLT3 receptor functions in the differentiation and proliferation of multipotent stem cells and their progeny in the myeloid, B cell, and T cell lineages. (Gilliland, G. D., and Griffin, J. D. The roles of FLT3 in hematopoesis and leukemia. Blood (2002) 100: 1532-42). FLT3 receptor expression is normally restricted to hematopoietic progenitors, and genetic ablation experiments have shown that FLT3 is required for the maturation of these early cells, but is not required in mature cells (Rosnet O., et al, Human FLT3/FLK2 receptor tyrosine kinase is expressed at the surface of normal and malignant hematopoietic cells. Leukemia (1996) 10; 238-48; Mackarehtschian K, et al. Targeted disruption of the flk2/flt3 gene leads to deficiencies in primitive hematopoietic progenitors. Immunity (1995) 3: 147-61).

Mutations in FLT3 are found in 25-45% of all AML patients (Renneville A., et al, Cooperating gene mutations in acute myeloid leukemia: a review of the literature. Leukemia (2008) 22: 915-31). Of the AML-associated FLT3 mutations, the most common is the internal tandem duplication (ITD), which is found in 25-35% of adult AML patients (Id). The ITD is an in-frame duplication of 3-400 nucleotides that encodes a lengthened FLT3 juxtamembrane domain (JMD) (Schnittger S., et al. FLT3 internal tandem duplication in 234 children with acute myeloid leukemia (AML): prognostic significance and relation to cellular drug resistance. Blood (2003) 102: 2387-94.). In vitro studies have shown that FLT3/ITDs promote ligand-independent receptor dimerization, leading to autonomous phosphorylation and constitutive activation of the receptor (Gilliand, G. D, and Griffin, J. D. Blood (2002) 100: 1532-42). Structural studies of FLT3 suggest that in the wild-type receptor, the JMD produces steric hindrance that prevents autodimerization (Griffith, J., et al. The Structural Basis for Autoinhibition of FLT3 by the Juxtamembrane Domain. Molecular Cell (2004) 13: 169-78). The ITD-associated lengthening of the JMD appears to remove this hindrance, resulting in autodimerization and constitutive FLT3 kinase activity. The second class of FLT3 mutation, found in 5-10% of AML patients, comprises missense point mutations in exon 20—commonly in codons D835, I836, N841, or Y842—which produce amino acid substitutions in the activation loop of the FLT3 tyrosine kinase domain (TKD) (Yamamoto Y., et al, Activating mutation of D835 within the activation loop of FLT3 in human hematologic malignancies. Blood (2001) 97: 2434-39). Investigators have also identified several AML-associated point mutations in the FLT3 JMD (Stirewalt D. L., et al. Novel FLT3 point mutations within exon 14 found in patients with acute myeloid leukemia. Br. J. Haematol (2004) 124: 481-84), and one in the N-terminal portion of the Tyrosine Kinase Domain (Schittenheim M. M., et al. FLT3 K663Q is a novel AML-associated oncogenic kinase: determination of biochemical properties and sensitivity to sunitnib. Leukemia (2006) 20: 2008-14.).

The AML-associated FLT3 mutations generally cause ligand-independent autophosphorylation of the FLT3 receptor and subsequent activation of downstream signaling pathways, such as PI3K, Ras, and JAK/STAT (Renneville, et al. (2008) 22: 915-31). However, the FLT3-ITD and TKD mutations are associated with significant biological differences (Renneville, et al. (2008) 22: 915-31). FLT3-ITD mutations constitutively induce STAT5 phosphorylation, while FLT3-TKD mutations only weakly induce STAT5 phosphorylation (Choudry, C. et al. AML-associated Flt3 kinase domain mutations show signal transduction differences compared with Flt3-ITD mutations. Blood (2005) 106: 265-73). Furthermore, FLT3-ITD, but not TKD mutations suppress expression of the transcription factors, c/EBPα and Pu.1, which function in myeloid differentiation. Additionally, neither class of FLT3 mutation is sufficient to induce AML, suggesting that additional mechanisms may be involved (Renneville, et al. (2008) 22: 915-31). Many investigational new drugs are targeted to FLT3 receptor kinase activity (Gilliland, G. D., and Griffin, J. D. Blood (2002) 100: 1532-42). However, the different cell signaling profiles of AML-associated mutations suggest that different AML patients will exhibit distinct responses to inhibition of FLT3 kinase activity. Pre-screening patient cell samples for a response to a FLT3 kinase inhibitor drug, for example by examining the effects of drug treatment on pSTAT5 levels, may predict whether a patient will respond to that drug.

Clinically, FLT3-TKD mutations correlate with shorter clinical response duration and worse overall survival than for patients carrying the FLT3-TKD or wild-type alleles (Meshinchi, S and Applebaum, F Clin. Can. Res. (2009) 13: 4263-4269; Frohling et al. Prognostic significance of activating FLT3 mutations in younger adults (16 to 60 years) with acute myeloid leukemia and normal cytogenetics: a study of the AML Study Group Ulm. Blood (2002) 100: 4372-80.). The presence of the FLT3-ITD mutation and the ratio of the FLT3-ITD mutation to other FLT3 alleles are predictive of clinical response duration, cumulative incidence of relapse, and patient overall survival (Renneville, et al. (2008) 22: 915-31).

In healthy myeloid lineages, G-CSF– promotes cell proliferation through activation of JAK/STAT signaling (Touw, I. P., and Marijke, B., Granulocyte colony-stimulating factor: key factor or innocent bystander in the development of secondary myeloid malignancy? (2007). J. Natl. Cancer. Inst. 99: 183-186). A class of AML-associated mutations produces truncated G-CSF receptor, and causes hyperreponsiveness to G-CSF stimulation (Gert-Jan, M. et al. G-CSF receptor truncations found in SCN/AML relieve SOCS3-controlled inhibition of STAT5 but leave suppression of STAT3 intact. Blood (2004) 104: 667-74.). Stimulation of AML patient blast cells with G-CSF in vitro revealed potentiated Stat3 and Stat5 phosphorylations that correlated with poor response to chemotherapy (Irish, J. M., et al. Single Cell Profiling of Potentiated Phospho-Protein Networks in Cancer Cells. Cell (2004) 118: 217-28.).

The process of angiogenesis may contribute to leukemic cell survival and a resultant resistance to chemotherapy-triggered cell death. Vascular endothelial growth factor (VEGF) is a major determinant of angiogenesis. A significant proportion of de novo and secondary AML blast populations produce and secrete VEGF protein. Moreover, blasts from some patients with newly diagnosed AML exhibit relative overexpresssion of VEGF Receptor R2 (Padro T, Bieker R, Ruiz S, et al. Overexpression of vascular endothelial growth factor (VEGF) and its cellular receptor KDR (VEGFR-2) in the bone marrow of patients with acute myeloid leukemia. Leukemia 2002; 16:1302). Furthermore, the incorporation of the anti-VEGF monoclonal antibody bevacizumab (Avastin) into an AML combination therapy reportedly improved tumor clearance rates. (Karp, J. E., et al. Targeting Vascular Endothelial Growth Factor for Relapsed and Refractory Adult Acute Myelogenous Leukemias. Clinical Cancer Res. (2004) 10: 3577-85).

In addition to Flt3, a variety of other genes are mutated in AML and can be divided into two classes based on whether they confer a favorable or non-favorable prognosis. Mutations in the chaperone protein-encoding gene NPM1 have been found in 30% of adults with de novo AML, but not in adults with secondary AML (Renneville, et al. (2008) 22: 915-31). Among patients with cytogenetically normal AML, NPM1 mutations are predictive of higher rates of response to induction therapy and longer overall survival, but only in the absence of FLT3-ITD mutations. Mutations in the basic region leucine zipper-encoding gene CEBPA are found in 15-19% of AML patients, and are predictive of longer overall survival and longer complete response duration (Baldus, C. D., et al. Clinical outcome of de novo acute myeloid leukemia patients with normal cytogenetics is affected by molecular genetic alterations: a concise review. *British J. Haematology* (2007) 137: 387-400).

Mutated genes that confer a non-favorable prognosis include ERG which encodes a transcription factor activated by signal transduction pathways that regulates cell differentiation, proliferation, and tissue invasion (Baldus, C. D., et al. *British J. Haematology* (2007) 137: 387-400.). Overexpression of ERG in AML patients is predictive of a higher rate of relapse and shorter overall survival (Marcucci et al, Overexpression of the ETS-related gene, ERG, predicts a worse outcome in acute myeloid leukemia with normal karyotype: a Cancer and Leukemia Group B study. *J. Clinical Oncology* (2005) 23: 9234-42). High expression of BAALC in younger AML patients (under 60 years old) is associated with lower rates of disease-free survival and overall survival (Baldus et al, BAALC expression predicts clinical outcome of de novo acute myeloid leukemia patients with normal cytogenetics: a Cancer and Leukemia Group B study. Blood (2003) 102: 1613-18). Overexpression of MN1 in AML patients is associated with a lower rate of response to induction therapy (Baldus, C. D., et al. *British J. Haematology* (2007) 137: 387-400.). Gain-of-function mutations in the receptor tyrosine kinase-encoding gene c-KIT are predictive of shorter overall complete response duration and overall survival in AML patients, and may also be predictive of response to treatment with tyrosine kinase inhibitors (Renneville, et al. (2008) 22: 915-31). Mutations in the Wilm's Tumor 1 (WT1) gene are found in 10-15% of AML cases, and in cytogenetically normal AML patients, are predictive of failure to achieve complete response to chemotherapy (Renneville, et al. (2008) 22: 915-31). Point mutations in the RAS oncogenes are found in 10-20% of AML patients, but prognostic uses of these mutations have not yet been identified (Renneville, et al. (2008) 22: 915-31).

RAS mutations: Ras proteins normally act as signaling switches, which alternate between the active (GTP-bound) and inactive (GDP-bound) states. Somatic point mutations in codons 12, 13 and 61 of the NRAS and KRAS genes occur in many myeloid malignancies, resulting in persistently active forms of the protein. Analyses of patients with MDS revealed a very high risk of transformation to AML in patients with N-RAS mutations, providing evidence that these mutations might represent an important progression factor in MDS. Under the two-hit model put forth by Gilliland et al., RAS mutations are likely to provide a growth advantage, which when combined with a secondary mutation that blocks differentiation, results in AML. Supporting this model, N-RAS or K-RAS mutations were found in 22% of cases of core binding factor AML (CBF-AML), which is defined by AML1-ETO or CBFβ-MYH11 gene fusions known to disrupt differentiation. (Boissel et al. Incidence and prognostic impact of c-Kit, FLT3 LIGAND, and Ras gene mutations in core binding factor acute myeloid leukemia (CBF-AML). Leukemia (2006) vol. 20 (6) pp. 965-970)

One embodiment of the invention will look at any of the cell signaling pathways described above in classifying diseases, such as AML. Modulators can be designed to investigate these pathways and any relevant parallel pathways.

In some embodiments, the invention provides a method for diagnosis, prognosis, determining progression, predicting response to treatment or choosing a treatment for AML, the method comprising the steps of (a) subjecting a cell population from the individual to a plurality of distinct modulators in separate cultures, (b) characterizing a plurality of pathways in one or more cells from the separate cultures comprising determining an activation level of at least one activatable element in at least three pathways, where the pathways are selected from the group consisting of apoptosis, cell cycle, signaling, or DNA damage pathways, and (c) correlating the characterization with diagnosis, prognosis, determining progression, predicting response to treatment or choosing a treatment for AML, in an individual, where the pathways characterization is indicative of the diagnosis, prognosis, determining progression, response to treatment or the appropriate treatment for AML. In some embodiments the activatable elements and modulators are selected from the activatable elements and modulators listed in Tables 1, 2, 3 or 5. In some embodiments, the activatable elements and modulators are selected from the activatable elements and modulators listed in Table 12 and are used to predict response duration in an individual after treatment. In some embodiments the modulator is selected from the group consisting of FLT3L, GM-CSF, SCF, G-CSF, SDF1a, LPS, PMA, Thapsigargin, IFNg, IFNa, IL-27, IL-3, IL-6, IL-10, ZVAD, $H_2O_2$, Staurosporine, Etoposide, Mylotarg, Daunorubicin, and AraC. In some embodiments, the individual has a predefined clinical parameter and the characterization of multiple pathways in combination with the clinical parameter is indicative of the diagnosis, prognosis, determining progression, predicting response to treatment or choosing a treatment for AML, in an individual. Examples of predetermined clinical parameters include, but are not limited to, age, de novo acute myeloid leukemia patient, secondary acute myeloid leukemia patient, or a biochemical/molecular marker. In some embodiments, the individual is over 60 years old. In some embodiments, the individual is under 60 years old. In some embodiments, when the individual is under 60 years old the activatable elements and modulators are selected from the activatable elements and modulators listed in Table 6. In some embodiments, where the individual is over 60 years the activatable elements and modulators are selected from the activatable elements and modulators listed in Table 7. In some embodiments, where the individual is a secondary acute myeloid leukemia patient the activatable elements and modulators are selected from the activatable elements and modulators listed in Table 8 and Table 9. In some embodiments, where the individual is a de novo acute myeloid leukemia patient the activatable elements and modulators are selected from the activatable elements and modulators listed in Table 10 and Table 11. In some embodiments, where the individual has a wild type FLT3 the activatable elements and modulators are selected from the activatable elements and modulators listed in Table 13.

In some embodiments, the activatable elements can demarcate AML cell subpopulations that have different genetic subclone origins. In some embodiments, the activatable elements can demarcate AML subpopulations that, in combination with additional surface molecules, can allow for surrogate identification of AML cell subpopulations. In some embodiments, the activatable elements can demarcate AML subpopulations that can be used to determine other protein, epitope-based, RNA, mRNA, siRNA, or metabolic markers that singly or coordinately allow for surrogate identification of AML cell subpopulations, disease stage of the individual from which the cells were derived, diagnosis, prognosis, response to treatment, or new druggable targets. In some embodiments, the pathways characterization allows for the delineation of AML cell subpopulations that are differentially susceptible to drugs or drug combinations. In other embodiments, the cell types or activatable elements from a given cell type will, in combination with activatable elements in other cell types, provide ratiometric or metrics that singly or coordinately allow for surrogate identification of AML cell subpopulations, disease stage of the individual from which the cells were derived, diagnosis, prognosis, response to treatment, or new druggable targets.

b. MDS

Regulation of hematopoiesis in MDS is complex and multiple factors are involved. Genetic alterations in signaling molecules have been extensively studied in MDS. These molecules include transcription factors, receptors for growth factors, RAS⁻ signaling molecules, and cell cycle regulators.

In the early stages of MDS, there is an increased frequency of apoptosis resulting in intramedullary apoptotic bodies. Advanced MDS, which may transform to AML, is characterized by increased proliferation and antiapoptotic factors, such as mutations in p53, RAS, C-MPL or FMS. (Aul et al. Evaluating the prognosis of patients with myelodysplastic syndromes. Ann Hematol (2002) vol. 81 (9) pp. 485-97)

Genetic alterations in the RAS signaling pathway are frequently seen in MDS. The RAS signaling pathway normally promotes cellular proliferation and differentiation. By contrast, pathogenic RAS pathway mutations generally cause continuous kinase activity and signal transduction. The cell surface receptor for macrophage colony stimulating factor (M-CSF), encoded by the FMS gene, normally promotes cellular proliferation and differentiation of monocyte and macrophages, and is upstream of RAS signaling. Activating mutations in this gene are found in 10% of MDS cases, and are associated with poor survival and increased risk of transformation to AML. (PADUA R A, et al. RAS, FMS and p53 mutations and poor clinical outcome in myelodysplasias: a 10-year follow-up. *Leukemia,* 1998, vol. 12, p. 887-892; TOBAL K, et al. Mutation of the human FMS gene (M-CSF receptor) in myelodysplastic syndromes and acute myeloid leukemia. *Leukemia,* 1990, vol. 4, p. 486-489.)

Activating mutations in FLT3, a receptor-type tyrosine kinase also upstream of RAS signaling, have been reported in 3-5% of MDS cases. (Georgiou et al. Serial determination of FLT3 mutations in myelodysplastic syndrome patients at diagnosis, follow up or acute myeloid leukemia transformation: incidence and their prognostic significance. Br J Haematol (2006) vol. 134 (3) pp. 302-6) Inactivation of the neurofibromatosis type 1 (NF1) gene, normally a negative regulator of RAS signaling, has also been implicated in the progression of MDS. (Stephenson J, et al. Possible co-existence of RAS activation and monosomy 7 in the leukemic transformation of myelodysplastic syndromes. *Leukemia Res* 1995; 19:741-8). Gain-of-function mutations have also been reported in PTPN11 in patients with MDS. (NEUBAUER A, et al. Mutations in the ras proto-oncogenes in patients with myelodysplastic syndromes. *Leukemia.* 1994, vol. 8, p. 638-641). Among the RAS genes themselves, mutations of the N-ras gene are the most frequent and are detected in 20 to 30 percent of human leukemias and approximately 16 percent of MDS cases. K-RAS mutations are found at approximately half that frequency. The majority of studies suggest that RAS mutations in MDS are associated with poor survival and increased probability of developing AML. (YUNIS J J, et al. Mechanisms of ras mutation in myelodysplastic syndrome. *Oncogene.* 1989, vol. 4, p. 609-614; Aul et al. Evaluating the prognosis of patients with myelodysplastic syndromes. Ann Hematol (2002) vol. 81 (9) pp. 485-97).

Although less frequently, AML1, C/EBPα, TEL (ETV6) and p53 genes are also a target of mutations in MDS. AML1-binding sites exist upstream of several genes encoding factors and receptors that determine the lineage specificity of hematopoietic cells. (OKUDA T, et al. AML1, the target of multiple chromosomal translocations in human leukemia, is essential for normal fetal liver hematopoiesis. *Cell.* 1996, vol. 84, p. 321-30.) C/EBPα is an important mediator of granulocyte differentiation and regulates the expression of multiple granulocyte-specific genes including the granulocyte colony-stimulating factor (G-CSF) receptor, neutrophil elastase and myeloperoxidase. C/EBPα knockout mice display a profound block in granulocyte differentiation (COLLINS S J, et al. Multipotent hematopoietic cell lines derived from C/EBPα (−/−) knockout mice display granulocyte macrophage-colony-stimulating factor, granulocyte-colony-stimulating factor and retinoic acid-induced granulocytic differentiation. *Blood.* 2001, vol. 98, p. 2382-8). This suggests that any mutation in C/EBPα will result in defective hematopoiesis. TEL function is essential for the establishment of hematopoiesis of all lineages in the bone marrow, suggesting a critical role for TEL in the normal transition of the hematopoietic activity from fetal liver to bone marrow. Experiments conducted on the role of TEL genes indicate an ineffective hematopoiesis in the case of an alteration in these genes. (WANG L C, et al. The TEL/ETV6 gene is required specifically for hematopoiesis in the bone marrow. *Genes and Development.* 1998, vol. 12, p. 2392-402). Mutations or deletions causing inactivation of the p53 gene in both the alleles have been shown to predispose the cells to neoplastic transformation. Inactivation is detected in 5 to 10 percent of cases of clinically advanced MDS, indicating that p53 mutations may play a role in leukemic progression of MDS. (SUGIMOTO K, et al. Mutations of the p53 gene in MDS and MDS-derived leukemia. *Blood.* 1993, vol. 81, p. 3022-6.)

Apoptotic genes (increased bcl-2 expression) (KUROTAKI H, et al. Apoptosis, bcl-2 expression and p53 accumulation in MDS, MDS derived acute myeloid leukemia and de novo acute myeloid leukemia. *Acta Haematologica,* 2000, vol. 102, p. 115-123.) And mutations in genes including CHK2, p53, MLL have been implicated in the pathogenesis of MDS (HOFMANN W K, et al. Mutation analysis of the DNA-damage checkpoint gene CHK2 in myelodysplastic syndromes and acute myeloid leukemias. *Leukemia Research,* 2001, vol. 25, p. 333-338; KIKUKAWA M, et al. Study of p53 in elderly patients with myelodysplastic syndromes by immunohistochemistry and DNA analysis. *American Journal of Pathology.* 1999, vol. 155, p. 717-721; POPPE B, et al. Expression analyses identify MEL as a prominent target of 11q23 amplification and support an etiologic role for MLL gain of function in myeloid malignancies. *Blood.* 2004, vol. 103, p. 229-235.)

Dysregulation of genes that encode angiogenic factors involved in the growth of hematopoietic cells may play important role in pathogenesis of MDS. (PRUNERI G, et al. Angiogenesis in myelodysplastic syndromes. *British Journal of Cancer,* 1999, vol. 81, p. 1398-1401.) The immunomodulatory cytokine, TNF-α has been shown to express strong inhibitory activity in hematopoiesis. (BROXMEYER H E, et al. The suppressive influences of human tumor necrosis factors on bone marrow hematopoietic progenitor cells from normal donors and patients with leukemia: synergism of tumor necrosis factor and interferon-gamma. *Journal of Immunology.* 1986, vol. 36, p. 4487-4495.) Other cytokines reportedly involved in the processes leading to ineffective hematopoiesis in MDSs include TGF-β, and TNF-related signaling molecules TRADD/FADD, RIP, and TNF-related apoptosis inducing ligand (TRAIL) (SAWANOBORI M, et al. Expression of TNF receptors and related signaling molecules in the bone marrow from patients with myelodysplastic syndromes. *Leukemia Research,* 2003, vol. 27, p. 583-591; PLASILOVA M, et al. TRAIL (Apo2L) suppresses growth of primary human leukemia and myelodysplasia progenitors. *Leukemia,* 2002, vol. 16, p. 67-73.)

One embodiment of the invention will look at any of the cell signaling pathways described above in classifying diseases, such as MDS. Modulators can be designed to investigate these pathways and any relevant parallel pathways.

In some embodiments, the invention provides a method for diagnosing, prognosing, determining progression, predicting response to treatment or choosing a treatment for MDS or rationale combinations of drugs, or identification of new potentially druggable targets the method, the method comprising the steps of (a) subjecting a cell population from the individual to a plurality of distinct modulators in separate cultures, (b) characterizing a plurality of pathways in one or more cells from the separate cultures comprising determining an activation level of at least one activatable element in at least three pathways, where the pathways are selected from the group consisting of apoptosis, cell cycle, signaling, or DNA damage pathways, and (c) correlating the characterization with diagnosing, prognosing, determining progression, predicting response to treatment or choosing a treatment for MDS, in an individual, where the pathways characterization is indicative of the diagnosing, prognosing, determining progression, response to treatment or the appropriate treatment for MDS. In some embodiments, the individual has a predefined clinical parameter and the characterization of multiple pathways in combination with the clinical parameter is indicative of the diagnosis, prognosis, determining progression, predicting response to treatment or choosing a treatment for MDS, in an individual. Examples of predetermined clinical parameters include, but are not limited to, biochemical/molecular markers. In some embodiments, the activatable elements can demarcate MDS cell subpopulations that have different genetic subclone origins. In some embodiments, the activatable elements can demarcate MDS subpopulations that, in combination with additional surface molecules, can allow for surrogate identification of MDS cell subpopulations. In some embodiments, the activatable elements can demarcate MDS subpopulations that can be used to determine other protein, epitope-based, RNA, mRNA, siRNA, or metabolic markers that singly or coordinately allow for surrogate identification of MDS cell subpopulations, disease stage of the individual from which the cells were derived, diagnosis, prognosis, response to treatment, or new druggable targets. In some embodiments, the pathways characterization allows for the delineation of MDS cell subpopulations that are differentially susceptible to drugs or drug combinations. In other embodiments, the cell types or activatable elements from a given cell type will, in combination with activatable elements in other cell types, provide ratiometric or metrics that singly or coordinately allow for surrogate identification of MDS cell subpopulations, disease stage of the individual from which the cells were derived, diagnosis, prognosis, response to treatment, or new druggable targets.

c. MPN

Dysregulation of the JAK-STAT signaling pathway has been implicated in the development and progression of MPN. Alterations in gene expression occur due to the activation of the JAK/STAT pathway by exogenous stimuli (sepsis or G-CSF treatment), or endogenously through activating mutations (e.g. JAK2-V617F. (ROBERT KRALOVICS, et. al. Altered gene expression in myeloproliferative neoplasms correlates with the activation of signaling by the V617F mutation of JAK2. *Blood.* November 2005, vol. 106, no. 10, p. 3374-3376.) Several distinct MPN, polycythemia vera, essential thrombocythemia, and myelofibrosis are found to have JAK2-V617F mutation, supporting the concept that hyperactivation of JAK-STAT signaling is involved in the development of MPN. JAK2 mutations are present in virtually all cases of polycythemia vera, 41 to 72 percent in essential thrombocythemia, and 39 to 57 percent in primary myelofibrosis. (BAXTER E J, et al. Acquired mutation of the tyrosine kinase JAK2 in human myeloproliferative neoplasms. *Lancet.* 2005, vol. 365, no. 9464, p. 1054-1061.) Studies have found 15 gene-expression markers which were elevated in patients with PV, including polycythemiarubra vera 1 (PRV1) and nuclear factor erythroid-derived 2 (NF-E2), as well as one marker, ANKRD15, which was downregulated. (ROBERT KRALOVICS, et. al. Altered gene expression in myeloproliferative neoplasms correlates with the activation of signaling by the V617F mutation of Jak2. *Blood.* November 2005, vol. 106, no. 10, p. 3374-3376.)

JAK3 important lymphoid development/myeloid differentiation. Loss of function of JAK3 leads to an autosomal recessive form of severe combined immunodeficiency. Gain of function mutations in JAK3 have been shown to lead to acute megakaryocytic leukemia. Leukemia and Lymphoma March 2008 49 (3):388-397

Phosphatases have been implicated in MPN biology. These include SHP-1(Src homology 2 domain containing tyrosine Phosphatase 1), SHP-2 (Src homology 2 domain containing tyrosine phosphatase 2), TC-PTP (T-cell PTP), RPTPα (Receptor protein tyrosine phosphatase a), DEP (Density enhanced phosphatase), PTP-MEG1(Protein tyrosine phosphatase MEG1), PTP-MEG2 (Protein tyrosine phosphatase MEG2). PTP-MEG2 is thought to be deregulated in Normally PTP-MEG2 decreases as cells differentiate, however PTP-MEG2 displays increased activity in PV.

One embodiment of the invention will look cell signaling pathways described above in classifying and diagnosing MPN and identification of new potentially druggable targets. Modulators can be designed to investigate these pathways and any relevant parallel pathways.

In some embodiments, the invention provides a method for diagnosing, prognosing, determining progression, predicting response to treatment or choosing a treatment for MPN or rationale combination of different drugs, the method comprising the steps of (a) subjecting a cell population from the individual to a plurality of distinct modulators in separate cultures, (b) characterizing a plurality of pathways in one or more cells from the separate cultures comprising determining an activation level of at least one activatable element in at least three pathways, where the pathways are selected from the group consisting of apoptosis, cell cycle, signaling, or DNA damage pathways, and (c) correlating the characterization with diagnosing, prognosing, determining progression, predicting response to treatment or choosing a treatment for MPN, in an individual, where the pathways characterization is indicative of the diagnosing, prognosing, determining progression, response to treatment or the appropriate treatment for MPN. In some embodiments, the individual has a predefined clinical parameter and the characterization of multiple pathways in combination with the clinical parameter is indicative of the diagnoses, prognoses, determining progression, predicting response to treatment or choosing a treatment for MPN, in an individual. Examples of predetermined clinical parameters include, but are not limited to, biochemical/molecular marker.

General Methods

Embodiments of the invention may be used to diagnose, predict or to provide therapeutic decisions for disease treatment, such as MDS, AML, or MPN. In some embodiments, the invention may be used to identify new druggable targets and to design drug combinations. The following will discuss instruments, reagents, kits, and the biology involved with these and other diseases. One aspect of the invention involves contacting a hematopoietic cell with a modulator; determining the activation states of a plurality of activatable elements in the cell; and classifying the cell based on said activation state.

In some embodiments, this invention is directed to methods and compositions, and kits for analysis, drug screening, diagnosis, prognosis, for methods of disease treatment and prediction. In some embodiments, the present invention involves methods of analyzing experimental data. In some embodiments, the physiological status of cells present in a sample (e.g. clinical sample) is used, e.g., in diagnosis or prognosis of a condition, patient selection for therapy using some of the agents identified above, to monitor treatment, modify therapeutic regimens, and to further optimize the selection of therapeutic agents which may be administered as one or a combination of agents. Hence, therapeutic regimens can be individualized and tailored according to the data obtained prior to, and at different times over the course of treatment, thereby providing a regimen that is individually appropriate. In some embodiments, a compound is contacted with cells to analyze the response to the compound.

In some embodiments, the present invention is directed to methods for classifying a sample derived from an individual having or suspected of having a condition, e.g., a neoplastic or a hematopoietic condition. The invention allows for identification of prognostically and therapeutically relevant subgroups of conditions and prediction of the clinical course of an individual. The methods of the invention provide tools useful in the treatment of an individual afflicted with a condition, including but not limited to methods for assigning a risk group, methods of predicting an increased risk of relapse, methods of predicting an increased risk of developing secondary complications, methods of choosing a therapy for an individual, methods of predicting duration of response, response to a therapy for an individual, methods of determining the efficacy of a therapy in an individual, and methods of determining the prognosis for an individual. The present invention provides methods that can serve as a prognostic indicator to predict the course of a condition, e.g. whether the course of a neoplastic or a hematopoietic condition in an individual will be aggressive or indolent, thereby aiding the clinician in managing the patient and evaluating the modality of treatment to be used. In another embodiment, the present invention provides information to a physician to aid in the clinical management of a patient so that the information may be translated into action, including treatment, prognosis or prediction.

In some embodiments, the invention is directed to methods of characterizing a plurality of pathways in single cells. Exemplary pathways include apoptosis, cell cycle, signaling, or DNA damage pathways. In some embodiments, the characterization of the pathways is correlated with diagnosing, prognosing or determining condition progression in an individual. In some embodiments, the characterization of the pathways is correlated with predicting response to treatment or choosing a treatment in an individual. In some embodiments, the characterization of the pathways is correlated with finding a new druggable target. In some embodiments, the pathways' characterization in combination with a predetermined clinical parameter is indicative of the diagnosis, prognosis or progression of the condition. In some embodiments, the pathways' characterization in combination with a predetermined clinical parameter is indicative of a response to treatment or of the appropriate treatment for an individual. In some embodiments, the characterization of the pathways in combination with a predetermined clinical parameter is indicative a new druggable target.

In some embodiments, the invention is directed to methods for determining the activation level of one or more activatable elements in a cell upon treatment with one or more modulators. The activation of an activatable element in the cell upon treatment with one or more modulators can reveal operative pathways in a condition that can then be used, e.g., as an indicator to predict course of the condition, to identify risk group, to predict an increased risk of developing secondary complications, to choose a therapy for an individual, to predict response to a therapy for an individual, to determine the efficacy of a therapy in an individual, and to determine the prognosis for an individual. In some embodiments, the operative pathways can reveal whether apoptosis, cell cycle, signaling, or DNA damage pathways are functional in an individual, where a pathway is functional if it is permissive for a response to a treatment. In some embodiments, when apoptosis, cell cycle, signaling, and DNA damage pathways are functional the individual can respond to treatment, and if at least one of the pathways is not functional the individual can not respond to treatment. In some embodiments, when the apoptosis and DNA damage pathways are functional the individual can respond to treatment. In some embodiments, the operative pathways can reveal new druggable targets.

In some embodiments, the invention is directed to methods of determining a phenotypic profile of a population of cells by exposing the population of cells to a plurality of modulators in separate cultures, determining the presence or absence of an increase in activation level of an activatable element in the cell population from each of the separate culture and classifying the cell population based on the presence or absence of the increase in the activation of the activatable element from each of the separate culture. In some embodiments at least one of the modulators is an inhibitor. In some embodiments, the presence or absence of an increase in activation level of a plurality of activatable elements is determined. In some embodiments, each of the activatable elements belongs to a particular pathway and the activation level of the activatable elements is used to characterize each of the particular pathways. In some embodiments, a plurality of pathways are characterized by exposing a population of cells to a plurality of modulators in separate cultures, determining the presence or absence of an increase in activation levels of a plurality of activatable elements in the cell population from each of the separate culture, wherein the activatable elements are within the pathways being characterized and classifying the cell population based on the characterizations of said multiple pathways. In some embodiments, the activatable elements and modulators are selected from the activatable elements and modulators listed in Tables 1, 2, 3 or 5. In some embodiments, the activatable elements and modulators are selected from the activatable elements and modulators listed in Table 12 and are used to predict response duration in an individual after treatment.

In some embodiments, the invention is directed to methods for classifying a cell by determining the presence or absence of an increase in activation level of an activatable element in the, in combination with additional expression markers. In some embodiments, expression markers or drug transporters, such as CD34, CD33, CD45, HLADR, CD11B FLT3 Ligand, c-KIT, ABCG2, MDR1, BCRP, MRP1, LRP, and others noted below, can also be used for stratifying responders and non-responders. The expression markers may be detected using many different techniques, for example using nodes from flow cytometry data (see the articles and patent applications referred to above). Other common techniques employ expression arrays (commercially available from Affymetrix, Santa Clara Calif.), taqman (commercially available from ABI, Foster City Calif.), SAGE (commercially available from Genzyme, Cambridge Mass.), sequencing techniques (see the commercial products from Helicos, 454, US Genomics, and ABI) and other commonly know assays. See Golub et al., Science 286: 531-537 (1999). Expression markers are measured in unstimulated cells to know whether they have an impact on functional apoptosis. This provides implications for treatment and prognosis for the disease. Under this hypothesis, the amount of drug transporters correlates with the response of the patient and non-responders may have more levels of drug transporters (to move a drug out of a cell) as compared to responders. In some embodiments, the invention is directed to methods of classifying a cell population by contacting the cell population with at least one modulator that affects signaling mediated by receptors selected from the group comprising of growth factors, mitogens and cytokines. In some embodiments, the invention is directed to methods of classifying a cell population by contacting the cell population with at least one modulator that affects signaling mediated by receptors selected from the group comprising SDF-1α, IFN-α, IFN-γ, IL-10, IL-6, IL-27, G-CSF, FLT-3L, IGF-1, M-CSF, SCF, PMA, and Thapsigargin; determining the activation states of a plurality of activatable elements in the cell comprising; and classifying the cell based on said activation states and expression levels. In some embodiments, the cell population is also exposed in a separate culture to at least one modulator that slows or stops the growth of cells and/or induces apoptosis of cells. In some embodiments, the modulator that slows or stops the growth of cells and/or induces apoptosis of cells is selected from the group consisting of, Etoposide, Mylotarg, AraC, daunorubicin, staurosporine, benzyloxycarbonyl-Val-Ala-Asp (OMe) fluoromethylketone (ZVAD), lenalidomide, EPO, and azacitadine, decitabine. In some embodiments, the cell population is also exposed in a separate culture to at least one modulator that is an inhibitor. In some embodiments the inhibitor is $H_2O_2$. In some embodiments, the expression of a growth factor receptor, cytokine receptor and/or a drug transporter is also measured. In some embodiments, the methods comprise determining the expression level at least one protein selected from the group comprising ABCG2, C-KIT receptor, and FLT3 LIGAND receptor. Another embodiment of the invention further includes using the modulators IL-3, IL-4, GM-CSF, EPO, LPS, TNF-α, and CD40L. In some embodiments, the cell population in a hematopoietic cell population. In some embodiments, the invention is directed to methods of correlating and/or classifying an activation state of an AML, MDS or MPN cell with a clinical outcome in an individual by subjecting the AML, MDS or MPN cell from the individual to a modulator, determining the activation levels of a plurality of activatable elements, and identifying a pattern of the activation levels of the plurality of activatable elements to determine the presence or absence of an alteration in signaling, where the presence of the alteration is indicative of a clinical outcome. In some embodiments, the activatable elements can demarcate AML, MDS or MPN cell subpopulations that have different genetic subclone origins. In some embodiments, the activatable elements can demarcate AML, MDS or MPN subpopulations that can be used to determine other protein, epitope-based, RNA, mRNA, siRNA, or metabolomic markers that singly or coordinately allow for surrogate identification of AML, MDS or MPN cell subpopulations, disease stage of the individual from which the cells were derived, diagnosis, prognosis, response to treatment, or new druggable targets. In some embodiments, the pathways characterization allows for the delineation of AML, MDS or MPN cell subpopulations that are differentially susceptible to drugs or drug combinations. In other embodiments, the cell types or activatable elements from a given cell type will, in combination with activatable elements in other cell types, provide ratiometric or metrics that singly or coordinately allow for surrogate identification of AML, MDS or MPN cell subpopulations, disease stage of the individual from which the cells were derived, diagnosis, prognosis, response to treatment, or new druggable targets.

The subject invention also provides kits for use in determining the physiological status of cells in a sample, the kit comprising one or more modulators, inhibitors, specific binding elements for signaling molecules, and may additionally comprise one or more therapeutic agents. The above reagents for the kit are all recited and listed in the present application below. The kit may further comprise a software package for data analysis of the cellular state and its physiological status, which may include reference profiles for comparison with the test profile and comparisons to other analyses as referred to above. The kit may also include instructions for use for any of the above applications.

In some embodiments, the invention provides methods, including methods to determine the physiological status of a cell, e.g., by determining the activation level of an activatable element upon contact with one or more modulators. In some embodiments, the invention provides methods, including methods to classify a cell according to the status of an activatable element in a cellular pathway. In some embodiments, the cells are classified by analyzing the response to particular modulators and by comparison of different cell states, with or without modulators. The information can be used in prognosis and diagnosis, including susceptibility to disease(s), status of a diseased state and response to changes, in the environment, such as the passage of time, treatment with drugs or other modalities. The physiological status of the cells provided in a sample (e.g. clinical sample) may be classified according to the activation of cellular pathways of interest. The cells can also be classified as to their ability to respond to therapeutic agents and treatments. The physiological status of the cells can provide new druggable targets for the development of treatments. These treatments can be used alone or in combination with other treatments. The physiological status of the cells can be used to design combination treatments.

One or more cells or cell types, or samples containing one or more cells or cell types, can be isolated from body samples. The cells can be separated from body samples by centrifugation, elutriation, density gradient separation, apheresis, affinity selection, panning, FACS, centrifugation with Hypaque, solid supports (magnetic beads, beads in columns, or other surfaces) with attached antibodies, etc. By using antibodies specific for markers identified with particular cell types, a relatively homogeneous population of cells may be obtained. Alternatively, a heterogeneous cell population can be used. Cells can also be separated by using filters. For example, whole blood can also be applied to filters that are engineered to contain pore sizes that select for the desired cell type or class. Rare pathogenic cells can be filtered out of diluted, whole blood following the lysis of red blood cells by using filters with pore sizes between 5 to 10 μm, as disclosed in U.S. patent application Ser. No. 09/790,673. Once a sample is obtained, it can be used directly, frozen, or maintained in appropriate culture medium for short periods of time. Methods to isolate one or more cells for use according to the methods of this invention are performed according to standard techniques and protocols well-established in the art. See also U.S. Ser. Nos. 61/048,886; 61/048,920; and 61/048,657. See also, the commercial products from companies such as BD and BCI as identified above.

See also U.S. Pat. Nos. 7,381,535 and 7,393,656. All of the above patents and applications are incorporated by reference as stated above.

In some embodiments, the cells are cultured post collection in a media suitable for revealing the activation level of an activatable element (e.g. RPMI, DMEM) in the presence, or absence, of serum such as fetal bovine serum, bovine serum, human serum, porcine serum, horse serum, or goat serum. When serum is present in the media it could be present at a level ranging from 0.0001% to 30%.

In some embodiments, the cells are hematopoietic cells. Examples of hematopoietic cells include but are not limited to pluripotent hematopoietic stem cells, B-lymphocyte lineage progenitor or derived cells, T-lymphocyte lineage progenitor or derived cells, NK cell lineage progenitor or derived cells, granulocyte lineage progenitor or derived cells, monocyte lineage progenitor or derived cells, megakaryocyte lineage progenitor or derived cells and erythroid lineage progenitor or derived cells.

The term "patient" or "individual" as used herein includes humans as well as other mammals. The methods generally involve determining the status of an activatable element. The methods also involve determining the status of a plurality of activatable elements.

In some embodiments, the invention provides a method of classifying a cell by determining the presence or absence of an increase in activation level of an activatable element in the cell upon treatment with one or more modulators, and classifying the cell based on the presence or absence of the increase in the activation of the activatable element. In some embodiments of the invention, the activation level of the activatable element is determined by contacting the cell with a binding element that is specific for an activation state of the activatable element. In some embodiments, a cell is classified according to the activation level of a plurality of activatable elements after the cell have been subjected to a modulator. In some embodiments of the invention, the activation levels of a plurality of activatable elements are determined by contacting a cell with a plurality of binding elements, where each binding element is specific for an activation state of an activatable element.

The classification of a cell according to the status of an activatable element can comprise classifying the cell as a cell that is correlated with a clinical outcome. In some embodiments, the clinical outcome is the prognosis and/or diagnosis of a condition. In some embodiments, the clinical outcome is the presence or absence of a neoplastic or a hematopoietic condition such as acute myeloid leukemia (AML), myelodysplastic syndrome (MDS) or myeloproliferative neoplasms (MPN). In some embodiments, the clinical outcome is the staging or grading of a neoplastic or hematopoietic condition. Examples of staging include, but are not limited to, aggressive, indolent, benign, refractory, Roman Numeral staging, TNM Staging, Rai staging, Binet staging, WHO classification, FAB classification, IPSS score, WPSS score, limited stage, extensive stage, staging according to cellular markers, occult, including information that may inform on time to progression, progression free survival, overall survival, or event-free survival.

The classification of a cell according to the status of an activatable element can comprise classifying a cell as a cell that is correlated to a patient response to a treatment. In some embodiments, the patient response is selected from the group consisting of complete response, partial response, nodular partial response, no response, progressive disease, stable disease and adverse reaction.

The classification of a rare cell according to the status of an activatable element can comprise classifying the cell as a cell that can be correlated with minimal residual disease or emerging resistance. See U.S. No. 61/048,886 which is incorporated by reference.

The classification of a cell according to the status of an activatable element can comprise selecting a method of treatment. Example of methods of treatments include, but are not limited to chemotherapy, biological therapy, radiation therapy, bone marrow transplantation, Peripheral stem cell transplantation, umbilical cord blood transplantation, autologous stem cell transplantation, allogeneic stem cell transplantation, syngeneic stem cell transplantation, surgery, induction therapy, maintenance therapy, watchful waiting, and other therapy.

A modulator can be an activator, an inhibitor or a compound capable of impacting cellular signaling networks. Modulators can take the form of a wide variety of environmental cues and inputs. Examples of modulators include but are not limited to growth factors, mitogens, cytokines, adhesion molecules, drugs, hormones, small molecules, polynucleotides, antibodies, natural compounds, lactones, chemotherapeutic agents, immune modulators, carbohydrates, proteases, ions, reactive oxygen species, radiation, physical parameters such as heat, cold, UV radiation, peptides, and protein fragments, either alone or in the context of cells, cells themselves, viruses, and biological and non-biological complexes (e.g. beads, plates, viral envelopes, antigen presentation molecules such as major histocompatibility complex). One exemplary set of modulators, include but are not limited to SDF-1α, IFN-α, IFN-γ, IL-10, IL-6, IL-27, G-CSF, FLT-3L, IGF-1, M-CSF, SCF, PMA, Thapsigargin, $H_2O_2$, Etoposide, Mylotarg, AraC, daunorubicin, staurosporine, benzyloxycarbonyl-Val-Ala-Asp (OMe) fluoromethylketone (ZVAD), lenalidomide, EPO, azacitadine, decitabine, IL-3, IL-4, GM-CSF, EPO, LPS, TNF-α, and CD40L.

In some embodiments, the modulator is an activator. In some embodiments the modulator is an inhibitor. In some embodiments, the invention provides methods for classifying a cell by contacting the cell with an inhibitor, determining the presence or absence of an increase in activation level of an activatable element in the cell, and classifying the cell based on the presence or absence of the increase in the activation of the activatable element. In some embodiments, a cell is classified according to the activation level of a plurality of activatable elements after the cells have been subjected to an inhibitor. In some embodiments, the inhibitor is an inhibitor of a cellular factor or a plurality of factors that participates in a signaling cascade in the cell. In some embodiments, the inhibitor is a phosphatase inhibitor. Examples of phosphatase inhibitors include, but are not limited to $H_2O_2$, siRNA, miRNA, Cantharidin, (−)-p-Bromotetramisole, Microcystin LR, Sodium Orthovanadate, Sodium Pervanadate, Vanadyl sulfate, Sodium oxodiperoxo(1,10-phenanthroline)vanadate, bis(maltolato)oxovanadium(IV), Sodium Molybdate, Sodium Perm olybdate, Sodium Tartrate, Imidazole, Sodium Fluoride, β-Glycerophosphate, Sodium Pyrophosphate Decahydrate, Calyculin A, Discodermia calyx, bpV(phen), mpV(pic), DMHV, Cypermethrin, Dephostatin, Okadaic Acid, NIPP-1, N-(9,10-Dioxo-9,10-dihydro-phenanthren-2-yl)-2,2-dimethyl-propionamide, α-Bromo-4-hydroxyacetophenone, 4-Hydroxyphenacyl Br, α-Bromo-4-methoxyacetophenone, 4-Methoxyphenacyl Br, α-Bromo-4-(carboxymethoxy)acetophenone, 4-(Carboxymethoxy)phenacyl Br, and bis(4-Trifluoromethylsulfonamidophenyl)-1,4-diisopropylbenzene, phenylarsine oxide, Pyrrolidine Dithiocarbamate, and Aluminium fluoride. In some embodiments, the phosphatase inhibitor is $H_2O_2$.

In some embodiments, the methods of the invention provide methods for classifying a cell population or determining the presence or absence of a condition in an individual by subjecting a cell from the individual to a modulator and an inhibitor, determining the activation level of an activatable element in the cell, and determining the presence or absence of a condition based on the activation level. In some embodiments, the activation level of a plurality of activatable elements in the cell is determined The inhibitor can be an inhibitor as described herein. In some embodiments, the inhibitor is a phosphatase inhibitor. In some embodiments, the inhibitor is $H_2O_2$. The modulator can be any modulator described herein. In some embodiments, the methods of the invention provides for methods for classifying a cell population by exposing the cell population to a plurality of modulators in separate cultures and determining the status of an activatable element in the cell population. In some embodiments, the status of a plurality of activatable elements in the cell population is determined In some embodiments, at least one of the modulators of the plurality of modulators is an inhibitor. The modulator can be at least one of the modulators described herein. In some embodiments, at least one modulator is selected from the group consisting of SDF-1α, IFN-α, IFN-γ, IL-10, IL-6, IL-27, G-CSF, FLT-3L, IGF-1, M-CSF, SCF, PMA, Thapsigargin, $H_2O_2$, Etoposide, Mylotarg, AraC, daunorubicin, staurosporine, benzyloxycarbonyl-Val-Ala-Asp (OMe) fluoromethylketone (ZVAD), lenalidomide, EPO, azacitadine, decitabine, IL-3, IL-4, GM-CSF, EPO, LPS, TNF-α, and CD40L or a combination thereof. In some embodiments of the invention, the status of an activatable element is determined by contacting the cell population with a binding element that is specific for an activation state of the activatable element. In some embodiments, the status of a plurality of activatable elements is determined by contacting the cell population with a plurality of binding elements, where each binding element is specific for an activation state of an activatable element.

In some embodiments, the methods of the invention provide methods for determining a phenotypic profile of a population of cells by exposing the population of cells to a plurality of modulators (recited herein) in separate cultures, determining the presence or absence of an increase in activation level of an activatable element in the cell population from each of the separate cultures and classifying the cell population based on the presence or absence of the increase in the activation of the activatable element from each of the separate culture. In some embodiments, the phenotypic profile is used to characterize multiple pathways in the population of cells.

Patterns and profiles of one or more activatable elements are detected using the methods known in the art including those described herein. In some embodiments, patterns and profiles of activatable elements that are cellular components of a cellular pathway or a signaling pathway are detected using the methods described herein. For example, patterns and profiles of one or more phosphorylated polypeptides are detected using methods known in art including those described herein.

In some embodiments, cells (e.g. normal cells) other than the cells associated with a condition (e.g. cancer cells) or a combination of cells are used, e.g., in assigning a risk group, predicting an increased risk of relapse, predicting an increased risk of developing secondary complications, choosing a therapy for an individual, predicting response to a therapy for an individual, determining the efficacy of a therapy in an individual, and/or determining the prognosis for an individual. That is that cells other than cells associated with a condition (e.g. cancer cells) are in fact reflective of the condition process. For instance, in the case of cancer, infiltrating immune cells might determine the outcome of the disease. Alternatively, a combination of information from the cancer cell plus the immune cells in the blood that are responding to the disease, or reacting to the disease can be used for diagnosis or prognosis of the cancer.

In some embodiments, the invention provides methods to carry out multiparameter flow cytometry for monitoring phospho-protein responses to various factors in acute myeloid leukemia, MDS, or MPN at the single cell level. Phospho-protein members of signaling cascades and the kinases and phosphatases that interact with them are required to initiate and regulate proliferative signals in cells. Apart from the basal level of protein phosphorylation alone, the effect of potential drug molecules on these network pathways was studied to discern unique cancer network profiles, which correlate with the genetics and disease outcome. Single cell measurements of phospho-protein responses reveal shifts in the signaling potential of a phospho-protein network, enabling categorization of cell network phenotypes by multidimensional molecular profiles of signaling. See U.S. Pat. No. 7,393,656. See also Irish et. al., Single cell profiling of potentiated phospho-protein networks in cancer cells. *Cell.* 2004, vol. 118, p. 1-20.

Flow cytometry is useful in a clinical setting, since relatively small sample sizes, as few as 10,000 cells, can produce a considerable amount of statistically tractable multidimensional signaling data and reveal key cell subsets that are responsible for a phenotype. See U.S. Pat. Nos. 7,381,535 and 7,393,656. See also Krutzik et al, 2004).

Cytokine response panels have been studied to survey altered signal transduction of cancer cells by using a multidimensional flow cytometry file which contained at least 30,000 cell events. In one embodiment, this panel is expanded and the effect of growth factors and cytokines on primary AML samples studied. See U.S. Pat. Nos. 7,381,535 and 7,393,656. See also Irish et. al., CELL July 23; 118(2):217-28. In some embodiments, the analysis involves working at multiple characteristics of the cell in parallel after contact with the compound. For example, the analysis can examine drug transporter function; drug transporter expression; drug metabolism; drug activation; cellular redox potential; signaling pathways; DNA damage repair; and apoptosis.

In some embodiments, the modulators include growth factors, cytokines, chemokines, phosphatase inhibitors, and pharmacological reagents. The response panel is composed of at least one of: SDF-1α, IFN-α, IFN-γ, IL-10, IL-6, IL-27, G-CSF, FLT-3L, IGF-1, M-CSF, SCF, PMA, Thapsigargin, $H_2O_2$, Etoposide, Mylotarg, AraC, daunorubicin, staurosporine, benzyloxycarbonyl-Val-Ala-Asp (OMe) fluoromethylketone (ZVAD), lenalidomide, EPO, azacitadine, decitabine, IL-3, IL-4, GM-CSF, EPO, LPS, TNF-α, and CD40L.

The response of each phospho-protein node is compared to the basal state and can be represented by calculating the $\log_2$ fold difference in the Median Fluorescence Intensity (MFI) of the stimulated sample divided by the unstimulated sample. The data can be analyzed using any of the metrics described herein including the metric described in FIG. 2. However, other statistical methods may be used. The growth factor and the cytokine response panel included detection of phosphorylated Stat1, Stat3, Stat5, Stat6, PLCγ2, S6, Akt, Erk1/2, CREB, p38, and NF-KBp-65. In some embodiments, a diagnosis, prognosis, a prediction of outcome such as response to treatment or relapse is performed by analyzing the two or more phosphorylation levels of two or more proteins each in response to one or more modulators. The phosphorylation levels of the independent proteins can be measured in response to the same or different modulators. Grouping of data points increases predictive value.

In some embodiments, the AML or other panel of modulators is further expanded to examine the process of DNA damage, apoptosis, drug transport, drug metabolism, and the use of peroxide to evaluate phosphatase activity. Analysis can assess the ability of the cell to undergo the process of apoptosis after exposure to the experimental drug in an in vitro assay as well as how quickly the drug is exported out of the cell or metabolized. The drug response panel can include but is not limited to detection of phosphorylated Chk2, Cleaved Caspase 3, Caspase 8, PARP and mitochondria-released Cytoplasmic Cytochrome C. Modulators may include Stauro, Etoposide, Mylotarg, AraC, and daunorubicin. Analysis can assess phosphatase activity after exposure of cells to phosphatase inhibitors including but not limited to hydrogen peroxide ($H_2O_2$), $H_2O_2$+SCF and $H_2O_2$+IFNα. The response panel to evaluate phosphatase activity can include but is not limited to the detection of phosphorylated Slp76, PLCg2, Lck, S6, Akt, Erk, Stat1, Sta3, and Stat5. Later, the samples may be analyzed for the expression of drug transporters such as MDR1/PGP, MRP1 and BCRP/ABCG2. Samples may also be examined for XIAP, Survivin, Bcl-2, MCL-1, Bim, Ki-67, Cyclin D1, ID1 and Myc.

Another method of the present invention is a method for determining the prognosis and therapeutic selection for an individual with acute myelogenous leukemia (AML). Using the signaling nodes and methodology described herein, multiparametric flow could separate a patient into "cytarabine responsive", meaning that a cytarabine based induction regimen would yield a complete response or "cytarabine non-responsive", meaning that the patient is unlikely to yield a complete response to a cytarabine based induction regimen. Furthermore, for those patients unlikely to benefit from cytarabine based therapy, the individual's blood or marrow sample could reveal signaling biology that corresponds to either in-vivo or in-vitro sensitivity to a class of drugs including but not limited to direct drug resistance modulators, anti-Bcl-2 or pro-apoptotic drugs, proteosome inhibitors, DNA methyl transferase inhibitors, histone deacetylase inhibitors, anti-angiogenic drugs, farnesyl transferase inhibitors, FLt3 ligand inhibitors, or ribonucleotide reductase inhibitors. An individual with AML with a complete response to induction therapy could further benefit from the present invention. The individual's blood or marrow sample could reveal signaling biology that corresponds to likelihood of benefit from further cytarabine based chemotherapy versus myeloablative therapy followed by and stem cell transplant versus reduced intensity therapy followed by stem cell transplantation.

In some embodiments, the invention provides a method for diagnosing, prognosing, determining progression, predicting response to treatment or choosing a treatment for AML, MDS or MPN in an individual where the individual has a predefined clinical parameter, the method comprising the steps of (a) subjecting a cell population from the individual to a plurality of distinct modulators in separate cultures, (b) characterizing a plurality of pathways in one or more cells from the separate cultures comprising determining an activation level of at least one activatable element in at least three pathways, where (i) the pathways are selected from the group consisting of apoptosis, cell cycle, signaling, or DNA damage pathways (ii) at least one of the pathways being characterized in at least one of the separate cultures is an apoptosis or DNA damage pathway, (iii) the distinct modulators independently activate or inhibit said one or more pathways being characterized, and (c) correlating the characterization with diagnosing, prognosing, determining progression, predicting response to treatment or choosing a treatment for AML, MDS or MPN in an individual, where the pathways characterization in combination with the clinical parameter is indicative of the diagnosing, prognosing, determining progression, response to treatment or the appropriate treatment for AML, MDS or MPN. Examples of predetermined clinical parameters include, but are not limited to, age, de novo acute myeloid leukemia patient, secondary acute myeloid leukemia patient, or a biochemical/molecular marker. In some embodiments, the individual is over 60 years old. In some embodiments, the individual is under 60 years old. In some embodiments the activatable elements and modulators are selected from the activatable elements and modulators listed in Tables 1, 2, 3 or 5. In some embodiments, the activatable elements and modulators are selected from the activatable elements and modulators listed in Table 12 and are used to predict response duration in an individual after treatment. In some embodiments the modulator is selected from the group consisting of FLT3L, GM-CSF, SCF, G-CSF, SDF1a, LPS, PMA, Thapsigargin, IFNg, IFNa, IL-27, IL-3, IL-6, IL-10, ZVAD, $H_2O_2$, Staurosporine, Etoposide, Mylotarg, Daunorubicin, and AraC. In some embodiments, when the individual is under 60 years old the activatable elements and modulators are selected from the activatable elements and modulators listed in Table 6. In some embodiments, where the individual is over 60 years the activatable elements and modulators are selected from the activatable elements and modulators listed in Table 7. In some embodiments, where the individual is a secondary acute myeloid leukemia patient the activatable elements and modulators are selected from the activatable elements and modulators listed in Table 8 and Table 9. In some embodiments, where the individual is a de novo acute myeloid leukemia patient the activatable elements and modulators are selected from the activatable elements and modulators listed in Table 10 and Table 11. In some embodiments, where the individual has a wild type FLT3 the activatable elements and modulators are selected from the activatable elements and modulators listed in Table 13.

In some embodiments, the invention provides a method for predicting a response to a treatment or choosing a treatment for AML, MDS or MPN in an individual, the method comprising the steps: (a) subjecting a cell population from the individual to at least two distinct modulators in separate cultures; (b) determining an activation level of at least one activatable element from each of at least three pathways selected from the group consisting of apoptosis, cell cycle, signaling, and DNA damage pathways in one or more cells from each said separate cultures, where at least one of the activatable elements is from an apoptosis or DNA damage pathway, and where the activatable elements measured in each separate culture are the same or the activatable elements measured in each separate culture are different; and (c) predicting a response to a treatment or choosing a therapeutic for AML, MDS or MPN in the individual based on the activation level of said activatable elements. In some embodiments, the method further comprises determining whether the apoptosis, cell cycle, signaling, or DNA damage pathways are functional in the individual based on the activation levels of the activatable elements, wherein a pathway is functional if it is permissive for a response to a treatment, where if the apoptosis, cell cycle, signaling, and DNA damage pathways are functional the individual can respond to treatment, and where if at least one of the pathways is not functional the individual can not respond to treatment. In some embodiments, the method further comprises determining whether the apoptosis, cell cycle, signaling, or DNA damage pathways are functional in the individual based on the activation levels of the activatable elements, wherein a pathway is functional if it is permissive for a response to a treatment, where if the apoptosis and DNA damage pathways are functional the individual can respond to treatment. In some embodiments, the method further comprises determining whether the apoptosis, cell cycle, signaling, or DNA damage pathways are functional in the individual based on the activation levels of the activatable elements, wherein a pathway is functional if it is permissive for a response to a treatment, where a therapeutic is chosen depending of the functional pathways in the individual. In some embodiments the activatable elements and modulators are selected from the activatable elements and modulators listed in Tables 1, 2, 3 or 5. In some embodiments, the activatable elements and modulators are selected from the activatable elements and modulators listed in Table 12 and are used to predict response duration in an individual after treatment. In some embodiments the modulator is selected from the group consisting of FLT3L, GM-CSF, SCF, G-CSF, SDF1a, LPS, PMA, Thapsigargin, IFNg, IFNa, IL-27, IL-3, IL-6, IL-10, ZVAD, $H_2O_2$, Staurosporine, Etoposide, Mylotarg, Daunorubicin, and AraC.

In some embodiments, the invention provides a method of predicting a response to a treatment or choosing a treatment for AML, MDS or MPN in an individual, the method comprising the steps of: (a) subjecting a cell population from said individual to at least three distinct modulators in separate cultures, wherein: (i) a first modulator is a growth factor or mitogen, (ii) a second modulator is a cytokine, (iii) a third modulator is a modulator that slows or stops the growth of cells and/or induces apoptosis of cells or, the third modulator is an inhibitor; (b) determining the activation level of at least one activatable element in one or more cells from each of the separate cultures, where: (i) a first activatable element is an activatable element within the PI3K/AKT, or MAPK pathways and the activation level is measured in response to the growth factor or mitogen, (ii) a second activatable element is an activatable element within the STAT pathway and the activation level is measured in response to the cytokine, (iii) a third activatable element is an activatable element within an apoptosis pathway and the activation level is measured in response to the modulator that slows or stops the growth of cells and/or induces apoptosis of cells, or the third activatable element is activatable element within the phospholipase C pathway and the activation level is measured in response to the inhibitor, or the third activatable element is a phosphatase and the activation level is measured in response to the inhibitor; and (c) correlating the activation levels of said activatable elements with a response to a treatment or with choosing a treatment for AML, MDS or MPN in the individual. Examples of predefined clinical parameters include age, de novo acute myeloid leukemia patient, secondary acute myeloid leukemia patient, or a biochemical/molecular marker. In some embodiments, the cytokine is selected from the group consisting of G-CSF, IFNg, IFNa, IL-27, IL-3, IL-6, and IL-10. In some embodiments, the growth factor is selected from the group consisting of FLT3L, SCF, G-CSF, and SDF1a. In some embodiments, the mitogen is selected from the group consisting of LPS, PMA, and Thapsigargin. In some embodiments, the modulator that slows or stops the growth of cells and/or induces apoptosis of cells is selected from the group consisting of Staurosporine, Etoposide, Mylotarg, Daunorubicin, and AraC.

In some embodiments, activation levels of an activatable element within the STAT pathway higher than a threshold level in response to a cytokine are indicative that an individual can not respond to treatment. In some embodiment, a treatment is chosen based on the ability of the cells to respond to treatment. In some embodiments, the activatable element within the STAT pathway is selected from the group consisting of p-Stat3, p-Stat5, p-Stat1, and p-Stat6 and the cytokine is selected from the group consisting of IFNg, IFNa, IL-27, IL-3, IL-6, IL-10, and G-CSF. In some embodiments, the activatable element within the STAT pathway is Stat 1 and the cytokine is IL-27 or G-CSF.

In some embodiments, activation levels of an activatable element within the PI3K/AKT, or MAPK pathway higher than a threshold level in response to a growth factor or mitogen is indicative that an individual can not respond to treatment. In some embodiment, a treatment is chosen based on the ability of the cells to respond to treatment with a modulator. In some embodiments, the activatable element within the PI3K/AKT, or MAPK pathway is selected from the group consisting of p-ERK, p38 and pS6 and the growth factor or mitogen is selected from the group consisting of FLT3L, SCF, G-CSF, SDF1a, LPS, PMA, and Thapsigargin.

In some embodiments, activation levels of an activatable element within the phospholipase C pathway higher than a threshold level in response to an inhibitor is indicative that an individual can respond to treatment. In some embodiment, a treatment is chosen based on the ability of the cells to respond to treatment. In some embodiments, the activatable element within the phospholipase C pathway is selected from the group consisting of p-Slp-76, and Plcg2 and the inhibitor is $H_2O_2$.

In some embodiments, activation levels of an activatable element within the apoptosis pathway higher than a threshold in response to a modulator that slows or stops the growth of cells and/or induces apoptosis of cells is indicative that an individual can respond to treatment. In some embodiment, a treatment is chosen based on the ability of the cells to respond to treatment. In some embodiments, the activatable element within the apoptosis pathway is selected from the group consisting of Parp+, Cleaved Caspase 8, and Cytoplasmic Cytochrome C, and the modulator that slows or stops the growth of cells and/or induces apoptosis of cells is selected from the group consisting of Staurosporine, Etoposide, Mylotarg, Daunorubicin, and AraC.

In some embodiments, activation levels of an activatable element within the apoptosis pathway higher than a threshold in response to a modulator that slows or stops the growth of cells and/or induces apoptosis of cells and activation levels of an activatable element within the STAT pathway higher than a threshold level in response to a cytokine is indicative that an individual can not respond to treatment. In some embodiments, the activatable element within the apoptosis pathway is selected from the group consisting of Parp+, Cleaved Caspase 8, and Cytoplasmic Cytochrome C, and the modulator that slows or stops the growth of cells and/or induces apoptosis of cells is selected from the group consisting of Staurosporine, Etoposide, Mylotarg, Daunorubicin, and AraC. In some embodiments, the activatable element within the STAT pathway is selected from the group consisting of p-Stat3, p-Stat5, p-Stat1, and p-Stat6 and the cytokine is selected from the group consisting of IFNg, IFNa, IL-27, IL-3, IL-6, IL-10, and G-CSF. In some embodiments, the activatable element within the STAT pathway is Stat 1 and the cytokine is IL-27 or G-CSF.

In some embodiments, the methods of the invention further comprise determining an activation level of an activatable element within a DNA damage pathway in response to a modulator that slows or stops the growth of cells and/or induces apoptosis of cells. In some embodiments, the activatable element within a DNA damage pathway is selected from the group consisting of Chk2, ATM, ATR and 14-3-3 and the modulator that slows or stops the growth of cells and/or induces apoptosis of cells is selected from the group consisting of Staurosporine, Etoposide, Mylotarg, Daunorubicin, and AraC.

In some embodiments, activation levels higher than a threshold of an activatable element within a DNA damage pathway and activation levels lower than a threshold of an activatable element within the apoptosis pathway in response to a modulator that slows or stops the growth of cells and/or induces apoptosis of cells are indicative of a communication breakdown between the DNA damage response pathway and the apoptotic machinery and that an individual can not respond to treatment. In some embodiment, a treatment is chosen based on the ability of the cells to respond to treatment.

In some embodiments, the methods of the invention further comprise determining an activation level of an activatable element within a cell cycle pathway in response to a modulator that slows or stops the growth of cells and/or induces apoptosis of cells. In some embodiments, the activatable element within a DNA damage pathway is selected from the group consisting of Cdc25, p53, CyclinA-Cdk2, CyclinE-Cdk2, CyclinB-Cdk1, p21, and Gadd45 and the modulator that slows or stops the growth of cells and/or induces apoptosis of cells is selected from the group consisting of Staurosporine, Etoposide, Mylotarg, Daunorubicin, and AraC.

In some embodiments, the methods of the invention further comprise determining the levels of a drug transporter and/or a cytokine receptor. In some embodiments, the cytokine receptors or drug transporters are selected from the group consisting of MDR1, ABCG2, MRP, P-Glycoprotein, CXCR4, FLT3, and c-kit. In some embodiments, levels higher than a threshold of the drug transporter and/or said cytokine receptor are indicative that an individual can not respond to treatment. In some embodiment, a treatment is chosen based on the ability of the cells to respond to treatment.

In some embodiments, the methods of the invention further comprise determining the activation levels of an activatable element within the Akt pathway in response to an inhibitor, where activation levels higher that a threshold of the activatable element within the Akt pathway in response to the inhibitor are indicative that the individual can not respond to treatment. In some embodiment, a treatment is chosen based on the ability of the cells to respond to treatment.

In some embodiments, activation levels higher than a threshold of an activatable element in the PI3K/AKT pathway in response to a growth factor is indicative that the individual can not respond to treatment. In some embodiments, the activatable element in the PI3K/Akt pathway is Akt and the growth factor is FLT3L.

In some embodiments, activation levels higher than a threshold of an activatable element in the apoptosis pathway in response to a modulator that slows or stops the growth of cells and/or induces apoptosis of cells is indicative that the individual can respond to treatment. In some embodiments, the activatable element within the apoptosis pathway is Parp+ and the modulator that slows or stops the growth of cells and/or induces apoptosis of cells is selected from the group consisting of Staurosporine, Etoposide, Mylotarg, Daunorubicin, and AraC.

In some embodiments, the invention provides a method of predicting a response to a treatment or choosing a treatment for AML in an individual where the individual is a secondary acute myeloid leukemia patient, the method comprising the steps of; (a) subjecting a cell population from the individual to IL-27 and G-CSF in separate cultures, (b) determining an activation level of pStat1 in one or more cells from each separate culture, (c) predicting a response to a treatment or choosing a treatment for AML, in the individual, where if the activation levels of pStat1 are higher than a threshold level in response to both IL-27 and G-CSF the individual can not respond to treatment and if the levels of pStat1 are lower than a threshold in response to both IL-27 and G-CSF the individual can respond to treatment. In some embodiments, the treatment is chemotherapy agent. Examples of chemotherapy agents include, but are not limited to, cytarabine (ara-C), daunorubicin (Daunomycin), idarubicin (Idamycin), mitoxantrone and 6-thioguanine. In some embodiments, the treatment is allogeneic stem cell transplant or autologous stem cell transplant.

In some embodiments, the invention provides a method of predicting a response to a treatment or choosing a treatment for AML, MDS or MPN in an individual, the method comprising the steps of: (a) subjecting a cell population from the individual to FLT3L, (b) determining an activation level of pAkt in one or more cells from the population (c) predicting a response to a treatment or choosing a treatment for AML, MDS or MPN in the individual, where if the activation levels of pAkt are higher than a predetermined threshold in response to FLT3L the individual can not respond to treatment. In some embodiments, the method further comprises the steps of: (d) subjecting a cell population from said individual to IL-27 in a separate culture, (e) determining an activation level of Stat1 in one or more cells from the separate culture, (f) predicting a response to a treatment or choosing a treatment for AML, MDS or MPN in the individual, where if the activation levels of pStat1 are higher than a predetermined threshold in response to IL-27 the individual can not respond to treatment. In some embodiments where the individual is over 60 years old the method further comprises the step of: (g) subjecting a cell population from the individual to H2O2 in a separate culture, (h) determining an activation level of Plcg2 in one or more cells from the separate culture (i) predicting a response to a treatment or choosing a treatment for AML, MDS or MPN in the individual, wherein if the activation levels of Plcg2 are higher than a predetermined threshold in response to H2O2 the individual can not respond to treatment. In some embodiments where the individual is under 60 years old the method further comprises the steps of (g) subjecting a cell population from said individual to Etoposide in a separate culture, (h) determining an activation level of Parp in one or more cells from the separate culture, and (i) predicting a response to a treatment for AML, MDS or MPN in said individual, where if the activation levels of Parp are higher than a predetermined threshold in response to Etoposide the individual can respond to treatment. In some embodiments, the treatment is chemotherapy agent. Examples of chemotherapy agents include, but are not limited to, cytarabine (ara-C), daunorubicin (Daunomycin), idarubicin (Idamycin), mitoxantrone and 6-thioguanine. In some embodiments, the treatment is allogeneic stem cell transplant or autologous stem cell transplant.

In some embodiments, the invention provides methods of prediction response to a treatment and/or risk of relapse for AML, MDS or MPN in an individual, the method comprising the steps of: (a) subjecting a cell population from the individual to SCF, (b) determining an activation level of pAkt and S6 in one or more cells from the population (c) predicting a response to a treatment, choosing a treatment or predicting risk of relapse for AML, MDS or MPN in the individual, where if the activation levels of pAkt and S6 are higher than a predetermined threshold in response to SCF the individual can not respond to treatment or will have a higher probability of relapse.

In some embodiments, a diagnosis, prognosis, a prediction of outcome such as response to treatment or relapse is performed by analyzing the two or more phosphorylation levels of two or more proteins each in response to one or more modulators. The phosphorylation levels of the independent proteins can be measured in response to the same or different modulators. Grouping of data points increases predictive value.

In some embodiments, the invention provides a method of diagnosing, prognosing or predicting a response to a treatment or choosing a treatment for AML, MDS or MPN in an individual, the method comprising the steps of: (a) subjecting a cell population from the individual in separate cultures to at least two modulators selected from the group consisting of Staurosporine, Etoposide, Mylotarg, Daunorubicin, AraC, CD40L, G-CSF, IGF-1, IFNg, IFNa, IL-27, IL-3, IL-6, IL-10, FLT3L, SCF, G-CSF, SDF1a, LPS, PMA, Thapsigargin and H2O2; b) determining the activation level of at least three activatable elements selected from the group consisting of p-Slp-76, p-Plcg2, p-Stat3, p-Stat5, p-Stat1, p-Stat6, p-Creb, Parp+, Chk2, p-65/RelA, p-Akt, p-S6, p-ERK, Cleaved Caspase 8, Cytoplasmic Cytochrome C, and p38; and (c) diagnosing, prognosing, or predicting a response to a treatment or choosing a treatment for AML, MDS or MPN based on the activation levels of the activatable elements. In some embodiments, the method further comprises determining the expression of a cytokine receptor or drug transporter selected from the group consisting of MDR1, ABCG2, MRP, P-Glycoprotein, CXCR4, FLT3, and c-Kit.

In some embodiments, the invention provides methods of diagnosing, prognosing, determining progression, predicting a response to a treatment or choosing a treatment for acute leukemia, myelodysplastic syndrome or myeloproliferative neoplasms in an individual, the methods comprising the steps of: (1) classifying one or more hematopoietic cells associated with acute leukemia, myelodysplastic syndrome or myeloproliferative neoplasms in the individual by a method comprising: a) subjecting a cell population comprising the one or more hematopoietic cells from the individual to CD40L, b) determining an activation level of at least one activatable element selected from the group consisting of p-CREB and p-Erk in one or more cells from the individual, and c) classifying the one or more hematopoietic cells based on the activation levels of the activatable element; and (2) making a decision regarding a diagnosis, prognosis, progression, response to a treatment or a selection of treatment for acute leukemia, myelodysplastic syndrome or myeloproliferative neoplasms in the individual based on the classification of said one or more hematopoietic cells.

In some embodiments, the inventions provides methods of diagnosing, prognosing, determining progression, predicting a response to a treatment or choosing a treatment for acute leukemia, myelodysplastic syndrome or myeloproliferative neoplasms in an individual, the methods comprising the steps of: (1) classifying one or more hematopoietic cells associated with acute leukemia, myelodysplastic syndrome or myeloproliferative neoplasms in the individual by a method comprising: a) subjecting a cell population comprising the one or more hematopoietic cells from the individual to FLT3L, b) determining an activation level of at least one activatable element selected from the group consisting of p-CREB, p-plcγ2, p-Stat5, p-Erk, p-Akt and p-S6 in one or more cells from the individual, and c) classifying said one or more hematopoietic cells based on the activation levels of the activatable element; and (2) making a decision regarding a diagnosis, prognosis, progression, response to a treatment or a selection of treatment for acute leukemia, myelodysplastic syndrome or myeloproliferative neoplasms in the individual based on said classification of said one or more hematopoietic cells. In some embodiment, the individual has a FLT3 mutation. In some embodiments, classifying further comprises identifying a difference in kinetics of said activation level.

In some embodiments, the invention provides methods of diagnosing, prognosing, determining progression, predicting a response to a treatment or choosing a treatment for acute leukemia, myelodysplastic syndrome or myeloproliferative neoplasms in an individual, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to G-CSF, b) determining an activation level of at least one activatable element selected from the group consisting of p-Stat 3, and p-Stat 5 in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to H2O2 and SCF, b) determining an activation level of at least one activatable element selected from the group consisting of p-Erk, p-plcγ2, and p-SLP 76 in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to H2O2, b) determining an activation level of p-Lck in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides method of diagnosing, prognosing, determining progression, predicting a response to a treatment or choosing a treatment for acute leukemia, myelodysplastic syndrome or myeloproliferative neoplasms in an individual, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to IGF-1, b) determining an activation level of at least one activatable element selected from the group consisting of p-CREB, and p-plcγ2 in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, said methods comprising the steps: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to a modulator selected from the group consisting of IL-27, IL-3 or IL-6, b) determining an activation level of at least one activatable element selected from the group consisting of p-CREB and p-Stat 3 in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, said methods comprising the steps: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to M-CSF, b) determining an activation level of at least one activatable elements selected from the group consisting of p-plcγ2, p-Akt and p-CREB in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, said methods comprising the steps of: (1) classifying one or more hematopoietic cells associated with acute leukemia, myelodysplastic syndrome or myeloproliferative neoplasms in said individual by a method comprising: a) determining the basal levels of at least one activatable element selected from the group consisting of p-CREB, p-Erk, p-plcγ2, p-Stat 3, and p-Stat 6 in one or more cells from said individual, and b) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides method of diagnosing, prognosing, determining progression, predicting a response to a treatment or choosing a treatment for acute leukemia, myelodysplastic syndrome or myeloproliferative neoplasms in an individual, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to SCF, b) determining an activation level of at least one activatable element selected from the group consisting of p-CREB, and p-plcγ2 in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to a modulator selected from the group consisting of SDF-1α and TNFα, b) determining an activation level of p-Erk in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to Thapsigargin, b) determining an activation level of p-CREB in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, said methods comprising the steps of: (1) classifying one or more hematopoietic cells associated with acute leukemia, myelodysplastic syndrome or myeloproliferative neoplasms in said individual by a method comprising: a) determining an activation level of at least three activatable elements in the presence of a modulator as listed in Tables 23 or 24, and b) classifying said one or more hematopoietic cells based on said activation levels of said activatable elements; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells. In some embodiments, the activation level of said at least three activatable elements being selected from the group consisting of (i) p-Akt in the presence of SCF, (ii) p-Akt in the presence of FLT3L, (iii) p-Chk2 in the presence of Etoposide; (iv) c-PARP+ in the presence of no modulator and (v) p-Erk 1/2 in the presence of PMA.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual is a De Novo patient or a patient with a FLT3 mutation, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to SCF or FLT3L, b) determining an activation level of at least one activatable element selected from the group consisting of p-S6, and p-plcγ2 in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells. In some embodiments, classifying further comprises identifying a difference in kinetics of said activation level.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual is a De Novo patient, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to Etoposide, b) determining an activation level of p-Chk2 in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual is a De Novo patient, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to FLT3L, b) determining an activation level of p-plcγ2 in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual is a De Novo patient, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to IL-3, b) determining an activation level of p-Stat 3 in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual is a De Novo patient, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to IL-6, b) determining an activation level p-Stat 5 in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual is a De Novo patient, said methods comprising the steps of: (1) classifying one or more hematopoietic cells associated with acute leukemia, myelodysplastic syndrome or myeloproliferative neoplasms in said individual by a method comprising: a) determining an activation level of at least one activatable element selected from the group consisting of p-Erk, and p-Stat 6 in one or more cells from said individual, and b) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual is a De Novo patient, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to SDF-1α, b) determining an activation level of p-CREB in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual is an individual with Secondary acute leukemia, myelodysplastic syndrome or myeloproliferative neoplasms, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to Etoposide, b) determining an activation level of at least one activatable element selected from the group consisting of p-Chk2, and c-PARP in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual is an individual with Secondary acute leukemia, myelodysplastic syndrome or myeloproliferative neoplasms, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to G-CSF; b) determining an activation level of p-Stat 1 in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides method of diagnosing, prognosing, determining progression, predicting a response to a treatment or choosing a treatment for acute leukemia, myelodysplastic syndrome or myeloproliferative neoplasms in an individual, wherein said individual is an individual with Secondary acute leukemia, myelodysplastic syndrome or myeloproliferative neoplasms, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to IFNα, b) determining an activation level of at least one activatable element selected from the group consisting of p-Stat 1, p-Stat 3 and p-Stat 5 in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual is an individual with Secondary acute leukemia, myelodysplastic syndrome or myeloproliferative neoplasms, said methods comprising the steps of: (1) classifying one or more hematopoietic cells associated with acute leukemia, myelodysplastic syndrome or myeloproliferative neoplasms in said individual by a method comprising: a) determining an activation level of at least one activatable element selected from the group consisting of p-Chk2, and c-PARP in one or more cells from said individual, and b) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual is an individual with Secondary acute leukemia, myelodysplastic syndrome or myeloproliferative neoplasms, said methods comprising the steps: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to PMA, b) determining an activation level of p-CREB in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual 60 years old or older, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to H2O2, b) determining an activation level of p-Akt in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual is 60 years old or older, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to IL-27, b) determining an activation level of p-Stat 3 in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual is 60 years old or older, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to LPS, b) determining an activation level of p-Erk in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual is less than 60 years old, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to a modulator selected from the group consisting of Daunorubicin, AraC, Etoposide and a combination thereof, b) determining an activation level of at least one activatable element selected from the group consisting of p-Chk2, and c-PARP in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual is less than 60 years old, said methods comprising the steps: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to a modulator selected from the group consisting of GM-CSF, IFNa, IFNg, IL-10 and IL-6, b) determining an activation level of at least one activatable element selected from the group consisting of p-Stat 1, p-Stat 3, and p-Stat 5 in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual is less than 60 years old, said methods comprising the steps of: (1) classifying one or more hematopoietic cells associated with acute leukemia, myelodysplastic syndrome or myeloproliferative neoplasms in said individual by a method comprising: a) determining an activation level of at least one activatable element selected from the group consisting of c-PARP, and p-Erk in one or more cells from said individual, and b) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual is less than 60 years old, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to a modulator selected from the group consisting of PMA and Thapsigargin, b) determining an activation level of at least one activatable element selected from the group consisting of p-CREB, and p-Erk in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual is less than 60 years old, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to a modulator selected from the group consisting of Staurosporine, ZVAD and a combination thereof, b) determining an activation level of at least one activatable element selected from the group consisting of cytochrome C, and c-PARP in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual has an intermediate or high risk cytogenetics, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to a modulator selected from the group consisting of G-CSF, IFNα, IFNg, IL-10, IL-27 and IL-6, b) determining an activation level of at least one activatable element selected from the group consisting of p-Stat 1, p-Stat 3, and p-Stat 5 in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual has an intermediate or high risk cytogenetics, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to H2O2, b) determining an activation level of at least one activatable element selected from the group consisting of p-Akt, and p-Slp 76 in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual has an intermediate or high risk cytogenetics, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to FLT3L or SCF, b) determining an activation level of at least one activatable element of p-Akt in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells. In some embodiments, classifying further comprises identifying a difference in kinetics of said activation level.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual has an intermediate or high risk cytogenetics, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to SDF-1α, b) determining an activation level of p-CREB in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual has an intermediate or high risk cytogenetics, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to FLT3L or PMA b) determining an activation level of p-CREB in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells. In some embodiments, the individual has a FLT3 mutation. In some embodiments, classifying further comprises identifying a difference in kinetics of said activation level.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual has an intermediate or high risk cytogenetics, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to Ara-C, Etoposide and Daunorubicin, b) determining an activation level of at least one activatable element selected from the group consisting of p-Chk2, and p-PARP in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual has an intermediate or high risk cytogenetics, said methods comprising the steps of: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to FLT3L, b) determining an activation level of p-Erk in one or more cells from said individual, and c) classifying said one or more hematopoietic cells based on said activation levels of said activatable element; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells. In some embodiments, classifying further comprises identifying a difference in kinetics of said activation level.

In some embodiments, the invention provides methods of diagnosing, prognosing, determining progression, predicting a response to a treatment or choosing a treatment for acute leukemia, myelodysplastic syndrome or myeloproliferative neoplasms in an individual, said methods comprising the steps of: (1) classifying one or more hematopoietic cells associated with acute leukemia, myelodysplastic syndrome or myeloproliferative neoplasms in said individual by a method comprising: a) determining an activation level of at least two activatable elements in the presence of a modulator as listed in FIG. 36, and b) classifying said one or more hematopoietic cells based on said activation levels of said activatable elements; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells. In some embodiments, at least one of the activatable elements is an activatable element from an apoptosis pathway.

In some embodiments, the invention provides methods of diagnosing, prognosing, determining progression, predicting a response to a treatment or choosing a treatment for acute leukemia, myelodysplastic syndrome or myeloproliferative neoplasms in an individual, said methods comprising the steps of: (1) classifying one or more hematopoietic cells associated with acute leukemia, myelodysplastic syndrome or myeloproliferative neoplasms in said individual by a method comprising: a) determining an activation level of at least three activatable elements in the presence of a modulator as listed in FIG. 36, and b) classifying said one or more hematopoietic cells based on said activation levels of said activatable elements; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells. In some embodiments, at least one of the activatable elements is an activatable element from an apoptosis pathway. In some embodiments, at least two of the activatable elements are activatable elements from an apoptosis pathway. In some embodiments, at least two of the activatable elements are activatable elements from an apoptosis pathway and the third activatable element is p-Erk 1/2 in the presence of PMA.

In some embodiments, the invention provides methods of diagnosing, prognosing, determining progression, predicting a response to a treatment or choosing a treatment for acute leukemia, myelodysplastic syndrome or myeloproliferative neoplasms in an individual, said methods comprising the steps of: (1) classifying one or more hematopoietic cells associated with acute leukemia, myelodysplastic syndrome or myeloproliferative neoplasms in said individual by a method comprising: a) determining an activation level of at least four activatable elements in the presence of a modulator as listed in FIG. 36, and b) classifying said one or more hematopoietic cells based on said activation levels of said activatable elements; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells. In some embodiments, at least one of the activatable elements is an activatable element from an apoptosis pathway. In some embodiments, at least two of the activatable elements are activatable elements from an apoptosis pathway.

In some embodiments, the invention provides methods of diagnosing, prognosing, determining progression, predicting a response to a treatment or choosing a treatment for acute leukemia, myelodysplastic syndrome or myeloproliferative neoplasms in an individual, wherein said individual has a FLT3 mutation, the method comprising: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to G-CSF, IL-6, IFNα, GM-CSF, IFNg, IL-10, or IL-27, b) determining an activation level of p-Stat 1, p-Stat 3 or p-Stat 5 in one or more cells from said individual, and c) classifying said one or more hematopoietic cells based on said activation levels; and (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells. In some embodiments, classifying further comprises identifying a difference in kinetics of said activation level.

In some embodiments, the invention provides methods for predicting response to a treatment for AML, MDS or MPN, wherein the positive predictive value (PPV) is higher than 60, 70, 80, 90, 95, or 99.9%. In some embodiments, the invention provides methods for predicting response to a treatment for AML, MDS or MPN, wherein the PPV is equal or higher than 95%. In some embodiments, the invention provides methods for predicting response to a treatment for AML, MDS or MPN, wherein the negative predictive value (NPV) is higher than 60, 70, 80, 90, 95, or 99.9%. In some embodiments, the invention provides methods for predicting response to a treatment for AML, MDS or MPN, wherein the NPV is higher than 85%.

In some embodiments, the invention provides methods for predicting risk of relapse at 2 years, wherein the PPV is higher than 60, 70, 80, 90, 95, or 99.9%. In some embodiments, the invention provides methods for predicting risk of relapse at 2 years, wherein the PPV is equal or higher than 95%. In some embodiments, the invention provides methods for predicting risk of relapse at 2 years, wherein the NPV is higher than 60, 70, 80, 90, 95, or 99.9%. In some embodiments, the invention provides methods for predicting risk of relapse at 2 years, wherein the NPV is higher than 80%. In some embodiments, the invention provides methods for predicting risk of relapse at 5 years, wherein the PPV is higher than 60, 70, 80, 90, 95, or 99.9%. In some embodiments, the invention provides methods for predicting risk of relapse at 5 years, wherein the PPV is equal or higher than 95%. In some embodiments, the invention provides methods for predicting risk of relapse at 5 years, wherein the NPV is higher than 60, 70, 80, 90, 95, or 99.9%. In some embodiments, the invention provides methods for predicting risk of relapse at 5 years, wherein the NPV is higher than 80%. In some embodiments, the invention provides methods for predicting risk of relapse at 10 years, wherein the PPV is higher than 60, 70, 80, 90, 95, or 99.9%. In some embodiments, the invention provides methods for predicting risk of relapse at 10 years, wherein the PPV is equal or higher than 95%. In some embodiments, the invention provides methods for predicting risk of relapse at 10 years, wherein the NPV is higher than 60, 70, 80, 90, 95, or 99.9%. In some embodiments, the invention provides methods for predicting risk of relapse at 10 years, wherein the NPV is higher than 80%.

In some embodiments, the p value in the analysis of the methods described herein is below 0.05, 04, 0.03, 0.02, 0.01, 0.009, 0.005, or 0.001. In some embodiments, the p value is below 0.001. Thus in some embodiments, the invention provides methods for diagnosing, prognosing, determining progression or predicting response for treatment of AML, MDS or MPN wherein the p value is below 0.05, 04, 0.03, 0.02, 0.01, 0.009, 0.005, or 0.001. In some embodiments, the p value is below 0.001. In some embodiments, the invention provides methods for diagnosing, prognosing, determining progression or predicting response for treatment of AML, MDS or MPN wherein the AUC value is higher than 0.5, 0.6, 07, 0.8 or 0.9. In some embodiments, the invention provides methods for diagnosing, prognosing, determining progression or predicting response for treatment of AML, MDS or MPN wherein the AUC value is higher than 0.7. In some embodiments, the invention provides methods for diagnosing, prognosing, determining progression or predicting response for treatment of AML, MDS or MPN wherein the AUC value is higher than 0.8. In some embodiments, the invention provides methods for diagnosing, prognosing, determining progression or predicting response for treatment of AML, MDS or MPN wherein the AUC value is higher than 0.9.

Another method of the present invention is a method for determining the prognosis and therapeutic selection for an individual with myelodysplasia or MDS. Using the signaling nodes and methodology described herein, multiparametric flow cytometry could separate a patient into one of five groups consisting of: "AML-like", where a patient displays signaling biology that is similar to that seen in acute myelogenous leukemia (AML) requiring intensive therapy, "Epo-Responsive", where a patient's bone marrow or potentially peripheral blood, shows signaling biology that corresponds to either in-vivo or in-vitro sensitivity to erythropoietin, "Lenalidomide responsive", where a patient's bone marrow or potentially peripheral blood, shows signaling biology that corresponds to either in-vivo or in-vitro sensitivity to Lenalidomide, "Auto-immune", where a patient's bone marrow or potentially peripheral blood, shows signaling biology that corresponds to sensitivity to cyclosporine A (CSA) and anti-thymocyte globulin (ATG).

In those cases where an individual is classified as "AML-like", the individual's blood or marrow sample could reveal signaling biology that corresponds to either in-vivo or in-vitro sensitivity to cytarabine or to a class of drugs including but not limited to direct drug resistance modulators, anti-Bcl-2 or pro-apoptotic drugs, proteosome inhibitors, DNA methyl transferase inhibitors, histone deacetylase inhibitors, anti-angiogenic drugs, farnesyl transferase inhibitors, FLt3 ligand inhibitors, or ribonucleotide reductase inhibitors.

In some embodiments of the invention, different gating strategies can be used in order to analyze only blasts in the sample of mixed population after treatment with the modulator. These gating strategies can be based on the presence of one or more specific surface marker expressed on each cell type. In some embodiments, the first gate eliminates cell doublets so that the user can focus on singlets. The following gate can differentiate between dead cells and live cells and subsequent gating of live cells classifies them into blasts, monocytes and lymphocytes. A clear comparison can be carried out to study the effect of potential modulators, such as G-SCF on activatable elements in: ungated samples, blasts, monocytes, granulocytes and lymphocytes by using two-dimensional contour plot representations of Stat5 and Stat3 phosphorylation (x and Y axis) of patient samples. The level of basal phosphorylation and the change in phosphorylation in both Stat3 and Stat5 phosphorylation in response to G-CSF can be compared. G-CSF increases both STAT3 and STAT5 phosphorylation and this dual signaling can occur concurrently (subpopulations with increases in both pSTAT 3 and pSTAT5) or individually (subpopulations with either an increase in phospho pSTAT 3 or pSTAT5 alone). The advantage of gating is to get a clearer picture and more precise results of the effect of various activatable elements on blasts.

Figure 5:
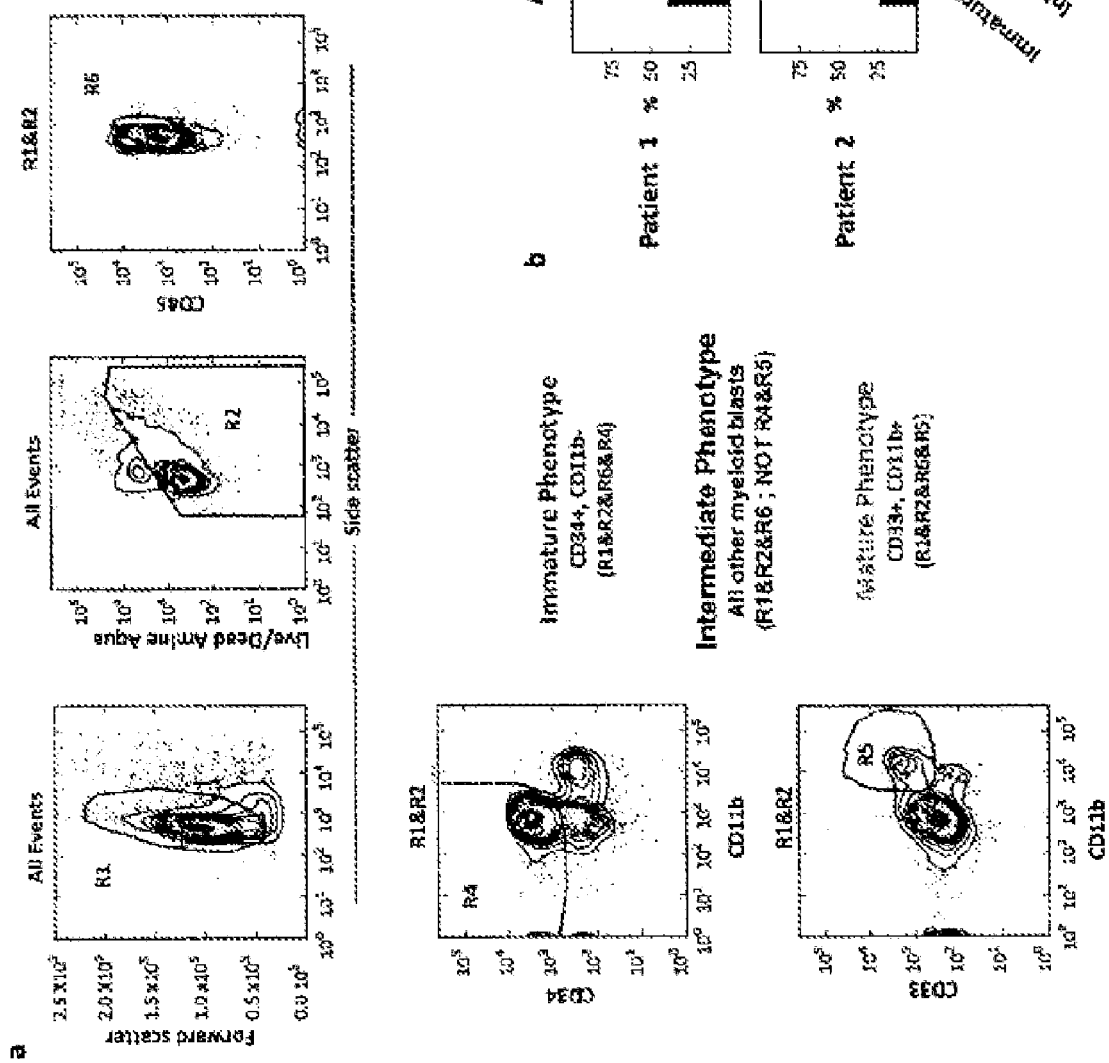
FIG. 5a depicts a gating analysis to define leukemic blast population.
FIG. 5b shows that cell surface markers did not identify resistance-associated myeloblasts subpopulations.

In some embodiments, a gate is established after learning from a responsive subpopulation. That is, a gate is developed from one data set. This gate can then be applied retrospectively or prospectively to other data sets (See FIGS. 5, 6, and 7). The cells in this gate can be used for the diagnosis or prognosis of a condition. The cells in this gate can also be used to predict response to a treatment or for treatment selection. The mere presence of cells in this gate may be indicative of a diagnosis, prognosis, or a response to treatment. In some embodiments, the presence of cells in this gate at a number higher than a threshold number may be indicative of a diagnosis, prognosis, or a response to treatment.

Figure 2A:
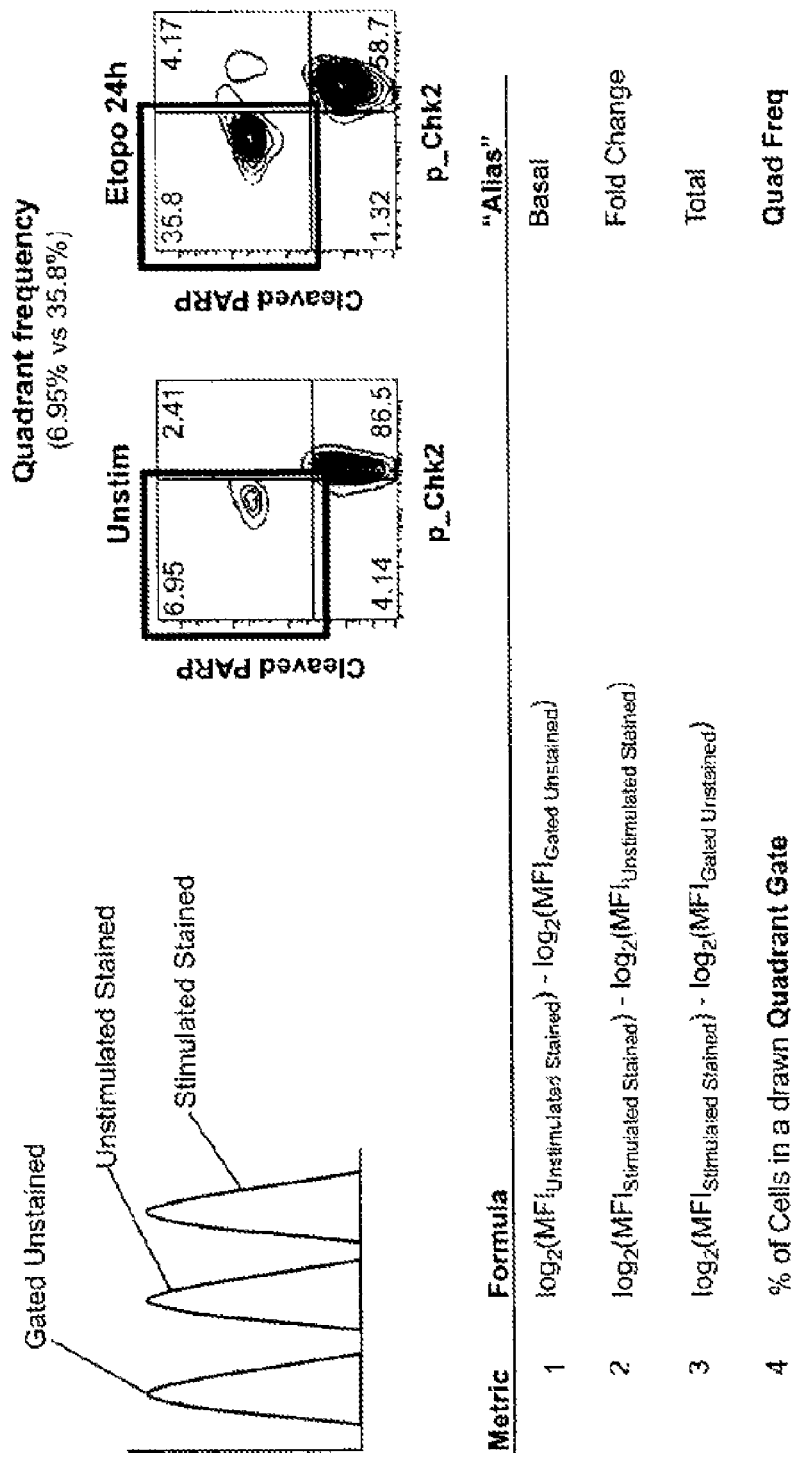
FIG. 2A shows the use of four metrics used to analyze data from cells that may be subject to a disease, such as AML. For these metrics the median (mean can be used as well) fluorescence intensity (MFI) was computed for the cells in one of the gated populations measured under various conditions of staining and stimulation. For example, the "basal" metric is calculated by subtracting the MFI of cells in the absence of a stimulant and stain (autofluorescence) from the MFI for cell measured in the absence of a stimulant (autofluorescence) ($\log_2(\mathrm{MFI}_{Unstimulated\ Stained})-\log_2(\mathrm{MFI}_{Gated\ Unstained})$). The "total phospho" metric is calculated by measuring the fluorescence of a cell that has been stimulated with a modulator and stained with a labeled antibody and then subtracting the value for autofluorescence ($\log_2(MFI_{stimulated\ Stained})-\log_2(MFI_{Gated\ Unstained})$. The "fold change" metric is the measurement of the fluorescence of a cell that has been stimulated with a modulator and stained with a labeled antibody and then subtracting the value for unstimulated stained cells ($\log_2(MFI_{stimulated\ Stained})-\log_2(MFI_{Unstimulated\ Stained})$. The "quadrant frequency" metric is the percentage of cells in each quadrant of the contour plot.
Figure 2B:
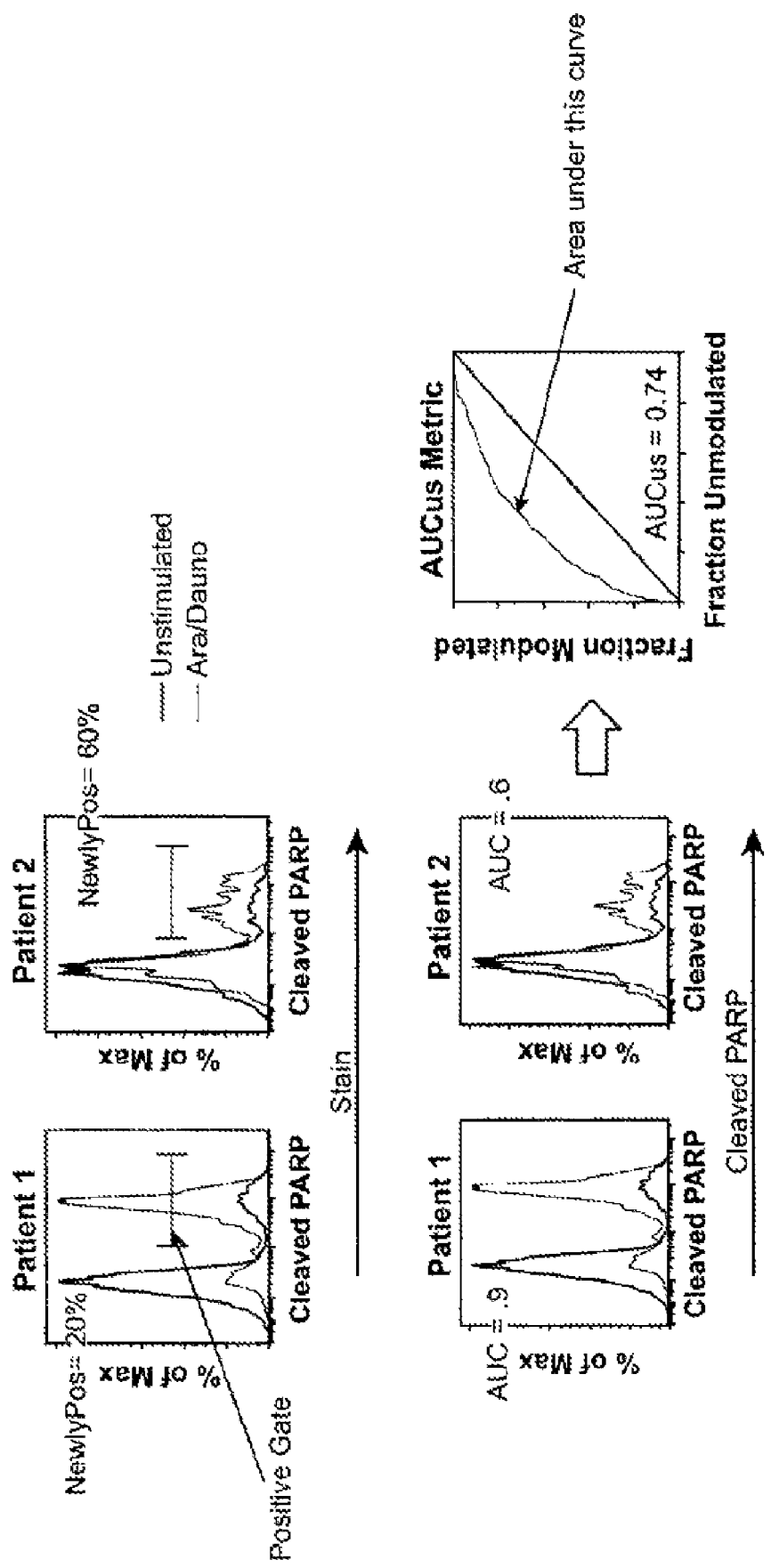
FIG. 2B shows that additional metrics can also be derived directly from the distribution of cell for a protein in a gated population for various conditions. NewlyPos=% of newly positive cells by modulator, based on a positive gate for a stain. AUC unstim=Area under the curve of frequency of un-modulated cells and modulated cells for a stain. NewlyPos: % Positive Cells modulated−% Positive Cellsunmodulated.

Some methods of analysis, also called metrics are: 1) measuring the difference in the log of the median fluorescence value between an unstimulated fluorochrome-antibody stained sample and a sample that has not been treated with a stimulant or stained ($\log(\mathrm{MFI}_{Unstimulated\ Stained})-\log(\mathrm{MFI}_{Gated\ Unstained})$), 2) measuring the difference in the log of the median fluorescence value between a stimulated fluorochrome-antibody stained sample and a sample that has not been treated with a stimulant or stained ($\log(\mathrm{MFI}_{Stimulated\ Stained})-\log(\mathrm{MFI}_{Gated\ Unstained})$), 3) Measuring the change between the stimulated fluorochrome-antibody stained sample and the unstimulated fluorochrome-antibody stained sample $\log(\mathrm{MFI}_{Stimulated\ Stained})-\log(\mathrm{MFI}_{Unstimulated\ Stained})$, also called "fold change in median fluorescence intensity", 4) Measuring the percentage of cells in a Quadrant Gate of a contour plot which measures multiple populations in one or more dimension 5) measuring MFI of phosphor positive population to obtain percentage positivity above the background; and 6) use of multimodality and spread metrics for large sample population and for subpopulation analysis. Other metrics used to analyze data are population frequency metrics measuring the frequency of cells with a described property such as cells positive for cleaved PARP (% PARP+), or cells positive for p-S6 and p-Akt (See FIG. 2B). Similarly, measurements examining the changes in the frequencies of cells may be applied such as the Change in % PARP+ which would measure the % PARP+$_{Stimulated\ Stained}$-% PARP+$_{Unstimulated\ Stained}$. The AUC$_{unstim}$ metric also measures changes in population frequencies measuring the frequency of cells to become positive compared to an unstimulated condition (FIG. 2B). The metrics described in FIG. 2B can be use to measure apoptosis. For example, these metrics can be applied to cleaved Caspase-3 and Caspase-8, e.g., Change in % Cleaved Caspase-3 or Cleaved Caspase-8.

Other possible metrics include third-color analysis (3D plots); percentage positive and relative expression of various markers; clinical analysis on an individual patient basis for various parameters, including, but not limited to age, race, cytogenetics, mutational status, blast percentage, CD34+ percentage, time of relapse, survival, etc. See FIG. 2. In alternative embodiments, there are other ways of analyzing data, such as third color analysis (3D plots), which can be similar to Cytobank 2D, plus third D in color.

Disease Conditions

The methods of the invention are applicable to any condition in an individual involving, indicated by, and/or arising from, in whole or in part, altered physiological status in a cell. The term "physiological status" includes mechanical, physical, and biochemical functions in a cell. In some embodiments, the physiological status of a cell is determined by measuring characteristics of cellular components of a cellular pathway. Cellular pathways are well known in the art. In some embodiments the cellular pathway is a signaling pathway. Signaling pathways are also well known in the art (see, e.g., Hunter T., Cell 100(1): 113-27 (2000); Cell Signaling Technology, Inc., 2002 Catalogue, Pathway Diagrams pgs. 232-253). A condition involving or characterized by altered physiological status may be readily identified, for example, by determining the state in a cell of one or more activatable elements, as taught herein.

In some embodiments, the present invention is directed to methods for classifying one or more cells in a sample derived from an individual having or suspected of having a condition. Example conditions include AML, MDS, or MPN. In some embodiments, the invention allows for identification of prognostically and therapeutically relevant subgroups of the conditions and prediction of the clinical course of an individual. In some embodiments, the invention provides methods of classifying a cell according to the activation levels of one or more activatable elements in a cell from an individual having or suspected of having a condition. In some embodiments, the classification includes classifying the cell as a cell that is correlated with a clinical outcome. The clinical outcome can be the prognosis and/or diagnosis of a condition, and/or staging or grading of a condition. In some embodiments, the classifying of the cell includes classifying the cell as a cell that is correlated with a patient response to a treatment. In some embodiments, the classifying of the cell includes classifying the cell as a cell that is correlated with minimal residual disease or emerging resistance.

Activatable Elements

The methods and compositions of the invention may be employed to examine and profile the status of any activatable element in a cellular pathway, or collections of such activatable elements. Single or multiple distinct pathways may be profiled (sequentially or simultaneously), or subsets of activatable elements within a single pathway or across multiple pathways may be examined (again, sequentially or simultaneously). In some embodiments, apoptosis, signaling, cell cycle and/or DNA damage pathways are characterized in order to classify one or more cells in an individual. The characterization of multiple pathways can reveal operative pathways in a condition that can then be used to classify one or more cells in an individual. In some embodiments, the classification includes classifying the cell as a cell that is correlated with a clinical outcome. The clinical outcome can be the prognosis and/or diagnosis of a condition, and/or staging or grading of a condition. In some embodiments, the classifying of the cell includes classifying the cell as a cell that is correlated with a patient response to a treatment. In some embodiments, the classifying of the cell includes classifying the cell as a cell that is correlated with minimal residual disease or emerging resistance.

As will be appreciated by those in the art, a wide variety of activation events can find use in the present invention. In general, the basic requirement is that the activation results in a change in the activatable protein that is detectable by some indication (termed an "activation state indicator"), preferably by altered binding of a labeled binding element or by changes in detectable biological activities (e.g., the activated state has an enzymatic activity which can be measured and compared to a lack of activity in the non-activated state). What is important is to differentiate, using detectable events or moieties, between two or more activation states (e.g. "off" and "on").

The activation state of an individual activatable element is either in the on or off state. As an illustrative example, and without intending to be limited to any theory, an individual phosphorylatable site on a protein can activate or deactivate the protein. Additionally, phosphorylation of an adapter protein may promote its interaction with other components/proteins of distinct cellular signaling pathways. The terms "on" and "off," when applied to an activatable element that is a part of a cellular constituent, are used here to describe the state of the activatable element, and not the overall state of the cellular constituent of which it is a part. Typically, a cell possesses a plurality of a particular protein or other constituent with a particular activatable element and this plurality of proteins or constituents usually has some proteins or constituents whose individual activatable element is in the on state and other proteins or constituents whose individual activatable element is in the off state. Since the activation state of each activatable element is measured through the use of a binding element that recognizes a specific activation state, only those activatable elements in the specific activation state recognized by the binding element, representing some fraction of the total number of activatable elements, will be bound by the binding element to generate a measurable signal. The measurable signal corresponding to the summation of individual activatable elements of a particular type that are activated in a single cell is the "activation level" for that activatable element in that cell. The measurable signal can be produced by the binding element and/or the activatable element. The measurable signal can be produced by the activatable element after the activatable element has been dissociated from the binding element.

Activation levels for a particular activatable element may vary among individual cells so that when a plurality of cells is analyzed, the activation levels follow a distribution. The distribution may be a normal distribution, also known as a Gaussian distribution, or it may be of another type. Different populations of cells may have different distributions of activation levels that can then serve to distinguish between the populations.

In some embodiments, the basis for classifying cells is that the distribution of activation levels for one or more specific activatable elements will differ among different phenotypes. A certain activation level, or more typically a range of activation levels for one or more activatable elements seen in a cell or a population of cells, is indicative that that cell or population of cells belongs to a distinctive phenotype. Other measurements, such as cellular levels (e.g., expression levels) of biomolecules that may not contain activatable elements, may also be used to classify cells in addition to activation levels of activatable elements; it will be appreciated that these levels also will follow a distribution, similar to activatable elements. Thus, the activation level or levels of one or more activatable elements, optionally in conjunction with levels of one or more levels of biomolecules that may or may not contain activatable elements, of cell or a population of cells may be used to classify a cell or a population of cells into a class. Once the activation level of intracellular activatable elements of individual single cells is known they can be placed into one or more classes, e.g., a class that corresponds to a phenotype. A class encompasses a class of cells wherein every cell has the same or substantially the same known activation level, or range of activation levels, of one or more intracellular activatable elements. For example, if the activation levels of five intracellular activatable elements are analyzed, predefined classes of cells that encompass one or more of the intracellular activatable elements can be constructed based on the activation level, or ranges of the activation levels, of each of these five elements. It is understood that activation levels can exist as a distribution and that an activation level of a particular element used to classify a cell may be a particular point on the distribution but more typically may be a portion of the distribution.

In some embodiments, the basis for classifying cells may use the position of a cell in a contour or density plot. The contour or density plot represents the number of cells that share a characteristic such as the activation level of activatable proteins in response to a modulator. For example, when referring to activation levels of activatable elements in response to one or more modulators, normal individuals and patients with a condition might show populations with increased activation levels in response to the one or more modulators. However, the number of cells that have a specific activation level (e.g. specific amount of an activatable element) might be different between normal individuals and patients with a condition. Thus, a cell can be classified according to its location within a given region in the contour or density plot. In other embodiments, the basis for classifying cells may use a series of population clusters whose centers, centroids, boundaries, relative positions describe the state of a cell, the diagnosis or prognosis of a patient, selection of treatment, or predicting response to treatment or to a combination of treatments, or long term outcome.

In some embodiments, the basis for classifying cells may use an N-dimensional Eigen map that describe the state of a cell, the diagnosis or prognosis of a patient, selection of treatment, or predicting response to treatment or to a combination of treatments, or long term outcome.

In other embodiments, the basis for classifying cells may use a Bayesian inference network of activatable elements interaction capabilities that together, or in part, describe the state of a cell, the diagnosis or prognosis of a patient, selection of treatment, or predicting response to treatment or to a combination of treatments, or long term outcome. See U.S. publication no. 2007/0009923 entitled Use of Bayesian Networks for Modeling Signaling Systems, incorporated herein by reference on its entirety.

In addition to activation levels of intracellular activatable elements, levels of intracellular or extracellular biomolecules, e.g., proteins, may be used alone or in combination with activation states of activatable elements to classify cells. Further, additional cellular elements, e.g., biomolecules or molecular complexes such as RNA, DNA, carbohydrates, metabolites, and the like, may be used in conjunction with activatable states or expression levels in the classification of cells encompassed here.

In some embodiments, cellular redox signaling nodes are analyzed for a change in activation level. Reactive oxygen species (ROS) are involved in a variety of different cellular processes ranging from apoptosis and necrosis to cell proliferation and carcinogenesis. ROS can modify many intracellular signaling pathways including protein phosphatases, protein kinases, and transcription factors. This activity may indicate that the majority of the effects of ROS are through their actions on signaling pathways rather than via non-specific damage of macromolecules. The exact mechanisms by which redox status induces cells to proliferate or to die, and how oxidative stress can lead to processes evoking tumor formation are still under investigation. See Mates, J M et al., Arch Toxicol. 2008 May:82(5):271-2; Galaris D., et al., Cancer Lett. 2008 Jul. 18; 266(1)21-9.

Reactive oxygen species can be measured. One example technique is by flow cytometry. See Chang et al., Lymphocyte proliferation modulated by glutamine: involved in the endogenous redox reaction; Clin Exp Immunol 1999 September; 117(3): 482-488. Redox potential can be evaluated by means of an ROS indicator, one example being 2',7'-dichlorofluorescein-diacetate (DCFH-DA) which is added to the cells at an exemplary time and temperature, such as 37° C. for 15 minutes. DCF peroxidation can be measured using flow cytometry. See Yang K D, Shaio M F. Hydroxyl radicals as an early signal involved in phorbol ester-induced monocyte differentiation of HL60 cells. Biochem Biophys Res Commun. 1994; 200:1650-7 and Wang J F, Jerrells T R, Spitzer J J. Decreased production of reactive oxygen intermediates is an early event during in vitro apoptosis of rat thymocytes. Free Radic Biol Med. 1996; 20:533-42.

In some embodiments, other characteristics that affect the status of a cellular constituent may also be used to classify a cell. Examples include the translocation of biomolecules or changes in their turnover rates and the formation and disassociation of complexes of biomolecule. Such complexes can include multi-protein complexes, multi-lipid complexes, homo- or hetero-dimers or oligomers, and combinations thereof. Other characteristics include proteolytic cleavage, e.g. from exposure of a cell to an extracellular protease or from the intracellular proteolytic cleavage of a biomolecule.

In some embodiments, cellular pH is analyzed. See June, C H and Moore, and J S, Curr Protoc Immulon, 2004 December; Chapter 5:Unit 5.5; Leyval, D et al., Flow cytometry for the intracellular pH measurement of glutamate producing Corynebacterium glutamicum, Journal of Microbiological Methods, Volume 29, Issue 2, 1 May 1997, Pages 121-127; Weider, E D, et al., Measurement of intracellular pH using flow cytometry with carboxy-SNARF-1. Cytometry, 1993 November; 14(8):916-21; and Valli, M, et al., Intracellular pH Distribution in *Saccharomyces cerevisiae* Cell Populations, Analyzed by Flow Cytometry, Applied and Environmental Microbiology, March 2005, p. 1515-1521, Vol. 71, No. 3.

In some embodiments, the activatable element is the phosphorylation of immunoreceptor tyrosine-based inhibitory motif (ITIM). An immunoreceptor tyrosine-based inhibition motif (ITIM), is a conserved sequence of amino acids (S/I/V/LxYxxI/V/L) that is found in the cytoplasmic tails of many inhibitory receptors of the immune system. After ITIM-possessing inhibitory receptors interact with their ligand, their ITIM motif becomes phosphorylated by enzymes of the Src family of kinases, allowing them to recruit other enzymes such as the phosphotyrosine phosphatases SHP-1 and SHP-2, or the inositol-phosphatase called SHIP. These phosphatases decrease the activation of molecules involved in cell signaling. See Barrow A, Trowsdale J (2006). "You say ITAM and I say ITIM, let's call the whole thing off: the ambiguity of immunoreceptor signalling". Eur J Immunol 36 (7): 1646-53. When phosphorylated, these phospho-tyrosine residues provide docking sites for the Shps which may result in transmission of inhibitory signals and effect the signaling of neighboring membrane receptor complexes (Paul et al., Blood (2000 96:483).

ITIMs can be analyzed by flow cytometry.

Additional elements may also be used to classify a cell, such as the expression level of extracellular or intracellular markers, nuclear antigens, enzymatic activity, protein expression and localization, cell cycle analysis, chromosomal analysis, cell volume, and morphological characteristics like granularity and size of nucleus or other distinguishing characteristics. For example, B cells can be further subdivided based on the expression of cell surface markers such as CD19, CD20, CD22 or CD23.

Alternatively, predefined classes of cells can be aggregated or grouped based upon shared characteristics that may include inclusion in one or more additional predefined class or the presence of extracellular or intracellular markers, similar gene expression profile, nuclear antigens, enzymatic activity, protein expression and localization, cell cycle analysis, chromosomal analysis, cell volume, and morphological characteristics like granularity and size of nucleus or other distinguishing cellular characteristics.

In some embodiments, the physiological status of one or more cells is determined by examining and profiling the activation level of one or more activatable elements in a cellular pathway. In some embodiments, a cell is classified according to the activation level of a plurality of activatable elements. In some embodiments, a hematopoietic cell is classified according to the activation levels of a plurality of activatable elements. In some embodiments, 1, 2, 3, 4, 5, 6, 7, 8, 9, 10 or more activatable elements may be analyzed in a cell signaling pathway. In some embodiments, the activation levels of one or more activatable elements of a hematopoietic cell are correlated with a condition. In some embodiments, the activation levels of one or more activatable elements of a hematopoietic cell are correlated with a neoplastic or hematopoietic condition as described herein. Examples of hematopoietic cells include, but are not limited to, AML, MDS or MPN cells.

In some embodiments, the activation level of one or more activatable elements in single cells in the sample is determined. Cellular constituents that may include activatable elements include without limitation proteins, carbohydrates, lipids, nucleic acids and metabolites. The activatable element may be a portion of the cellular constituent, for example, an amino acid residue in a protein that may undergo phosphorylation, or it may be the cellular constituent itself, for example, a protein that is activated by translocation, change in conformation (due to, e.g., change in pH or ion concentration), by proteolytic cleavage, degradation through ubiquitination and the like. Upon activation, a change occurs to the activatable element, such as covalent modification of the activatable element (e.g., binding of a molecule or group to the activatable element, such as phosphorylation) or a conformational change. Such changes generally contribute to changes in particular biological, biochemical, or physical properties of the cellular constituent that contains the activatable element. The state of the cellular constituent that contains the activatable element is determined to some degree, though not necessarily completely, by the state of a particular activatable element of the cellular constituent. For example, a protein may have multiple activatable elements, and the particular activation states of these elements may overall determine the activation state of the protein; the state of a single activatable element is not necessarily determinative. Additional factors, such as the binding of other proteins, pH, ion concentration, interaction with other cellular constituents, and the like, can also affect the state of the cellular constituent.

In some embodiments, the activation levels of a plurality of intracellular activatable elements in single cells are determined In some embodiments, at least about 2, 3, 4, 5, 6, 7, 8, 9, 10 or more than 10 intracellular activatable elements are determined.

Activation states of activatable elements may result from chemical additions or modifications of biomolecules and include biochemical processes such as glycosylation, phosphorylation, acetylation, methylation, biotinylation, glutamylation, glycylation, hydroxylation, isomerization, prenylation, myristoylation, lipoylation, phosphopantetheinylation, sulfation, ISGylation, nitrosylation, palmitoylation, SUMOylation, ubiquitination, neddylation, citrullination, amidation, and disulfide bond formation, disulfide bond reduction. Other possible chemical additions or modifications of biomolecules include the formation of protein carbonyls, direct modifications of protein side chains, such as o-tyrosine, chloro-, nitrotyrosine, and dityrosine, and protein adducts derived from reactions with carbohydrate and lipid derivatives. Other modifications may be non-covalent, such as binding of a ligand or binding of an allosteric modulator.

One example of a covalent modification is the substitution of a phosphate group for a hydroxyl group in the side chain of an amino acid (phosphorylation). A wide variety of proteins are known that recognize specific protein substrates and catalyze the phosphorylation of serine, threonine, or tyrosine residues on their protein substrates. Such proteins are generally termed "kinases." Substrate proteins that are capable of being phosphorylated are often referred to as phosphoproteins (after phosphorylation). Once phosphorylated, a substrate phosphoprotein may have its phosphorylated residue converted back to a hydroxyl one by the action of a protein phosphatase that specifically recognizes the substrate protein. Protein phosphatases catalyze the replacement of phosphate groups by hydroxyl groups on serine, threonine, or tyrosine residues. Through the action of kinases and phosphatases a protein may be reversibly phosphorylated on a multiplicity of residues and its activity may be regulated thereby. Thus, the presence or absence of one or more phosphate groups in an activatable protein is a preferred readout in the present invention.

Another example of a covalent modification of an activatable protein is the acetylation of histones. Through the activity of various acetylases and deacetylases the DNA binding function of histone proteins is tightly regulated. Furthermore, histone acetylation and histone deactelyation have been linked with malignant progression. See Nature, 2004 May 27; 429(6990): 457-63.

Another form of activation involves cleavage of the activatable element. For example, one form of protein regulation involves proteolytic cleavage of a peptide bond. While random or misdirected proteolytic cleavage may be detrimental to the activity of a protein, many proteins are activated by the action of proteases that recognize and cleave specific peptide bonds. Many proteins derive from precursor proteins, or proproteins, which give rise to a mature isoform of the protein following proteolytic cleavage of specific peptide bonds. Many growth factors are synthesized and processed in this manner, with a mature isoform of the protein typically possessing a biological activity not exhibited by the precursor form. Many enzymes are also synthesized and processed in this manner, with a mature isoform of the protein typically being enzymatically active, and the precursor form of the protein being enzymatically inactive. This type of regulation is generally not reversible. Accordingly, to inhibit the activity of a proteolytically activated protein, mechanisms other than "reattachment" must be used. For example, many proteolytically activated proteins are relatively short-lived proteins, and their turnover effectively results in deactivation of the signal. Inhibitors may also be used. Among the enzymes that are proteolytically activated are serine and cysteine proteases, including cathepsins and caspases respectively.

In one embodiment, the activatable enzyme is a caspase. The caspases are an important class of proteases that mediate programmed cell death (referred to in the art as "apoptosis"). Caspases are constitutively present in most cells, residing in the cytosol as a single chain proenzyme. These are activated to fully functional proteases by a first proteolytic cleavage to divide the chain into large and small caspase subunits and a second cleavage to remove the N-terminal domain. The subunits assemble into a tetramer with two active sites (Green, Cell 94:695-698, 1998). Many other proteolytically activated enzymes, known in the art as "zymogens," also find use in the instant invention as activatable elements.

In an alternative embodiment the activation of the activatable element involves prenylation of the element. By "prenylation", and grammatical equivalents used herein, is meant the addition of any lipid group to the element. Common examples of prenylation include the addition of farnesyl groups, geranylgeranyl groups, myristoylation and palmitoylation. In general these groups are attached via thioether linkages to the activatable element, although other attachments may be used.

In alternative embodiment, activation of the activatable element is detected as intermolecular clustering of the activatable element. By "clustering" or "multimerization", and grammatical equivalents used herein, is meant any reversible or irreversible association of one or more signal transduction elements. Clusters can be made up of 2, 3, 4, etc., elements. Clusters of two elements are termed dimers. Clusters of 3 or more elements are generally termed oligomers, with individual numbers of clusters having their own designation; for example, a cluster of 3 elements is a trimer, a cluster of 4 elements is a tetramer, etc.

Clusters can be made up of identical elements or different elements. Clusters of identical elements are termed "homo" dimers, while clusters of different elements are termed "hetero" clusters. Accordingly, a cluster can be a homodimer, as is the case for the $\beta_2$-adrenergic receptor.

Alternatively, a cluster can be a heterodimer, as is the case for $GABA_{B-R}$. In other embodiments, the cluster is a homotrimer, as in the case of TNFα, or a heterotrimer such the one formed by membrane-bound and soluble CD95 to modulate apoptosis. In further embodiments the cluster is a homo-oligomer, as in the case of Thyrotropin releasing hormone receptor, or a hetero-oligomer, as in the case of TGFβ1.

In a preferred embodiment, the activation or signaling potential of elements is mediated by clustering, irrespective of the actual mechanism by which the element's clustering is induced. For example, elements can be activated to cluster a) as membrane bound receptors by binding to ligands (ligands including both naturally occurring and synthetic ligands), b) as membrane bound receptors by binding to other surface molecules, or c) as intracellular (non-membrane bound) receptors binding to ligands.

In some embodiments, the activatable element is a protein. Examples of proteins that may include activatable elements include, but are not limited to kinases, phosphatases, lipid signaling molecules, adaptor/scaffold proteins, cytokines, cytokine regulators, ubiquitination enzymes, adhesion molecules, cytoskeletal/contractile proteins, heterotrimeric G proteins, small molecular weight GTPases, guanine nucleotide exchange factors, GTPase activating proteins, caspases, proteins involved in apoptosis, cell cycle regulators, molecular chaperones, metabolic enzymes, vesicular transport proteins, hydroxylases, isomerases, deacetylases, methylases, demethylases, tumor suppressor genes, proteases, ion channels, molecular transporters, transcription factors/DNA binding factors, regulators of transcription, and regulators of translation. Examples of activatable elements, activation states and methods of determining the activation level of activatable elements are described in US Publication Number 20060073474 entitled "Methods and compositions for detecting the activation state of multiple proteins in single cells" and US Publication Number 20050112700 entitled "Methods and compositions for risk stratification" the content of which are incorporate here by reference. See also U.S.

Ser. Nos. 61/048,886; 61/048,920; and Shulz et al., Current Protocols in Immunology 2007, 78:8.17.1-20.

In some embodiments, the protein is selected from the group consisting of HER receptors, PDGF receptors, Kit receptor, FGF receptors, Eph receptors, Trk receptors, IGF receptors, Insulin receptor, Met receptor, Ret, VEGF receptors, TIE1, TIE2, FAK, Jak1, Jak2, Jak3, Tyk2, Src, Lyn, Fyn, Lck, Fgr, Yes, Csk, Abl, Btk, ZAP70, Syk, IRAKs, cRaf, ARaf, BRAF, Mos, Lim kinase, ILK, Tpl, ALK, TGFβ receptors, BMP receptors, MEKKs, ASK, MLKs, DLK, PAKs, Mek 1, Mek 2, MKK3/6, MKK4/7, ASK1, Cot, NIK, Bub, Myt 1, Wee1, Casein kinases, PDK1, SGK1, SGK2, SGK3, Akt1, Akt2, Akt3, p90Rsks, p70S6 Kinase, Prks, PKCs, PKAs, ROCK 1, ROCK 2, Auroras, CaMKs, MNKs, AMPKs, MELK, MARKs, Chk1, Chk2, LKB-1, MAPKAPKs, Pim1, Pim2, Pim3, IKKs, Cdks, Jnks, Erks, IKKs, GSK3α, GSK3β, Cdks, CLKs, PKR, PI3-Kinase class 1, class 2, class 3, mTor, SAPK/JNK1,2,3, p38s, PKR, DNA-PK, ATM, ATR, Receptor protein tyrosine phosphatases (RPTPs), LAR phosphatase, CD45, Non receptor tyrosine phosphatases (NRPTPs), SHPs, MAP kinase phosphatases (MKPs), Dual Specificity phosphatases (DUSPs), CDC25 phosphatases, Low molecular weight tyrosine phosphatase, Eyes absent (EYA) tyrosine phosphatases, Slingshot phosphatases (SSH), serine phosphatases, PP2A, PP2B, PP2C, PP1, PP5, inositol phosphatases, PTEN, SHIPs, myotubularins, phosphoinositide kinases, phopsholipases, prostaglandin synthases, 5-lipoxygenase, sphingosine kinases, sphingomyelinases, adaptor/scaffold proteins, Shc, Grb2, BLNK, LAT, B cell adaptor for PI3-kinase (BCAP), SLAP, Dok, KSR, MyD88, Crk, CrkL, GAD, Nck, Grb2 associated binder (GAB), Fas associated death domain (FADD), TRADD, TRAF2, RIP, T-Cell leukemia family, IL-2, IL-4, IL-8, IL-6, interferon γ, interferon α, suppressors of cytokine signaling (SOCs), Cbl, SCF ubiquitination ligase complex, APC/C, adhesion molecules, integrins, Immunoglobulin-like adhesion molecules, selectins, cadherins, catenins, focal adhesion kinase, p130CAS, fodrin, actin, paxillin, myosin, myosin binding proteins, tubulin, eg5/KSP, CENPs, β-adrenergic receptors, muscarinic receptors, adenylyl cyclase receptors, small molecular weight GTPases, H-Ras, K-Ras, N-Ras, Ran, Rac, Rho, Cdc42, Arfs, RABs, RHEB, Vav, Tiam, Sos, Dbl, PRK, TSC1,2, Ras-GAP, Arf-GAPs, Rho-GAPs, caspases, Caspase 2, Caspase 3, Caspase 6, Caspase 7, Caspase 8, Caspase 9, Bcl-2, Mcl-1, Bcl-XL, Bcl-w, Bcl-B, A1, Bax, Bak, Bok, Bik, Bad, Bid, Bim, Bmf, Hrk, Noxa, Puma, IAPs, XIAP, Smac, Cdk4, Cdk 6, Cdk 2, Cdk1, Cdk 7, Cyclin D, Cyclin E, Cyclin A, Cyclin B, Rb, p16, p14Arf, p27KIP, p21CIP, molecular chaperones, Hsp90s, Hsp70, Hsp27, metabolic enzymes, Acetyl-CoAa Carboxylase, ATP citrate lyase, nitric oxide synthase, caveolins, endosomal sorting complex required for transport (ESCRT) proteins, vesicular protein sorting (Vsps), hydroxylases, prolyl-hydroxylases PHD-1, 2 and 3, asparagine hydroxylase FIH transferases, Pin1 prolyl isomerase, topoisomerases, deacetylases, Histone deacetylases, sirtuins, histone acetylases, CBP/P300 family, MYST family, ATF2, DNA methyl transferases, Histone H3K4 demethylases, H3K27, JHDM2A, UTX, VHL, WT-1, p53, Hdm, PTEN, ubiquitin proteases, urokinase-type plasminogen activator (uPA) and uPA receptor (uPAR) system, cathepsins, metalloproteinases, esterases, hydrolases, separase, potassium channels, sodium channels, multi-drug resistance proteins, P-Gycoprotein, nucleoside transporters, Ets, Elk, SMADs, Rel-A (p65-NFKB), CREB, NFAT, ATF-2, AFT, Myc, Fos, Sp1, Egr-1, T-bet, β-catenin, HIFs, FOXOs, E2Fs, SRFs, TCFs, Egr-1, β-catenin, FOXO STAT1, STAT 3, STAT 4, STAT 5, STAT 6, p53, WT-1, HMGA, pS6, 4EPB-1, eIF4E-binding protein, RNA polymerase, initiation factors, elongation factors.

In another embodiment the activatable element is a nucleic acid. Activation and deactivation of nucleic acids can occur in numerous ways including, but not limited to, cleavage of an inactivating leader sequence as well as covalent or non-covalent modifications that induce structural or functional changes. For example, many catalytic RNAs, e.g. hammerhead ribozymes, can be designed to have an inactivating leader sequence that deactivates the catalytic activity of the ribozyme until cleavage occurs. An example of a covalent modification is methylation of DNA. Deactivation by methylation has been shown to be a factor in the silencing of certain genes, e.g. STAT regulating SOCS genes in lymphomas. See Leukemia. See February 2004; 18(2): 356-8. SOCS1 and SHP1 hypermethylation in mantle cell lymphoma and follicular lymphoma: implications for epigenetic activation of the Jak/STAT pathway. Chim C S, Wong K Y, Loong F, Srivastava G.

In another embodiment the activatable element is a small molecule, carbohydrate, lipid or other naturally occurring or synthetic compound capable of having an activated isoform. In addition, as pointed out above, activation of these elements need not include switching from one form to another, but can be detected as the presence or absence of the compound. For example, activation of cAMP (cyclic adenosine mono-phosphate) can be detected as the presence of cAMP rather than the conversion from non-cyclic AMP to cyclic AMP.

In some embodiments of the invention, the methods described herein are employed to determine the activation level of an activatable element, e.g., in a cellular pathway. Methods and compositions are provided for the classification of a cell according to the activation level of an activatable element in a cellular pathway. The cell can be a hematopoietic cell. Examples of hematopoietic cells include but are not limited to pluripotent hematopoietic stem cells, granulocyte lineage progenitor or derived cells, monocyte lineage progenitor or derived cells, macrophage lineage progenitor or derived cells, megakaryocyte lineage progenitor or derived cells and erythroid lineage progenitor or derived cells.

In some embodiments, the cell is classified according to the activation level of an activatable element, e.g., in a cellular pathway comprises classifying the cell as a cell that is correlated with a clinical outcome. In some embodiments, the clinical outcome is the prognosis and/or diagnosis of a condition. In some embodiments, the clinical outcome is the presence or absence of a neoplastic or a hematopoietic condition. In some embodiments, the clinical outcome is the staging or grading of a neoplastic or hematopoietic condition. Examples of staging include, but are not limited to, aggressive, indolent, benign, refractory, Roman Numeral staging, TNM Staging, Rai staging, Binet staging, WHO classification, FAB classification, IPSS score, WPSS score, limited stage, extensive stage, staging according to cellular markers such as ZAP70 and CD38, occult, including information that may inform on time to progression, progression free survival, overall survival, or event-free survival.

In some embodiments, methods and compositions are provided for the classification of a cell according to the activation level of an activatable element, e.g., in a cellular pathway wherein the classification comprises classifying a cell as a cell that is correlated to a patient response to a treatment. In some embodiments, the patient response is selected from the group consisting of complete response, partial response, nodular partial response, no response, progressive disease, stable disease and adverse reaction.

In some embodiments, methods and compositions are provided for the classification of a cell according to the activation level of an activatable element, e.g., in a cellular pathway wherein the classification comprises classifying the cell as a cell that is correlated with minimal residual disease or emerging resistance.

In some embodiments, methods and compositions are provided for the classification of a cell according to the activation level of an activatable element, e.g., in a cellular pathway wherein the classification comprises selecting a method of treatment. Example of methods of treatments include, but are not limited to, chemotherapy, biological therapy, radiation therapy, bone marrow transplantation, Peripheral stem cell transplantation, umbilical cord blood transplantation, autologous stem cell transplantation, allogeneic stem cell transplantation, syngeneic stem cell transplantation, surgery, induction therapy, maintenance therapy, and watchful waiting.

Generally, the methods of the invention involve determining the activation levels of an activatable element in a plurality of single cells in a sample.

Signaling Pathways

In some embodiments, the methods of the invention are employed to determine the status of an activatable element in a signaling pathway. In some embodiments, a cell is classified, as described herein, according to the activation level of one or more activatable elements in one or more signaling pathways. Signaling pathways and their members have been described. See (Hunter T. Cell Jan. 7, 2000; 100(1): 13-27). Exemplary signaling pathways include the following pathways and their members: The MAP kinase pathway including Ras, Raf, MEK, ERK and elk; the PI3K/Akt pathway including PI-3-kinase, PDK1, Akt and Bad; the NF-κB pathway including IKKs, IkB and the Wnt pathway including frizzled receptors, beta-catenin, APC and other co-factors and TCF (see Cell Signaling Technology, Inc. 2002 Catalog pages 231-279 and Hunter T., supra.). In some embodiments of the invention, the correlated activatable elements being assayed (or the signaling proteins being examined) are members of the MAP kinase, Akt, NFkB, WNT, RAS/RAF/MEK/ERK, JNK/SAPK, p38 MAPK, Src Family Kinases, JAK/STAT and/or PKC signaling pathways. See FIG. 1 generally.

In some embodiments, the status of an activatable element within the PI3K/AKT, or MAPK pathways in response to a growth factor or mitogen is determined. In some embodiments, the activatable element within the PI3K/AKT or MAPK pathway is selected from the group consisting of Akt, p-Erk, p38 and pS6 and the growth factor or mitogen is selected from the group consisting of FLT3L, SCF, G-CSF, SCF, G-CSF, SDF1a, LPS, PMA and Thapsigargin.

In some embodiments, the status of an activatable element within JAk/STAT pathways in response to a cytokine is determined In some embodiments, the activatable element within the JAK/STAT pathway is selected from the group consisting of p-Stat3, p-Stat5, p-Stat1, and p-Stat6 and the cytokine is selected from the group consisting of IFNg, IFNa, IL-27, IL-3, IL-6, IL-10, and G-CSF. In some embodiments, the activatable element within the STAT pathway is Stat 1 and the cytokine is IL-27 or G-CSF.

In some embodiments, the status of an activatable element within the phospholipase C pathway in response to an inhibitor is determined. In some embodiments, the activatable element within the phospholipase C pathway is selected from the group consisting of p-Slp-76, and Plcg2 and the inhibitor is H2O2.

In some embodiments, the status of a phosphatase in response to an inhibitor is determined. In some embodiments, the inhibitor is H2O2.

In some embodiments, the methods of the invention are employed to determine the status of a signaling protein in a signaling pathway known in the art including those described herein. Exemplary types of signaling proteins within the scope of the present invention include, but are not limited to kinases, kinase substrates (i.e. phosphorylated substrates), phosphatases, phosphatase substrates, binding proteins (such as 14-3-3), receptor ligands and receptors (cell surface receptor tyrosine kinases and nuclear receptors)). Kinases and protein binding domains, for example, have been well described (see, e.g., Cell Signaling Technology, Inc., 2002 Catalogue "The Human Protein Kinases" and "Protein Interaction Domains" pgs. 254-279).

Nuclear Factor-kappaB (NF-κB) Pathway: Nuclear factor-kappaB (NF-kappaB) transcription factors and the signaling pathways that activate them are central coordinators of innate and adaptive immune responses. More recently, it has become clear that NF-kappaB signaling also has a critical role in cancer development and progression. NF-kappaB provides a mechanistic link between inflammation and cancer, and is a major factor controlling the ability of both pre-neoplastic and malignant cells to resist apoptosis-based tumor-surveillance mechanisms. In mammalian cells, there are five NF-κB family members, RelA (p65), RelB, c-Rel, p50/p105 (NF-κB1) and p52/p100 (NF-κB2) and different NF-κB complexes are formed from their homo and heterodimers. In most cell types, NF-κB complexes are retained in the cytoplasm by a family of inhibitory proteins known as inhibitors of NF-κB (IκBs). Activation of NF-κB typically involves the phosphorylation of IκB by the IκB kinase (IKK) complex, which results in IκB ubiquitination with subsequent degradation. This releases NF-κB and allows it to translocate freely to the nucleus. The genes regulated by NF-κB include those controlling programmed cell death, cell adhesion, proliferation, the innate- and adaptive-immune responses, inflammation, the cellular-stress response and tissue remodeling. However, the expression of these genes is tightly coordinated with the activity of many other signaling and transcription-factor pathways. Therefore, the outcome of NF-κB activation depends on the nature and the cellular context of its induction. For example, it has become apparent that NF-κB activity can be regulated by both oncogenes and tumor suppressors, resulting in either stimulation or inhibition of apoptosis and proliferation. See Perkins, N. *Integrating cell-signaling pathways with NF-κB and IKK function*. Reviews: Molecular Cell Biology. January 2007; 8(1): 49-62, hereby fully incorporated by reference in its entirety for all purposes. Hayden, M. *Signaling to NF-κB*. Genes & Development. 2004; 18: 2195-2224, hereby fully incorporated by reference in its entirety for all purposes. Perkins, N. *Good Cop, Bad Cop: The Different Faces of NF-κB*. Cell Death and Differentiation. 2006; 13: 759-772, hereby fully incorporated by reference in its entirety for all purposes.

Phosphatidylinositol 3-kinase (PI3-K)/AKT Pathway: PI3-Ks are activated by a wide range of cell surface receptors to generate the lipid second messengers phosphatidylinositol 3,4-biphosphate ($PIP_2$) and phosphatidylinositol 3,4,5-trisphosphate ($PIP_3$). Examples of receptor tyrosine kinases include but are not limited to FLT3 LIGAND, EGFR, IGF-1R, HER2/neu, VEGFR, and PDGFR. The lipid second messengers generated by PI3Ks regulate a diverse array of cellular functions. The specific binding of $PI3,4P_2$ and $PI3,4,5P_3$ to target proteins is mediated through the pleckstrin homology (PH) domain present in these target proteins. One key downstream effector of PI3-K is Akt, a serine/threonine kinase, which is activated when its PH domain interacts with $PI3, 4P_2$ and $PI3,4,5P_3$ resulting in recruitment of Akt to the plasma membrane. Once there, in order to be fully activated, Akt is phosphorylated at threonine 308 by 3-phosphoinositide-dependent protein kinase-1 (PDK-1) and at serine 473 by several PDK2 kinases. Akt then acts downstream of PI3K to regulate the phosphorylation of a number of substrates, including but not limited to forkhead box O transcription factors, Bad, GSK-3β, I-κB, mTOR, MDM-2, and S6 ribosomal subunit. These phosphorylation events in turn mediate cell survival, cell proliferation, membrane trafficking, glucose homeostasis, metabolism and cell motility. Deregulation of the PI3K pathway occurs by activating mutations in growth factor receptors, activating mutations in a PI3-K gene (e.g. PIK3CA), loss of function mutations in a lipid phosphatase (e.g. PTEN), up-regulation of Akt, or the impairment of the tuberous sclerosis complex (TSC1/2). All these events are linked to increased survival and proliferation. See Vivanco, I. *The Phosphatidylinositol 3-Kinase-AKT Pathway in Human Cancer*. Nature Reviews: Cancer. July, 2002; 2: 489-501 and Shaw, R. *Ras, PI(3)K and mTOR signaling controls tumor cell growth*. Nature. May, 2006; 441: 424-430, Marone et al., Biochimica et Biophysica Acta, 2008; 1784, p 159-185 hereby fully incorporated by reference in their entirety for all purposes.

Wnt Pathway: The Wnt signaling pathway describes a complex network of proteins well known for their roles in embryogenesis, normal physiological processes in adult animals, such as tissue homeostasis, and cancer. Further, a role for the Wnt pathway has been shown in self-renewal of hematopoietic stem cells (Reya T et al., Nature. 2003 May 22; 423(6938):409-14). Cytoplasmic levels of β-catenin are normally kept low through the continuous proteosomal degradation of β-catenin controlled by a complex of glycogen synthase kinase 3β (GSK-3β), axin, and adenomatous polyposis coli (APC). When Wnt proteins bind to a receptor complex composed of the Frizzled receptors (Fz) and low density lipoprotein receptor-related protein (LRP) at the cell surface, the GSK-3/axin/APC complex is inhibited. Key intermediates in this process include disheveled (Dsh) and axin binding the cytoplasmic tail of LRP. Upon Wnt signaling and inhibition of the β-catenin degradation pathway, β-catenin accumulates in the cytoplasm and nucleus. Nuclear β-catenin interacts with transcription factors such as lymphoid enhanced-binding factor 1 (LEF) and T cell-specific transcription factor (TCF) to affect transcription of target genes. See Gordon, M. *Wnt Signaling: Multiple Pathways, Multiple Receptors, and Multiple Transcription Factors*. J of Biological Chemistry. June, 2006; 281(32): 22429-22433, Logan C Y, Nusse R: The Wnt signaling pathway in development and disease. Annu Rev Cell Dev Biol 2004, 20:781-810, Clevers H: Wnt/beta-catenin signaling in development and disease. Cell 2006, 127:469-480. Hereby fully incorporated by reference in its entirety for all purposes.

Protein Kinase C (PKC) Signaling: The PKC family of serine/threonine kinases mediates signaling pathways following activation of receptor tyrosine kinases, G-protein coupled receptors and cytoplasmic tyrosine kinases. Activation of PKC family members is associated with cell proliferation, differentiation, survival, immune function, invasion, migration and angiogenesis. Disruption of PKC signaling has been implicated in tumorigenesis and drug resistance. PKC isoforms have distinct and overlapping roles in cellular functions. PKC was originally identified as a phospholipid and calcium-dependent protein kinase. The mammalian PKC superfamily consists of 13 different isoforms that are divided into four subgroups on the basis of their structural differences and related cofactor requirements cPKC (classical PKC) isoforms (α, βI, βII and γ), which respond both to Ca2+ and DAG (diacylglycerol), nPKC (novel PKC) isoforms (δ, ε, θ and η), which are insensitive to Ca2+, but dependent on DAG, atypical PKCs (aPKCs, ι/λ, ζ), which are responsive to neither co-factor, but may be activated by other lipids and through protein-protein interactions, and the related PKN (protein kinase N) family (e.g. PKN1, PKN2 and PKN3), members of which are subject to regulation by small GTPases. Consistent with their different biological functions, PKC isoforms differ in their structure, tissue distribution, subcellular localization, mode of activation and substrate specificity. Before maximal activation of its kinase, PKC requires a priming phosphorylation which is provided constitutively by phosphoinositide-dependent kinase 1 (PDK-1). The phospholipid DAG has a central role in the activation of PKC by causing an increase in the affinity of classical PKCs for cell membranes accompanied by PKC activation and the release of an inhibitory substrate (a pseudo-substrate) to which the inactive enzyme binds. Activated PKC then phosphorylates and activates a range of kinases. The downstream events following PKC activation are poorly understood, although the MEK-ERK (mitogen activated protein kinase kinase-extracellular signal-regulated kinase) pathway is thought to have an important role. There is also evidence to support the involvement of PKC in the PI3K-Akt pathway. PKC isoforms probably form part of the multi-protein complexes that facilitate cellular signal transduction. Many reports describe dysregulation of several family members. For example alterations in PKCε have been detected in thyroid cancer, and have been correlated with aggressive, metastatic breast cancer and PKCι was shown to be associated with poor outcome in ovarian cancer. (Knauf J A, et al. Isozyme-Specific Abnormalities of PKC in Thyroid Cancer: Evidence for Post-Transcriptional Changes in PKC Epsilon. *The Journal of Clinical Endocrinology & Metabolism*. Vol. 87, No. 5, pp 2150-2159; Zhang L et al. *Integrative Genomic Analysis of Protein Kinase C (PKC) Family Identifies PKC{iota} as a Biomarker and Potential Oncogene in Ovarian Carcinoma*. Cancer Res. 2006, Vol 66, No. 9, pp 4627-4635)

Mitogen Activated Protein (MAP) Kinase Pathways: MAP kinases transduce signals that are involved in a multitude of cellular pathways and functions in response to a variety of ligands and cell stimuli. (Lawrence et al., Cell Research (2008) 18: 436-442). Signaling by MAPKs affects specific events such as the activity or localization of individual proteins, transcription of genes, and increased cell cycle entry, and promotes changes that orchestrate complex processes such as embryogenesis and differentiation. Aberrant or inappropriate functions of MAPKs have now been identified in diseases ranging from cancer to inflammatory disease to obesity and diabetes. MAPKs are activated by protein kinase cascades consisting of three or more protein kinases in series: MAPK kinase kinases (MAP3Ks) activate MAPK kinases (MAP2Ks) by dual phosphorylation on S/T residues; MAP2Ks then activate MAPKs by dual phosphorylation on Y and T residues MAPKs then phosphorylate target substrates on select S/T residues typically followed by a proline residue. In the ERK1/2 cascade the MAP3K is usually a member of the Raf family. Many diverse MAP3Ks reside upstream of the p38 and the c-Jun N-terminal kinase/stress-activated protein kinase (JNK/SAPK) MAPK groups, which have generally been associated with responses to cellular stress. Downstream of the activating stimuli, the kinase cascades may themselves be stimulated by combinations of small G proteins, MAP4Ks, scaffolds, or oligomerization of the MAP3K in a pathway. In the ERK1/2 pathway, Ras family members usually bind to Raf proteins leading to their activation as well as to the subsequent activation of other downstream members of the pathway.

a. Ras/RAF/MEK/ERK Pathway:

Classic activation of the RAS/Raf/MAPK cascade occurs following ligand binding to a receptor tyrosine kinase at the cell surface, but a vast array of other receptors have the ability to activate the cascade as well, such as integrins, serpentine receptors, heterotrimeric G-proteins, and cytokine receptors. Although conceptually linear, considerable cross talk occurs between the Ras/Raf/MAPK/Erk kinase (MEK)/Erk MAPK pathway and other MAPK pathways as well as many other signaling cascades. The pivotal role of the Ras/Raf/MEK/Erk MAPK pathway in multiple cellular functions underlies the importance of the cascade in oncogenesis and growth of transformed cells. As such, the MAPK pathway has been a focus of intense investigation for therapeutic targeting. Many receptor tyrosine kinases are capable of initiating MAPK signaling. They do so after activating phosphorylation events within their cytoplasmic domains provide docking sites for src-homology 2 (SH2) domain-containing signaling molecules. Of these, adaptor proteins such as Grb2 recruit guanine nucleotide exchange factors such as SOS-1 or CDC25 to the cell membrane. The guanine nucleotide exchange factor is now capable of interacting with Ras proteins at the cell membrane to promote a conformational change and the exchange of GDP for GTP bound to Ras. Multiple Ras isoforms have been described, including K-Ras, N-Ras, and H-Ras. Termination of Ras activation occurs upon hydrolysis of RasGTP to RasGDP. Ras proteins have intrinsically low GTPase activity. Thus, the GTPase activity is stimulated by GTPase-activating proteins such as NF-1 GTPase-activating protein/neurofibromin and p120 GTPase activating protein thereby preventing prolonged Ras stimulated signaling. Ras activation is the first step in activation of the MAPK cascade. Following Ras activation, Raf (A-Raf, B-Raf, or Raf-1) is recruited to the cell membrane through binding to Ras and activated in a complex process involving phosphorylation and multiple cofactors that is not completely understood. Raf proteins directly activate MEK1 and MEK2 via phosphorylation of multiple serine residues. MEK1 and MEK2 are themselves tyrosine and threonine/serine dual-specificity kinases that subsequently phosphorylate threonine and tyrosine residues in Erk1 and Erk2 resulting in activation. Although MEK1/2 have no known targets besides Erk proteins, Erk has multiple targets including Elk-1, c-Ets1, c-Ets2, p90RSK1, MNK1, MNK2, and TOB. The cellular functions of Erk are diverse and include regulation of cell proliferation, survival, mitosis, and migration. McCubrey, J. *Roles of the Raf/MEK/ERK pathway in cell growth, malignant transformation and drug resistance*. Biochimica et Biophysica Acta. 2007; 1773: 1263-1284, hereby fully incorporated by reference in its entirety for all purposes, Friday and Adjei, Clinical Cancer Research (2008) 14, p 342-346.

b c-Jun N-Terminal Kinase (JNK)/Stress-Activated Protein Kinase (SAPK) Pathway:

The c-Jun N-terminal kinases (JNKs) were initially described as a family of serine/threonine protein kinases, activated by a range of stress stimuli and able to phosphorylate the N-terminal transactivation domain of the c-Jun transcription factor. This phosphorylation enhances c-Jun dependent transcriptional events in mammalian cells. Further research has revealed three JNK genes (JNK1, JNK2 and JNK3) and their splice-forms as well as the range of external stimuli that lead to JNK activation. JNK1 and JNK2 are ubiquitous, whereas JNK3 is relatively restricted to brain. The predominant MAP2Ks upstream of JNK are MEK4 (MKK4) and MEK7 (MKK7). MAP3Ks with the capacity to activate JNK/SAPKs include MEKKs (MEKK1, -2, -3 and -4), mixed lineage kinases (MLKs, including MLK1-3 and DLK), Tpl2, ASKs, TAOs and TAK1. Knockout studies in several organisms indicate that different MAP3Ks predominate in JNK/SAPK activation in response to different upstream stimuli. The wiring may be comparable to, but perhaps even more complex than, MAP3K selection and control of the ERK1/2 pathway. JNK/SAPKs are activated in response to inflammatory cytokines; environmental stresses, such as heat shock, ionizing radiation, oxidant stress and DNA damage; DNA and protein synthesis inhibition; and growth factors. JNKs phosphorylate transcription factors c-Jun, ATF-2, p53, Elk-1, and nuclear factor of activated T cells (NFAT), which in turn regulate the expression of specific sets of genes to mediate cell proliferation, differentiation or apoptosis. JNK proteins are involved in cytokine production, the inflammatory response, stress-induced and developmentally programmed apoptosis, actin reorganization, cell transformation and metabolism. Raman, M. *Differential regulation and properties of MAPKs*. Oncogene. 2007; 26: 3100-3112, hereby fully incorporated by reference in its entirety for all purposes.

c. p38 MAPK Pathway:

Several independent groups identified the p38 Map kinases, and four p38 family members have been described ($\alpha$, $\beta$, $\gamma$, $\delta$). Although the p38 isoforms share about 40% sequence identity with other MAPKs, they share only about 60% identity among themselves, suggesting highly diverse functions. p38 MAPKs respond to a wide range of extracellular cues particularly cellular stressors such as UV radiation, osmotic shock, hypoxia, pro-inflammatory cytokines and less often growth factors. Responding to osmotic shock might be viewed as one of the oldest functions of this pathway, because yeast p38 activates both short and long-term homeostatic mechanisms to osmotic stress. p38 is activated via dual phosphorylation on the TGY motif within its activation loop by its upstream protein kinases MEK3 and MEK6. MEK3/6 are activated by numerous MAP3Ks including MEKK1-4, TAOs, TAK and ASK. p38 MAPK is generally considered to be the most promising MAPK therapeutic target for rheumatoid arthritis as p38 MAPK isoforms have been implicated in the regulation of many of the processes, such as migration and accumulation of leucocytes, production of cytokines and pro-inflammatory mediators and angiogenesis, that promote disease pathogenesis. Further, the p38 MAPK pathway plays a role in cancer, heart and neurodegenerative diseases and may serve as promising therapeutic target. Cuenda, A. *p38 MAP-Kinases pathway regulation, function, and role in human diseases*. Biochimica et Biophysica Acta. 2007; 1773: 1358-1375; Thalhamer et al., Rheumatology 2008; 47:409-414; Roux, P. *ERK and p38 MAPK-Activated Protein Kinases: a Family of Protein Kinases with Diverse Biological Functions*. Microbiology and Molecular Biology Reviews. June, 2004; 320-344 hereby fully incorporated by reference in its entirety for all purposes.

Src Family Kinases: Src is the most widely studied member of the largest family of nonreceptor protein tyrosine kinases, known as the Src family kinases (SFKs). Other SFK members include Lyn, Fyn, Lck, Hck, Fgr, Blk, Yrk, and Yes. The Src kinases can be grouped into two sub-categories, those that are ubiquitously expressed (Src, Fyn, and Yes), and those which are found primarily in hematopoietic cells (Lyn, Lck, Hck, Blk, Fgr). (Benati, D. *Src Family Kinases as Potential Therapeutic Targets for Malignancies and Immunological Disorders*. Current Medicinal Chemistry. 2008; 15: 1154-1165) SFKs are key messengers in many cellular pathways, including those involved in regulating proliferation, differentiation, survival, motility, and angiogenesis. The activity of SFKs is highly regulated intramolecularly by interactions between the SH2 and SH3 domains and intermolecularly by association with cytoplasmic molecules. This latter activation may be mediated by focal adhesion kinase (FAK) or its molecular partner Crk-associated substrate (CAS), which plays a prominent role in integrin signaling, and by ligand activation of cell surface receptors, e.g. epidermal growth factor receptor (EGFR). These interactions disrupt intramolecular interactions within Src, leading to an open conformation that enables the protein to interact with potential substrates and downstream signaling molecules. Src can also be activated by dephosphorylation of tyrosine residue Y530. Maximal Src activation requires the autophosphorylation of tyrosine residue Y419 (in the human protein) present within the catalytic domain. Elevated Src activity may be caused by increased transcription or by deregulation due to overexpression of upstream growth factor receptors such as EGFR, HER2, platelet-derived growth factor receptor (PDGFR), fibroblast growth factor receptor (FGFR), vascular endothelial growth factor receptor, ephrins, integrin, or FAK. Alternatively, some human tumors show reduced expression of the negative Src regulator, Csk. Increased levels, increased activity, and genetic abnormalities of Src kinases have been implicated in both solid tumor development and leukemias. Ingley, E. *Src family kinases: Regulation of their activities, levels and identification of new pathways*. Biochimica et Biophysica Acta. 2008; 1784 56-65, hereby fully incorporated by reference in its entirety for all purposes. Benati and Baldari., Curr Med Chem. 2008; 15(12):1154-65, Finn (2008) Ann Oncol. May 16, hereby fully incorporated by reference in its entirety for all purposes.

Janus kinase (JAK)/Signal transducers and activators of transcription (STAT) pathway: The JAK/STAT pathway plays a crucial role in mediating the signals from a diverse spectrum of cytokine receptors, growth factor receptors, and G-protein-coupled receptors. Signal transducers and activators of transcription (STAT) proteins play a crucial role in mediating the signals from a diverse spectrum of cytokine receptors growth factor receptors, and G-protein-coupled receptors. STAT directly links cytokine receptor stimulation to gene transcription by acting as both a cytosolic messenger and nuclear transcription factor. In the Janus Kinase (JAK)-STAT pathway, receptor dimerization by ligand binding results in JAK family kinase (JFK) activation and subsequent tyrosine phosphorylation of the receptor, which leads to the recruitment of STAT through the SH2 domain, and the phosphorylation of conserved tyrosine residue. Tyrosine phosphorylated STAT forms a dimer, translocates to the nucleus, and binds to specific DNA elements to activate target gene transcription, which leads to the regulation of cellular proliferation, differentiation, and apoptosis. The entire process is tightly regulated at multiple levels by protein tyrosine phosphatases, suppressors of cytokine signaling and protein inhibitors of activated STAT. In mammals seven members of the STAT family (STAT1, STAT2, STAT3, STAT4, STAT5a, STAT5b and STAT6) have been identified. JAKs contain two symmetrical kinase-like domains; the C-terminal JAK homology 1 (JH1) domain possesses tyrosine kinase function while the immediately adjacent JH2 domain is enzymatically inert but is believed to regulate the activity of JH1. There are four JAK family members: JAK1, JAK2, JAK3 and tyrosine kinase 2 (Tyk2). Expression is ubiquitous for JAK1, JAK2 and TYK2 but restricted to hematopoietic cells for JAK3. Mutations in JAK proteins have been described for several myeloid malignancies. Specific examples include but are not limited to: Somatic JAK3 (e.g. JAK3A572V, JAK3V7221, JAK3P132T) and fusion JAK2 (e.g., ETV6-JAK2, PCM1-JAK2, BCR-JAK2) mutations have respectively been described in acute megakaryocytic leukemia and acute leukemia/chronic myeloid malignancies, JAK2 (V617F, JAK2 exon 12 mutations) and MPL MPLW515L/K/S, MPLS505N) mutations associated with myeloproliferative disorders and myeloproliferative neoplasms. JAK2 mutations, primarily JAK2V617F, are invariably associated with polycythemia vera (PV). This mutation also occurs in the majority of patients with essential thrombocythemia (ET) or primary myelofibrosis (PMF) (Tefferi n., Leukemia & Lymphoma, March 2008; 49(3): 388-397). STATs can be activated in a JAK-independent manner by src family kinase members and by oncogenic FLt3 ligand-ITD (Hayakawa and Naoe, Ann N Y Acad Sci. 2006 November; 1086:213-22; Choudhary et al. Activation mechanisms of STAT5 by oncogenic FLt3 ligand-ITD. Blood (2007) vol. 110 (1) pp. 370-4). Although mutations of STATs have not been described in human tumors, the activity of several members of the family, such as STAT1, STAT3 and STAT5, is dysregulated in a variety of human tumors and leukemias. STAT3 and STAT5 acquire oncogenic potential through constitutive phosphorylation on tyrosine, and their activity has been shown to be required to sustain a transformed phenotype. This was shown in lung cancer where tyrosine phosphorylation of STAT3 was JAK-independent and mediated by EGF receptor activated through mutation and Src. (Alvarez et al., Cancer Research, Cancer Res 2006; 66) STAT5 phosphorylation was also shown to be required for the long-term maintenance of leukemic stem cells. (Schepers et al. STAT5 is required for long-term maintenance of normal and leukemic human stem/progenitor cells. Blood (2007) vol. 110 (8) pp. 2880-2888) In contrast to STAT3 and STAT5, STAT1 negatively regulates cell proliferation and angiogenesis and thereby inhibits tumor formation. Consistent with its tumor suppressive properties, STAT 1 and its downstream targets have been shown to be reduced in a variety of human tumors (Rawlings, J. *The JAK/STAT signaling pathway*. J of Cell Science. 2004; 117 (8):1281-1283, hereby fully incorporated by reference in its entirety for all purposes).

Drug Transporters

A key issue in the treatment of many cancers is the development of resistance to chemotherapeutic drugs. Of the many resistance mechanisms, two classes of transporters play a major role. The human ATP-binding cassette (ABC) superfamily of proteins consists of 49 membrane proteins that transport a diverse array of substrates, including sugars, amino acids, bile salts lipids, sterols, nucleotides, endogenous metabolites, ions, antibiotics drugs and toxins out of cells using the energy of hydrolysis of ATP. ATP-binding-cassette (ABC) transporters are evolutionary extremely well-conserved transmembrane proteins that are highly expressed in hematopoietic stem cells (HSCs). The physiological function in human stem cells is believed to be protection against genetic damage caused by both environmental and naturally occurring xenobiotics. Additionally, ABC transporters have been implicated in the maintenance of quiescence and cell fate decisions of stem cells. These physiological roles suggest a potential role in the pathogenesis and biology of stem cell-derived hematological malignancies such as acute and chronic myeloid leukemia (Raaijmakers, Leukemia (2007) 21, 2094-2102, Zhou et al., Nature Medicine, 2001, 7, p 1028-1034

Several ABC proteins are multidrug efflux pumps that not only protect the body from exogenous toxins, but also play a role in uptake and distribution of therapeutic drugs. Expression of these proteins in target tissues causes resistance to treatment with multiple drugs. (Gillet et al., Biochimica et Biophysica Acta (2007) 1775, p 237, Sharom (2008) Pharmacogenomics 9 p 105). A more detailed discussion of the ABC family members with critical roles in resistance and poor outcome to treatment is discussed below.

The second class of plasma membrane transporter proteins that play a role in the uptake of nucleoside-derived drugs are the Concentrative and Equilibrative Nucleoside Transporters (CNT and ENT, respectively), encoded by gene families SLC28 and SLC29 (Pastor-Anglada (2007) J. Physiol. Biochem 63, p 97). They mediate the uptake of natural nucleosides and a variety of nucleoside-derived drugs, mostly used in anti-cancer therapy. In vitro studies, have shown that one mechanism of nucleoside resistance can be mediated through mutations in the gene for ENT1/SLC29A1 resulting in lack of detectable protein (Cai et al., Cancer Research (2008) 68, p 2349). Studies have also described in vivo mechanisms of resistance to nucleoside analogues involving low or non-detectable levels of ENT 1 in Acute Myeloid Leukemia (AML), Mantle Cell lymphoma and other leukemias (Marce et al., Malignant Lymphomas (2006), 91, p 895).

Of the ABC transporter family, three family members account for most of the multiple drug resistance (MDR) in humans; P-gycoprotein (Pgp/MDR1/ABCB1), MDR-associated protein (MRP1, ABCC1) and breast cancer resistance protein (BCRP, ABCG2 or MXR). Pgp/MDR1 and ABCG2 can export both unmodified drugs and drug conjugates, whereas MRP1 exports glutathione and other drug conjugates as well as unconjugated drugs together with free glutathione. All three ABC transporters demonstrate export activity for a broad range of structurally unrelated drugs and display both distinct and overlapping specificities. For example, MRP1 promotes efflux of drug-glutathione conjugates, vinca alkaloids, camptothecin, but not taxol. Examples of drugs exported by ABCG2 include mitoxantrone, etoposide, daunorubicin as well as the tyrosine kinase inhibitors Gleevec and Iressa. In treatment regimens for leukemias, one of the main obstacles to achieving remission is intrinsic and acquired resistance to chemotherapy mediated by the ABC drug transporters. Several reports have described correlations between transporter expression levels as well as their function, evaluated through the use of fluorescent dyes, with resistance of patients to chemotherapy regimens. Notably, in AML, studies have shown that expression of Pgp/MDR1 is associated with a lower rate of complete response to induction chemotherapy and a higher rate of resistant disease in both elderly and younger AML patients (Leith et al., Blood (1997) 89 p 3323, Leith et al., Blood (1999) 94, p 1086). Legrand et al., (Blood (1998) 91, p 4480) showed that Pgp/MDR1 and MRP1 function in CD34+ blast cells are negative prognostic factors in AML and further, the same group showed that a high level of simultaneous activity of Pgp/MDR1 and MRP1 was predictive of poor treatment outcome (Legrand et al., (Blood (1999) 94, p 1046). In two more recent studies, elevated expression of Pgp/MDR1 and BCRP in CD34+/CD38− AML subpopulations were found in 8 out of 10 non-responders as compared to 0 out of 10 in responders to induction chemotherapy (Ho et al., Experimental Hematology (2008) 36, p 433). In a second study, evaluation of Pgp/MDR1, MRP1, BCRP/ABCG2 and lung resistance protein showed that the more immature subsets of leukemic stem cells expressed higher levels of these proteins compared more mature leukemic subsets (Figueiredo-Pontes et al., Clinical Cytometry (2008) 74B p 163).

Experimentally, it is possible to correlate expression of transporter proteins with their function by the use of inhibitors including but not limited to cyclosporine (measures Pgp function), probenecid (measures MRP1 function), fumitremorgin C, and a derivative Ko143, reserpine (measures ABCG2 function). Aalthough these molecules inhibit a variety of transporters, they do permit some correlations to be made between protein expression and function (Legrand et al., (Blood (1998) 91, p 4480), Legrand et al., (Blood (1999) 94, p 1046, Zhou et al., Nature Medicine, 2001, 7, p 1028-1034, Sarkardi et al., Physiol Rev 2006 86: 1179-1236).

Extending the use of these inhibitors, they can be used to make correlations within subpopulations of cells gated both for phenotypic markers denoting stages of development along hematopoietic and lymphoid lineages, as well as reagents that recognize the transporter proteins themselves. Thus it will be possible to simultaneously measure protein expression and function.

Expression levels of drug transporters and receptors may not be as informative by themselves for disease management as analysis of activatable elements, such as phosphorylated proteins. However, expression information may be useful in combination with the analysis of activatable elements, such as phosphorylated proteins. In some embodiments, the methods described herein analyze the expression of drug transporters and receptors in combination with the analysis of one or more activatable elements for the diagnosis, prognosis, selection of treatment, or predicting response to treatment for a condition.

DNA Damage and Apoptosis

The response to DNA damage is a protective measure taken by cells to prevent or delay genetic instability and tumorigenesis. It allows cells to undergo cell cycle arrest and gives them an opportunity to either: repair the broken DNA and resume passage through the cell cycle or, if the breakage is irreparable, trigger senescence or an apoptotic program leading to cell death (Wade Harper et al., Molecular Cell, (2007) 28 p 739-745, Bartek J et al., Oncogene (2007)26 p 7773-9).

Several protein complexes are positioned at strategic points within the DNA damage response pathway and act as sensors, transducers or effectors of DNA damage. Depending on the nature of DNA damage for example; double stranded breaks, single strand breaks, single base alterations due to alkylation, oxidation etc, there is an assembly of specific DNA damage sensor protein complexes in which activated ataxia telangiectasia mutated (ATM) and ATM- and Rad3 related (ATR) kinases phosphorylate and subsequently activate the checkpoint kinases Chk1 and Chk2. Both of these DNA-signal transducer kinases amplify the damage response by phosphorylating a multitude of substrates. Both checkpoint kinases have overlapping and distinct roles in orchestrating the cell's response to DNA damage.

Maximal kinase activation of Chk2 involves phosphorylation and homo-dimerization with ATM-mediated phosphorylation of T68 on Chk2 as a preliminary event. This in turn activates the DNA repair. As mentioned above, in order for DNA repair to proceed, there must be a delay in the cell cycle. Chk2 seems to have a role at the G1/S and G2/M junctures and may have overlapping functions with Chk1. There are multiple ways in which Chk1 and Chk2 mediate cell cycle suspension. In one mechanism Chk2 phosphorylates the CDC25A and CDC25C phosphatases resulting in their removal from the nucleus either by proteosomal degradation or by sequestration in the cytoplasm by 14-3-3. These phosphatases are no longer able to act on their nuclear CDK substrates. If DNA repair is successful cell cycle progression is resumed (Antoni et al., Nature reviews cancer (2007) 7, p 925-936).

When DNA repair is no longer possible the cell undergoes apoptosis with participation from Chk2 in p53 independent and dependent pathways. Chk2 substrates that operate in a p53-independent manner include the E2F1 transcription factor, the tumor suppressor promyelocytic leukemia (PML) and the polo-like kinases 1 and 3 (PLK1 and PLK3). E2F1 drives the expression of a number of apoptotic genes including caspases 3, 7, 8 and 9 as well as the pro-apoptotic Bcl-2 related proteins (Bim, Noxa, PUMA).

In its response to DNA damage, the p53 activates the transcription of a program of genes that regulate DNA repair, cell cycle arrest, senescence and apoptosis. The overall functions of p53 are to preserve fidelity in DNA replication such that when cell division occurs tumorigenic potential can be avoided. In such a role, p53 is described as "The Guardian of the Genome" (Riley et al., Nature Reviews Molecular Cell Biology (2008) 9 p 402-412). The diverse alarm signals that impinge on p53 result in a rapid increase in its levels through a variety of post translational modifications. Worthy of mention is the phosphorylation of amino acid residues within the amino terminal portion of p53 such that p53 is no longer under the regulation of Mdm2 The responsible kinases are ATM, Chk1 and Chk2. The subsequent stabilization of p53 permits it to transcriptionally regulate multiple pro-apoptotic members of the Bcl-2 family, including Bax, Bid, Puma, and Noxa (Discussion below).

The series of events that are mediated by p53 to promote apoptosis including DNA damage, anoxia and imbalances in growth-promoting signals are sometimes termed the "intrinsic apoptotic" program since the signals triggering it originate within the cell. An alternate route of activating the apoptotic pathway can occur from the outside of the cell mediated by the binding of ligands to transmembrane death receptors. This extrinsic or receptor mediated apoptotic program acting through their receptor death domains eventually converges on the intrinsic, mitochondrial apoptotic pathway as discussed below (Sprick et al., Biochim Biophys Acta. (2004) 1644 p 125-32).

Key regulators of apoptosis are proteins of the Bcl-2 family. The founding member, the Bcl-2 proto-oncogene was first identified at the chromosomal breakpoint of t(14:18) bearing human follicular B cell lymphoma. Unexpectedly, expression of Bcl-2 was proved to block rather than promote cell death following multiple pathological and physiological stimuli (Danial and Korsemeyer, Cell (2204) 116, p 205-219). The Bcl-2 family has at least 20 members which are key regulators of apoptosis, functioning to control mitochondrial permeability as well as the release of proteins important in the apoptotic program. The ratio of anti- to pro-apoptotic molecules such as Bcl-2/Bax constitutes a rheostat that sets the threshold of susceptibility to apoptosis for the intrinsic pathway, which utilizes organelles such as the mitochondrion to amplify death signals. The family can be divided into 3 subclasses based on structure and impact on apoptosis. Family members of subclass 1 including Bcl-2, Bcl-$X_L$ and Mcl-1 are characterized by the presence of 4 Bcl-2 homology domain (BH1, BH2, BH3 and BH4) and are anti-apoptotic. The structure of the second subclass members is marked for containing 3 BH domains and family members such as Bax and Bak possess pro-apoptotic activities. The third subclass, termed the BH3-only proteins include Noxa, Puma, Bid, Bad and Bim. They function to promote apoptosis either by activating the pro-apoptotic members of group 2 or by inhibiting the anti-apoptotic members of subclass 1 (Er et al., Biochimica et Biophysica Act (2006) 1757, p 1301-1311, Fernandez-Luna Cellular Signaling (2008) Advance Publication Online).

The role of mitochondria in the apoptotic process was clarified as involving an apoptotic stimulus resulting in depolarization of the outer mitochondrial membrane leading to a leak of cytochrome C into the cytoplasm. Association of Cytoplasmic cytochrome C molecules with adaptor apoptotic protease activating factor (APAF) forms a structure called the apoptosome which can activate enzymatically latent pro-caspase 9 into a cleaved activated form. Caspase 9 is one member of a family of cysteine aspartyl-specific proteases; genes encoding 11 of these proteases have been mapped in the human genome. Activated caspase 9, classified as an intiator caspase, then cleaves procaspase 3 which cleaves more downstream procaspases, classified as executioner caspases, resulting in an amplification cascade that promotes cleavage of death substrates including poly(ADP-ribose) polymerase 1 (PARP). The cleavage of PARP produces 2 fragments both of which have a role in apoptosis (Soldani and Scovassi Apoptosis (2002) 7, p 321). A further level of apoptotic regulation is provided by smac/Diablo, a mitochondrial protein that inactivates a group of anti-apoptotic proteins termed inhibitors of apoptosis (IAPs) (Huang et al., Cancer Cell (2004) 5 p 1-2). IAPs operate to block caspase activity in 2 ways; they bind directly to and inhibit caspase activity and in certain cases they can mark caspases for ubiquitination and degradation.

Members of the caspase gene family (cysteine proteases with aspartate specificity) play significant roles in both inflammation and apoptosis. Caspases exhibit catalytic and substrate recognition motifs that have been highly conserved. These characteristic amino acid sequences allow caspases to interact with both positive and negative regulators of their activity. The substrate preferences or specificities of individual caspases have been exploited for the development of peptides that successfully compete for caspase binding. In addition to their distinctive aspartate cleavage sites at the P1 position, the catalytic domains of the caspases require at least four amino acids to the left of the cleavage site with P4 as the prominent specificity-determining residue. WEHD, VDVAD, and DEVD are examples of peptides that preferentially bind caspase-1, caspase-2 and caspase-3, respectively. It is possible to generate reversible or irreversible inhibitors of caspase activation by coupling caspase-specific peptides to certain aldehyde, nitrile or ketone compounds. These caspase inhibitors can successfully inhibit the induction of apoptosis in various tumor cell lines as well as normal cells. Fluoromethyl ketone (FMK)-derivatized peptides act as effective irreversible inhibitors with no added cytotoxic effects. Inhibitors synthesized with a benzyloxycarbonyl group (also known as BOC or Z) at the N-terminus and O-methyl side chains exhibit enhanced cellular permeability thus facilitating their use in both in vitro cell culture as well as in vivo animal studies. Benzyloxycarbonyl-Val-Ala-Asp (OMe) fluoromethylketone (ZVAD) is a caspase inhibitor. See Misaghi, et al., z-VAD-fmk inhibits peptide:N-glycanase and may result in ER stress Cell Death and Differentiation (2006) 13, 163-165.

The balance of pro- and anti-apoptotic proteins is tightly regulated under normal physiological conditions. Tipping of this balance either way results in disease. An oncogenic outcome results from the inability of tumor cells to undergo apoptosis and this can be caused by over-expression of anti-apoptotic proteins or reduced expression or activity of pro-apoptotic protein.

Figure 3:
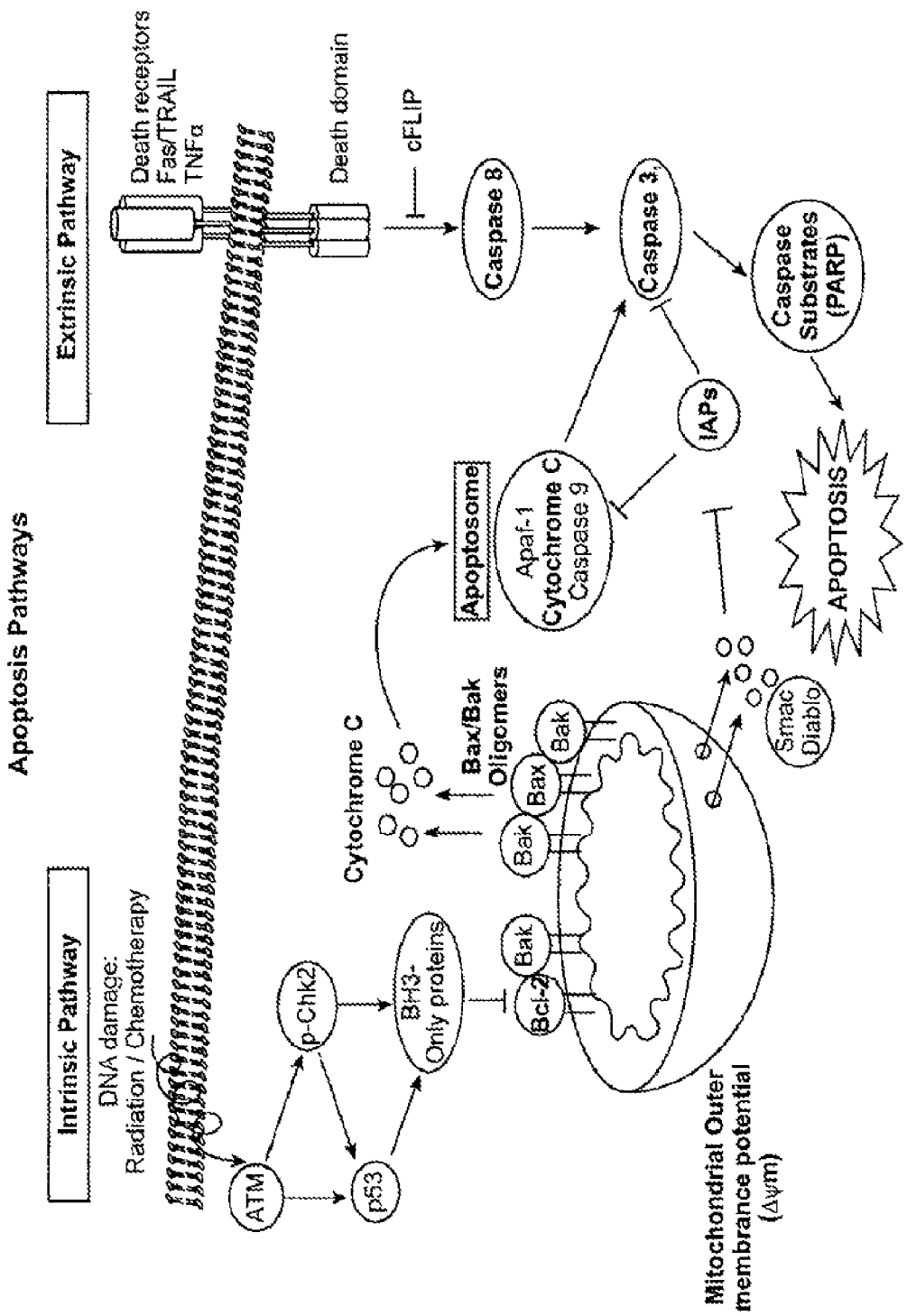
FIG. 3 shows a diagram of apoptosis pathways.

FIG. 3 shows the role of apoptosis in AML.

In some embodiments, the status of an activatable element within an apoptosis pathway in response to a modulator that slows or stops the growth of cells and/or induces apoptosis of cells is determined. In some embodiments, the activatable element within the apoptosis pathway is selected from the group consisting of PARP+, Cleaved Caspase 8, and Cytoplasmic Cytochrome C, and the modulator that slows or stops the growth of cells and/or induces apoptosis of cells is selected from the group consisting of Staurosporine, Etoposide, Mylotarg, Daunorubicin, and AraC.

In some embodiments, the status of an activatable element within a DNA damage pathway in response to a modulator that slows or stops the growth of cells and/or induces apoptosis of cells is determined. In some embodiments, the activatable element within a DNA damage pathway is selected from the group consisting of Chk1, Chk2, ATM, and ATR and the modulator that slows or stops the growth of cells and/or induces apoptosis of cells is selected from the group consisting of Staurosporine, Etoposide, Mylotarg, Daunorubicin, and AraC.

In some embodiments, interrogation of the apoptotic machinery will also be performed by etoposide with or without ZVAD, an inhibitor of caspases, or a combination of Cytarabine and Daunorubicin at clinically relevant concentrations based on peak plasma drug levels. The standard dose of Cytarabine, 100 mg/m2, yields a peak plasma concentration of approximately 40 nM, whereas high dose Cytarabine, 3 g/m2, yields a peak plasma concentration of 2 uM. Daunorubicin at 25 mg/m2 yields a peak plasma concentration of 50 ng/ml and at 50 mg/m2 yields a peak plasma concentration of 200 ng/ml. Our in vitro apoptosis assay will use concentrations of Cytarabine up to 2 uM, and concentrations of Daunorubicin up to 200 ng/ml.

Etoposide phosphate (brand names: Eposin, Etopophos, Vepesid, VP-16) is an inhibitor of the enzyme topoisomerase II and a semisynthetic derivative of podophyllotoxin, a substance extracted from the mandrake root Podophyllum peltatum. Possessing potent antineoplastic properties, etoposide binds to and inhibits topoisomerase II and its function in ligating cleaved DNA molecules, resulting in the accumulation of single- or double-strand DNA breaks, the inhibition of DNA replication and transcription, and apoptotic cell death. Etoposide acts primarily in the G2 and S phases of the cell cycle. See the NCI Drug Dictionary at http://www.cancer.gov/Templates/drugdictionary.aspx?CdrID=39207.

Cell Cycle

The cell cycle, or cell-division cycle, is the series of events that take place in a cell leading to its division and duplication (replication). The cell cycle consists of five distinct phases: G1 phase, S phase (synthesis), G2 phase (collectively known as interphase) and M phase (mitosis). M phase is itself composed of two tightly coupled processes: mitosis, in which the cell's chromosomes are divided between the two daughter cells, and cytokinesis, in which the cell's cytoplasm divides forming distinct cells. Activation of each phase is dependent on the proper progression and completion of the previous one. Cells that have temporarily or reversibly stopped dividing are said to have entered a state of quiescence called G0 phase.

Regulation of the cell cycle involves processes crucial to the survival of a cell, including the detection and repair of genetic damage as well as the prevention of uncontrolled cell division. The molecular events that control the cell cycle are ordered and directional; that is, each process occurs in a sequential fashion and it is impossible to "reverse" the cycle.

Two key classes of regulatory molecules, cyclins and cyclin-dependent kinases (CDKs), determine a cell's progress through the cell cycle. Many of the genes encoding cyclins and CDKs are conserved among all eukaryotes, but in general more complex organisms have more elaborate cell cycle control systems that incorporate more individual components. Many of the relevant genes were first identified by studying yeast, especially Saccharomyces cerevisiae genetic nomenclature in yeast dubs many these genes cdc (for "cell division cycle") followed by an identifying number, e.g., cdc25.

Cyclins form the regulatory subunits and CDKs the catalytic subunits of an activated heterodimer; cyclins have no catalytic activity and CDKs are inactive in the absence of a partner cyclin. When activated by a bound cyclin, CDKs perform a common biochemical reaction called phosphorylation that activates or inactivates target proteins to orchestrate coordinated entry into the next phase of the cell cycle. Different cyclin-CDK combinations determine the downstream proteins targeted. CDKs are constitutively expressed in cells whereas cyclins are synthesised at specific stages of the cell cycle, in response to various molecular signals.

Upon receiving a pro-mitotic extracellular signal, G1 cyclin-CDK complexes become active to prepare the cell for S phase, promoting the expression of transcription factors that in turn promote the expression of S cyclins and of enzymes required for DNA replication. The G1 cyclin-CDK complexes also promote the degradation of molecules that function as S phase inhibitors by targeting them for ubiquitination. Once a protein has been ubiquitinated, it is targeted for proteolytic degradation by the proteasome. Active S cyclin-CDK complexes phosphorylate proteins that make up the pre-replication complexes assembled during G1 phase on DNA replication origins. The phosphorylation serves two purposes: to activate each already-assembled pre-replication complex, and to prevent new complexes from forming This ensures that every portion of the cell's genome will be replicated once and only once. The reason for prevention of gaps in replication is fairly clear, because daughter cells that are missing all or part of crucial genes will die. However, for reasons related to gene copy number effects, possession of extra copies of certain genes would also prove deleterious to the daughter cells.

Mitotic cyclin-CDK complexes, which are synthesized but inactivated during S and G2 phases, promote the initiation of mitosis by stimulating downstream proteins involved in chromosome condensation and mitotic spindle assembly. A critical complex activated during this process is an ubiquitin ligase known as the anaphase-promoting complex (APC), which promotes degradation of structural proteins associated with the chromosomal kinetochore. APC also targets the mitotic cyclins for degradation, ensuring that telophase and cytokinesis can proceed. Interphase: Interphase generally lasts at least 12 to 24 hours in mammalian tissue. During this period, the cell is constantly synthesizing RNA, producing protein and growing in size. By studying molecular events in cells, scientists have determined that interphase can be divided into 4 steps: Gap 0 (G0), Gap 1 (G1), S (synthesis) phase, Gap 2 (G2).

Cyclin D is the first cyclin produced in the cell cycle, in response to extracellular signals (e.g. growth factors). Cyclin D binds to existing CDK4, forming the active cyclin D-CDK4 complex. Cyclin D-CDK4 complex in turn phosphorylates the retinoblastoma susceptibility protein (Rb). The hyperphosphorylated Rb dissociates from the E2F/DP1/Rb complex (which was bound to the E2F responsive genes, effectively "blocking" them from transcription), activating E2F. Activation of E2F results in transcription of various genes like cyclin E, cyclin A, DNA polymerase, thymidine kinase, etc. Cyclin E thus produced binds to CDK2, forming the cyclin E-CDK2 complex, which pushes the cell from G1 to S phase (G1/S transition). Cyclin B along with cdc2 (cdc2-fission yeasts (CDK1-mammalia)) forms the cyclin B-cdc2 complex, which initiates the G2/M transition. Cyclin B-cdc2 complex activation causes breakdown of nuclear envelope and initiation of prophase, and subsequently, its deactivation causes the cell to exit mitosis.

Two families of genes, the Cip/Kip family and the INK4a/ARF (Inhibitor of Kinase 4/Alternative Reading Frame) prevent the progression of the cell cycle. Because these genes are instrumental in prevention of tumor formation, they are known as tumor suppressors.

The Cip/Kip family includes the genes p21, p27 and p57. They halt cell cycle in G1 phase, by binding to, and inactivating, cyclin-CDK complexes. p21 is a p53 response gene (which, in turn, is triggered by DNA damage eg. due to radiation). p27 is activated by Transforming Growth Factor β (TGF β), a growth inhibitor.

The INK4a/ARF family includes p16INK4a, which binds to CDK4 and arrests the cell cycle in G1 phase, and p14arf which prevents p53 degradation.

Cell cycle checkpoints are used by the cell to monitor and regulate the progress of the cell cycle. Checkpoints prevent cell cycle progression at specific points, allowing verification of necessary phase processes and repair of DNA damage. The cell cannot proceed to the next phase until checkpoint requirements have been met.

Several checkpoints are designed to ensure that damaged or incomplete DNA is not passed on to daughter cells. Two main checkpoints exist: the G1/S checkpoint and the G2/M checkpoint. G1/S transition is a rate-limiting step in the cell cycle and is also known as restriction point. An alternative model of the cell cycle response to DNA damage has also been proposed, known as the postreplication checkpoint. p53 plays an important role in triggering the control mechanisms at both G1/S and G2/M checkpoints.

A disregulation of the cell cycle components may lead to tumor formation. As mentioned above, some genes like the cell cycle inhibitors, RB, p53 etc., when they mutate, may cause the cell to multiply uncontrollably, forming a tumor. Although the duration of cell cycle in tumor cells is equal to or longer than that of normal cell cycle, the proportion of cells that are in active cell division (versus quiescent cells in G0 phase) in tumors is much higher than that in normal tissue. Thus there is a net increase in cell number as the number of cells that die by apoptosis or senescence remains the same.

In some embodiments, the status of an activatable element within a cell cycle pathway in response to a modulator that slows or stops the growth of cells and/or induces apoptosis of cells is determined. In some embodiments, the activatable element within a DNA damage pathway is selected from the group consisting of, Cdc25, p53, CyclinA-Cdk2, CyclinE-Cdk2, CyclinB-Cdk1, p21, and Gadd45. In some embodiments, the modulator that slows or stops the growth of cells and/or induces apoptosis of cells is selected from the group consisting of Staurosporine, Etoposide, Mylotarg, Daunorubicin, and AraC.

Modulators

In some embodiments, the methods and composition utilize a modulator. A modulator can be an activator, a therapeutic compound, an inhibitor or a compound capable of impacting a cellular pathway. Modulators can also take the form of environmental cues and inputs.

Modulation can be performed in a variety of environments. In some embodiments, cells are exposed to a modulator immediately after collection. In some embodiments where there is a mixed population of cells, purification of cells is performed after modulation. In some embodiments, whole blood is collected to which a modulator is added. In some embodiments, cells are modulated after processing for single cells or purified fractions of single cells. As an illustrative example, whole blood can be collected and processed for an enriched fraction of lymphocytes that is then exposed to a modulator. Modulation can include exposing cells to more than one modulator. For instance, in some embodiments, cells are exposed to at least 2, 3, 4, 5, 6, 7, 8, 9, or 10 modulators. See U.S. Patent Application 61/048,657 which is incorporated by reference.

In some embodiments, cells are cultured post collection in a suitable media before exposure to a modulator. In some embodiments, the media is a growth media. In some embodiments, the growth media is a complex media that may include serum. In some embodiments, the growth media comprises serum. In some embodiments, the serum is selected from the group consisting of fetal bovine serum, bovine serum, human serum, porcine serum, horse serum, and goat serum. In some embodiments, the serum level ranges from 0.0001% to 30%. In some embodiments, the growth media is a chemically defined minimal media and is without serum. In some embodiments, cells are cultured in a differentiating media.

Modulators include chemical and biological entities, and physical or environmental stimuli. Modulators can act extracellularly or intracellularly. Chemical and biological modulators include growth factors, mitogens, cytokines, drugs, immune modulators, ions, neurotransmitters, adhesion molecules, hormones, small molecules, inorganic compounds, polynucleotides, antibodies, natural compounds, lectins, lactones, chemotherapeutic agents, biological response modifiers, carbohydrate, proteases and free radicals. Modulators include complex and undefined biologic compositions that may comprise cellular or botanical extracts, cellular or glandular secretions, physiologic fluids such as serum, amniotic fluid, or venom. Physical and environmental stimuli include electromagnetic, ultraviolet, infrared or particulate radiation, redox potential and pH, the presence or absences of nutrients, changes in temperature, changes in oxygen partial pressure, changes in ion concentrations and the application of oxidative stress. Modulators can be endogenous or exogenous and may produce different effects depending on the concentration and duration of exposure to the single cells or whether they are used in combination or sequentially with other modulators. Modulators can act directly on the activatable elements or indirectly through the interaction with one or more intermediary biomolecule. Indirect modulation includes alterations of gene expression wherein the expressed gene product is the activatable element or is a modulator of the activatable element.

In some embodiments the modulator is selected from the group consisting of growth factors, mitogens, cytokines, adhesion molecules, drugs, hormones, small molecules, polynucleotides, antibodies, natural compounds, lactones, chemotherapeutic agents, immune modulators, carbohydrates, proteases, ions, reactive oxygen species, peptides, and protein fragments, either alone or in the context of cells, cells themselves, viruses, and biological and non-biological complexes (e.g. beads, plates, viral envelopes, antigen presentation molecules such as major histocompatibility complex). In some embodiments, the modulator is a physical stimuli such as heat, cold, UV radiation, and radiation. Examples of modulators, include but are not limited to SDF-1α, IFN-α, IFN-γ, IL-10, IL-6, IL-27, G-CSF, FLT-3L, IGF-1, M-CSF, SCF, PMA, Thapsigargin, $H_2O_2$, Etoposide, Mylotarg, AraC, daunorubicin, staurosporine, benzyloxycarbonyl-Val-Ala-Asp (OMe) fluoromethylketone (ZVAD), lenalidomide, EPO, azacitadine, decitabine, IL-3, IL-4, GM-CSF, EPO, LPS, TNF-α, and CD40L.

In some embodiments, the modulator is an activator. In some embodiments the modulator is an inhibitor. In some embodiments, cells are exposed to one or more modulator. In some embodiments, cells are exposed to at least 2, 3, 4, 5, 6, 7, 8, 9, or 10 modulators. In some embodiments, cells are exposed to at least two modulators, wherein one modulator is an activator and one modulator is an inhibitor. In some embodiments, cells are exposed to at least 2, 3, 4, 5, 6, 7, 8, 9, or 10 modulators, where at least one of the modulators is an inhibitor.

In some embodiments, the cross-linker is a molecular binding entity. In some embodiments, the molecular binding entity is a monovalent, bivalent, or multivalent is made more multivalent by attachment to a solid surface or tethered on a nanoparticle surface to increase the local valency of the epitope binding domain.

In some embodiments, the inhibitor is an inhibitor of a cellular factor or a plurality of factors that participates in a cellular pathway (e.g. signaling cascade) in the cell. In some embodiments, the inhibitor is a phosphatase inhibitor. Examples of phosphatase inhibitors include, but are not limited to $H_2O_2$, siRNA, miRNA, Cantharidin, (−)-p-Bromotetramisole, Microcystin LR, Sodium Orthovanadate, Sodium Pervanadate, Vanadyl sulfate, Sodium oxodiperoxo(1,10-phenanthroline)vanadate, bis(maltolato)oxovanadium(IV), Sodium Molybdate, Sodium Perm olybdate, Sodium Tartrate, Imidazole, Sodium Fluoride, β-Glycerophosphate, Sodium Pyrophosphate Decahydrate, Calyculin A, Discodermia calyx, bpV(phen), mpV(pic), DMHV, Cypermethrin, Dephostatin, Okadaic Acid, NIPP-1, N-(9,10-Dioxo-9,10-dihydro-phenanthren-2-yl)-2,2-dimethyl-propionamide, α-Bromo-4-hydroxyacetophenone, 4-Hydroxyphenacyl Br, α-Bromo-4-methoxyacetophenone, 4-Methoxyphenacyl Br, α-Bromo-4-(carboxymethoxy)acetophenone, 4-(Carboxymethoxy)phenacyl Br, and bis(4-Trifluoromethylsulfonamidophenyl)-1,4-diisopropylbenzene, phenylarsine oxide, Pyrrolidine Dithiocarbamate, and Aluminium fluoride. In some embodiments, the phosphatase inhibitor is $H_2O_2$.

In some embodiments, the activation level of an activatable element in a cell is determined by contacting the cell with at least 2, 3, 4, 5, 6, 7, 8, 9, or 10 modulators. In some embodiments, the activation level of an activatable element in a cell is determined by contacting the cell with at least 2, 3, 4, 5, 6, 7, 8, 9, or 10 modulators where at least one of the modulators is an inhibitor. In some embodiments, the activation level of an activatable element in a cell is determined by contacting the cell with an inhibitor and a modulator, where the modulator can be an inhibitor or an activator. In some embodiments, the activation level of an activatable element in a cell is determined by contacting the cell with an inhibitor and an activator. In some embodiments, the activation level of an activatable element in a cell is determined by contacting the cell with two or more modulators.

In some embodiments, a phenotypic profile of a population of cells is determined by measuring the activation level of an activatable element when the population of cells is exposed to a plurality of modulators in separate cultures. In some embodiments, the modulators include $H_2O_2$, PMA, SDF1α, CD40L, IGF-1, IL-7, IL-6, IL-10, IL-27, IL-4, IL-2, IL-3, thapsigardin and/or a combination thereof. For instance a population of cells can be exposed to one or more, all or a combination of the following combination of modulators: $H_2O_2$, PMA; SDF1α; CD40L; IGF-1; IL-7; IL-6; IL-10; IL-27; IL-4; IL-2; IL-3; thapsigardin. In some embodiments, the phenotypic profile of the population of cells is used to classify the population as described herein.

Gating

In another embodiment, a user may analyze the signaling in subpopulations based on surface markers. For example, the user could look at: "stem cell populations" by CD34+CD38− or CD34+ CD33− expressing cells; drug transporter positive cells; i.e. FLT3 LIGAND+ cells; or multiple leukemic subclones based on CD33, CD45, HLA-DR, CD11b and analyzing signaling in each subpopulation. In another alternative embodiment, a user may analyze the data based on intracellular markers, such as transcription factors or other intracellular proteins; based on a functional assay (i.e. dye negative "side population" aka drug transporter+cells, or fluorescent glucose uptake, or based on other fluorescent markers. In some embodiments, a gate is established after learning from a responsive subpopulation. That is, a gate is developed from one data set after finding a population that correlates with a clinical outcome. This gate can then be applied retrospectively or prospectively to other data sets.

In some embodiments where flow cytometry is used, prior to analyzing of data the populations of interest and the method for characterizing these populations are determined. For instance, there are at least two general ways of identifying populations for data analysis: (i) "Outside-in" comparison of Parameter sets for individual samples or subset (e.g., patients in a trial). In this more common case, cell populations are homogenous or lineage gated in such a way as to create distinct sets considered to be homogenous for targets of interest. An example of sample-level comparison would be the identification of signaling profiles in tumor cells of a patient and correlation of these profiles with non-random distribution of clinical responses. This is considered an outside-in approach because the population of interest is pre-defined prior to the mapping and comparison of its profile to other populations. (ii) "Inside-out" comparison of Parameters at the level of individual cells in a heterogeneous population. An example of this would be the signal transduction state mapping of mixed hematopoietic cells under certain conditions and subsequent comparison of computationally identified cell clusters with lineage specific markers. This could be considered an inside-out approach to single cell studies as it does not presume the existence of specific populations prior to classification. A major drawback of this approach is that it creates populations which, at least initially, require multiple transient markers to enumerate and may never be accessible with a single cell surface epitope. As a result, the biological significance of such populations can be difficult to determine. The main advantage of this unconventional approach is the unbiased tracking of cell populations without drawing potentially arbitrary distinctions between lineages or cell types.

Each of these techniques capitalizes on the ability of flow cytometry to deliver large amounts of multiparameter data at the single cell level. For cells associated with a condition (e.g. neoplastic or hematopoietic condition), a third "meta-level" of data exists because cells associated with a condition (e.g. cancer cells) are generally treated as a single entity and classified according to historical techniques. These techniques have included organ or tissue of origin, degree of differentiation, proliferation index, metastatic spread, and genetic or metabolic data regarding the patient.

In some embodiments, the present invention uses variance mapping techniques for mapping condition signaling space. These methods represent a significant advance in the study of condition biology because it enables comparison of conditions independent of a putative normal control. Traditional differential state analysis methods (e.g., DNA microarrays, subtractive Northern blotting) generally rely on the comparison of cells associated with a condition from each patient sample with a normal control, generally adjacent and theoretically untransformed tissue. Alternatively, they rely on multiple clusterings and reclusterings to group and then further stratify patient samples according to phenotype. In contrast, variance mapping of condition states compares condition samples first with themselves and then against the parent condition population. As a result, activation states with the most diversity among conditions provide the core parameters in the differential state analysis. Given a pool of diverse conditions, this technique allows a researcher to identify the molecular events that underlie differential condition pathology (e.g., cancer responses to chemotherapy), as opposed to differences between conditions and a proposed normal control.

In some embodiments, when variance mapping is used to profile the signaling space of patient samples, conditions whose signaling response to modulators is similar are grouped together, regardless of tissue or cell type of origin. Similarly, two conditions (e.g. two tumors) that are thought to be relatively alike based on lineage markers or tissue of origin could have vastly different abilities to interpret environmental stimuli and would be profiled in two different groups.

When groups of signaling profiles have been identified it is frequently useful to determine whether other factors, such as clinical responses, presence of gene mutations, and protein expression levels, are non-randomly distributed within the groups. If experiments or literature suggest such a hypothesis in an arrayed flow cytometry experiment, it can be judged with simple statistical tests, such as the Student's t-test and the $X^2$ test. Similarly, if two variable factors within the experiment are thought to be related, the Pearson, and/or Spearman are used to measure the degree of this relationship.

Examples of analysis for activatable elements are described in US publication number 20060073474 entitled "Methods and compositions for detecting the activation state of multiple proteins in single cells" and US publication number 20050112700 entitled "Methods and compositions for risk stratification" the content of which are incorporate here by reference.

Detection

In practicing the methods of this invention, the detection of the status of the one or more activatable elements can be carried out by a person, such as a technician in the laboratory. Alternatively, the detection of the status of the one or more activatable elements can be carried out using automated systems. In either case, the detection of the status of the one or more activatable elements for use according to the methods of this invention is performed according to standard techniques and protocols well-established in the art.

One or more activatable elements can be detected and/or quantified by any method that detect and/or quantitates the presence of the activatable element of interest. Such methods may include radioimmunoassay (RIA) or enzyme linked immunoabsorbance assay (ELISA), immunohistochemistry, immunofluorescent histochemistry with or without confocal microscopy, reversed phase assays, homogeneous enzyme immunoassays, and related non-enzymatic techniques, Western blots, whole cell staining, immunoelectronmicroscopy, nucleic acid amplification, gene array, protein array, mass spectrometry, patch clamp, 2-dimensional gel electrophoresis, differential display gel electrophoresis, microsphere-based multiplex protein assays, label-free cellular assays and flow cytometry, etc. U.S. Pat. No. 4,568,649 describes ligand detection systems, which employ scintillation counting. These techniques are particularly useful for modified protein parameters. Cell readouts for proteins and other cell determinants can be obtained using fluorescent or otherwise tagged reporter molecules. Flow cytometry methods are useful for measuring intracellular parameters.

In some embodiments, the present invention provides methods for determining an activatable element's activation profile for a single cell. The methods may comprise analyzing cells by flow cytometry on the basis of the activation level of at least two activatable elements. Binding elements (e.g. activation state-specific antibodies) are used to analyze cells on the basis of activatable element activation level, and can be detected as described below. Alternatively, non-binding elements systems as described above can be used in any system described herein.

Detection of cell signaling states may be accomplished using binding elements and labels. Cell signaling states may be detected by a variety of methods known in the art. They generally involve a binding element, such as an antibody, and a label, such as a fluorchrome to form a detection element. Detection elements do not need to have both of the above agents, but can be one unit that possesses both qualities. These and other methods are well described in U.S. Pat. Nos. 7,381,535 and 7,393,656 and U.S. Ser. Nos. 10/193,462; 11/655,785; 11/655,789; 11/655,821; 11/338,957, 61/048,886; 61/048,920; and 61/048,657 which are all incorporated by reference in their entireties.

In one embodiment of the invention, it is advantageous to increase the signal to noise ratio by contacting the cells with the antibody and label for a time greater than 5, 6, 7, 8, 9, 10, 11, 12, 13, 14, 15, 16, 17, 18, 19, 20, 24 or up to 48 or more hours.

When using fluorescent labeled components in the methods and compositions of the present invention, it will recognized that different types of fluorescent monitoring systems, e.g., Cytometric measurement device systems, can be used to practice the invention. In some embodiments, flow cytometric systems are used or systems dedicated to high throughput screening, e.g. 96 well or greater microtiter plates. Methods of performing assays on fluorescent materials are well known in the art and are described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N. J., Modern Molecular Photochemistry, Menlo Park: Benjamin/Cummings Publishing Col, Inc. (1978), pp. 296-361.

Fluorescence in a sample can be measured using a fluorimeter. In general, excitation radiation, from an excitation source having a first wavelength, passes through excitation optics. The excitation optics cause the excitation radiation to excite the sample. In response, fluorescent proteins in the sample emit radiation that has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation. In general, known robotic systems and components can be used.

Other methods of detecting fluorescence may also be used, e.g., Quantum dot methods (see, e.g., Goldman et al., J. Am. Chem. Soc. (2002) 124:6378-82; Pathak et al. J. Am. Chem. Soc. (2001) 123:4103-4; and Remade et al., Proc. Natl. Sci.

USA (2000) 18:553-8, each expressly incorporated herein by reference) as well as confocal microscopy. In general, flow cytometry involves the passage of individual cells through the path of a laser beam. The scattering the beam and excitation of any fluorescent molecules attached to, or found within, the cell is detected by photomultiplier tubes to create a readable output, e.g. size, granularity, or fluorescent intensity.

In some embodiments, the activation level of an activatable element is measured using Inductively Coupled Plasma Mass Spectrometer (ICP-MS). A binding element that has been labeled with a specific element binds to the activatable. When the cell is introduced into the ICP, it is atomized and ionized. The elemental composition of the cell, including the labeled binding element that is bound to the activatable element, is measured. The presence and intensity of the signals corresponding to the labels on the binding element indicates the level of the activatable element on that cell (Tanner et al. Spectrochimica Acta Part B: Atomic Spectroscopy, 2007 March; 62(3):188-195.).

The detecting, sorting, or isolating step of the methods of the present invention can entail fluorescence-activated cell sorting (FACS) techniques, where FACS is used to select cells from the population containing a particular surface marker, or the selection step can entail the use of magnetically responsive particles as retrievable supports for target cell capture and/or background removal. A variety of FACS systems are known in the art and can be used in the methods of the invention (see e.g., WO99/54494, filed Apr. 16, 1999; U.S. Ser. No. 20010006787, filed Jul. 5, 2001, each expressly incorporated herein by reference).

In some embodiments, a FACS cell sorter (e.g. a FACS-Vantage™ Cell Sorter, Becton Dickinson Immunocytometry Systems, San Jose, Calif.) is used to sort and collect cells based on their activation profile (positive cells) in the presence or absence of an increase in activation level in an activatable element in response to a modulator. Other flow cytometers that are commercially available include the LSR II and the Canto II both available from Becton Dickinson. See Shapiro, Howard M., Practical Flow Cytometry, 4th Ed., John Wiley & Sons, Inc., 2003 for additional information on flow cytometers.

In some embodiments, the cells are first contacted with fluorescent-labeled activation state-specific binding elements (e.g. antibodies) directed against specific activation state of specific activatable elements. In such an embodiment, the amount of bound binding element on each cell can be measured by passing droplets containing the cells through the cell sorter. By imparting an electromagnetic charge to droplets containing the positive cells, the cells can be separated from other cells. The positively selected cells can then be harvested in sterile collection vessels. These cell-sorting procedures are described in detail, for example, in the FACSVantage™ Training Manual, with particular reference to sections 3-11 to 3-28 and 10-1 to 10-17, which is hereby incorporated by reference in its entirety. See the patents, applications and articles referred to, and incorporated above for detection systems.

Fluorescent compounds such as Daunorubicin and Enzastaurin are problematic for flow cytometry based biological assays due to their broad fluorescence emission spectra. These compounds get trapped inside cells after fixation with agents like paraformaldehyde, and are excited by one or more of the lasers found on flow cytometers. The fluorescence emission of these compounds is often detected in multiple PMT detectors which complicates their use in multiparametric flow cytometry. A way to get around this problem is to compensate out the fluorescence emission of the compound from the PMT detectors used to measure the relevant biological markers. This is achieved using a PMT detector with a bandpass filter near the emission maximum of the fluorescent compound, and cells incubated with the compound as the compensation control when calculating a compensation matrix. The cells incubated with the fluorescent compound are fixed with paraformaldehyde, then washed and permeabilized with 100% methanol. The methanol is washed out and the cells are mixed with unlabeled fixed/permed cells to yield a compensation control consisting of a mixture of fluorescent and negative cell populations.

In another embodiment, positive cells can be sorted using magnetic separation of cells based on the presence of an isoform of an activatable element. In such separation techniques, cells to be positively selected are first contacted with specific binding element (e.g., an antibody or reagent that binds an isoform of an activatable element). The cells are then contacted with retrievable particles (e.g., magnetically responsive particles) that are coupled with a reagent that binds the specific element. The cell-binding element-particle complex can then be physically separated from non-positive or non-labeled cells, for example, using a magnetic field. When using magnetically responsive particles, the positive or labeled cells can be retained in a container using a magnetic filed while the negative cells are removed. These and similar separation procedures are described, for example, in the Baxter Immunotherapy Isolex training manual which is hereby incorporated in its entirety.

In some embodiments, methods for the determination of a receptor element activation state profile for a single cell are provided. The methods comprise providing a population of cells and analyze the population of cells by flow cytometry. Preferably, cells are analyzed on the basis of the activation level of at least two activatable elements. In some embodiments, a multiplicity of activatable element activation-state antibodies is used to simultaneously determine the activation level of a multiplicity of elements.

In some embodiment, cell analysis by flow cytometry on the basis of the activation level of at least two elements is combined with a determination of other flow cytometry readable outputs, such as the presence of surface markers, granularity and cell size to provide a correlation between the activation level of a multiplicity of elements and other cell qualities measurable by flow cytometry for single cells.

As will be appreciated, the present invention also provides for the ordering of element clustering events in signal transduction. Particularly, the present invention allows the artisan to construct an element clustering and activation hierarchy based on the correlation of levels of clustering and activation of a multiplicity of elements within single cells. Ordering can be accomplished by comparing the activation level of a cell or cell population with a control at a single time point, or by comparing cells at multiple time points to observe subpopulations arising out of the others.

The present invention provides a valuable method of determining the presence of cellular subsets within cellular populations. Ideally, signal transduction pathways are evaluated in homogeneous cell populations to ensure that variances in signaling between cells do not qualitatively nor quantitatively mask signal transduction events and alterations therein. As the ultimate homogeneous system is the single cell, the present invention allows the individual evaluation of cells to allow true differences to be identified in a significant way.

Thus, the invention provides methods of distinguishing cellular subsets within a larger cellular population. As outlined herein, these cellular subsets often exhibit altered biological characteristics (e.g. activation levels, altered response to modulators) as compared to other subsets within the population. For example, as outlined herein, the methods of the invention allow the identification of subsets of cells from a population such as primary cell populations, e.g. peripheral blood mononuclear cells that exhibit altered responses (e.g. response associated with presence of a condition) as compared to other subsets. In addition, this type of evaluation distinguishes between different activation states, altered responses to modulators, cell lineages, cell differentiation states, etc.

As will be appreciated, these methods provide for the identification of distinct signaling cascades for both artificial and stimulatory conditions in complex cell populations, such a peripheral blood mononuclear cells, or naive and memory lymphocytes.

When necessary cells are dispersed into a single cell suspension, e.g. by enzymatic digestion with a suitable protease, e.g. collagenase, dispase, etc; and the like. An appropriate solution is used for dispersion or suspension. Such solution will generally be a balanced salt solution, e.g. normal saline, PBS, Hanks balanced salt solution, etc., conveniently supplemented with fetal calf serum or other naturally occurring factors, in conjunction with an acceptable buffer at low concentration, generally from 5-25 mM. Convenient buffers include HEPES1 phosphate buffers, lactate buffers, etc. The cells may be fixed, e.g. with 3% paraformaldehyde, and are usually permeabilized, e.g. with ice cold methanol; HEPES-buffered PBS containing 0.1% saponin, 3% BSA; covering for 2 min in acetone at −200 C; and the like as known in the art and according to the methods described herein.

In some embodiments, one or more cells are contained in a well of a 96 well plate or other commercially available multiwell plate. In an alternate embodiment, the reaction mixture or cells are in a cytometric measurement device. Other multiwell plates useful in the present invention include, but are not limited to 384 well plates and 1536 well plates. Still other vessels for containing the reaction mixture or cells and useful in the present invention will be apparent to the skilled artisan.

The addition of the components of the assay for detecting the activation level or activity of an activatable element, or modulation of such activation level or activity, may be sequential or in a predetermined order or grouping under conditions appropriate for the activity that is assayed for. Such conditions are described here and known in the art. Moreover, further guidance is provided below (see, e.g., in the Examples).

In some embodiments, the activation level of an activatable element is measured using Inductively Coupled Plasma Mass Spectrometer (ICP-MS). A binding element that has been labeled with a specific element binds to the activatable. When the cell is introduced into the ICP, it is atomized and ionized. The elemental composition of the cell, including the labeled binding element that is bound to the activatable element, is measured. The presence and intensity of the signals corresponding to the labels on the binding element indicates the level of the activatable element on that cell (Tanner et al. Spectrochimica Acta Part B: Atomic Spectroscopy, 2007 March; 62(3):188-195.).

As will be appreciated by one of skill in the art, the instant methods and compositions find use in a variety of other assay formats in addition to flow cytometry analysis. For example, DNA microarrays are commercially available through a variety of sources (Affymetrix, Santa Clara Calif.) or they can be custom made in the lab using arrayers which are also know (Perkin Elmer). In addition, protein chips and methods for synthesis are known. These methods and materials may be adapted for the purpose of affixing activation state binding elements to a chip in a prefigured array. In some embodiments, such a chip comprises a multiplicity of element activation state binding elements, and is used to determine an element activation state profile for elements present on the surface of a cell.

In some embodiments, a chip comprises a multiplicity of the "second set binding elements," in this case generally unlabeled. Such a chip is contacted with sample, preferably cell extract, and a second multiplicity of binding elements comprising element activation state specific binding elements is used in the sandwich assay to simultaneously determine the presence of a multiplicity of activated elements in sample. Preferably, each of the multiplicity of activation state-specific binding elements is uniquely labeled to facilitate detection.

In some embodiments confocal microscopy can be used to detect activation profiles for individual cells. Confocal microscopy relies on the serial collection of light from spatially filtered individual specimen points, which is then electronically processed to render a magnified image of the specimen. The signal processing involved confocal microscopy has the additional capability of detecting labeled binding elements within single cells, accordingly in this embodiment the cells can be labeled with one or more binding elements. In some embodiments the binding elements used in connection with confocal microscopy are antibodies conjugated to fluorescent labels, however other binding elements, such as other proteins or nucleic acids are also possible.

In some embodiments, the methods and compositions of the instant invention can be used in conjunction with an "In-Cell Western Assay." In such an assay, cells are initially grown in standard tissue culture flasks using standard tissue culture techniques. Once grown to optimum confluency, the growth media is removed and cells are washed and trypsinized. The cells can then be counted and volumes sufficient to transfer the appropriate number of cells are aliquoted into microwell plates (e.g., Nunc™ 96 Microwell™ plates). The individual wells are then grown to optimum confluency in complete media whereupon the media is replaced with serum-free media. At this point controls are untouched, but experimental wells are incubated with a modulator, e.g. EGF. After incubation with the modulator cells are fixed and stained with labeled antibodies to the activation elements being investigated. Once the cells are labeled, the plates can be scanned using an imager such as the Odyssey Imager (LiCor, Lincoln Nebr.) using techniques described in the Odyssey Operator's Manual v1.2., which is hereby incorporated in its entirety. Data obtained by scanning of the multiwell plate can be analyzed and activation profiles determined as described below.

In some embodiments, the detecting is by high pressure liquid chromatography (HPLC), for example, reverse phase HPLC, and in a further aspect, the detecting is by mass spectrometry.

These instruments can fit in a sterile laminar flow or fume hood, or are enclosed, self-contained systems, for cell culture growth and transformation in multi-well plates or tubes and for hazardous operations. The living cells may be grown under controlled growth conditions, with controls for temperature, humidity, and gas for time series of the live cell assays. Automated transformation of cells and automated colony pickers may facilitate rapid screening of desired cells.

Flow cytometry or capillary electrophoresis formats can be used for individual capture of magnetic and other beads, particles, cells, and organisms.

Flexible hardware and software allow instrument adaptability for multiple applications. The software program modules allow creation, modification, and running of methods.

The system diagnostic modules allow instrument alignment, correct connections, and motor operations. Customized tools, labware, and liquid, particle, cell and organism transfer patterns allow different applications to be performed. Databases allow method and parameter storage. Robotic and computer interfaces allow communication between instruments.

In some embodiment, the methods of the invention include the use of liquid handling components. The liquid handling systems can include robotic systems comprising any number of components. In addition, any or all of the steps outlined herein may be automated; thus, for example, the systems may be completely or partially automated. See U.S. Ser. No. 61/048,657.

As will be appreciated by those in the art, there are a wide variety of components which can be used, including, but not limited to, one or more robotic arms; plate handlers for the positioning of microplates; automated lid or cap handlers to remove and replace lids for wells on non-cross contamination plates; tip assemblies for sample distribution with disposable tips; washable tip assemblies for sample distribution; 96 well loading blocks; cooled reagent racks; microtiter plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation. In some embodiments, chemically derivatized particles, plates, cartridges, tubes, magnetic particles, or other solid phase matrix with specificity to the assay components are used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In some embodiments, platforms for multi-well plates, multi-tubes, holders, cartridges, minitubes, deep-well plates, microfuge tubes, cryovials, square well plates, filters, chips, optic fibers, beads, and other solid-phase matrices or platform with various volumes are accommodated on an upgradable modular platform for additional capacity. This modular platform includes a variable speed orbital shaker, and multi-position work decks for source samples, sample and reagent dilution, assay plates, sample and reagent reservoirs, pipette tips, and an active wash station. In some embodiments, the methods of the invention include the use of a plate reader.

In some embodiments, thermocycler and thermoregulating systems are used for stabilizing the temperature of heat exchangers such as controlled blocks or platforms to provide accurate temperature control of incubating samples from 0° C. to 100° C.

In some embodiments, interchangeable pipet heads (single or multi-channel) with single or multiple magnetic probes, affinity probes, or pipetters robotically manipulate the liquid, particles, cells, and organisms. Multi-well or multi-tube magnetic separators or platforms manipulate liquid, particles, cells, and organisms in single or multiple sample formats.

In some embodiments, the instrumentation will include a detector, which can be a wide variety of different detectors, depending on the labels and assay. In some embodiments, useful detectors include a microscope(s) with multiple channels of fluorescence; plate readers to provide fluorescent, ultraviolet and visible spectrophotometric detection with single and dual wavelength endpoint and kinetics capability, fluorescence resonance energy transfer (FRET), luminescence, quenching, two-photon excitation, and intensity redistribution; CCD cameras to capture and transform data and images into quantifiable formats; and a computer workstation.

In some embodiments, the robotic apparatus includes a central processing unit which communicates with a memory and a set of input/output devices (e.g., keyboard, mouse, monitor, printer, etc.) through a bus. Again, as outlined below, this may be in addition to or in place of the CPU for the multiplexing devices of the invention. The general interaction between a central processing unit, a memory, input/output devices, and a bus is known in the art. Thus, a variety of different procedures, depending on the experiments to be run, are stored in the CPU memory.

These robotic fluid handling systems can utilize any number of different reagents, including buffers, reagents, samples, washes, assay components such as label probes, etc.

Any of the steps above can be performed by a computer program product that comprises a computer executable logic that is recorded on a computer readable medium. For example, the computer program can execute some or all of the following functions: (i) exposing reference population of cells to one or more modulators, (ii) exposing reference population of cells to one or more binding elements, (iii) detecting the activation levels of one or more activatable elements, (iv) characterizing one or more cellular pathways and/or (v) classifying one or more cells into one or more classes based on the activation level.

The computer executable logic can work in any computer that may be any of a variety of types of general-purpose computers such as a personal computer, network server, workstation, or other computer platform now or later developed. In some embodiments, a computer program product is described comprising a computer usable medium having the computer executable logic (computer software program, including program code) stored therein. The computer executable logic can be executed by a processor, causing the processor to perform functions described herein. In other embodiments, some functions are implemented primarily in hardware using, for example, a hardware state machine. Implementation of the hardware state machine so as to perform the functions described herein will be apparent to those skilled in the relevant arts.

The program can provide a method of determining the status of an individual by accessing data that reflects the activation level of one or more activatable elements in the reference population of cells.

Analysis

Advances in flow cytometry have enabled the individual cell enumeration of up to thirteen simultaneous parameters (De Rosa et al., 2001) and are moving towards the study of genomic and proteomic data subsets (Krutzik and Nolan, 2003; Perez and Nolan, 2002). Likewise, advances in other techniques (e.g. microarrays) allow for the identification of multiple activatable elements. As the number of parameters, epitopes, and samples have increased, the complexity of experiments and the challenges of data analysis have grown rapidly. An additional layer of data complexity has been added by the development of stimulation panels which enable the study of activatable elements under a growing set of experimental conditions. See Krutzik et al, Nature Chemical Biology February 2008. Methods for the analysis of multiple parameters are well known in the art. See U.S. Ser. No. 61/079,579 for gating analysis.

In some embodiments where flow cytometry is used, flow cytometry experiments are performed and the results are expressed as fold changes using graphical tools and analyses, including, but not limited to a heat map or a histogram to facilitate evaluation. One common way of comparing changes in a set of flow cytometry samples is to overlay histograms of one parameter on the same plot. Flow cytometry experiments ideally include a reference sample against which experimental samples are compared. Reference samples can include normal and/or cells associated with a condition (e.g. tumor cells). See also U.S. Ser. No. 61/079,537 for visualization tools.

The patients are stratified based on nodes that inform the clinical question using a variety of metrics. To stratify the patients between those patients with No Response (NR) versus a Complete Response (CR), a prioritization of the nodes can be made according to statistical significance (such as p-value from a t-test or Wilcoxon test or area under the receiver operator characteristic (ROC) curve) or their biological relevance. See FIG. 2, and the methods described herein for methods for analyzing the cell signaling pathway data. For example, FIG. 2 shows four methods to analyze data, such as from AML patients. Other characteristics such as expression markers may also be used. For example the fold over isotype can be used (e.g., log 2(MFIstain)–Log 2(MFIisotype)) or % positive above Isotype.

FIG. 2 shows the use of four metrics used to analyze data from cells that may be subject to a disease, such as AML. For example, the "basal" metric is calculated by measuring the autofluorescence of a cell that has not been stimulated with a modulator or stained with a labeled antibody. The "total phospho" metric is calculated by measuring the autofluorescence of a cell that has been stimulated with a modulator and stained with a labeled antibody. The "fold change" metric is the measurement of the total phospho metric divided by the basal metric. The quadrant frequency metric is the frequency of cells in each quadrant of the contour plot.

A user may also analyze multimodal distributions to separate cell populations. In some embodiments, metrics can be used for analyzing bimodal and spread distribution. In some embodiments, a Mann-Whitney U Metric is used.

In some embodiments, metrics that calculate the percent of positive above unstained and metrics that calculate MFI of positive over untreated stained can be used.

A user can create other metrics for measuring the negative signal. For example, a user may analyze a "gated unstained" or ungated unstained autofluorescence population as the negative signal for calculations such as "basal" and "total". This is a population that has been stained with surface markers such as CD33 and CD45 to gate the desired population, but is unstained for the fluorescent parameters to be quantitatively evaluated for node determination. However, every antibody has some degree of nonspecific association or "stickyness" which is not taken into account by just comparing fluorescent antibody binding to the autofluorescence. To obtain a more accurate "negative signal", the user may stain cells with isotype-matched control antibodies. In addition to the normal fluorescent antibodies, in one embodiment, (phospho) or non phosphopeptides which the antibodies should recognize will take away the antibody's epitope specific signal by blocking its antigen binding site allowing this "bound" antibody to be used for evaluation of non-specific binding. In another embodiment, a user may block with unlabeled antibodies. This method uses the same antibody clones of interest, but uses a version that lacks the conjugated fluorophore. The goal is to use an excess of unlabeled antibody with the labeled version. In another embodiment, a user may block other high protein concentration solutions including, but not limited to fetal bovine serum, and normal serum of the species in which the antibodies were made, i.e. using normal mouse serum in a stain with mouse antibodies. (It is preferred to work with primary conjugated antibodies and not with stains requiring secondary antibodies because the secondary antibody will recognize the blocking serum). In another embodiment, a user may treat fixed cells with phosphatases to enzymatically remove phosphates, then stain.

In alternative embodiments, there are other ways of analyzing data, such as third color analysis (3D plots), which can be similar to Cytobank 2D, plus third D in color.

One embodiment of the present invention is software to examine the correlations among phosphorylation or expression levels of pairs of proteins in response to stimulus or modulation. The software examines all pairs of proteins for which phosphorylation and/or expression was measured in an experiment. The Total phospho metric (sometimes called "FoldAF") is used to represent the phosphorylation or expression data for each protein; this data is used either on linear scale or log 2 scale. See FIG. 2, metric 3 for Total Phospho.

For each protein pair under each experimental condition (unstimulated, stimulated, or treated with drug/modulator), the Pearson correlation coefficient and linear regression line fit are computed. The Pearson correlation coefficients for samples representing responding and non-responding patients are calculated separately for each group and compared to the unperturbed (unstimulated) data. The following additional metrics are derived:

1. Delta CRNR unstim: the difference between Pearson correlation coefficients for each protein pair for the responding patients and for the non-responding patients in the basal or unstimulated state.
2. Delta CRNR stim: the difference between Pearson correlation coefficients for each protein pair for the responding patients and for the non-responding patients in the stimulated or treated state.
3. DeltaDelta CRNR: the difference between Delta CRNRstim and Delta CRNRunstim.

The correlation coefficients, line fit parameters (R, p-value, and slope), and the three derived parameters described above are computed for each protein-protein pair. Protein-protein pairs are identified for closer analysis by the following criteria:

1. Large shifts in correlations within patient classes as denoted by large positive or negative values (top and bottom quartile or $10^{th}$ and $90^{th}$ percentile) of the DeltaDelta CRNR parameter.
2. Large positive or negative (top and bottom quartile or $10^{th}$ and $90^{th}$ percentile) Pearson correlation for at least one patient group in either unstimulated or stimulated/treated condition.
3. Significant line fit (p-value<=0.05 for linear regression) for at least one patient group in either unstimulated or stimulated/treated condition.

All pair data is plotted as a scatter plot with axes representing phosphorylation or expression level of a protein. Data for each sample (or patient) is plotted with color indicating whether the sample represents a responder (generally blue) or non-responder (generally red). Further line fits for responders, non-responders and all data are also represented on this graph, with significant line fits (p-value<=0.05 in linear regression) represented by solid lines and other fits represented by dashed line, enabling rapid visual identification of significant fits. Each graph is annotated with the Pearson correlation coefficient and linear regression parameters for the individual classes and for the data as a whole. The resulting plots are saved in PNG format to a single directory for browsing using Picassa. Other visualization software can also be used.

Each protein pair can be further annotated by whether the proteins comprising the pair are connected in a "canonical" pathway. In the current implementation canonical pathways are defined as the pathways curated by the NCI and Nature Publishing Group. This distinction is important; however, it is likely not an exclusive way to delineate which protein pairs to examine. High correlation among proteins in a canonical pathway in a sample may indicate the pathway in that sample is "intact" or consistent with the known literature. One embodiment of the present invention identifies protein pairs that are not part of a canonical pathway with high correlation in a sample as these may indicate the non-normal or pathological signaling. This method will be used to identify stimulator/modulator-stain-stain combinations that distinguish classes of patients.

In some embodiments, nodes and/or nodes/metric combinations can be analyzed and compared across sample for their ability to distinguish among different groups (e.g., CR vs. NR patients) using classification algorithms. Any suitable classification algorithm known in the art can be used. Examples of classification algorithms that can be used include, but are not limited to, multivariate classification algorithms such as decision tree techniques: bagging, boosting, random forest, additive techniques: regression, lasso, bblrs, stepwise regression, nearest neighbors or other methods such as support vector machines.

In some embodiments, nodes and/or nodes/metric combinations can be analyzed and compared across sample for their ability to distinguish among different groups (e.g., CR vs. NR patients) using random forest algorithm. Random forest (or random forests) is an ensemble classifier that consists of many decision trees and outputs the class that is the mode of the class's output by individual trees. The algorithm for inducing a random forest was developed by Leo Breiman (Breiman, Leo (2001). "Random Forests". Machine Learning 45 (1): 5-32. doi:10.1023/A:1010933404324) and Adele Cutler. The term came from random decision forests that was first proposed by Tin Kam Ho of Bell Labs in 1995. The method combines Breiman's "bagging" idea and the random selection of features, introduced independently by Ho (Ho, Tin (1995). "Random Decision Forest". 3rd Int'l Conf. on Document Analysis and Recognition. pp. 278-282; Ho, Tina (1998). "The Random Subspace Method for Constructing Decision Forests". IEEE Transactions on Pattern Analysis and Machine Intelligence 20 (8): 832-844. doi:10.1109/34.709601) and Amit and Geman (Amit, Y.; Geman, D. (1997). "Shape quantization and recognition with randomized trees". Neural Computation 9 (7): 1545-1588. doi:10.1162/neco.1997.9.7.1545) in order to construct a collection of decision trees with controlled variation.

In some embodiments, nodes and/or nodes/metric combinations can be analyzed and compared across sample for their ability to distinguish among different groups (e.g., CR vs. NR patients) using lasso algorithm. The method of least squares is a standard approach to the approximate solution of overdetermined systems, i.e. sets of equations in which there are more equations than unknowns. "Least squares" means that the overall solution minimizes the sum of the squares of the errors made in solving every single equation. The best fit in the least-squares sense minimizes the sum of squared residuals, a residual being the difference between an observed value and the fitted value provided by a model.

In some embodiments, nodes and/or nodes/metric combinations can be analyzed and compared across sample for their ability to distinguish among different groups (e.g., CR vs. NR patients) using BBLRS model building methodology.

a. Description of the BBLRS Model Building Methodology

Production of bootstrap samples: A large number of bootstrap samples are first generated with stratification by outcome status to insure that all bootstrap samples have a representative proportion of outcomes of each type. This is particularly important when the number of observations is small and the proportion of outcomes of each type is unbalanced. Stratification under such a scenario is especially critical to the composition of the out of bag (OOB) samples, since only about one-third of observations from the original sample will be included in each OOB sample.

Best subsets selection of main effects: Best subsets selection is used to identify the combination of predictors that yields the largest score statistic among models of a given size in each bootstrap sample. Models having from 1 to 2×N/10 are typically entertained at this stage, where N is the number of observations. This is much larger than the number of predictors generally recommended when building a generalized linear prediction model (Harrell, 2001) but subsequent model building rules are applied to reduce the likelihood of overfitting. At the conclusion of this step, there will be a "best" main effects model of each size for each bootstrap sample, though the number of unique models of each size may be considerably fewer.

Determination of the optimal model size (for main effects): Each of the unique "best" models of each size, identified in the previous step, are fit to each of a subset of the bootstrap samples, where the number of bootstrap samples in the subset is under the control of the user (i.e. a tuning parameter) so that the processing time required at this step can be controlled. For each of the bootstrap samples in the subset, the median SBC of the "best" models of the same size is calculated and the model size yielding the lowest median SBC in that bootstrap sample is identified. The optimal model size is then determined as the size for which the median SBC is smallest most often over the subset of bootstrap samples.

Identification of the top models of the best size: At this stage, all previously identified "best" models of the optimal size are fit to every bootstrap sample. A number of top models are then selected as those with the highest values of the margin statistic (a measure from the logistic model of the difference in the predicted probabilities of CR, between NR patients with the highest predicted probabilities and CR patients with the lowest predicted probabilities). In order to limit the processing time required in subsequent steps, the number of top models selected is under the control of the user.

Identification of important two-way interactions: For each of the top main effects models identified in the previous step, models are constructed on every bootstrap sample, with main effects forced into the model and with stepwise selection used to identify important two-way interactions among the set of all possible pair-wise combinations of the main effects. The nominal significance level for entry and removal of interaction terms is under the control of the user. Significance levels greater than 0.05 are often used for entry because of the low power many studies have to detect interactions and because safeguards against over-fitting are applied subsequently.

At this stage, collections of full models (main effects and possibly some two-way interactions among them) have been constructed (on the set of all bootstrap samples) for each unique set of main effects identified in the previous step. The top full models in each collection are then chosen as those constructed most frequently over all bootstrap samples, where winners are decided among tied models by the lowest mean SBC and then the highest mean AUROC. The number of full models in each collection that are advanced to the next step is under the control of the user.

Selection of the effects in the final model: Each full model advanced to this step is fit to every bootstrap sample and the median margin statistic for each model over the bootstrap samples is calculated. The model with the highest median margin statistic is selected as the final model. If there are ties, the model with the lowest mean SBC is selected.

Technically, the procedure described here results in the selection of the effects (main effects and possibly two-way interactions) to be included in the final model, but not specification of the model itself. The latter includes the effects and the specific regression coefficients associated with the intercept and each of the model effects.

Specification of the final model: The effects in the final model are then fit to the complete dataset using Firth's method to apply shrinkage to the regression coefficient estimates. The model effects and their estimated regression coefficients (plus the estimate of the intercept) comprise the final model.

Another method of the present invention relates to display of information using scatter plots. Scatter plots are known in the art and are used to visually convey data for visual analysis of correlations. See U.S. Pat. No. 6,520,108. The scatter plots illustrating protein pair correlations can be annotated to convey additional information, such as one, two, or more additional parameters of data visually on a scatter plot.

Previously, scatter plots used equal size plots to denote all events. However, using the methods described herein two additional parameters can be visualized as follows. First, the diameter of the circles representing the phosphorylation or expression levels of the pair of proteins may be scaled according to another parameter. For example they may be scaled according to expression level of one or more other proteins such as transporters (if more than one protein, scaling is additive, concentric rings may be used to show individual contributions to diameter).

Second, additional shapes may be used to indicate subclasses of patients. For example they could be used to denote patients who responded to a second drug regimen or where CRp status. Another example is to show how samples or patients are stratified by another parameter (such as a different stim-stain-stain combination). Many other shapes, sizes, colors, outlines, or other distinguishing glyphs may be used to convey visual information in the scatter plot.

In this example the size of the dots is relative to the measured expression and the box around a dot indicates a NRCR patient that is a patient that became CR (Responsive) after more aggressive treatment but was initially NR (Non-Responsive). Patients without the box indicate a NR patient that stayed NR.

Applying the methods of the present invention, the Total Phospho metric for p-Akt and p-Stat1 are correlated in response to peroxide ("HOOH") treatment. (Total phoshpho is calculated as shown in FIG. 2, metric #3). On log 2 scale the Pearson correlation coefficient for p-Akt and p-Stat1 in response to HOOH for samples from patients who responded to first treatment is 0.89 and the p-value for linear regression line fit is 0.0075. In contrast there appeared to be no correlation observed for p-Akt and p-Stat1 in HOOH treated samples from patients annotated as "NR" (non-responder) or "NRCR" (initial non-responder, who responded to later more intensive treatment). Further there are no significant correlations observed for these proteins in any patient class for untreated samples.

The Total phospho metric for p-Erk and p-CREB also appeared to be correlated in response to IL-3, IL-6, and IL-27 treatment in samples from non-responding patients (NR and NR-CR). When considering all data in log 2 scale the Pearson correlation coefficients for p-Erk and p-CREB in response to IL-3, IL-6, and IL-27 for samples from patients who did not respond to first treatment are 0.74, 0.76, 0.81, respectively, and the respective p-values for linear regression line fits are <0.0001, <0.0001, and <0.0001. In contrast there appeared to be no correlation observed for p-Erk and p-Creb in IL-3, IL-6, and IL-27 experiments for patients annotated as "CR". (Not shown). Table 2 below shows nodes identified by a fold change metric. Table 3 below shows node identified by a variety of methods. In some embodiments, the nodes depicted in Table 2 and 3 are used according to the methods described herein for classification, diagnosis, prognosis of AML, MDS or MPN or for the selection of treatment and/or predict outcome after administering a therapeutic.

TABLE 2

Nodes Identified by Fold Change Metric

| Node | Metric | Relevant Biology/ Known Role in AML | p-Val | AUC |
|---|---|---|---|---|
| SDF-1 → p-Akt | Fold Change | BM Chemokine | .025 | .71 |
| SCF → p-Akt | Fold Change | Stem Cell Growth Factor Upreg, Mutated In AML | .018 | .809 |
| SCF → p-S6 | Fold Change | Stem Cell Growth Factor Upreg, Mutated In AML | .055 | .66 |
| FLT3L → p-Akt | Fold Change | Growth Factor Mutated In AML | .003 | .82 |
| FLT3L → p-S6 | Fold Change | Growth Factor Mutated In AML | .026 | .66 |
| G-CSF → p-Stat3 | Fold Change | Myeloid Growth Factor | .090 | .68 |
| G-CSF → p-Stat5 | Fold Change | Myeloid Growth Factor | .038 | .70 |
| Peroxide → p-Slp-76 | Fold Change | Phosphatase Inhibition Novel AML Biology | .02 | .78 |
| Peroxide → p-Plcγ2 | Fold Change | Phosphatase Inhibition Novel AML Biology | .09 | .75 |
| IFNα → p-Stat1 | Fold Change | | .017 | .747 |
| IFNγ → p-Stat1 | Fold Change | | .038 | .707 |
| Thapsi → p-S6 | Fold Change | Pharmacological stim | .020 | .707 |
| PMA → p-Erk | Fold Change | Pharmacological stim | .062 | .702 |

TABLE 3

Nodes Identified by Variety of Metrics

| Node | Metric | Relevant Biology/ Known Role in AML | p-Val | AUC |
|---|---|---|---|---|
| Etoposide → cleaved PARP+ p-Chk2- | Quadrant Gate Frequency | DNA damage & Apoptosis | .001 | .82 |
| p-Creb | Basal | Over-expressed in AML | .0005 | .87 |
| p-Erk | Basal | Activated in AML | .02 | .77 |
| p-Stat6 | Basal | Novel AML Biology | .008 | .76 |
| p-Plcγ2 | Basal | Novel AML Biology | .007 | .79 |
| p-Stat3 | Basal | Activated in AML | .005 | .81 |
| IL-27 → p-Stat3 | Total | p-Stat3 Active in AML | .00004 | .80 |

TABLE 3-continued

Nodes Identified by Variety of Metrics

| Node | Metric | Relevant Biology/Known Role in AML | p-Val | AUC |
|---|---|---|---|---|
| IL-10 → p-Stat3 | Total | p-Stat3 Active in AML | .0009 | .84 |
| IL-6 → p-Stat3 | Total | p-pStat3 Active in AML | .001 | .77 |
| Etopo + Zvad → Cleaved Caspse 3 | Total | Apoptosis | | |
| ABCG2 | % Positive Above Isotype | Drug Transporter | .00093 | .75 |
| C-KITR | Fold over Isotype | Growth Factor Receptor | .012 | .78 |
| FLT3R | Fold over Isotype | Growth Factor Receptor | .0004 | .82 |

In some embodiments, analyses are performed on healthy cells. In some embodiments, the health of the cells is determined by using cell markers that indicate cell health. In some embodiments, cells that are dead or undergoing apoptosis will be removed from the analysis. In some embodiments, cells are stained with apoptosis and/or cell death markers such as PARP or Aqua dyes. Cells undergoing apoptosis and/or cells that are dead can be gated out of the analysis. In other embodiments, apoptosis is monitored over time before and after treatment. For example, in some embodiments, the percentage of healthy cells can be measured at time zero and then at later time points and conditions such as: 24 h with no modulator, and 24 h with Ara-C/Daunorubicin. In some embodiments, the measurements of activatable elements are adjusted by measurements of sample quality for the individual sample, such as the percent of healthy cells present.

In some embodiments, a regression equation will be used to adjust raw node readout scores for the percentage of healthy cells at 24 hours post-thaw. In some embodiments, means and standard deviations will be used to standardize the adjusted node readout scores.

Before applying the SCNP classifier, raw node-metric signal readouts (measurements) for samples will be adjusted for the percentage of healthy cells and then standardized. The adjustment for the percentage of healthy cells and the subsequent standardization of adjusted measurements is applied separately for each of the node-metrics in the SCNP classifier.

The following formula can be used to calculate the adjusted, normalized node-metric measurement (z) for each of the node-metrics of each sample.

$$z = ((x - (b_0 + b_1 \times pcthealthy)) - residual\_mean)/residual\_sd,$$

where x is the raw node-metric signal readout, $b_0$ and $b_1$ are the coefficients from the regression equation used to adjust for the percentage of healthy cells (pcthealthy), and residual_mean and residual_sd are the mean and standard deviation, respectively, for the adjusted signal readouts in the training set data. The values of $b_0$, $b_1$, residual_mean, and residual_sd for each node-metric are included in the embedded object below, with values of the latter two parameters stored in variables by the same name. The values of the $b_0$ and $b_1$ parameters are contained on separate records in the variable named "estimate". The value for $b_0$ is contained on the record where the variable "parameter" is equal to "Intercept" and the value for $b_1$ is contained on the record where the variable "parameter" is equal to "percenthealthy24Hrs". The value of pcthealthy will be obtained for each sample as part of the standard assay output. The SCNP classifier will be applied to the z values for the node-metrics to calculate the continuous SCNP classifier score and the binary induction response assignment (pNR or pCR) for each sample.

In some embodiments, the measurements of activatable elements are adjusted by measurements of sample quality for the individual cell populations or individual cells, based on markers of cell health in the cell populations or individual cells. Examples of analysis of healthy cells can be found in U.S. application Ser. No. 61/374,613 filed Aug. 18, 2010, the content of which is incorporated herein by reference in its entirety for all purposes.

In some embodiments, the invention provides methods of diagnosing, prognosing, determining progression, predicting a response to a treatment or choosing a treatment for acute leukemia, myelodysplastic syndrome or myeloproliferative neoplasms in an individual, the method comprising: (1) classifying one or more hematopoietic cells associated with acute leukemia, myelodysplastic syndrome or myeloproliferative neoplasms in said individual by a method comprising: a) subjecting a cell population comprising said one or more hematopoietic cells from said individual to modulator conditions, b) determining an activation level of activatable elements in one or more cells from said individual, and c) classifying said one or more hematopoietic cells based on said activation levels in response to modulator conditions using multivariate classification algorithms such as decision tree techniques: bagging, boosting, random forest, additive techniques: regression, lasso, bblrs, stepwise regression, nearest neighbors or other methods such as support vector machines (2) making a decision regarding a diagnosis, prognosis, progression, response to a treatment or a selection of treatment for acute leukemia, myelodysplastic syndrome or myeloproliferative neoplasms in said individual based on said classification of said one or more hematopoietic cells. In some embodiments, classifying further comprises identifying a difference in kinetics of said activation level. In some embodiments, the measurements of activatable elements are made only in healthy cells as determined using markers of cell health. In some embodiments, the measurements of activatable elements are adjusted by measurements of sample quality for the individual sample, such as the percent of healthy cells present.

Drug Screening

Another embodiment of the present invention is a method for screening drugs that are in development and indicated for patients that have been diagnosed with acute myelogenous leukemia (AML), myelodysplasia (MDS) or myelodyspastic syndrome (MPN).

Using the signaling nodes and methodology described herein, multiparametric flow cytometry could be used in-vitro to predict both on and off-target cell signaling effects. Using an embodiment of the present invention, the bone marrow or peripheral blood obtained from a patient diagnosed with AML, MDS or MPN could be divided and part of the sample subjected to a therapeutic. Modulators (e.g. GM-CSF or PMA) could then be added to the untreated and treated specimens. Activatable elements (e.g. JAKs/STATs/AKT), including the proposed target of the therapeutic, or those that may be affected by the therapeutic (off-target) can then be assessed for an activation state. This activation state can be used to predict the therapeutics' potential for on and off target effects prior to first in human studies.

Using the signaling nodes and methodology described herein, one embodiment of the present invention, such as multiparametric flow cytometry, could be used after in-vivo exposure to a therapeutic in development for patients that have been diagnosed with AML, MDS or MPN to determine both on and off-target effects. Using an embodiment of the present invention, the bone marrow or peripheral blood (fresh, frozen, ficoll purified, etc.) obtained from a patient diagnosed with AML or MDS at time points before and after exposure to a given therapeutic may be subjected to a modulator as above. Activatable elements (e.g. JAKs/STATs/ AKT), including the proposed target of the therapeutic, or those that may be affected by the therapeutic (off-target) can then be assessed for an activation state. This activation state can then be used to determine the on and off target signaling effects on the bone marrow or blast cells.

The apoptosis and peroxide panel study may reveal new biological classes of stratifying nodes for drug screening. Some of the important nodes could include changes on levels of p-Lck, pSlp-76, p PLCγ2, in response to peroxide alone or in combination with growth factors or cytokines. These important nodes are induced Cleaved Caspase 3 and Cleaved Caspase 8, and etoposide induced p-Chk2, peroxide ($H_2O_2$) induced p-SLP-76, peroxide ($H_2O_2$) induced p-PLCγ2 and peroxide ($H_2O_2$) induced P-Lck. The apoptosis panel may include but is not limited to, detection of changes in phosphorylation of Chk2, changes in amounts of cleaved caspase 3, cleaved caspase 8, cleaved poly (ACP ribose) polymerase PARP, cytochrome C released from the mitochondria these apoptotic nodes are measured in response to agents that included but are not limited to DNA damaging agents such as Etoposide, Mylotarg, AraC and daunorubicin either alone or in combination as well as to the global kinase inhibitor staurosporine.

Using the signaling nodes and methodology described herein, multiparametric flow cytometry could be used to find new target for treatment (e.g. new druggable targets). Using an embodiment of the present invention, the bone marrow or peripheral blood obtained from a patient diagnosed with AML, MDS or MPN could be divided and part of the sample subjected to one or more modulators (e.g. GM-CSF or PMA). Activatable elements (e.g. JAKs/STATs/AKT) can then be assessed for an activation state. This activation state can be used to predict find new target molecule for new existing therapeutics. These therapeutics can be used alone or in combination with other treatments for the treatment of AML, MDS or MPN.

Kits

In some embodiments the invention provides kits. Kits provided by the invention may comprise one or more of the state-specific binding elements described herein, such as phospho-specific antibodies. A kit may also include other reagents that are useful in the invention, such as modulators, fixatives, containers, plates, buffers, therapeutic agents, instructions, and the like.

In some embodiments, the kit comprises one or more of the phospho-specific antibodies specific for the proteins selected from the group consisting of PI3-Kinase (p85, p110a, p110b, p110d), Jak1, Jak2, SOCs, Rac, Rho, Cdc42, Ras-GAP, Vav, Tiam, Sos, Dbl, Nck, Gab, PRK, SHP1, and SHP2, SHIP1, SHIP2, sSHIP, PTEN, Shc, Grb2, PDK1, SGK, Akt1, Akt2, Akt3, TSC1,2, Rheb, mTor, 4EBP-1, p70S6Kinase, S6, LKB-1, AMPK, PFK, Acetyl-CoAa Carboxylase, DokS, Rafs, Mos, Tpl2, MEK1/2, MLK3, TAK, DLK, MKK3/6, MEKK1, 4, MLK3, ASK1, MKK4/7, SAPK/JNK1,2,3, p38s, Erk1/2, Syk, Btk, BLNK, LAT, ZAP70, Lck, Cbl, SLP-76, PLCγ1, PLCγ 2, STAT1, STAT 3, STAT 4, STAT 5, STAT 6, FAK, p130CAS, PAKs, LIMK1/2, Hsp90, Hsp70, Hsp27, SMADs, Rel-A (p65-NFKB), CREB, Histone H2B, HATs, HDACs, PKR, Rb, Cyclin D, Cyclin E, Cyclin A, Cyclin B, P16, p14Arf, p27KIP, p21CIP, Cdk4, Cdk6, Cdk7, Cdk1, Cdk2, Cdk9, Cdc25,A/B/C, Abl, E2F, FADD, TRADD, TRAF2, RIP, Myd88, BAD, Bcl-2, Mcl-1, Bcl-XL, Caspase 2, Caspase 3, Caspase 6, Caspase 7, Caspase 8, Caspase 9, IAPs, Smac, Fodrin, Actin, Src, Lyn, Fyn, Lck, NIK, IκB, p65 (RelA), IKKα, PKA, PKCα, PKCβ, PKC↓, PKCδ, CAMK, Elk, AFT, Myc, Egr-1, NFAT, ATF-2, Mdm2, p53, DNA-PK, Chk1, Chk2, ATM, ATR, βcatenin, CrkL, GSK3α, GSK3β, and FOXO. In some embodiments, the kit comprises one or more of the phospho-specific antibodies specific for the proteins selected from the group consisting of Erk, Syk, Zap70, Lck, Btk, BLNK, Cbl, PLCγ2, Akt, RelA, p38, S6. In some embodiments, the kit comprises one or more of the phospho-specific antibodies specific for the proteins selected from the group consisting of Akt1, Akt2, Akt3, SAPK/JNK1,2,3, p38s, Erk1/2, Syk, ZAP70, Btk, BLNK, Lck, PLCγ, PLCγ 2, STAT1, STAT 3, STAT 4, STAT 5, STAT 6, CREB, Lyn, p-S6, Cbl, NF-KB, GSK3β, CARMA/Bc110 and Tcl-1.

Kits provided by the invention may comprise one or more of the modulators described herein. In some embodiments, the kit comprises one or more modulators selected from the group consisting of $H_2O_2$, PMA, BAFF, April, SDF1 α, CD40L, IGF-1, Imiquimod, polyCpG, IL-7, IL-6, IL-10, IL-27, IL-4, IL-2, IL-3, thapsigardin and a combination thereof.

The state-specific binding element of the invention can be conjugated to a solid support and to detectable groups directly or indirectly. The reagents may also include ancillary agents such as buffering agents and stabilizing agents, e.g., polysaccharides and the like. The kit may further include, where necessary, other members of the signal-producing system of which system the detectable group is a member (e.g., enzyme substrates), agents for reducing background interference in a test, control reagents, apparatus for conducting a test, and the like. The kit may be packaged in any suitable manner, typically with all elements in a single container along with a sheet of printed instructions for carrying out the test.

Such kits enable the detection of activatable elements by sensitive cellular assay methods, such as IHC and flow cytometry, which are suitable for the clinical detection, prognosis, and screening of cells and tissue from patients, such as leukemia patients, having a disease involving altered pathway signaling.

Such kits may additionally comprise one or more therapeutic agents. The kit may further comprise a software package for data analysis of the physiological status, which may include reference profiles for comparison with the test profile.

Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

In some embodiments, the invention provides a kit comprising: (a) at least two modulators selected from the group consisting of Staurosporine, Etoposide, Mylotarg, Daunorubicin, AraC, G-CSF, IFNg, IFNa, IL-27, IL-3, IL-6, IL-10, FLT3L, SCF, G-CSF, SCF, G-CSF, SDF1a, LPS, PMA, Thapsigargin and H2O2; b) at least three binding elements specific to a particular activation state of the activatable element selected from the group consisting of p-Slp-76, p-Plcg2, p-Stat3, p-Stat5, p-Stat1, p-Stat6, P-Creb, Parp+, Chk2, Rel-A (p65-NFKB), p-AKT, p-S6, p-ERK, Cleaved Caspase 8, Cytoplasmic Cytochrome C, and p38; and (c) instructions for diagnosis, prognosis, determining acute myeloid leukemia progression and/or predicting response to a treatment for acute myeloid leukemia in an individual. In some embodiments, the kit further comprises a binding element specific for a cytokine receptor or drug transporter are selected from the group consisting of MDR1, ABCG2, MRP, P-Glycoprotein, CXCR4, FLT3, and c-kit. In some embodiments, the binding element is an antibody.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are expressly incorporated by reference in their entireties.

EXAMPLES

Example 1

Materials and Methods

The present illustrative example represents how to analyze cells in one embodiment of the present invention. There are several steps in the process, such as the stimulation step, the staining step and the flow cytometry step. The stimulation step of the phospho-flow procedure can start with vials of frozen cells and end with cells fixed and permeabilized in methanol. Then the cells can be stained with an antibody directed to a particular protein of interest and then analyzed using a flow cytometer.

The materials used in this invention include thawing medium which comprises PBS-CMF+10% FBS+2 mM EDTA; 70 um Cell Strainer (BD); anti-CD45 antibody conjugated to Alexa 700 (Invitrogen) used at 1 ul per sample; propidium iodide (PI) solution (Sigma 10 ml, 1 mg/me used at 1 ug/ml; RPMI+1% FBS medium; media A comprising RPMI+1% FBS+1× Penn/Strep; Live/Dead Reagent, Amine Aqua (Invitrogen); 2 ml, 96-Deep Well, U-bottom polypropylene plates (Nunc); 300 ul 96-Channel Extended-Length D.A.R.T. tips for Hydra (Matrix); Phosphate Buffered Saline (PBS) (MediaTech); 16% Paraformaldehyde (Electron Microscopy Sciences); 100% Methanol (EMD) stored at −20 C; Transtar 96 dispensing apparatus (Costar); Transtar 96 Disposable Cartridges (Costar, Polystyrene, Sterile); Transtar reservoir (Costar); and foil plate sealers.

a. Thawing Cell and Live/Dead Staining:

Frozen cells are thawed in a 37° C. water bath and gently resuspended in the vial and transferred to the 15 mL conical tube. The 15 mL tube is centrifuged at 930 RPM (200×g) for 8 minutes at room temperature. The supernatant is aspirated and the pellet is gently resuspended in 1 mL media A. The cell suspension is filtered through a 70 um cell strainer into a new 15 mL tube. The cell strainer is rinsed with 1 mL media A and another 12 ml of media A into the 15 mL tube. The cells are mixed into an even suspension. A 20 µL aliquot is immediately removed into a 96-well plate containing 180 µL PBS+ 4% FBS+CD45 Alexa 700+PI to determine cell count and viability post spin. After the determination, the 15 mL tubes are centrifuged at 930 RPM (200×g) for 8 minutes at room temperature. The supernatant is aspirated and the cell pellet is gently resuspended in 4 mL PBS+4 µL Amine Aqua and incubated for 15 min in a 37° C. incubator. 10 mL RPMI+1% FBS is added to the cell suspension and the tube is inverted to mix the cells. The 15 mL tubes are centrifuged at 930 RPM (200×g) for 8 minutes at room temperature. The cells are resuspended in Media A at the desired cell concentration ($1.25 \times 10^6$/mL). For samples with low numbers of cells ($<18.5 \times 10^6$), the cells are resuspended up to 15 mL media. For samples with high numbers of cells ($>18.5 \times 10^6$), the volume is raised to 10 mL with media A and the desired volume is transferred to a new 15 mL tube, and the cell concentration is adjusted to $1.25 \times 10^6$ cells/ml. 1.6 mL of the above cell suspension (concentration at $1.25 \times 10^6$ cells/nil) is transferred into of a multi-well plate. From this plate, 80 ul is dispensed into each well of a subsequent plate. The plates are covered with a lid (Nunc) and placed in a 37° C. incubator for 2 hours to rest.

b. Cell Stimulation:

A concentration for each stimulant that is five folds more (5×) than the final concentration is prepared using Media A as diluent. 5× stimuli are arrayed into wells of a standard 96 well v-bottom plate that correspond to the wells on the plate with cells to be stimulated.

Preparation of fixative: Stock vial contains 16% paraformaldehyde which is diluted with PBS to a concentration that is 1.5×. The stock vial is placed in a 37° C. water bath.

Adding the stimulant: The cell plate(s) are taken out of the incubator and placed in a 37° C. water bath next to the pipette apparatus. The cell plate is taken from the water bath and gently swirled to resuspend any settled cells. With pipettor, the stimulant is dispensed into the cell plate and vortexed at "7" for 5 seconds. The deep well plate is put back into the water bath.

Adding Fixative: 200 µl of the fixative solution (final concentration at 1.6%) is dispensed into wells and then mixed on the titer plate shaker on high for 5 seconds. The plate is covered with foil sealer and incubated in a 37° C. water bath for 10 minutes. The plate is spun for 6 minutes at 2000 rpm at room temperature. The cells are aspirated using a 96 well plate aspirator (VP Scientific). The plate is vortexed to resuspend cell pellets in the residual volume. The pellet is ensured to be dispersed before the Methanol step (see cell permeabilization) or clumping will occur.

Cell Permeabilization: Permeability agent, for example methanol, is added slowly and while the plate is vortexing. To do this, the cell plate is placed on titer plate shaker and made sure it is secure. The plate is set to shake using the highest setting. A pipetter is used to add 0.6 mls of 100% methanol to the plate wells. The plate(s) are put on ice until this step has been completed for all plates. Plates are covered with a foil seal using the plate roller to achieve a tight fit. At this stage the plates may be stored at −80° C.

c. Staining Protocol

Reagents for staining include FACS/Stain Buffer-PBS+ 0.1% Bovine serum albumen (BSA)+0.05% Sodium Azide; Diluted Bead Mix-1 mL FACS buffer+1 drop anti-mouse Ig Beads+1 drop negative control beads. The general protocol for staining cells is as follows, although numerous variations on the protocol may be used for staining cells:

Cells are thawed if frozen. Cells are pelleted at 2000 rpm 5 minutes. Supernatant is aspirated with vacuum aspirator. Plate is vortexed on a "plate vortex" for 5-10 seconds. Cells are washed with 1 mL FACS buffer. Repeat the spin, aspirate and vortex steps as above. 50 µL of FACS/stain buffer with the desired, previously optimized, antibody cocktail is added to two rows of cells at a time and agitate the plate. The plate is covered and incubated in a shaker for 30 minutes at room temperature (RT). During this incubation, the compensation plate is prepared. For the compensation plate, in a standard 96 well V-bottom plate, 20 µL of "diluted bead mix" is added per well. Each well gets 5 μL of 1 fluorophor conjugated control IgG (examples: Alexa488, PE, Pac Blue, Aqua, Alexa647, Alexa700). For the Aqua well, add 200 μL of Aqua−/+ cells. Incubate the plate for 10 minutes at RT. Wash by adding 200 μL FACS/stain buffer, centrifuge at 2000 rpm for 5 minutes, and remove supernatant. Repeat the washing step and resuspend the cells/beads in 200 μL FACS/stain buffer and transfer to a U-bottom 96 well plate. After 30 min, 1 mL FACS/stain buffer is added and the plate is incubated on a plate shaker for 5 minutes at room temperature. Centrifuge, aspirate and vortex cells as described above. 1 mL FACS/stain buffer is added to the plate and the plate is covered and incubated on a plate shaker for 5 minutes at room temperature. Repeat the above two steps and resuspend the cells in 75 μl FACS/stain buffer. The cells are analyzed using a flow cytometer, such as a LSRII (Becton Disckinson). All wells are selected and Loader Settings are described below: Flow Rate: 2 uL/sec; Sample Volume: 40 uL; Mix volume: 40 uL; Mixing Speed: 250 uL/sec; # Mixes: 5; Wash Volume: 800 uL; STANDARD MODE. When a plate has completed, a Batch analysis is performed to ensure no clogging.

d. Gating Protocol

Data acquired from the flow cytometer are analyzed with Flowjo software (Treestar, Inc). The Flow cytometry data is first gated on single cells (to exclude doublets) using Forward Scatter Characteristics Area and Height (FSC-A, FSC-H). Single cells are gated on live cells by excluding dead cells that stain positive with an amine reactive viability dye (Aqua-Invitrogen). Live, single cells are then gated for subpopulations using antibodies that recognize surface markers as follows: CD45++, CD33− for lymphocytes, CD45++, CD33++ for monocytes+granulocytes and CD45+, CD33+ for leukemic blasts. Signaling, determined by the antibodies that interact with intracellular signaling molecules, in these subpopulation gates that select for "lymphs", "monos+grans", and "blasts" is analyzed.

e. Gating of Flow Cytometry Data to Identify Live Cells and the Lymphoid and Myeloid Subpopulations:

Flow cytometry data can be analyzed using several commercially available software programs including FACS-Diva™, FlowJo, and Winlist™. The initial gate is set on a two-parameter plot of forward light scatter (FSC) versus side light scatter (SSC) to gate on "all cells" and eliminate debris and some dead cells from the analysis. A second gate is set on the "live cells" using a two-parameter plot of Amine Aqua (a dye that brightly stains dead cells, commercially available from Invitrogen) versus SSC to exclude dead cells from the analysis. Subsequent gates are be set using antibodies that recognize cell surface markers and in so doing define cell sub-sets within the entire population. A third gate is set to separate lymphocytes from all myeloid cells (acute myeloid leukemia cells reside in the myeloid gate). This is done using a two-parameter plot of CD45 (a cell surface antigen found on all white blood cells) versus SSC. The lymphocytes are identified by their characteristic high CD45 expression and low SSC. The myeloid population typically has lower CD45 expression and a higher SSC signal allowing these different populations to be discriminated. The gated region containing the entire myeloid population is also referred to as the P1 gate.

f. Phenotypic Gating to Identify Subpopulations of Acute Myeloid Leukemia Cells:

The antibodies used to identify subpopulations of AML blast cells are CD34, CD33, and CD11b. The CD34$^+$CD11b$^-$ blast population represents the most immature phenotype of AML blast cells. This population is gated on CD34 high and CD11b negative cells using a two-parameter plot of CD34 versus CD11b. The CD33 and CD11b antigens are used to identify AML blast cells at different stages of monocytic differentiation. All cells that fall outside of the CD34$^+$CD11b$^-$ gate described above (called "Not CD34+") are used to generate a two-parameter plot of CD33 versus CD11b. The CD33$^+$CD11b$^{hi}$ myeloid population represents the most differentiated monocytic phenotype. The CD33$^+$CD11b$^{intermediate}$ and CD33$^+$CD11b$^{lo}$ populations represent less differentiated monocytic phenotypes.

The data can then be analyzed using various metrics, such as basal level of a protein or the basal level of phosphorylation in the absence of a stimulant, total phosphorylated protein, or fold change (by comparing the change in phosphorylation in the absence of a stimulant to the level of phosphorylation seen after treatment with a stimulant), on each of the cell populations that are defined by the gates in one or more dimensions. These metrics are then organized in a database tagged by: the Donor ID, plate identification (ID), well ID, gated population, stain, and modulator. These metrics tabulated from the database are then combined with the clinical data to identify nodes that are correlated with a pre-specified clinical variable (for example; response or non response to therapy) of interest.

Example 2

Multi-parameter flow cytometric analysis was performed on peripheral blasts taken at diagnosis from 9 AML patients who achieved a complete response (CR) and 24 patients who were non-responders (NR) to one cycle of standard 7+3 induction therapy (100-200 mg/m2 cytarabine and 60 mg/m2 daunorubicin). The signal nodes were organized into 4 biological categories: 1) Protein expression of receptors and drug transporters 2) Response to cytokines and growth factors, 3) Phosphatase activity, and 4) Apoptotic signaling pathways.

The data showed that expression of the receptors for c-Kit and FLT3 Ligand and the drug transporter ABCG2, were increased in patients who achieved an NR versus CR (data not shown). Readouts from the cytokine-Stat response panels and the growth factor-Map kinase and PI3-Kinase response panels (see Table 4) revealed increased signaling in blasts taken from NR patients versus blasts taken from patients who clinically responded to therapy. To determine the role of phosphatases, peroxide, ($H_2O_2$) a physiologic phosphatase inhibitor revealed increased phosphatase activity in CRs versus NRs for some signaling molecules and increased phosphatase activity in NRs versus CRs for others. In the absence of treatment with $H_2O_2$, CRs had lower levels of phosphorylated PLCγ2 and SLP-76 versus NRs, and attained higher levels of phosphorylated PLCγ2 and SLP-76 upon $H_2O_2$ treatment. In contrast, $H_2O_2$ revealed higher levels of p-Akt in NR patients versus CR patients. Lastly, interrogation of the apoptotic machinery using agents such as staurosporine and etoposide showed that NR patient blasts failed to undergo cell death, as determined by cleaved PARP and cleaved Caspase 8. Of note, in NR patient blasts, these agents did promote an increase in phosphorylated Chk2 suggesting a communication breakdown between the DNA damage response pathway and the apoptotic machinery. In contrast, blasts from CR patients showed significant populations of cells with cleaved PARP and caspase 8 consistent with their clinical outcomes.

In this study, 152 signaling nodes per patient sample were measured by multi-parameter flow cytometry and revealed distinct signaling profiles that correlate with patient response to ara-C based induction therapy. This study identified 29 individuals nodes strongly associated (i.e. AUC>0.7, p value 0.05) with clinical response to 1 cycle of ara-C based induction therapy. Most of these nodes were highly correlated.

Table 4 below shows 26 of the 29 nodes strongly associated with clinical responses. Expression levels of c-Kit, Flt-3L receptors and ABCG2 drug transporter also associated with clinical responses.

Alterations were seen in expression for the c-Kit and Flt-3L receptors, the ABCG2 drug transporter, cytokine and growth factor pathway response, phosphatase activity and apoptotic response, all of which could stratify the NR from the CR patient subsets.

Figure 4:
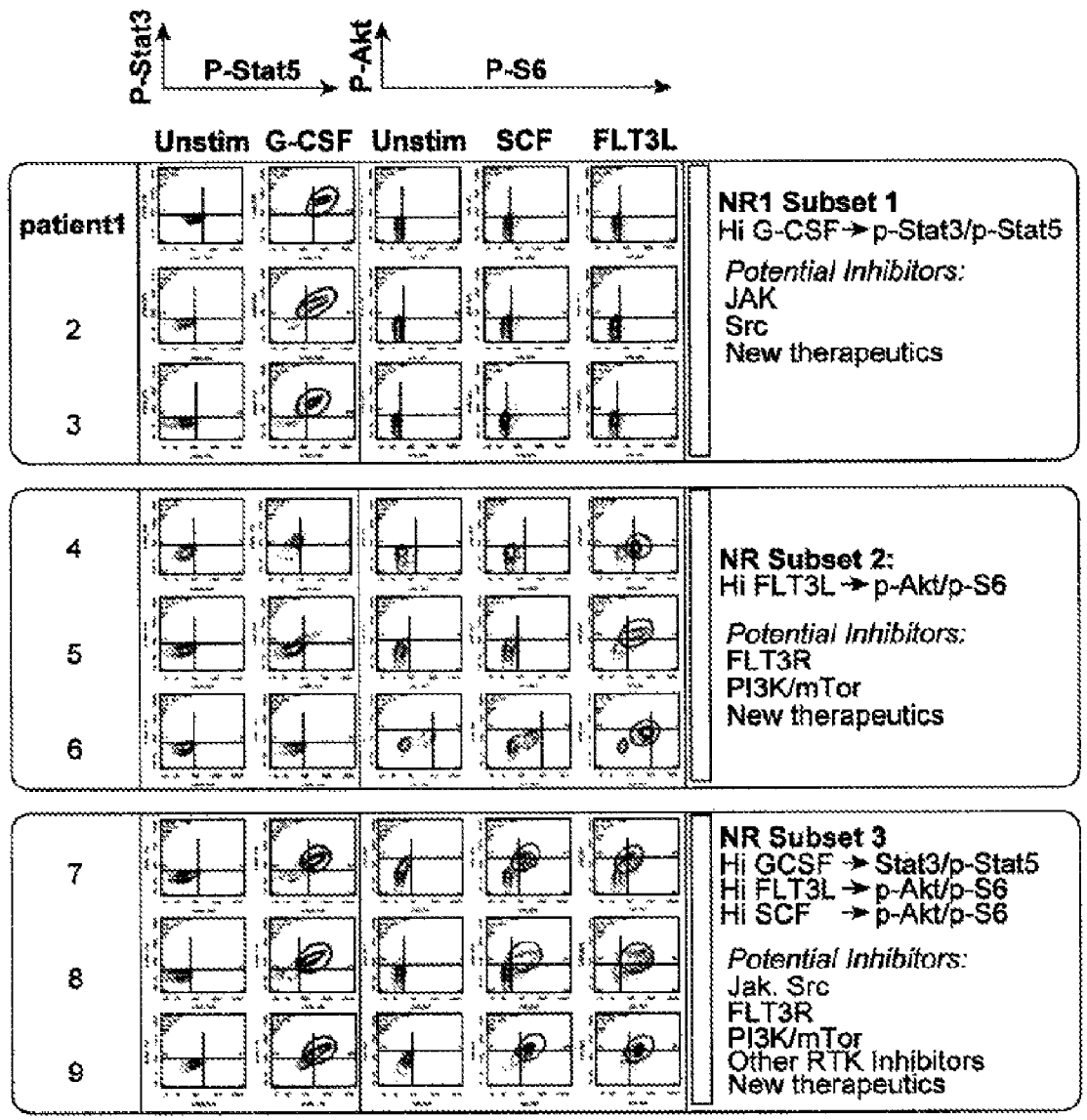
FIG. 4 shows the use of signaling nodes to select patients for specific targeted therapies.

It was also determined that evoked signaling to biologically relevant modulators reveals nodes that stratify non-responding patients from complete responders in this AML sample set. For example, FIG. 4 shows different activation profiles for NR patients. The operative pathways in these ease/potential response to therapy. Combination of two independent nodes, p-Stat5-C SF and p-Akt-FLT3L, can classify correctly all CR (but one CRp) and misclassify only 5 NR (not shown).

Additionally, Phospho-Flow technology allows detection of multiple signaling subpopulations within the AML blast population which could be instrumental in disease monitoring and following rare populations after therapy. See FIG. 4 and not shown. Overall, phospho-flow identifies patient subgroups of AML with different clinical outcomes to induction therapy, reveals mechanisms of potential pathophysiology, and provides a tool for personalized treatment options based on unique patient-specific signaling networks and for disease monitoring under therapeutic pressure.

TABLE 4

| | Un-stim | IFNa | IFNg | IL-27 | IL-6 | IL-10 | G-CSF | FLT-3L | SCF | SDF-1a | Thap-sigargin | PMA | Stauro-sporine | Etopo-side | $H_2O_2$ |
|---|---|---|---|---|---|---|---|---|---|---|---|---|---|---|---|
| p-Stat1(Y701) | | NR | NR | | | | | | | | | | | | |
| p-Stat3(Y703) | NR | | | NR | NR | NR | NR | | | | | | | | |
| p-Stat5(Y694) | | | | | | | NR | | | | | | | | |
| p-Stat6(Y641) | NR | | | | | | | | | | | | | | |
| p-S6(S235/236) | | | | | | | | NR | NR | | NR | | | | |
| p-Akt(S473) | | | | | | | | NR | NR | NR | | | | | |
| p-Erk (T202/Y204) | NR | | | | | | | | | | | NR | | | |
| p-PLCg2(Y759) | NR | | | | | | | | | | | | | | CR |
| p-SLP76 (Y128) | | | | | | | | | | | | | | | CR |
| p-CREB(S133) | NR | | | | | | | | | | | | | | |
| Cleaved PARP | | | | | | | | | | | | | CR | CR | |
| Cleaved Caspase 8 | | | | | | | | | | | | | CR | | |
| Cleaved Caspase 3 | | | | | | | | | | | | | CR | CR | |

NR = Nodes in which activation is greater in a NR patient than in a CR patient
CR = Nodes in which activation is greater in a CR patient than an NR patient patients can be used to predict response to a treatment or to choose a specific treatment for the patients. FIG. 4 shows that NR patients in subset 1 have high levels of p-Stat3 and p-Stat5 in response to G-CSF. This suggests that JAK, Src and other new therapeutics could be good candidates for the treatment of these patients. In addition, FIG. 4 shows that NR patients in subset 2 have high levels of p-Akt and p-S6 in response to FLT3L. This suggests that inhibitors to FLT3R, PI-3K/mTor and other new therapeutics could be good candidates for the treatment of these patients. FIG. 4 also shows that NR patients in subset 2 have high levels of p-Stat3 and p-Stat5 in response to G-CSF, high levels of p-Akt and p-S6 in response to FLT3L, and high levels of p-Akt and p-S6 in response to SCF. This suggests that inhibitors to JAK, Src, FLT3R, PI-3K/mTor, RKT inhibitors and other new therapeutics could be good candidates for the treatment of these patients.

However, some patients with a functional apoptosis response to Etoposide as measured by p-Chk2 and cleaved PARP have a CR phenotype despite having high levels of p-Stat3 and p-Stat5 in response to G-CSF (data not shown). Even though high levels of p-Stat3 and p-Stat5 in response to G-CSF is associated with NR, if the apoptotic machinery is still active the patient might be able to respond to treatment. This suggests that there may be a requirement for more than one signaling pathway to prevent or veto apoptosis. In this case G-CSF signaling is not able alone to prevent apoptosis. These results indicate that multivariate analysis of signaling nodes can improve the specificity of the patient stratification.

Although univariate analysis of signaling nodes can stratify patients based on response to induction therapy as several predictive nodes were independent of each other, multivariate analysis of signaling nodes can improve specificity while providing insight into the pathophysiology of the dis- Example 3

An analysis of a heterogeneous population of AML patients may be conducted as outlined above. The results may show the following. In some embodiments, univariate analysis is performed on relatively homogeneous clinical groups, such as patents over 60 years old, patients under 60 years old, de novo AML patients, and secondary AML patients. In other embodiments the groups may be molecularly homogeneous groups, such as Flt-3-ITD WT. For example, in patients over 60 years old, NRs may have a higher $H_2O_2$ response than CRs and/or a higher FLT3L response than CRs. In patients under 60, NRs may have a higher IL-27 response than CRs and/or CRs may induce apoptosis to Etoposide or Ara-C/Daunorubicin more than NRs. In de novo AML, CRs may induce apoptosis (cleaved PARP) in response to Etoposide or Ara-C/Daunorubicin, they may have higher total p-S6 levels than NRs, or NRs may have higher $H_2O_2$ response than CRs. In secondary AML, NRs may have higher $H_2O_2$ responses than CRs, NRs may have higher FLT3L, SCF response than CRs, NRs may have higher G-CSF, IL-27 response than CRs, and there may be overlapping nodes with the over 60 patient set. The following tables may illustrate the above. The tables show the node, metric, and patient subpopulations. For example, the node can be shown as the node (readout) followed by the stimulant/modulator, and in some instances the receptor through which they act (Table 11 also lists some labels that can be employed in the readout). The metric is the way the result may be calculated (see definitions above and in the figures; ppos is percent positive). The leukemic blast cell subpopulations are: P1 all leukemic cells, S1 most immature blast population, S3 most mature blast population and S2 median mature blast population. All nodes: AUC≧0.7, p values≦0.05, lowest N=4

TABLE 5

Univariate analysis of All patients can reveal predictive signaling nodes for Response
Failed Pts removed, NR = Resistant only

| Node | Metric | P1 | S1 | S2 | S3 |
|---|---|---|---|---|---|
| Cleaved.PARP.Ara.C.Daunorubicin.-HCl | Fold | X |  | X |  |
|  | TotalPhospho | X |  | X |  |
| Cleaved.PARP.Etoposide | Fold |  |  | X |  |
| Flt3.CD135.Mouse.IgG1 | ppos |  | X |  |  |
| p.Akt.Hydrogen.Peroxide | Fold |  |  |  | X |
| p.Chk2..Ara.C.Daunorubicin.HCl | Fold |  |  | X |  |
| p.CREB.SDF.1a.CXCL12 | Fold |  |  |  | X |
|  | TotalPhospho |  |  | X |  |
| p.PLCg2.Hydrogen.Peroxide | Fold |  |  |  | X |
| p.S6.SCF | TotalPhospho |  |  | X |  |
| p.SLP.76.Hydrogen.Peroxide | Fold |  |  |  | X |
| p.Stat1.IL.27 | Fold |  | X |  |  |
|  | TotalPhospho | X | X |  |  |
| p.Stat3.IL.27 | Fold | X | X |  |  |
|  | TotalPhospho |  | X |  |  |
| p.Stat5.IL.27 | Fold |  | X |  |  |
| SCF.R.c.kit.CD117.IgG1. | Fold |  |  |  | X |
| SCF.R.c.kit.CD117.IgG2b | Fold |  | X |  |  |
|  | ppos |  | X | X |  |
| MDR.Family.ABCG2.BRCP1.IgG1. | ppos |  | X |  |  |
| P.glycoprotein.MDR1.IgG1 | Fold |  | X |  |  |

TABLE 6

Univariate analysis of Young Pts (Age < 60) can reveal predictive signaling nodes for Response
Failed Pts removed, NR = Resistant only

| Node | Metric | P1 | S1 | S2 |
|---|---|---|---|---|
| Cleaved.PARP.Etoposide | Fold | X | X | X |
|  | TotalPhospho | X | X |  |
| Cleaved.PARP.No.Modulator | TotalPhospho | X |  |  |
| p.Akt.SCF | Fold |  |  | X |
| p.CREB.SDF.1a.CXCL12 | Fold |  | X |  |
| p.ERK.FLT.3.Ligand | Fold |  | X |  |
| p.Stat1.IL.27 | Fold | X | X |  |
|  | TotalPhospho | X | X |  |
| p.Stat3.IL.27 | Fold | X | X |  |
|  | TotalPhospho | X | X |  |

TABLE 7

Univariate analysis of Age > 60 patients can reveal predictive signaling nodes CR vs. NR:
Failed Pts removed, NR = Resistant only

| Node | Metric | P1 | S2 | S3 |
|---|---|---|---|---|
| p.Akt.Hydrogen.Peroxide | Fold | X |  |  |
| p.Akt.FLT.3.Ligand | Fold | X | X | X |
| p.ERK.FLT.3.Ligand | Fold | X |  |  |
| p.PLCg2.Hydrogen.Peroxide | TotalPhospho | X |  |  |
| p.S6.FLT.3.Ligand | Fold | X | X | X |
| p.S6.SCF | Fold | X | X |  |
| p.SLP.76.Hydrogen.Peroxide | Fold | X |  |  |

TABLE 8

Univariate analysis of 2ndary AML pts can reveal predictive signaling nodes for Response:
Including Failed Pts

| Node | Metric | P1 | S1 | S2 | S3 |
|---|---|---|---|---|---|
| p.Akt.Hydrogen.Peroxide | Fold |  |  |  | X |
| p.Akt.FLT.3.Ligand | Fold |  | X |  |  |
| p.Akt.SDF.1a.CXCL12 | Fold |  |  | X |  |
| p.ERK.FLT.3.Ligand | Fold |  | X | X |  |
| p.PLCg2.Hydrogen.Peroxide | Fold |  |  |  | X |
|  | TotalPhospho |  |  |  | X |
| p.S6.FLT.3.Ligand | Fold |  | X |  |  |
| p.S6.A.SCF | Fold |  | X |  |  |
| p.SLP.76.Hydrogen.Peroxide | Fold |  |  |  | X |
| p.Stat1.G.CSF | Fold |  | X |  |  |
| p.Stat1.A.IL.27 | Fold |  | X | X |  |
|  | TotalPhospho |  | X |  |  |
| p.Stat3.A.G.CSF | Fold |  | X |  |  |
| p.Stat3.IL.27 | Fold |  | X |  |  |
|  | TotalPhospho |  | X |  |  |
| p.Stat5.G.CSF | Fold |  | X |  |  |
|  | TotalPhospho |  | X |  |  |
| SCF.R.c.kit.CD117.Mouse.IgG1. | Fold |  |  | X |  |
|  | ppos |  |  | X | X |

TABLE 9

Univariate analysis of 2ndary AML pts can reveal predictive signaling nodes for Response:
Failed Pts removed, NR = Resistant only

| Node | Metric | P1 | S1 | S2 | S3 |
|---|---|---|---|---|---|
| p.Akt.Hydrogen.Peroxide | Fold |  |  |  | X |
| p.Akt.FLT.3.Ligand | Fold | X |  |  |  |
| p.Akt.SCF | TotalPhospho | X |  |  |  |
| p.ERK.FLT.3.Ligand | Fold | X | X |  |  |
| p.ERK.SCF | Fold | X |  |  |  |
| p.PLCg2.Hydrogen.Peroxide | Fold |  |  |  | X |
| p.S6.FLT.3.Ligand | Fold | X |  |  |  |
| p.S6.SCF | Fold | X | X |  |  |
| p.Stat1.IL.27 | Fold | X |  | X |  |
|  | TotalPhospho | X |  |  |  |
| p.Stat3.G.CSF | Fold | X |  |  |  |
| p.Stat3.IL.27 | Fold | X |  |  |  |
| p.Stat5.G.CSF | Fold | X |  |  |  |
| SCF.R.c.kit.CD117.Mouse.IgG1. | Fold |  |  | X |  |
|  | ppos |  |  | X | X |

TABLE 10

Univariate analysis of DeNovo AML can reveal predictive signaling nodes for Response:
Including Failed Pts

| Node | Metric | P1 | S1 | S2 | S3 |
|---|---|---|---|---|---|
| Cleaved.PARP.Etoposide | Fold |  | X |  |  |
| Cytochrome.C.Staurosporine.Z.-VAD.Caspase.Inhibitor | Fold |  |  | X |  |
|  | TotalPhospho | X |  | X |  |
| Cytochrome.C. No.Modulator | TotalPhospho |  |  | X | X |
| p.Akt.Hydrogen.Peroxide | Fold |  | X |  |  |
| p.Akt.FLT.3.Ligand | TotalPhospho |  |  |  | X |
| p.Akt.SCF | Fold | X |  | X |  |
|  | TotalPhospho |  |  |  | X |
| p.Akt.SDF.1a.CXCL12 | Fold |  |  | X |  |
| p.CREB.SDF.1a.CXCL12 | Fold |  |  | X |  |
| p.ERK.Thapsigargin | Fold | X |  |  | X |
| p.ERK.No.Modulator | TotalPhospho | X |  |  |  |
| p.Stat1.GM.CSF | TotalPhospho |  |  |  | X |
| p.Stat1.IL.10 | Fold |  |  | X |  |
|  | TotalPhospho |  |  | X |  |
| p.Stat1.IL.3 | TotalPhospho | X |  |  |  |
| p.Stat1.A.IL.6 | Fold | X |  |  |  |
|  | TotalPhospho | X |  | X | X |

TABLE 10-continued

Univariate analysis of DeNovo AML can reveal predictive signaling nodes for Response:
Including Failed Pts

| Node | Metric | P1 | S1 | S2 | S3 |
|---|---|---|---|---|---|
| p.Stat3.GM.CSF | TotalPhospho | X | | X | X |
| p.Stat3.IFN.g | Fold | X | | X | X |
| | TotalPhospho | X | | X | X |
| p.Stat3.Y705.PE.A.IL.10 | Fold | X | | X | X |
| | TotalPhospho | X | | X | X |
| p.Stat3.Y705.PE.A.IL.3 | TotalPhospho | X | | | |
| p.Stat3.Y705.PE.A.IL.6 | Fold | | | | X |
| | TotalPhospho | X | | | X |
| p.Stat5.G.CSF | Fold | | | | X |
| | TotalPhospho | | | | X |
| p.Stat5.IL.10 | Fold | X | | X | X |
| p.Stat5.IL.3 | Fold | X | | | |
| p.Stat5.IL.6 | Fold | X | | X | X |
| p.Stat6.No.Modulator | TotalPhospho | X | | X | |
| pERK.LPS | Fold | | | X | |
| SCF.R.c.kit.CD117.IgG1. | Fold | | | X | |
| | ppos | | | X | X |
| SCF.R.c.kit.CD117.IgG2b | Fold | X | | X | |
| | ppos | | | X | X |
| X.MDR.Family.MRP.1.IgG2a | Fold | X | | | |
| | ppos | X | | | |
| P.glycoprotein.MDR1.IgG2a | Fold | X | | | |

TABLE 11

Univariate analysis of De Novo AML patients can reveals predictive signaling nodes CR vs. NR:
Removed Failed Pts. NR = Resistant

| Node | Metric | P1 | S1 | S2 | S3 |
|---|---|---|---|---|---|
| Cleaved.PARP.Cytosine.b.arabino.furanoside.Daunorubicin.HCl | Fold | | | X | |
| | TotalPhospho | | | X | |
| Cleaved.PARP.D214.FITC.A.Etoposide | Fold | X | X | X | |
| p.Akt.S473.Alexa.Fluor.488.A.Hydrogen.Peroxide | Fold | | X | | |
| p.Akt.S473.Alexa.Fluor.647.A.FLT.3.Ligand | TotalPhospho | | | | X |
| p.Akt.S473.Alexa.Fluor.647.A.SCF | Fold | X | | X | |
| | TotalPhospho | | | | X |
| p.Akt.S473.Alexa.Fluor.647.A.SDF.1a.CXCL12 | Fold | | | X | |
| p.CREB.S133.PE.A.SDF.1a.CXCL12 | Fold | | | X | |
| p.S6.S235.236.Alexa.Fluor.488.A.FLT.3.Ligand | TotalPhospho | X | | X | |
| p.S6.S235.236.Alexa.Fluor.488.A.PMA | TotalPhospho | X | | X | |
| p.S6.S235.236.Alexa.Fluor.488.A.SCF | TotalPhospho | X | | X | |
| p.S6.S235.236.Alexa.Fluor.488.A.Thapsigargin | TotalPhospho | | | X | X |
| p.SLP.76.Y128.Alexa.Fluor.647.A.Hydrogen.Peroxide | Fold | X | | | |
| p.Stat5.Y694.Alexa.Fluor.647.A.G.CSF | TotalPhospho | | | | X |
| p.Stat5.Y694.Alexa.Fluor.647.A.IFN.a.2b | Fold | | | X | |
| SCF.R.c.kit.CD117.APC.A.Mouse.IgG2b | Fold | | | X | |

TABLE 12

Univariate analysis of All patients can reveal predictive signaling nodes for Response Duration

| Node | Metric | P1 | S1 | S2 | S3 |
|---|---|---|---|---|---|
| Cleaved.PARP.araC.Daunorubicin.-HCl | Fold | X | | | |
| Cleaved.PARP.Etoposide | Fold | X | | | |
| CXCR4.IgG1 | Fold | | X | X | X |
| CXCR4.IgG1 | ppos | | X | | |
| p.Akt.Hydrogen.Peroxide | Fold | | X | | X |
| | TotalPhospho | | X | | |
| p.Akt.SDF.1a.CXCL12 | TotalPhospho | | X | | |
| p.ERK.FLT.3.Ligand | Fold | | | X | |
| p.PLCg2.Hydrogen.Peroxide | TotalPhospho | | X | X | |
| p.S6.Thapsigargin | TotalPhospho | | X | | |
| p.SLP.76.Hydrogen.Peroxide | TotalPhospho | | X | | X |
| p.Stat3.IL.10 | Fold | | | X | |
| p.Stat5.IL.6 | TotalPhospho | | X | | |
| MDR.Family.ABCG2.BRCP1.IgG1. | Fold | | | | X |
| MDR.Family.ABCG2.IgG2b | ppos | | | X | X |

TABLE 13

Univariate analysis of Flt3 WT Pts can reveal predictive signaling nodes for Response Duration

| Node | Metric | P1 | S1 | S2 | S3 |
|---|---|---|---|---|---|
| Cleaved.PARP.araC.Daunorubicin.-HCl | Fold | X | | X | |
| Cleaved.PARP.Etoposide | Fold | X | | | |
| | TotalPhospho | | X | | |
| CXCR4.IgG1 | Fold | | | X | X |
| | ppos | | | X | X |
| CXCR4.IgG1 | Fold | | | X | |
| CXCR4.No.Modulator | TotalPhospho | | | X | X |
| p.Akt.Hydrogen.Peroxide | Fold | | X | | |
| | TotalPhospho | | X | | |
| p.ERK.FLT.3.Ligand | Fold | | | X | X |
| p.PLCg2.Hydrogen.Peroxide | Fold | X | | | |
| | TotalPhospho | | X | | |
| p.S6.Thapsigargin | TotalPhospho | | X | | |
| p.SLP.76.Hydrogen.Peroxide | TotalPhospho | | X | | |
| MDR.Family.ABCG2.BRCP1.IgG2b | ppos | | | X | X |
| MDR.Family.MRP.IgG2a | Fold | | | | X |

Example 4

Multi-parameter flow cytometric analysis was performed on BMMC samples taken at diagnosis from 61 AML patients.

The samples were balanced for complete response (CR) and non-responders (NR) after 1 to 3 cycles of induction therapy and de novo versus secondary AML. Nodes in Tables 2 to 10 were examined.

10 nodes are common in stratifying NR and CR between the studies in Example 2 and these studies. Table 14 shows the common stratifying nodes.

TABLE 14

| Cytokine Pathways: 5 Nodes | |
|---|---|
| IL-27 | p-Stat 3 and p-Stat 1 |
| IL-27 | p-Stat 1 |
| IL-6 | p-Stat 3 |
| IL-10 | p-Stat 3 |
| IFNa | p-Stat 1 |
| Growth Factors: 4 Nodes | |
| Flt3L | p-Akt and p-S6 |
| SCF | p-Akt and p-S6 |
| Apoptosis Pathways | |
| Etoposide or AraC/Dauno | Cleaved PARP+ |

In secondary analysis patient subpopulations were stratified by clinical variables. Patients are stratified by age, de novo acute myeloid leukemia patient, secondary acute myeloid leukemia patient, or a biochemical/molecular marker.

Patients were stratified by age (as split variable <60 years old vs. >60 years old and as co-variate). In patients younger than 60 years old, NRs have higher H2O2 and FLT3L responses than CRs. In patients younger than 60 years old, NRs have higher IL-27 response than CRs. In addition, in patients younger than 60 years old, CRs induce apoptosis to Etoposide or Ara-C/Daunorubicin more than NRs.

Patients were stratified by de novo versus secondary AML. Stratifying nodes for de novo group show overlapping nodes with patients younger than 60 year old. Stratifying nodes for secondary group show overlapping nodes with patients older than 60 year old group.

Patients were stratified by FLT3 ITD mutation vs. FLT3 wild type phenotypes. The signaling was significantly different between the patients with FLT3 ITD mutation vs. FLT3 wild type. Parp-cytosine.b.arabino.furanoside is an example of an identified node informative on relapse risk in patients who achieved CR and have FLT3 WT and normal karyotype disease (not shown).

Individual nodes can be combined for analysis. Several methods can be used for the analysis.

The nodes can be analyzed using additive linear models to discover combinations that provide better accuracy of prediction for response to induction therapy than the individual nodes. These models can also include clinical covariates like age, gender, secondary AML that may already be predictive of the outcome. Only nodes that add to the accuracy of the model after accounting for these clinical covariates are considered to be useful. The formula below is an example of how additive linear models can be used $$\text{Response (CR or NR)} = a + b^*C_1 + c^*C_2 + d^*\text{Node}_1 + e^*\text{Node}_2$$

C1 and C2 are the clinical covariates that are considered to be predictive of response, Node1 and Node2 are the two nodes from the biological data. The coefficient a, b, c, d, e are determined by the regression process. The significance of the coefficients if tested against them being equal to zero; i.e. if the p-value for d=0 if very small (say <0.05), then the contribution from the Node1 –is considered to the important. Several such models can be explored to find combinations of nodes that are complimentary. Examples of methods for exploring multiple such models include bootstrapping, and stepwise regression.

Analysis methods can include additive lineal models, such as the model represented in the following equations $$\text{CR or NR} = a + b^*\text{Age(categorical)} + c^*\text{Node for "all blast" population}$$

Incorporating age as a clinical variable increases the significance of the resulting combination model (not shown).

The nodes can be analyzed using independent combinations of nodes. This method seeks threshold along different node axes independently. This model among clinical subgroups improves predictive value (not shown).

The nodes can be analyzed using decision trees model. This model involves the hierarchical splitting of data. This model might mimic a more natural decision process. Each node is evaluated on sub-set of data at each level of the tree.

Both independent node combinations and decision tree provide node combinations of interest.

Results from the BMMC samples were compared with PBMC samples from the same patients in 10 of the patients. The samples were compared for sub-populations and signaling. The same phenotypic sub-populations are present in PBMC and BMMC, but in different percentage. It was observed that ⅔ of nodes correlate (i.e. Pearson>0.8 or Spearman>0.8) in "all blast" population of PBMC vs. BMMC. The correlations are node and subpopulation specific.

Example 5

This example evaluated whether single cell network profiling (SCNP), in which cells are modulated and their signaling response ascertained by multiparametric flow cytometry, could be used to functionally characterize signaling pathways associated with in vivo AML chemotherapy resistance. Morphologic and functional heterogeneity of myeloblasts was observed in paired samples obtained from two patients at diagnosis and at first relapse. Notably, a subpopulation of leukemic cells characterized by simultaneous SCF-mediated increases in the levels of phosphorylated (p-) Akt and p-S6 (SCF:p-Akt/p-S6), was identified in the relapsed samples from both patients. This SCF responsive subpopulation, although dominant in the relapse samples, was present and detectable at a much lower frequency in the diagnostic samples. Application of this finding to an independent set of 47 AML diagnostic samples identified seven patients, six of whom experienced disease relapse. The presence of an SCF:pAkt/p-S6 subpopulation was independent from c-Kit (SCF receptor) expression levels on the AML blasts and from patient age, cytogenetics and FLT-3 mutational status. This example shows that longitudinal SCNP analysis can provide unique insights into the nature of AML chemoresistance allowing for the identification of subpopulations of cells present at diagnosis with unique signaling characteristics predictive of higher rates of relapse.

Materials and Methods

Patient Samples

All AML bone marrow mononuclear cells (BMMC) were derived from the bone marrow (BM) of AML patients treated at MD Anderson Cancer Center (MDACC) between September 1999 and September 2006. Clinical data were de-identified in compliance with Health Insurance Portability and Accountability Act regulations. Patient/sample inclusion criteria required a diagnosis of French-American-British (FAB) classification of M0 through M7 AML (excluding M3) AML, collection prior to therapy initiation and at least 50% viability upon sample thaw. For the identification of chemoresistant signaling profiles, two longitudinally paired BMMC samples at diagnosis (collection prior to the initiation of induction chemotherapy) and first relapse, were examined. An independent test set comprised of 47 BMMC samples collected at diagnosis from AML patients with a disease response of CR after high dose cytarabine based chemotherapy was used to assess the ability of the identified signaling profiles to predict disease relapse. Healthy, unstimulated BMMC (n=2) were purchased from a commercial source (All Cells) to serve as a control. All samples underwent fractionation over Ficoll-Hypaque prior to cryopreservation with 90% fetal bovine serum and 10% dimethyl sulfoxide and storage in liquid nitrogen.

SCNP Assay

The SCNP assay measured response to growth factors and cytokines involved in hematopoietic progenitor or myeloid biology (SCF, FLT3L, G-CSF, IL-27), drug transporter (ABCG2, MRP-1) and chemokine receptors (CXCR4) associated with adverse disease prognosis in AML, and the c-Kit growth factor receptor for SCF. The SCF and FLT3L-mediated PI3K/Akt and MAPK pathway is important for maintaining the hematopoietic stem cell pool; G-CSF-mediated Jak/STAT pathway activation is important for neutrophilic differentiation of hematopoietic progenitor cells; interleukin (IL)-27 mediated Jak/STAT pathway activation is important in regulating proliferation and differentiation of hematopoietic stem cells; CXCR4 expression is associated with disease relapse and decreased survival; and drug transporter expression levels (i.e. ABCG2 and MRP-1) are known to be associated with adverse prognosis in AML. All together, approximately 20 signaling nodes were evaluated in each sample.

SCNP assays were performed as described previously. Cryopreserved samples were thawed at 37° C. and washed once in warm PBS containing 10% FBS (HyClone, Waltham, Mass., USA) and 2 mM EDTA. The cells were re-suspended, filtered to remove debris and washed in RPMI 1640 (MediaTech, Manassas, Va., USA) cell culture media containing 1% FBS before staining with Aqua LIVE/DEAD viability dye (Invitrogen, Carlsbad, Calif., USA) to distinguish non-viable cells. The cells were re-suspended in RPMI containing 1% FBS, aliquoted to 100,000 cells/condition and rested for 1-2 hours at 37° C. Cells were incubated for 15 minutes at 37° C. with each of the following signaling modulators: fms-like tyrosine kinase receptor-3 ligand (FLT3L, 50 ng/ml; eBiosciences, San Diego, Calif., USA); granulocyte colony-stimulating factor (G-CSF, 50 ng/ml; R&D Systems, Minneapolis, Minn., USA); interleukin-27 (IL-27, 50 ng/ml, R&D Systems); stem cell factor (SCF, 20 ng/ml, R&D Systems). After exposure to modulators, cells were fixed with a final concentration of 1.6% paraformaldehyde (Electron Microscopy Sciences, Hatfield, Pa., USA) for 10 minutes at 37° C. Cells were pelleted and then permeabilized with 100% ice-cold methanol (Sigma-Aldrich, St. Louis, Mo., USA) and stored at −80° C. overnight. Subsequently, cells were washed with FACS buffer containing phosphate buffered saline (PBS, Fisher Scientific, Waltham, Mass., USA), 0.5% bovine serum albumin (BSA, Ankeny, Iowa, USA), 0.05% NaN3 (Mallinckrodt, Hazelwood, Mo., USA), pelleted and stained with cocktails of fluorochrome-conjugated antibodies. As an exploratory effort, when sufficient number of cells were available, simultaneous measurement of c-Kit expression and SCF induced signaling was also performed. Antibodies were available from commercial vendors such as BD, Bechman Coulter, Invitrogen and R&D Systems.

Flow Cytometry Data Acquisition and Analysis

Flow cytometry data was acquired on an LSR II and/or CANTO II flow cytometer using the FACS DIVA software (BD Biosciences, San Jose, Calif.). All flow cytometry data were gated using either FlowJo (TreeStar Software, Ashland, Oreg.), or WinList (Verity House Software, Topsham, Me.). 3D Visual analysis was performed using Spotfire (Tibco, Somerville, Mass., USA). Dead cells and debris were excluded by forward scatter, side scatter, and Aqua viability dye staining. Surface markers consisting of CD45, CD34, CD11b and CD33 and right-angle light-scatter characteristics identified phenotypes consistent with myeloid leukemia cells. The percentage of cells expressing c-Kit was calculated by the frequency of cells with an intensity level greater than the 95th percentile for isotype control antibody staining. CXCR4, MRP-1, and ABCG2 expression levels were calculated as a fold difference compared to the mean fluorescent intensity value obtained by the corresponding isotype control antibody.

Gating applied to the second data set to assay SCF, FLT3L, G-CSF, and IL-27 responsiveness was defined by the basal state (unstimulated) fluorescence of downstream readouts (e.g. p-Akt, p-S6, STAT3). This gating was performed on healthy BM samples which were run in each study as controls since absolute values were not comparable between the studies due to differences in experimental configurations (e.g. reagent and cytometer calibrations). The choice of normal BM to define the cut off for the activated subpopulation in AML marrow was based on the potential for constitutively activated pathways in AML samples.

Statistical Analysis

Given the relatively small number of samples, comparisons between the readouts from diagnostic and relapse samples were performed visually. After resistance-associated nodes were identified, Fisher's exact test was applied to compute the probability of association of the nodes with disease relapse occurring by chance in an independent data set. R statistics package was used for this purpose.

Results

Patient and Sample Characteristics

Modulated SCNP was evaluated on longitudinally paired diagnosis and relapse AML samples from two patients with AML. Clinical characteristics of the patients are shown in Table 15. Both patients received high dose cytarabine based induction chemotherapy with disease response of CR followed by relapse within one year. Cytogenetic analysis revealed prognostically unfavorable translocations of AML1-EV11 and DEK-NUP214 [t(6;9)] in patients one and two respectively. In addition, patient two had FLT3-ITD positive leukemia, a known poor prognostic marker for relapse risk and overall survival and associated with the DEK-NUP214 translocation in the majority of cases.

Healthy control BMMC (N=2) were derived from young healthy male volunteers (age=18 and 20 years respectively).

TABLE 15

Clinical Characteristics of Patient Donors for Longitudinally Paired Diagnosis and Relapse Samples

| Donor | Age (Years) | Gender | Sample Source | Secondary AML | FAB | Cytogenetics | Cytogenetic group | FLT3 ITD | Induction Chemotherapy | Induction Response | Relapse | CR Duration (Weeks) |
|---|---|---|---|---|---|---|---|---|---|---|---|---|
| 1 | 77.8 | M | BM | No | M0 | 46, XY, t(3; 21) (q26; q22) | unfavorable | NEG | IDA + HDAC* | CR | Yes | 46.143 |
| 2 | 34.8 | F | BM | No | M2 | t(6; 9) | unfavorable | POS | IA + ZARNESTRA** | CR | Yes | 11.143 |

*Idarubicin + high dose Ara-C
**Idarubicin + Ara-C + Zarnestra

Comparison of Diagnosis and Relapse AML Samples

Longitudinally paired diagnostic and relapse samples from two AML patients were processed as described in Materials and Methods to assess whether specific cell subpopulations could be identified (using cell surface phenotypes and/or signaling profiles) in the relapsed sample in a greater percentage than observed in the corresponding diagnostic sample. Next, in an independent and larger group of diagnostic patient samples, the presence of blasts with the previously identified cell profiles were examined for their association with disease relapse.

Myeloblast Subpopulations Defined by Surface Markers

The two diagnostic and first relapse samples were first compared for expression of conventional surface markers used to define myeloblast maturity as shown in FIG. 5a. Samples from both patients displayed different proportions of CD34+ CD11b- (immature), CD33+CD11b+ (mature) and all other blasts (intermediate—neither mature nor immature) phenotypes from each other and between diagnosis and relapse. Subpopulations based on these characteristics of myeloblast maturity were not informative of relapse risk for either patient sample (FIG. 5b). The levels of the chemokine receptor CXCR4 and drug transporters ABCG2 and MRP-1 were similar between diagnosis and relapse samples and were also not informative for disease relapse (not shown).

Myeloblast Subpopulations Defined by Intracellular Signaling Profiles

Figure 6:
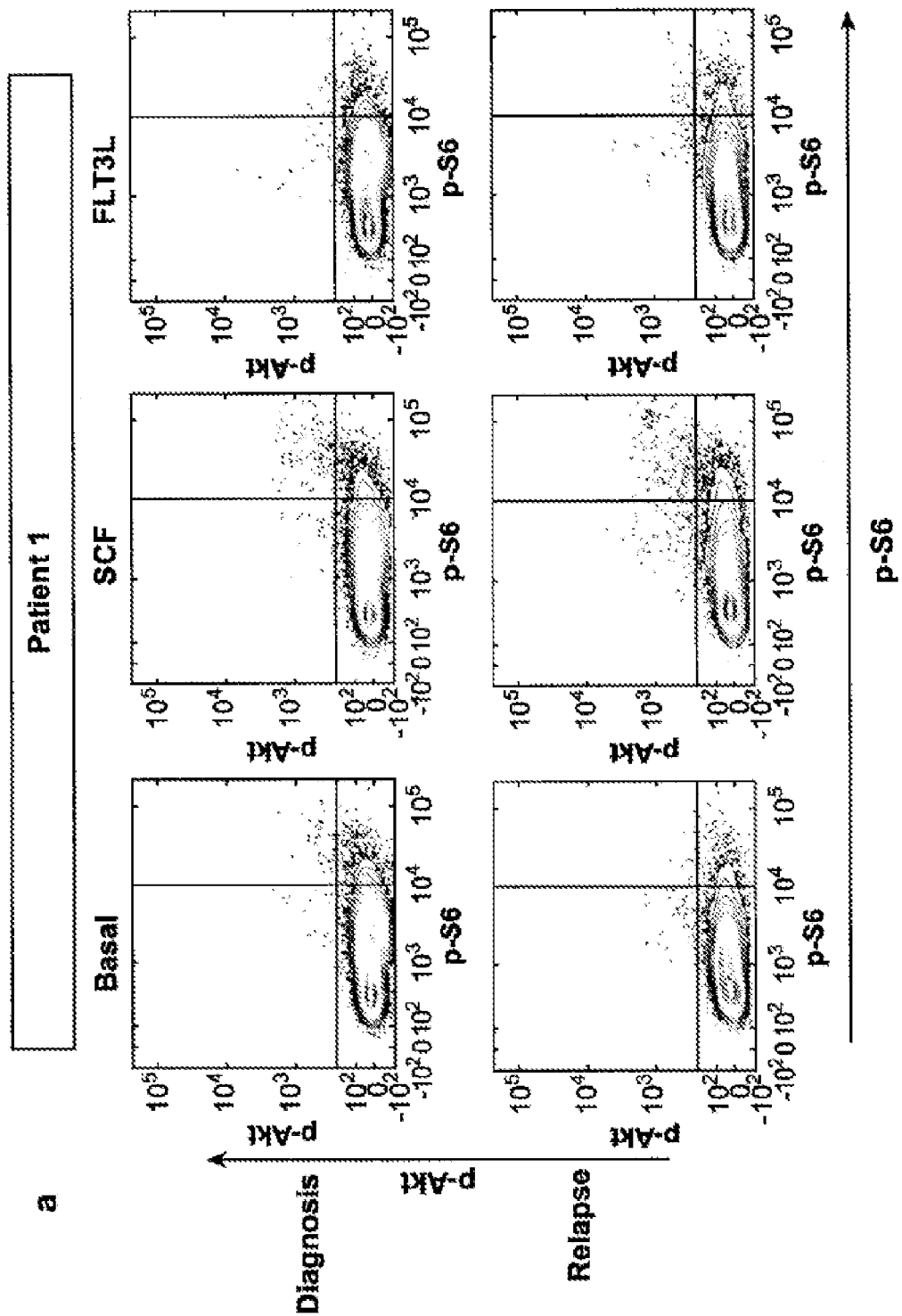
FIG. 6 shows that an examination of signaling profiles revealed differences in relapse and diagnosis samples for SCF and FLT3L.
Figure 7:
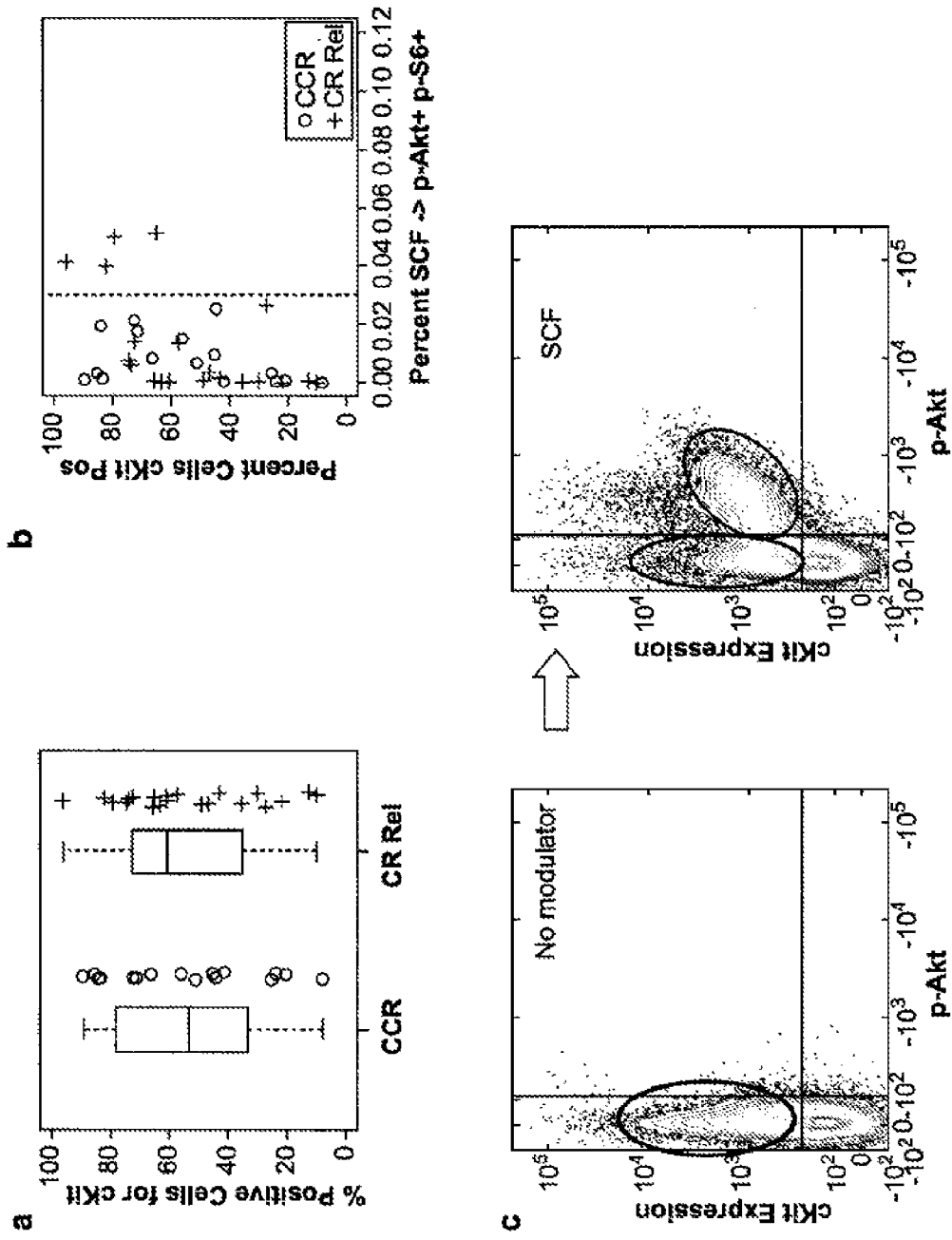
FIG. 7 shows that c-kit expression is not predictive of SCF responsiveness.

Examination of intracellular signaling profiles revealed functionally distinct cell subsets in the otherwise phenotypically similar relapse and diagnosis samples (FIG. 6). Specifically, when the relapse samples from Patient 1 and Patient 2 were modulated using SCF, both p-Akt and p-S6 were induced in 3.2% and 31.7% of cells respectively (FIG. 6). A similar finding of an increased percentage of myeloblasts subpopulations defined by intracellular signaling profiles in relapse versus diagnosis samples was observed when FLT3L (inducing p-S6 and p-Akt, FIG. 6), and IL-27 or G-SCF (inducing p-STAT3 and p-STAT5) were used as modulators (not shown).

To investigate whether similar cells were present at the time of diagnosis, which would support the concept of selection, or absent, supporting the idea of an induced change, we looked for the presence of cells with similar functional responses to SCF, FLT3L, IL-27 and G-CSF in the corresponding diagnosis samples. While no IL-27 responsive subpopulation was identified, SCF, FLT3L and G-CSF responsive cells were observed in the diagnostic AML bone marrow samples (FIG. 6), although in much lower percentage (~1%). Back-gating of the SCF responsive cells in the relapse samples revealed that the SCF:p-Akt/p-S6 signaling profile was found in phenotypically diverse cell subpopulations despite similar categorization by conventional surface markers (not shown, CD34+CD33+CD11b- for both Patient 1 and Patient 2 yet each patient displays distinct SCF-responsive cell subpopulation). In the two normal BM samples, an SCF-responsive subpopulation was present and was comparable between the samples; These SCF responsive cells were phenotypically distinct from the SCF-responsive cells in the leukemia samples and characterized by CD34+ CD33- CD11b- (not shown).

Testing the Predictive Value at Diagnosis for Disease Relapse of Resistance-Associated Signaling Nodes After identifying the resistance-associated signaling nodes in the relapsed samples, we analyzed the nodes in the valuer for being predictive for poor outcome [early relapse].

Predictive Value of SCF:p-Akt/p-S6 Subpopulation in an Independent Sample Set

We first applied the SCF:p-Akt/p-S6 gating scheme (as defined in Materials and Methods) to an independent set of diagnostic AML samples. All patients received high dose cytarabine based induction chemotherapy with disease response of complete remission. Of these, 27 experienced disease relapse (CR Rel) while 20 remained in complete continuous remission (CCR) for two or more years. Patients from whom this independent sample set was obtained were young (41/47<60) and a high proportion (20/47) had FAB M2 AML.

In seven diagnostic AML samples a subset of leukemic blast cells, which responded to SCF modulation by phosphorylation of p-Akt and p-S6, were observed (not shown). Of those seven, six patients experienced disease relapse within two years (p=0.21, Fisher's exact test) from remission while the seventh patient had a complete remission lasting more than two years; interestingly this AML sample had favorable cytogenetics t(8;21) (not shown). Of note, all of the patients with this SCF responsive profile were less than 60 years old and with the exception mentioned above, they all had intermediate or high risk cytogenetics; six out of seven also had an early myeloid FAB classification of M1 or M2. Also of note, the occurrence of the SCF:pAkt/pS6 subpopulation was independent of the presence of FLT3-ITD: only one of the six samples was positive for FLT3-ITD mutation. Importantly, the predictive value of the combination of FLT3-ITD and SCF:p-Akt/p-S6 for disease relapse was greater than either biomarker individually (p=0.03, Fisher's Exact Test).

c-Kit (SCF Receptor) Expression is Not Predictive of SCF Responsiveness

We next examined whether expression of c-Kit, the receptor for SCF, could function as a surrogate marker for the SCF:p-Akt/p-S6 phenotype. Although only samples that expressed c-Kit were able to respond to SCF, no association between c-Kit expression levels and likelihood of leukemia relapse (FIG. 7a) was observed suggesting that c-Kit expression is a necessary but not sufficient condition for intracellular signaling. In line with this observation, the removal of non-c-Kit expressing samples improved relapse prediction (FIG. 7b). Furthermore, when blast cells from an AML sample were simultaneously examined for c-Kit and the downstream signaling marker p-Akt, intra-patient heterogeneity in c-Kit expression and response to SCF within c-kit expressing cells was observed (FIG. 7c).

Predictive Value of Other Resistance-Associated Signaling Node Subpopulations in an Independent Sample Set We also examined whether FLT3L:p-Akt/p-S6, G-CSF:p-STAT3/5 or IL-27:p-STAT3/5 signaling nodes predicted poor outcome in the same independent set of diagnostic AML samples. Unlike SCF: p-Akt/p-S6 gate, no association was found with disease relapse (not shown).

Discussion

Relapse due to chemoresistant residual disease is a major cause of death in both adult and pediatric patients with AML and aberrant signal transduction within pathways that control cell proliferation and survival is thought to play an important role in secondary chemoresistance. In this study we used SCNP as a strategy to identify specific signaling pathway profiles associated with in vivo chemoresistance using paired diagnosis and relapse samples. While performed on a limited number of paired AML samples, our study provides unique insights into the nature of AML secondary chemoresistance in rare cell populations, identifying a functionally characterized cell subset associated with likelihood of early relapse when the assay was applied in a separate patient cohort.

A subset of leukemia cells with enhanced activity within the PI3 kinase/Akt cascade (SCF:p-Akt/p-S6) was found to be commonly expanded in the two leukemia samples collected at relapse. Importantly, the presence of cell subpopulations expressing this same signaling profile at diagnosis was associated with disease relapse after complete response to induction chemotherapy in an independent sample set of AML diagnostic samples. Although the SCF:p-Akt/p-S6 profile was not present in all patients with relapsed disease, all but one sample that contained a subpopulation of >3% SCF:p-Akt/p-S6 cells relapsed within two years of remission. These data support the marked biologic heterogeneity at the basis of AML secondary chemoresistance and lend merit to the approach of studying signaling profiles in functionally distinct subpopulations in longitudinally collected AML samples before and after therapy to identify poor-prognostic cell populations. While the SCF:p-Akt/p-S6 profile was predictive for relapse, other profiles (i.e. G-CSF:p-STAT 3/5, FLT3L:p-Akt/p-S6 and IL-27:p-STAT 3/5) were not associated with poor outcome in this sample set. Whether these nodes have clinical significance remains to be determined. Analysis of additional paired samples is likely to reveal other pathway nodes predictive of chemoresistance or relapse. The data also supports the concept that the cells that give rise to resistance are selected from amongst the diversity of leukemic blasts present at diagnosis, as opposed to induction of cells with new characteristics. This implies that recognition of resistance prone characteristics at diagnosis could be used to select and apply therapies that target these cells mechanistically on an individualized basis at the time of diagnosis. Thus, the results described herein coul be used to prevent chemoresistance from emerging and improve clinical outcome.

PI3K/Akt signaling is known to play a fundamental role in opposing apoptosis and has been shown to be associated with resistance to a variety of chemotherapeutic agents, including those used to induce remission in AML and with inferior survival in AML. Importantly, the prognostic value of the presence of the SCF:p-Akt/p-S6 profile was independent from other known prognostic factors for relapse in AML including age and the presence of FLT3 ITD mutation. In the tested sample set the combination of the SCF:p-Akt/p-S6 phenotype with FLT-3 ITD mutational status resulted in higher predictive value for disease relapse than that either marker alone. Further studies are warranted to determine whether these findings, including the significance of this phenotype occurring predominantly in early myeloid (FAB M1-M2) leukemia, hold true in larger independent sample sets.

The receptor tyrosine kinase Kit and its ligand SCF are expressed on early hematopoietic cells and are essential for the proliferation and survival of these cells. (34) Kit is expressed on over 70% of pediatric and adult AML and activating mutations of c-Kit are associated with poor outcome in the core binding factor subset of adult AML. While this study did not examine molecular aberrations aside from FLT-3 mutational status, we show that c-Kit expression could not substitute for the poor prognostic SCF:p-Akt/p-S6 phenotype. In addition, heterogeneity of c-Kit was observed within individual leukemia samples with some blast subpopulations expressing high levels and other populations showing no cell surface c-Kit expression. Furthermore, the simultaneous examination of c-Kit and p-Akt revealed distinct c-Kit positive cell populations within an individual AML sample that had different signaling capabilities. This strategy will provide the ability to examine signaling in future studies only in the cells that express c-Kit. Taken together, these data reveal the diversity of c-Kit expression and function in the context of AML, underscore the complexity and heterogeneity of each individual's AML, and suggest further studies incorporating dual cell surface and intracellular profiling.

Currently there are no measures to indicate why patients with similar clinically appearing disease have different responses to therapy with some remaining disease free while others undergo disease relapse and ultimately succumb. SCNP permits an accurate characterization of each individual's leukemia signaling pathway phenotype and biologic heterogeneity allowing for a more efficient delineation of the normality or pathology of leukemic subpopulations. This study shows that leukemic cell populations differ quantitatively and qualitatively before and after in-vivo therapeutic pressure in AML and that SCNP offers a novel approach to identify chemotherapy-resistant subpopulations that may predispose patients to disease relapse.

Example 6 a. Exposure of AML Blasts in vitro to Staurosporine and Etoposide Reveals Three Distinct Apoptosis Profiles Jak/Stat and PI3 kinase pathways are tied to cancer cell survival. For this reason, apoptotic proficiency in AML samples was determined in response to etoposide and staurosporine exposure in vitro. In addition, the ability of etoposide and staurosporine to induce a DNA damage response was also evaluated for these samples.

Single cell network profiling using flow cytometry was used to determine DNA damage response and apoptosis in AML blasts after in vitro exposure to staurosporine and etoposide. After treatment of samples with staurosporine for 6 h or etoposide for 24 hours, cells were stained with Amine Aqua viability dye then fixed, permeabilized and incubated with a cocktail of fluorochrome-conjugated antibodies that delineated AML blasts by their surface markers and measured levels of intracellular signaling molecules within the canonical intrinsic apoptosis pathway: cleavage products of Caspase 3, Caspase-8, and PARP.

The data showed three distinct apoptosis responses of AML blasts after in vitro exposure to staurosporine and etoposide (not shown). The metric used to analyze this data was "Apoptosis" and is a measure of apoptosis and cell death induced by a drug. A viable cell will be Aqua negative and PARP negative and a measure of cell death is PARP and/or Aqua positivity.

"Apoptosis"=% of PARP$^-$ Aqua$^-$$_{unstim}$–% of PARP$^-$ Aqua$^-$$_{Drug}$.

If initially before exposure to a drug a sample has 80% of cells that are PARP$^-$ Aqua$^-$ (live/healthy) and after treatment the sample has 30% of cells that are PARP$^-$ Aqua$^-$ then the drug induced an apoptotic response in 50% of the cells.

In the first profile, staurosporine, a multi-kinase inhibitor and inducer of apoptosis, failed to induce apoptosis (Staurosporine Resistant profile). Samples responsive to staurosporine were then classified by their responses to Etoposide, a topoisomerase 11 inhibitor which identified a second signature in which AML blasts were competent to undergo an apoptotic response to staurosporine but not to etoposide (Etoposide Resistant Profile). The third profile described AML blasts that were competent to undergo apoptosis in response to both agents (Apoptosis Competent Profile).

Co-incubation of samples with a pan-Caspase inhibitor, Z-VAD, revealed different apoptotic mechanisms among leukemic samples. Various changes in the levels of Cleaved Caspase-3 and PARP were observed upon co-incubation with Z-VAD revealing contributions of both caspase-dependent (Z-VAD sensitive) and caspase-independent (Z-VAD insensitive) pathways of apoptosis, (not shown). For example, Z-VAD inhibited cleavage of caspase 3 and PARP to near completion (0341,0521) suggesting that in these samples apoptosis was predominantly caspase-dependent. In other samples (8303, 8402) PARP cleavage was only partially inhibited by Z-VAD treatment suggesting the presence of caspase-independent mechanisms of apoptosis. Samples that were classified by the "Apoptosis Competent profile" were enriched for Z-VAD in sensitive samples, suggesting the presence of both caspase dependent and independent cell death pathways in these samples suggesting that in these samples cells have a choice of cell death pathways (not shown).

Mechanistically, treatment of cells with etoposide (but not staurosporine) will result in DNA damage which will halt the cell cycle through activation of cell cycle checkpoint kinases and give the cell time to repair the damage. If attempts to repair DNA are unsuccessful, cells undergo apoptosis (Huang et al., Molecular Cancer therapeutics 2008 and see references therein). In this study DNA damage was determined by measuring the ATM phosphorylation site, T68, on Chk2. In this AML sample set different DNA Damage and Apoptosis in responses were seen between samples exposed in vitro to Etoposide. The spectrum of responses included samples which failed to elicit a DNA damage and apoptosis response (8314), samples in which there was a DNA damage response but no apoptosis (0521, 8390) and samples in which both responses were intact (5688, 8303, 8402). Analysis of the in vitro apoptotic responses in the context of FLT3 mutations revealed a range of apoptosis responses in both molecular classes. Notably, samples in which staurosporine and etoposide induced the greatest apoptotic responses were those that expressed FLT3 ITD. As discussed above, given the range of signaling responses within a molecularly classified group, in this case FLT3 ITD mutations, further analysis of networks should be performed to characterize samples and classify patients and their potential response to therapeutic agents.

The apoptosis profile revealed for each AML sample after in vitro exposure to staurosporine and etoposide was compared to the clinical response documented post induction therapy. Strikingly, the "Staurosporine Resistant" and "Etoposide Resistant" apoptosis profiles were completely comprised of AML samples from clinical NR patient samples. In contrast, the "Apoptosis Competent" profile comprised all samples from clinical CR patients. Of note, several samples from NR patients fell into the "Apoptosis CompetentProfile". Thus, in vitro apoptosis assays in leukemic samples could potentially model in vivo clinical responsiveness to chemotherapy.

b. Jak/Stat and PI3K Signaling Confer Resistance to Apoptosis in AML Blasts

To understand how proliferation and survival signaling relate to apoptotic potential, JAK/STAT and PI3K/S6 pathway activity in leukemic samples was analyzed in the context of the apoptotic profiles described above. While some differences in the basal unstimulated levels of phosphorylated STAT proteins were observed between apoptotic signature groups, stimulation with cytokines revealed variable JAK/STAT activity among the apoptosis categories described above. Robust Jak/Stat responses were seen upon treatment with G-CSF (p-Stat3, p-Stat5) or GM-CSF (p-Stat5) in all samples from the "Staurosporine Resistant" apoptosis category, consistent with Stat proteins providing a survival function. In the two other apoptotic categories, the G-CSF-mediated increases in p-Stat3 and p-Stat5 were variable suggesting that in these patients, G-CSF signaling provides an apoptosis-independent pathway for analysis and potential patient stratification.

Consistent with the role of augmented Stat signaling in "staurosporine resistant" samples, IL-27-induced levels of total p-Stat1 and p-Stat3 were all greater in this apoptotic sub-category. "Etoposide Resistant" samples had varying levels of IL-27-mediated Stat signaling and the lowest levels of induced Stat phosphorylation were observed in the "Apoptosis Competent" category (not shown).

The NR patients within the "apoptosis Competent" Profile displayed higher IL-27 induced p-Stat than CR patients again emphasizing the need to evaluate multiple pathways in patient samples in order to reach meaningful clinical decisions.

Consistent with their roles in survival, there was an inverse correlation between levels of growth factor-mediated-p-Akt and p-S6 signaling and apoptotic response. Greater induced p-Akt and p-S6 levels were observed in samples where there was a low level of induced apoptosis (Staurosporine and/or Etoposide Resistant categories). In contrast in the "Apoptosis Competent Profile" there were low levels of growth factor-mediated increases in p-Akt and p-S6 (not shown).

Other myeloid cytokines and chemokines known to stimulate the PI3K/S6 and pathway are G-CSF, GM-CSF, and SDF-1α. Overall, these modulators mediated the greatest increase in p-Akt and p-S6 levels in the "Staurosporine Resistant" category consistent with the survival role conferred by the PI3K pathway. Notably, two different cytokines, G-CSF and GM-CSF provided a similar signaling output (p-Stat5, p-S6) in this apoptotic category. Pathway characterization of AML blasts highlights the different signaling mechanisms utilized to evade apoptosis (for example: sample 8093, NR, "Etoposide resistant", induced Jak/Stat signaling elevated, sample 0521, NR, "Etoposide Resistant", induced PI3K/S6 signaling elevated, sample 4353, NR, "Staurosporine Resistant", induced Jak/Stat and PI3K/S6 pathways elevated.

c. Analysis of Signaling and Apoptosis in the Context of FLT3 Mutations

Analysis of the in vitro apoptotic responses in the context of FLT3 mutations revealed that AML samples expressing FLT3 ITD have relatively intact apoptotic machinery compared with AML samples expressing wild type FLT3 (not shown). However, apoptosis responses to both staurosporine and etoposide varied between samples within FLT3 ITD+ or WT subgroups, demonstrating that molecular characterization alone is not sufficient to classify patients and their potential response to therapeutics. In other analyses FLT3-ITD patients had higher basal p-Stat5 and cytokine induced p-Stat5 levels than FLT3-WT patients although a large spread of responses was seen in either FLT3-ITD or FLT3-WT patients. Also, FLT3-ITD patients had lower basal and FLT3L induced p-S6 than FLT3-WT patients. Again a spread of responses was seen within FLT3 WT or FLT3-ITD subgroups demonstrating how single cell network profiling can further characterize samples within a molecularly-defined patient subgroup.

Example 7

Scenarios of how this invention might be used to advance the diagnosis or prognosis of disease, or the ability to predict or assess response to therapy are outlined in the following two paragraphs.

A 49 year-old individual presents to their primary medical doctor with the chief complaint of fatigue and bruising. A complete blood count reveals increased white blood cells, decreased hemoglobin and hematocrit, low platelets and circulating blasts. A bone marrow aspirate is obtained and flow cytometry reveals an immature myeloid blast population. The patient is diagnosed with acute myeloid leukemia and the physician and patient must determine the best course of therapy. Using an embodiment of the present invention, the bone marrow or peripheral blood of the patient might be removed and modulators such as GMCSF or PMA added. Activatable elements such asp-Stat3, p-Stat5 and p-Akt might classify this patient as one of the 25% of patients diagnosed with AML less than 60 years old who will not benefit from cytarabine based induction therapy. This invention may also reveal signaling biology within this patient's blasts population that suggests to the physician that the patient should be treated with a DNA methyl transferase inhibitor. With this invention, the patient would then be spared the toxicities associated with cytarabine therapy and could be placed on a clinical trial where he would receive a therapy from which he would likely benefit.

A 52 year-old female presents to her primary medical doctor with the chief complaint of fatigue and bruising. A complete blood count reveals normal numbers of white blood cells, decreased hemoglobin and hematocrit, and low platelets. A bone marrow aspirate and biopsy is obtained and flow cytometry and histology reveals tri-lineage myelodysplasia. The patient is diagnosed with MDS. Using an embodiment of the present invention, the bone marrow or peripheral blood of the patient might be removed and modulators such as GMCSF or PMA added. Activatable elements such as STAT3, STAT5 and AKT might reveal that the biology associated with this patient's MDS is likely of auto-immune origin. The physician promptly places this patient on CSA and ATG. Within 6 weeks she shows complete normalization of her complete blood count.

Example 8

This example relates to the publication "Dynamic Single-Cell Network Profiles in Acute Myelogenous Leukemia Are Associated with Patient Response to Standard Induction Therapy". Kornblau S M, Minden M D, Rosen D B, Putta S, Cohen A, Covey T, Spellmeyer D C, Fantl W J, Gayko U, Cesano A. Clinical Cancer Research. 2010 Jul. 15; 16(14): 3721-33 January 31. This publication is incorporate herein by reference in its entirety for all purposes.

Traditional prognostic markers in acute myeloid leukemia (AML) use static features present at diagnosis. This study reports measurements of single cell network profiling (SCNP) in response to external modulators as a new tool to recognize and interpret disease heterogeneity in the context of therapeutic applications. Intracellular signaling profiles from two sequential training cohorts of diagnostic non-M3 AML patient samples (n=34 and 88) showed high reproducibility (Pearson correlation coefficients≧0.8). In the first training study univariate analysis identified multiple "nodes" (modulated readouts of proteins in signaling pathways) relevant to myeloid biology and correlated with disease response to conventional induction therapy (i.e. AUC of ROC>0.66; p<0.05). Importantly combining independently predictive nodes improved disease response stratification (AUC of ROC up to 1.0). Extrapolation of the assay to a second independent set of samples revealed similar findings after accounting for clinical covariates. In particular, for patients <60 years old, the presence of intact apoptotic pathways was associated with complete response (CR), while FLT3 ligand mediated increase in phospho (p)-Akt and p-Erk correlated to NRs in patients >60 years. Findings were independent of cytogenetic and FLT3 mutational status. These data support the value of SCNP in AML disease characterization and management.

Introduction

Acute Myeloid Leukemia (AML) displays biologic and clinical heterogeneity due to a complex range of cytogenetic and molecular aberrations resulting in downstream effects on gene expression, protein function and cell signal transduction pathways, ultimately affecting proliferation and cellular differentiation. While morphology and cytochemical stains historically have formed the basis for AML classification, and emerging technologies such as gene expression profiling, microRNA profiling, epigenetic profiling and more recently proteomic profiling have been used to elucidate the biologic heterogeneity of AML, and have provided useful insights into the disease biology and its correlation with clinical outcomes. While individual molecular changes have shown to be associated with disease-free and overall survival, only karyotype, high expression levels of the brain and acute leukemia cytoplasmic (BAALC), and meningioma 1 (MN 1) genes at presentation have demonstrated an association with response to induction chemotherapy. (Marcucci et al. Curr Opin Hematol. 2005; 12:68-75; Langer C, Marcucci et al. J Clin Oncol. 2009; 27:3198-3204.) However, although these findings offer directionally predictive information at a population level, no validated means currently exist to predict the disease response to standard AML induction chemotherapy at the individual patient level.

Recently, reverse-phase protein arrays (RPPA) generated proteomic profiles that characterized aberrantly regulated signaling networks in AML samples and were found to correlate with known morphologic features, cytogenetics and outcome. (Kornblau et al. Blood. 2009; 113:154-164.) Single cell network profiling (SCNP) using multiparametric flow cytometry is a newer approach for analyzing and interpreting protein expression and post-translational protein modifications under modulated conditions at the single cell level. This approach interrogates the physiology of signaling pathways by measuring network properties beyond those detected in resting cells (e.g. failure of a pathway to become activated, hyper/hyposensitivity of the pathway to physiologic stimulators, altered response kinetics and rewiring of canonical pathways), thus revealing otherwise unseen functional heterogeneity in apparently morphologically and molecularly homogeneous disease groups. When applied to pathways shown to be important in disease pathology, this method of mapping signaling networks has potential applications in the development of predictive/diagnostic tests for therapeutic response and for improved efficiency of drug development. (Irish et al. Cell. 2004; 118:217-228; Irish et al. Nat Rev Cancer. 2006; 6:146-155; Krutzik et al. Nat Methods. 2006; 3:361-368; and Sachs et al. Science. 2005; 308:523-529.)

To utilize modulated SCNP to reveal AML network biology as a guide for disease management, two independent sample sets from newly diagnosed adult patients with AML (non-M3) were tested sequentially. Since multiple signaling pathways may be dysregulated in AML and impact responsiveness to therapy, a wide range of pathways that regulate proliferation, survival, DNA damage, apoptosis and drug transport were evaluated in response to modulators important in myeloid biology. Analyses evaluated assay performance, identified a signaling profile associated with response to standard induction chemotherapy (first training study) and extrapolated the identified profile to a fully independent set of AML samples (second training study). The results of the two studies illustrate the value of quantitatively measuring single cell signaling networks under modulated conditions to stratify AML patients for outcome to standard induction chemotherapy.

Materials and Methods
Patient Samples

Two independent sets of cryopreserved samples were analyzed sequentially. The first set consisted of 35 peripheral blood mononuclear cell (PBMC) samples derived from AML patients. The second set consisted of 134 cryopreserved bone marrow mononuclear cell (BMMC) samples derived from AML patients. These samples were the same samples used in the previous examples. Sample inclusion criteria required collection prior to initiation of induction chemotherapy, AML classification by the French-American-British (FAB) criteria as M0 through M7 (excluding M3) and availability of clinical annotations.

In the first study, induction chemotherapy consisted of at least one cycle of standard cytarabine-based induction therapy (i.e. daunorubicin 60 mg/m$^2$×3 days, cytarabine 100-200 mg/m$^2$ continuous infusion×7 days); responses were measured after one cycle of induction therapy. In the second study, cytarabine (200 mg/m$^2$ to 3 g/m$^2$) was used in combination with an anthracycline (daunorubicin or idarubicin) or an additional anti-metabolite (e.g. fludarabine or troxacitabine), and sometimes, an experimental agent (Table 16). Responses in this set were measured after completion of induction therapy (>90% after one cycle). Standard clinical and laboratory criteria were used for defining complete response (CR) in both studies. Leukemia samples obtained from patients who did not meet the criteria for CR or samples obtained from those who died during induction therapy were considered non-complete response (NR) for the primary analyses. Both studies had one patient that met all the criteria for a clinical CR, with the exception of platelet recovery. Classified as "CRp," these samples were included in the CR group for all primary analysis. The univariate analyses were also repeated with the CRp patients classified into the NR sample group for sensitivity analysis.

TABLE 16

Demographic and Baseline Characteristics for Evaluable Patients/Samples in Both Studies

| | Characteristic | CR No. 1 | NR No. 1 | All Pts No. 1 | P No. 1 | CR No. 2 | NR No. 2 | All Pts No. 2 | P No. 2 |
|---|---|---|---|---|---|---|---|---|---|
| | N | 9 | 25 | 34 | | 57 | 31 | 88 | |
| Age (yr) | Median | 57 | 47.4 | 49.1 | 0.084 | 51.2 | 61.6 | 55.2 | 0.004 |
| | Range | 38.2-74.8 | 20.7-70.2 | 20.7-74.8 | | 27.0-79.0 | 25.0-76.3 | 25.0-79.0 | |
| Age Group | <60 yr | 5 (56%) | 20 (80%) | 25 (74%) | 0.201 | 51 (89%) | 15 (48%) | 66 (75%) | <.001 |
| | >=60 yr | 4 (44%) | 5 (20%) | 9 (26%) | | 6 (11%) | 16 (52%) | 22 (25%) | |
| Sex | F | 7 (78%) | 14 (56%) | 21 (62%) | 0.427 | 32 (56%) | 16 (52%) | 48 (55%) | 0.823 |
| | M | 2 (22%) | 11 (44%) | 13 (38%) | | 25 (44%) | 15 (48%) | 40 (45%) | |
| Cytogentic | Favorable | 0 (0%) | 1 (4%) | 1 (3%) | 0.639 | 7 (12%) | 0 (0%) | 7 (8%) | 0.004 |
| Group | Intermediate | 8 (89%) | 18 (72%) | 26 (76%) | | 29 (51%) | 9 (29%) | 38 (43%) | |
| | Unfavorable | 0 (0%) | 3 (12%) | 3 (9%) | | 21 (37%) | 22 (71%) | 43 (49%) | |
| | Not Done | 1 (11%) | 3 (12%) | 4 (12%) | | 0 (0%) | 0 (0%) | 0 (0%) | |
| FAB | M0 | 0 (0%) | 2 (8%) | 2 (6%) | 0.474 | 1 (2%) | 1 (3%) | 2 (2%) | 0.794 |
| | M1 | 2 (22%) | 2 (8%) | 4 (12%) | | 8 (14%) | 1 (3%) | 9 (10%) | |
| | M2 | 1 (11%) | 5 (20%) | 6 (18%) | | 22 (39%) | 14 (45%) | 36 (41%) | |
| | M4 | 1 (11%) | 7 (28%) | 8 (24%) | | 14 (25%) | 8 (26%) | 22 (25%) | |
| | M5 | 3 (33%) | 2 (8%) | 5 (15%) | | 8 (14%) | 4 (13%) | 12 (14%) | |
| | M6 | 0 (0%) | 0 (0%) | 0 (0%) | | 2 (4%) | 2 (6%) | 4 (5%) | |
| | Other/Unknown | 2 (22%) | 7 (28%) | 9 (27%) | | 2 (4%) | 1 (3%) | 3 (3%) | |
| Race | White | 3 (33%) | 17 (68%) | 20 (59%) | 0.201 | 15 (26%) | 15 (48%) | 30 (34%) | 0.127 |
| | Asian | 5 (56%) | 5 (20%) | 10 (29%) | | 1 (2%) | 1 (3%) | 2 (2%) | |
| | Other* | 1 (11%) | 2 (8%) | 3 (9%) | | 10 (18%) | 1 (3%) | 11 (13%) | |
| | Unknown | 0 (0%) | 1 (4%) | 1 (3%) | | 31 (54%) | 14 (45%) | 45 (51%) | |
| FLT3-ITD | Negative | 4 (44%) | 14 (56%) | 18 (53%) | 0.641 | 44 (77%) | 23 (74%) | 67 (76%) | 0.477 |
| | Positive | 5 (56%) | 10 (40%) | 15 (44%) | | 11 (19%) | 5 (16%) | 16 (18%) | |
| | Unknown | 0 (0%) | 1 (4%) | 1 (3%) | | 2 (4%) | 3 (10%) | 5 (3%) | |
| Secondary | No | 8 (89%) | 25 (100%) | 33 (97%) | 0.265 | 47 (82%) | 14 (45%) | 61 (69%) | <.001 |
| AML | Yes | 1 (11%) | 0 (0%) | 1 (3%) | | 10 (18%) | 17 (55%) | 27 (31%) | |
| Poor | No | 5 (56%) | 18 (72%) | 23 (68%) | 0.425 | 22 (39%) | 3 (10%) | 25 (28%) | 0.004 |
| Prognosis† | Yes | 4 (44%) | 7 (28%) | 11 (32%) | | 35 (61%) | 28 (90%) | 63 (72%) | |
| Induction | Standard 3 + 7 | 9 (100%) | 25 (100%) | 34 (100%) | n/a | 0 (0%) | 0 (0%) | 0 (0%) | 0.222 |
| Therapy | Fludarabine + HDAC | 0 (0%) | 0 (0%) | 0 (0%) | | 11 (19%) | 2 (6%) | 13 (15%) | |
| | IA + Zarnestra | 0 (0%) | 0 (0%) | 0 (0%) | | 18 (32%) | 9 (29%) | 27 (31%) | |

TABLE 16-continued

Demographic and Baseline Characteristics for Evaluable Patients/Samples in Both Studies

| Characteristic | CR No. 1 | NR No. 1 | All Pts No. 1 | P No. 1 | CR No. 2 | NR No. 2 | All Pts No. 2 | P No. 2 |
|---|---|---|---|---|---|---|---|---|
| IDA + HDAC | 0 (0%) | 0 (0%) | 0 (0%) | | 17 (30%) | 9 (29%) | 26 (30%) | |
| Other | 0 (0%) | 0 (0%) | 0 (0%) | | 11 (19%) | 11 (35%) | 22 (25%) | |

There are 25 primary refractory patients and 6 failed patients in Study No. 2. The two-sample t-test was used to compare mean ages of CR and NR patients.
Fisher's Exact test was used to compare CR and NR patients with respect to categorical variables with two levels. The standard Chi-Square test was used to compare CR and NR patients with respect to categorical variables with three or more levels.
*The "Other" values for race are based on Black and Hispanic sub groups
†Poor prognosis is defined as having one or more of the following high risk features: age ≧60 years, unfavorable cytogenetics, FLT3 ITD positive or secondary AML SCNP Assays Cocktails of fluorochrome-conjugated antibodies were used to measure phosphorylated intracellular signaling molecules, cell lineage markers, and drug transporters in AML cells. Measurements were taken at basal state and after extracellular modulation with growth factors or cytokines.

A pathway "node" (FIG. 1) was defined as a combination of specific proteomic readout in the presence or absence of a specific modulator. Up to 147 nodes (including eight surface receptors and transporters) using 27 modulators were assessed in the two studies (Table 17).

Samples with 6.8 and 4.7 million cells were required to test all planned experimental nodes in the first and second studies, respectively. In both studies, evaluable samples were defined as those that yielded a minimum of 100,000 viable cells. In addition, 500 cells were required in the myeloid blast population for any condition to be included in analysis for a given sample. In the first set, 34 of 35 patients had evaluable samples, although some samples did not have enough cells for the testing of all planned nodes (Table 17). There were also two cryopreserved vials of each sample, allowing for assessment of assay reproducibility. In the second set, the number of viable cells recovered after thawing (median 1.1 million cells) was significantly less than expected and only 88 of the 134 samples were evaluable.

TABLE 17

All Nodes, with Biological Categories, Flouorochrome Read-Outs, and Number of Patients Assessed in Both Studies

| Modulator | Biological Category | Num. Pts No. 1 | Num. Pts No. 2 | Read-Out (antibody) Dye: Alexa 488 or FITC | Read-Out (antibody) Dye: PE | Read-Out (antibody) Dye: Alexa 647 or APC |
|---|---|---|---|---|---|---|
| Ara-C & Daunorubicin | Apoptosis | n/a | 42 | c-PARP | Dauno | p-Chk2 (T68) |
| CD40L | CCG | 34 | n/a | p-S6 (S235) | p-CREB (S133) | p-Erk 1/2 (T202/204)* |
| CD40L | CCG | 34 | n/a | p-p38 (T180/Y182) | p-Erk 1/2 (T202/204)* | p-NFkB p 65 (S529) |
| EPO | CCG | 34 | n/a | p-Stat1 (Y701) | p-Stat3 (Y705) | p-Stat5 (Y694) |
| Etoposide | Apoptosis | n/a | 62 | c-PARP | n/a | p-Chk2 (T68) |
| Etoposide | Apoptosis | 28 | n/a | BCL-2 | c-PARP* | p-Chk2 (T68) |
| Etoposide | Apoptosis | 27 | n/a | c-Caspase 3 | c-PARP* | None |
| Etoposide + ZVAD | Apoptosis | 28 | n/a | BCL-2 | c-PARP* | p-Chk2 (T68) |
| Etoposide + ZVAD | Apoptosis | 29 | n/a | c-Caspase 3 | c-PARP* | n/a |
| Flt3L | CCG | 34 | 76 | p-S6 (S235) | p-Erk 1/2 (T202/204) | p-Akt (S473) |
| Flt3L | CCG | 34 | n/a | p-CREB (S133) | p-Plcγ2 (Y759) | p-Stat5 (Y694) |
| Flt3L | CCG | n/a | 9 | p-Plcγ2 (Y759) | p-CREB (S133) | p-Stat5 (Y694) |
| G-CSF | CCG | 34 | 63 | p-Stat1 (Y701) | p-Stat3 (Y705) | p-Stat5 (Y694) |
| G-CSF | CCG | 34 | n/a | p-S6 (S235) | p-Erk 1/2 (T202/204) | p-Akt (S473) |
| GM-CSF | CCG | 34 | 14 | p-Stat1 (Y701) | p-Stat3 (Y705) | p-Stat5 (Y694) |
| GM-CSF | CCG | 34 | n/a | p-S6 (S235) | p-Erk 1/2 (T202/204) | p-Akt (S473) |
| $H_2O_2$ | Phosphatase | n/a | 65 | p-Akt (S473) | p-Plcγ2 (Y759) | p-SLP76 (Y128) |
| $H_2O_2$ | Phosphatase | 29 | n/a | p-Stat1 (Y701) | p-Stat3 (Y705) | p-Stat5 (Y694) |
| $H_2O_2$ | Phosphatase | 29 | n/a | p-Lck (Y505) | p-Plcγ2 (Y759) | p-SLP76 (Y128) |
| $H_2O_2$ | Phosphatase | 29 | n/a | p-S6 (S235) | p-Erk 1/2 (T202/204) | p-Akt (S473) |
| $H_2O_2$ + IFNα | Phosphatase | 29 | n/a | p-Stat1 (Y701) | p-Stat3 (Y705) | p-Stat5 (Y694) |
| $H_2O_2$ + SCF | Phosphatase | 29 | n/a | p-Lck (Y505) | p-Plcγ2 (Y759) | p-SLP76 (Y128) |
| $H_2O_2$ + SCF | Phosphatase | 29 | n/a | p-S6 (S235) | p-Erk 1/2 (T202/204) | p-Akt (S473) |
| IFNα | CCG | 34 | 46 | p-Stat1 (Y701) | p-Stat3 (Y705) | p-Stat5 (Y694) |
| IFNγ | CCG | 34 | 21 | p-Stat1 (Y701) | p-Stat3 (Y705) | p-Stat5 (Y694) |
| IGF-1 | CCG | 34 | n/a | p-S6 (S235) | p-CREB (S133)* | p-Erk 1/2 (T202/204) |
| IGF-1 | CCG | 34 | n/a | p-CREB (S133)* | p-Plcγ2 (Y759) | p-Stat5 (Y694) |
| IL-10 | CCG | 34 | 24 | p-Stat1 (Y701) | p-Stat3 (Y705) | p-Stat5 (Y694) |
| IL-27 | CCG | 34 | 56 | p-Stat1 (Y701) | p-Stat3 (Y705) | p-Stat5 (Y694) |
| IL-27 | CCG | 34 | n/a | p-S6 (S235) | p-CREB (S133) | p-Erk 1/2 (T202/204) |
| IL-3 | CCG | 34 | 13 | p-Stat1 (Y701) | p-Stat3 (Y705) | p-Stat5 (Y694) |
| IL-3 | CCG | 34 | n/a | p-S6 (S235) | p-CREB (S133) | p-Erk 1/2 (T202/204) |
| IL-4 | CCG | 34 | 9 | None | p-Stat6 (Y641) | p-Stat5 (Y694) |
| IL-6 | CCG | 34 | 15 | p-Stat1 (Y701) | p-Stat3 (Y705) | p-Stat5 (Y694) |
| IL-6 | CCG | 34 | n/a | p-S6 (S235) | p-CREB (S133) | p-Erk 1/2 (T202/204) |
| LPS | CCG | 34 | 27 | p-p38 (T180/Y182) | p-Erk 1/2 (T202/204) | p-NFkB p 65 (S529) |
| M-CSF | CCG | 34 | 9 | p-S6 (S235) | p-Erk 1/2 (T202/204) | p-Akt (S473) |
| M-CSF | CCG | 34 | n/a | p-CREB (S133) | p-Plcγ2 (Y759) | p-Stat5 (Y694) |
| None/Phenotypic | Surface Markers | n/a | 48 | CXCR4 | MRP1 | ABCG2 |
| None/Phenotypic Stain | Surface Markers | n/a | 51 | Flt3R | n/a | C-Kit |

TABLE 17-continued

All Nodes, with Biological Categories, Flouorochrome Read-Outs, and Number of Patients Assessed in Both Studies

| Modulator | Biological Category | Num. Pts No. 1 | Num. Pts No. 2 | Read-Out (antibody) Dye: Alexa 488 or FITC | Read-Out (antibody) Dye: PE | Read-Out (antibody) Dye: Alexa 647 or APC |
| --- | --- | --- | --- | --- | --- | --- |
| None/Phenotypic Stain | Surface Markers | 31 | n/a | EPO-R | Flt3R | C-Kit |
| None/Phenotypic Stain | Surface Markers | 31 | n/a | n/a | CXCR4 | ABCG2 |
| None/Phenotypic Stain | Surface Markers | 31 | n/a | MCSF-R | TNF-R | CD40 |
| PMA | CCG | 34 | 46 | p-S6 (S235) | p-CREB (S133) | p-Erk 1/2 (T202/204) |
| SCF | CCG | 34 | 74 | p-S6 (S235) | p-Erk 1/2 (T202/204) | p-Akt (S473) |
| SCF | CCG | 34 | n/a | p-CREB (S133) | p-Plcγ2 (Y759) | p-Stat5 (Y694) |
| SCF | CCG | n/a | 9 | p-Plcγ2 (Y759) | p-CREB (S133) | p-Stat5 (Y694) |
| SDF-1α | CCG | n/a | 93 | n/a | p-CREB (S133) | p-Akt (S473) |
| SDF-1α | CCG | 34 | n/a | p-S6 (S235) | p-Erk 1/2 (T202/204) | p-Akt (S473) |
| Stauro | Apoptosis | n/a | 9 | c-Caspase 8 | c-PARP | Cytochrome C |
| Stauro | Apoptosis | 26 | n/a | BCL-2 | c-PARP* | c-Caspase 8 |
| Stauro | Apoptosis | 30 | n/a | c-Caspase 3 | c-PARP* | None |
| Stauro + ZVAD | Apoptosis | n/a | 16 | c-Caspase 8 | c-PARP | Cytochrome C |
| Stauro + ZVAD | Apoptosis | 26 | n/a | BCL-2 | c-PARP* | c-Caspase 8 |
| Stauro + ZVAD | Apoptosis | 30 | n/a | c-Caspase 3 | c-PARP* | n/a |
| Thapsigargin | CCG | 34 | 43 | p-S6 (S235) | p-CREB (S133 | p-Erk 1/2 (T202/204) |
| TNF | CCG | 34 | 9 | p-p38 (T180/Y182) | p-Erk 1/2 (T202/204) | p-NFkB p 65 (S529) |

*Read-Out was assessed twice and all data was included for analysis.

Metrics are defined in Materials and Methods

Each modulator and read-out combination is a node. Unmodulated, basal levels were also measured. In #1, there were 18 basal, 121 modulated, and 8 surface markers for a total node count of 147. In #2, there were 16 basal, 69 modulated, and 5 surface markers for a total node count of 90.

Akt indicates protein kinase B;

APC, allophyco-cyanin;

Ara-C, cytarabine;

ATP-binding cassette, subfamily G, member 2;

BCL, CD, cluster of differentiation;

c-, cleaved-;

CCG, cytokine, chemokine, growth factor;

C-kit, CD117;

CREB, cAMP response element binding;

CXCR, CXC chemokine receptor;

EPO, erythropoietin;

Erk, Extracellular signal-regulated kinase;

FITC, fluorescein isothiocyanate;

FLT3, fms-like tyrosine kinase;

G-CSF, granulocyte colony stimulating factor;

GM-CSF, granulocyte macrophage stimulating factor;

H2O2, hydrogen peroxide;

IFN, interferon;

IGF, insulin-like growth factor;

IL, interleukin;

M-CSF, macrophage colony stimulating factor;

MDR, p-glycoprotein;

NFkB, Nuclear Factor-Kappa B;

p-, phospho-;

p38, map kinase family protein 38;

PARP, Extracellular signal-regulated kinase;

PE, phycoerythrin;

Plcγ, phospholipase c-gamma;

S6, ribosomal protein S6;

SCF, stem cell factor;

SDF, stromal cell derived factor;

Stat, signal transducer and activator of transcription;

Stauro, staurosporine;

TNF, tumor necrosis factor;

ZVAD, ZVAD-FMK caspase inhibitor

Cyropreserved samples were thawed at 37° C., washed and centrifuged in PBS, 10% FBS and 2 mM EDTA. The cells were re-suspended, filtered to remove debris and washed in RPMI cell culture media, 1% FBS, then stained with Live/Dead Fixable Aqua Viability Dye to distinguish non-viable cells. The cells were then re-suspended in RPMI, 1% FBS, aliquoted to 100,000 cells/condition and rested for 1-2 hours at 37° C. prior to SCNP assays. Each condition included two to five phenotypic markers for cell population gating (eg, CD45, CD33), up to three intracellular stains or up to three additional surface markers or control antibodies for an eight-color flow cytometry assay.

Functional assays were performed as previously described. Cells were incubated with modulators (Table 18), at 37° C. for 3-15 minutes, fixed with 1.6% paraformaldehyde (final concentration) for 10 minutes at 37° C., pelleted and permeabilized with 100% ice-cold methanol and stored at −80° C. For functional apoptosis assays, cells were incubated for 24 hours with cytotoxic drugs (i.e. etoposide or Ara-C and daunorubicin), re-stained with Live/Dead Fixable Aqua Viability Dye before fixation and permeabilization, washed with FACS Buffer (PBS, 0.5% BSA, 0.05% $NaN_3$), pelleted and stained with fluorescent dye-conjugated antibodies to both surface antigens (CD33, CD45) and the signaling protein targets (Table 18B).

TABLE 18A

List of Modulators and Technical Conditions of Use in Both Studies

| Modulator | Final Concentration | Modulator Treatment Duration | Manufacturer (Location) |
| --- | --- | --- | --- |
| Ara-C | 0.5 ug/mL | 24 h | Sigma Aldrich (St Louis, MO) |
| CD40L | 0.5 ug/mL | 7.5' and 15' | R&D (Minneapolis, MN) |
| Daunorubicin | 100 ng/mL | 24 h | Sigma Aldrich (St Louis, MO) |
| Erythropoetin | 1 IU/mL | 15' | R&D (Minneapolis, MN) |
| Etoposide | 30 mg/mL | 24 h | Sigma Aldrich (St Louis, MO) |
| FCS | 1.0% | various | HyClone (Waltham, MA) |
| Flt3L | 50 ng/mL | 15' | eBiosciences (San Diego, CA) |
| G-CSF | 50 ng/mL | 15' | R&D (Minneapolis, MN) |
| G-CSF | 50 ng/mL | 15' | Pepro (Rocky Hill, NJ) |
| GM-CSF | 2 ng/mL | 15' | BD (San Jose, CA) |
| H2O2 | 3 mM | 15' | JT Baker (Phillipsburg, NJ) |
| IFNα | 10000 IU/ML | 15' | Schering (Kenilworth, NJ) |
| IFNγ | 5 ng/mL | 15' | BD (San Jose, CA) |
| IGF-1 | 6.66 ng/mL | 15' | R&D (Minneapolis, MN) |
| IL-10 | 25 ng/mL | 15' | BD (San Jose, CA) |
| IL-27 | 50 ng/mL | 15' | R&D (Minneapolis, MN) |
| IL-3 | 50 ng/mL | 15' | BD (San Jose, CA) |
| IL-4 | 5 ng/mL | 15' | BD (San Jose, CA) |
| IL-6 | 25 ng/mL | 15' | R&D (Minneapolis, MN) |
| LPS | 1 ug/mL | 7.5' | Sigma Aldrich (St Louis, MO) |
| M-CSF | 2 ng/mL | 15' | R&D (Minneapolis, MN) |
| PMA | 400 nM | 15' | Sigma Aldrich (St Louis, MO) |
| SCF | 20 ng/mL | 15' | R&D (Minneapolis, MN) |
| SDF-1α | 2 ng/mL | 3' | R&D (Minneapolis, MN) |
| Stauro | 2.33 ug/mL | 6 h | Sigma Aldrich (St Louis, MO) |
| Thapsigargin | 1 uM | 15' | EMD Biosciences (Darmstadt, Germany) |
| TNFα | 20 ng/mL | 7.5' | BD (San Jose, CA) |
| Z-VAD-FMK Caspase Inhibitor | 100 uM | 24 h | R&D (Minneapolis, MN) |

TABLE 18B

Antibodies Used in Both Studies

| Antibody | Species & Isotype | Manufacturer (Location) | Label |
| --- | --- | --- | --- |
| ABCG2 | Mouse IgG2b | R&D (Minneapolis, MN) | APC |
| BCL-2 | Mouse IgG1, k | BD (San Jose, CA) | FITC |
| CD11b | Mouse IgG1 | Beckman (Miami, FL) | Pac Blue |
| CD33 | Mouse IgG1 | Beckman (Miami, FL) | Biotin |
| CD33 | Mouse IgG1 | BD (San Jose, CA) | Pac Blue |
| CD34 | Mouse IgG1 | BD (San Jose, CA) | PerCP |
| CD40 | Mouse IgG1, k | BD (San Jose, CA) | APC |
| CD45 | Mouse IgG1 | Invitrogen (Carlsbad, CA) | Ax700 |
| C-Kit | Mouse IgG1 | R&D (Minneapolis, MN) | APC |
| c-Caspase 3 | Rabbit IgG | BD (San Jose, CA) | FITC |
| c-Caspase 8 (Asp391) | Rabbit IgG | CST (Danvers, MA) | Unlabeled |
| c-PARP(Asp214) | Mouse IgG1, k | BD (San Jose, CA) | PE |
| c-PARP(Asp214) | Mouse IgG1, k | BD (San Jose, CA) | FITC |
| Control Ig | Ms IgG1 | eBio (San Diego, CA) | FITC |
| Control Ig | Mouse IgG2a, k | BD (San Jose, CA) | PE |
| Control Ig | Rat IgG1 | MBL (Woburn, MA) | FITC |
| Control Ig | Mouse IgG2b | R&D (Minneapolis, MN) | APC |

TABLE 18B-continued

Antibodies Used in Both Studies

| | | | |
|---|---|---|---|
| Control Ig | Mouse IgG1 | BD (San Jose, CA) | PE |
| Control Ig | Mouse IgG1, k | BD (San Jose, CA) | FITC |
| Control Ig | Mouse IgG1, k | BD (San Jose, CA) | APC |
| Control Ig | Mouse IgG1, k | BD (San Jose, CA) | PE |
| CXCR4 | Mouse IgG2a, k | BD (San Jose, CA) | PE |
| CXCR4 | Rat IgG1 | MBL (Woburn, MA) | FITC |
| Cytochrome C | Mouse IgG2b, k | BD (San Jose, CA) | Ax647 |
| EpoR | Mouse IgG2b | R&D (Minneapolis, MN) | FITC |
| Flt3R | Mouse igG1 | R&D (Minneapolis, MN) | PE |
| Flt3R | Mouse IgG1 | Ebio (San Diego, CA) | FITC |
| goat anti-rabbit | Goat IgG | Invitrogen (Carlsbad, CA) | Ax488 |
| goat anti-rabbit | Goat IgG | Invitrogen (Carlsbad, CA) | Ax647 |
| M-CSFR | Mouse IgG1 | R&D (Minneapolis, MN) | FITC |
| MRP-1 | Mouse IgG1 | R&D (Minneapolis, MN) | PE |
| p-Akt (S473) | Rabbit IgG | CST (Danvers, MA) | Ax647 |
| p-Akt (S473) | Rabbit IgG | CST (Danvers, MA) | Ax488 |
| p-Chk2 (T68) | Rabbit IgG | CST (Danvers, MA) | Unlabeled |
| p-CREB (pS133) | Rabbit IgG | CST (Danvers, MA) | Ax488 |
| p-CREB (pS133) | Mouse IgG1, k | BD (San Jose, CA) | PE |
| p-Erk ½ (T202/204) | Mouse IgG1 | BD (San Jose, CA) | Ax647 |
| p-Erk ½ (T202/204) | Mouse IgG1 | BD (San Jose, CA) | PE |
| p-Lck (Y505) | Mouse IgG1 | BD (San Jose, CA) | Ax488 |
| p-NF-kB p65 (pS529) | Mouse IgG2b, k | BD (San Jose, CA) | Ax647 |
| p-p38 MAPK (pT180/pY182) | Mouse IgG1 | BD (San Jose, CA) | Ax488 |
| p-Plcγ2 (Y759) | Mouse IgG1, k | BD (San Jose, CA) | PE |
| p-Plcγ2 (Y759) | Mouse IgG1, k | BD (San Jose, CA) | Ax488 |
| p-S6 (S235/236) | Rabbit IgG | CST (Danvers, MA) | Ax488 |
| p-SLP76 (pY128) | Mouse IgG1, k | BD (San Jose, CA) | Ax647 |
| p-Stat1 (pY701) | Mouse IgG2a | BD (San Jose, CA) | Ax488 |
| p-Stat3 (pY705) | Mouse IgG2a, k | BD (San Jose, CA) | PE |
| p-Stat5 (pY694) | Mouse IgG1 | BD (San Jose, CA) | Ax647 |
| p-Stat6 (pY641) | Mouse IgG2a | BD (San Jose, CA) | PE |
| TNF-R1 | Mouse IgG2a | Beckman (Miami, FL) | PE |
| Non-Antibody Stains | n/a | Manufacturer (Location) | Dye |
| Amine Aqua Viability Dye | n/a | Invitrogen (Carlsbad, CA) | Aqua |
| Streptavidin-Qdot 605 | n/a | Invitrogen (Carlsbad, CA) | Qdot 605 |

Abbreviations are defined in Table 17

Data Acquisition and Cytometry Analysis

Data was acquired using FACS DIVA software on both LSR II and CANTO II Flow Cytometers (BD). For all analyses, dead cells and debris were excluded by forward scatter (FSC), side scatter (SSC), and Amine Aqua Viability Dye measurement. Leukemic cells were identified as cells that lacked the characteristics of mature lymphocytes (CD45$^{++}$, CD33$^-$) and that fit the CD45 and CD33 versus right-angle light-scatter characteristics consistent with myeloid leukemia cells.

Statistical Analysis and Stratifying Node Selection a) Metrics

The median fluorescence intensity (MFI) was computed for each node from the fluorescence intensity levels for the cells in the myeloid population. The MFI values were then used to compute a variety of metrics by comparing them to baseline or background values, including the unmodulated condition, cellular autofluorescence and antibody isotype controls. The following metrics were computed:

1. Basal MFI ("Basal")=$\log_2(MFI_{Unmodulated\ Stained})-\log_2(MFI_{Gated\ Unstained\ (Autofluoresence)})$, designed to measure the basal levels of a certain protein under unmodulated conditions.
2. Fold Change MFI ("Fold")=$\log_2(MFI_{Modulated\ Stained})-\log_2(MFI_{Unmodulated\ Stained})$, a measure of the change in the activation state of a protein under modulated conditions.
3. Total Phospho MFI ("Total Phospho")= $\log_2(MFI_{Modulated\ Stained})-\log_2(MFI_{Gated\ Unstained\ (Autofluorescence)})$, a measure of the total levels of a protein under modulated conditions.
4. Relative Protein Expression ("Rel. Expression")=$\log_2(MFI_{stain})-\log_2(MFI_{Control})$, a measure of the levels of surface marker staining relative to control antibody staining.
5. Percent Cell Positivity ("PercentPos")=a measure of the frequency of cells that have surface markers staining at an intensity level greater than the 95$^{th}$ percentile for isotype control antibody staining.
6. An additional metric was designed to measure the levels of cellular apoptosis in response to cytotoxic drugs: Quadrant ("Quad")=a measure of the percentage of cells in a flow cytometry quadrant region defined by p-Chk2 and c-PARP i.e. the % of cells that are both p-Chk2− and c-PARP+.

b) Reproducibility Analysis

In the first study, two cryopreserved vials for all evaluable patient samples (n=34) were processed separately to assess overall assay reproducibility. Pearson and Spearman rank correlations were computed for each node/metric combination between the two data sets.

c) Univariate Analysis

Figure 8:
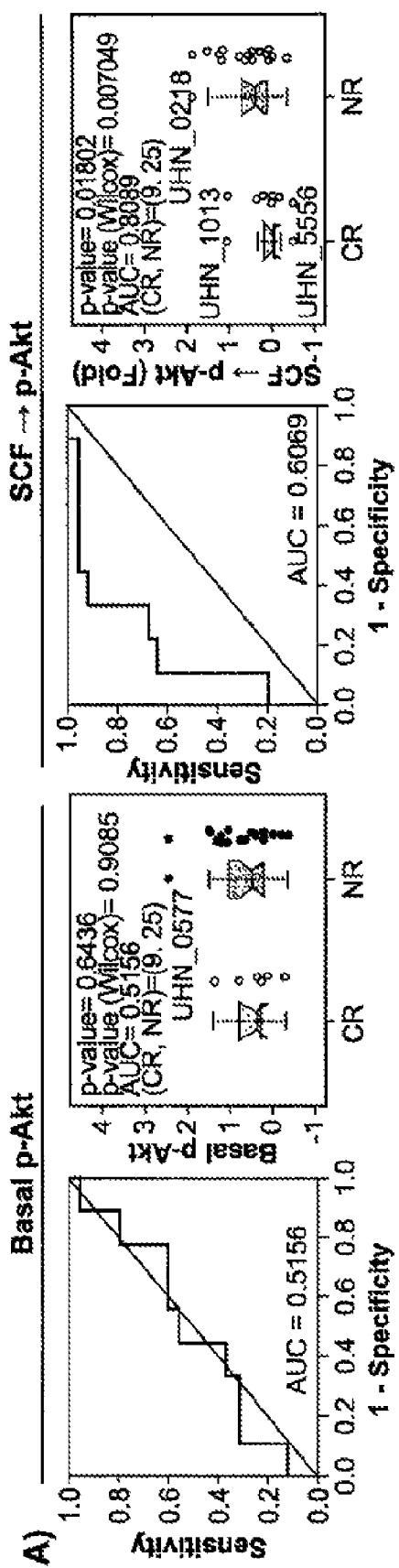
FIG. 8 shows univariate analysis for first study. Univariate analysis of modulated signaling and functional apoptosis nodes stratify NR and CR patient groups. (A) Stratification of NR and CR patient groups with SCF modulated, but not Basal, p-Akt signaling. (B) Stratification of NR and CR patients using functional apoptosis assays. The frequency of p-CHK2-, Cleaved PARP+ (c-PARP+) Apoptotic cells (upper left quadrant of the flow cytometry plots) after overnight exposure to Etoposide is used to quantify apoptosis. The circle in the lower right quadrant highlights cells that mount a DNA Damage Response but fail to undergo apoptosis.
Figure 8:
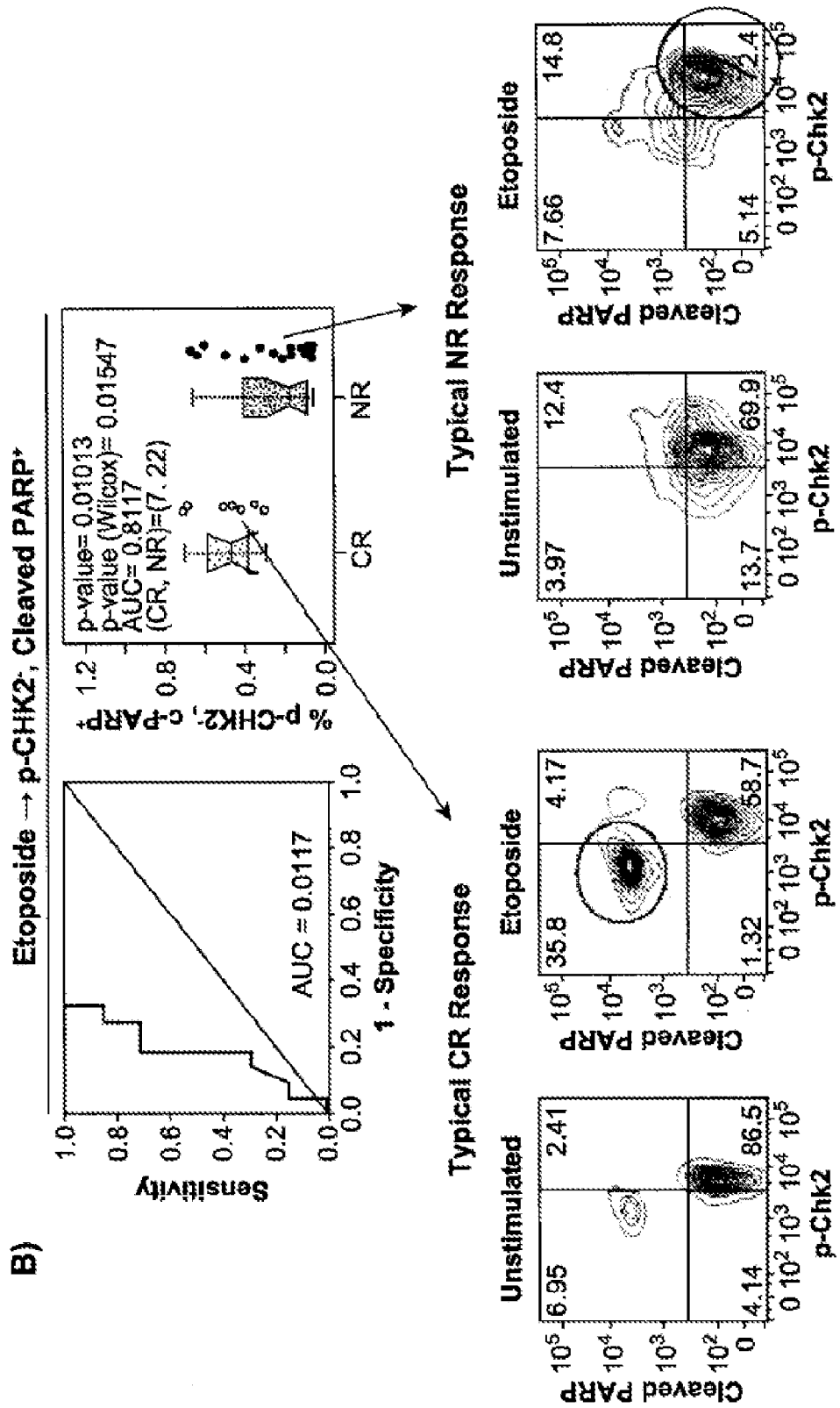

All node/metric combinations were analyzed and compared across samples for their ability to distinguish between the CR and NR sample groups. Student t-test and Wilcoxon p values were computed for each node/metric combination. In addition, the area under the receiver operator characteristic (ROC) curve was computed to assess the diagnostic accuracy of each node/metric combination (FIG. 8).

In the first study a total of 304 node/metric combinations were independently tested for differences between patient samples whose response to standard induction therapy was CR vs. NR. No corrections for multiple testing were applied to the p-values. Instead, simulations were performed by randomly permuting the clinical variable to estimate the number of node/metric combinations that might appear to be significant by chance. For each node/metric combination NC donors were randomly chosen (without replacement) and assigned to the CR category (where NC is the number of actual CRs in the original data set for that node/metric) and the remaining donors were assigned to the NR category. By comparing each node/metric to the permuted clinical variable, the student t-test p-values were computed. This process was repeated 10,000 times. The results were used to estimate the number of node/metrics expected to be significant by chance at the various p-values and compared with the empirical p-values for the number of node/metric combination found to be significant from the original data.

The statistical software package R, version 2.7.0 was used.

d) Correlations Between Node/Metric Combinations:

Correlations between all pairs of node/metric combination were assessed by computing Pearson and Spearman rank correlations.

e) Combinations of Node/Metrics

Nodes that can potentially complement each other to improve the accuracy of prediction of response to therapy were also explored. Given the small size of the data set, a straightforward "corner classifier" approach for picking combinations was adopted. Combinations that had an AUC greater than any included individual node/metric were tested for their robustness via a bootstrapping approach.

The corners classifier is a rule-based algorithm for dividing subjects into two classes (in this case the dichotomized response to induction therapy) using one or more numeric variables (defined in our study as a node/metric combination). This method works by setting a threshold on each variable, then combining the resulting intervals with "and" operator (e.g. X<10, and Y>50). This creates a rectangular region expected to hold most members of the class previously identified as the target (in this study clinical CR or NR sample groups). Threshold values can be chosen by minimizing an error criterion, however here in order to capture all CRs these values were set to either the maximum or the minimum value for each node/metric for all CRs. The accuracy of the corner classifier was measured by ranking the donors by their distance to the boundary. Donors that were inside the boundary were assigned a negative distance. This ranked list was used to compute an AUC under the ROC for the classifier. This AUC will be referred to as the 'minimum distance AUC'.

A "bagging", aka "bootstrapped aggregation", was used to internally cross-validate the results of the above statistical model. Bootstrap resamples were drawn 1,000 times. For each resample a new corner classifier was computed, which was used to predict the class membership of those patients excluded from the resample. After repeating the resampling operation, each patient acquires a list of predicted class memberships based on classifiers computed using other patients. These predicted values were used to create an ROC curve and to calculate its AUC, which will be referred to as the 'Bootstrap AUC'. The minimum distance AUC and bootstrap AUC together provide an estimate of the accuracy as well as the robustness of a combination of node/metrics.

Results

First Study:

a) Patient and Sample Characteristics.

Thirty-four evaluable AML PBMC samples were tested in the first study (Table 16 and 19). The sample set in this study was biased toward younger (<60 years), female patients whose leukemia did not respond to induction chemotherapy. Compared to the typical distribution of AML patients, Asian ethnicity (29%) and intermediate-risk cytogenetic (76%) samples were overrepresented, though ethnicity was in alignment with the Toronto population. Furthermore, 10 of 18 (56%) cytogenetically normal (CN) samples tested expressed the FLT3 ITD phenotype, overall indicating a poor prognostic group of patients[17-19].

SUPPLEMENTAL TABLE 19

Demographic and Baseline Characteristics for All Patients (Intend To Diagnose) in Both Studies

| Characteristic | | CR 1 | NR 1 | All Pts 1 | P 1 | CR 2 | NR 2 | All Pts 2 | P 2 |
|---|---|---|---|---|---|---|---|---|---|
| | N | 10 | 25 | 35 | | 88 | 46 | 134 | |
| Age (yr) | Median | 59.9 | 47.4 | 49.8 | 0.050 | 51.8 | 61.7 | 55.5 | |
| | Range | 38.2-74.8 | 20.7-70.2 | 20.7-74.8 | | 27.0-79.0 | 25.0-85.2 | 25.0-85.2 | <.001 |
| Age Group | <60 yr | 5 (50%) | 20 (80%) | 25 (71%) | 0.107 | 71 (81%) | 22 (48%) | 93 (69%) | <.001 |
| | >=60 yr | 5 (50%) | 5 (20%) | 10 (29%) | | 17 (19%) | 24 (52%) | 41 (31%) | |
| Sex | F | 7 (70%) | 14 (56%) | 21 (60%) | 0.704 | 46 (52%) | 24 (52%) | 70 (52%) | 1.000 |
| | M | 3 (30%) | 11 (44%) | 14 (40%) | | 42 (48%) | 22 (48%) | 64 (48%) | |
| Cytogentic Group | Favorable | 0 (0%) | 1 (4%) | 1 (3%) | 0.588 | 10 (11%) | 0 (0%) | 10 (7%) | <.001 |
| | Intermediate | 9 (90%) | 18 (72%) | 27 (77%) | | 48 (55%) | 12 (26%) | 60 (45%) | |
| | Unfavorable | 0 (0%) | 3 (12%) | 3 (9%) | | 30 (34%) | 34 (74%) | 64 (48%) | |
| | Not Done | 1 (10%) | 3 (12%) | 4 (11%) | | 0 (0%) | 0 (0%) | 0 (0%) | |
| FAB | M0 | 0 (0%) | 2 (8%) | 2 (6%) | 0.316 | 2 (2%) | 1 (2%) | 3 (2%) | 0.697 |
| | M1 | 2 (20%) | 2 (8%) | 4 (11%) | | 13 (15%) | 3 (7%) | 16 (12%) | |
| | M2 | 1 (10%) | 5 (20%) | 6 (17%) | | 31 (35%) | 22 (48%) | 53 (40%) | |
| | M4 | 1 (10%) | 7 (28%) | 8 (23%) | | 21 (24%) | 11 (24%) | 32 (24%) | |
| | M5 | 4 (40%) | 2 (8%) | 6 (17%) | | 15 (17%) | 5 (11%) | 20 (15%) | |
| | M6 | 0 (0%) | 0 (0%) | 0 (0%) | | 3 (3%) | 2 (4%) | 5 (4%) | |
| | Other & Unk. | 2 (20%) | 7 (28%) | 9 (26%) | | 3 (3%) | 2 (4%) | 5 (4%) | |
| Race | White | 4 (40%) | 17 (68%) | 21 (60%) | 0.306 | 30 (34%) | 20 (43%) | 50 (37%) | 0.473 |
| | Other & Unk.* | 6 (60%) | 8 (32%) | 14 (40%) | | 58 (66%) | 26 (57%) | 84 (63%) | |
| FLT3-ITD | Negative | 4 (40%) | 14 (56%) | 18 (51%) | 0.615 | 67 (76%) | 35 (76%) | 102 (76%) | 0.867 |
| | Positive | 5 (50%) | 10 (40%) | 15 (43%) | | 17 (19%) | 8 (17%) | 25 (19%) | |
| | Unknown | 1 (10%) | 1 (4%) | 2 (6%) | | 4 (5%) | 3 (7%) | 7 (5%) | |
| Secondary AML | No | 9 (90%) | 25 (100%) | 34 (97%) | 0.286 | 73 (83%) | 20 (43) | 93 (69%) | <.001 |
| | Yes | 1 (10%) | 0 (0%) | 1 (3%) | | 15 (17%) | 26 (57%) | 41 (31%) | |

SUPPLEMENTAL TABLE 19-continued

Demographic and Baseline Characteristics for All Patients (Intend To Diagnose) in Both Studies

| Characteristic | | CR 1 | NR 1 | All Pts 1 | P 1 | CR 2 | NR 2 | All Pts 2 | P 2 |
|---|---|---|---|---|---|---|---|---|---|
| Poor Prognosis† | No | 2 (20%) | 11 (44%) | 13 (37%) | 0.184 | 28 (32%) | 3 (7%) | 31 (23%) | <.001 |
| | Yes | 8 (80%) | 14 (56%) | 22 (63%) | | 60 (68%) | 43 (93%) | 103 (77%) | |
| Induction Therapy | 7 + 3 Ara-C/Dauno | 10 (100%) | 25 (100%) | 35 (100%) | n/a | 0 (0%) | 0 (0%) | 0 (0%) | |
| | Fludarabine + HDAC | 0 (0%) | 0 (0%) | 0 (0%) | | 18 (20%) | 2 (4%) | 20 (15%) | 0.075 |
| | IA + Zarnestra | 0 (0%) | 0 (0%) | 0 (0%) | | 20 (23%) | 11 (24%) | 31 (23%) | |
| | IDA + HDAC | 0 (0%) | 0 (0%) | 0 (0%) | | 24 (27%) | 15 (33%) | 39 (29%) | |
| | Other | 0 (0%) | 0 (0%) | 0 (0%) | | 26 (30%) | 18 (39%) | 44 (33%) | |

There were 38 primary refractory patients and 8 failed patients in Study No 2. The two sample t-test was used to compare mean ages of CR and NR patients. Fishers Exact test was used to compare CR and NR patient samples with respect to categorical variables with two levels. The standard Chi-Square test was used to compare CR and NR patients with respect to categorical variables with three or more levels.
*The "Other" values for race are based on Black, Asian, and Hispanic sub groups
†Poor prognosis is defined as having one ore more of the following high risk features: age >60 years, unfavorable cytogenetics, FLT3 ITD positive or secondary AML b) Assay Reproducibility.

Good correlation (Pearson coefficient≧0.8) was found between the data from the repeated assays (covering the thawing, stimulating, staining, gating and data analysis steps of the assays) performed using duplicate vials. As expected, assay reproducibility was better for nodes with a large range of signaling (not shown) as measured by standard deviation (SD), e.g. read outs for: SCF/p-Akt, FLT3L/p-Akt and G-CSF/p-Stat5. Node/metric combinations with less reproducible results included those with a very low range of signaling and SD, including G-CSF/p-Stat1, Il27/p-CREB, SDF1-α/p-Erk (Table 20).

TABLE 20

Reproducibility: Study No. 1

| Node: Modulator/Read-Out | Metric | Biological Category | Num. Pts | Pearson Coefficient | Spearman Coefficient | R2 | SD Value |
|---|---|---|---|---|---|---|---|
| FLT3L/p-Akt | Fold | CCG | 34 | 0.92 | 0.82 | 0.84 | 0.59 |
| FLT3L/p-Akt | TotalPhospho | CCG | 34 | 0.92 | 0.94 | 0.85 | 0.95 |
| FLT3L/p-Erk | Fold | CCG | 34 | 0.69 | 0.56 | 0.48 | 0.23 |
| FLT3L/p-Erk | TotalPhospho | CCG | 34 | 0.63 | 0.61 | 0.39 | 0.58 |
| FLT3L/p-S6 | Fold | CCG | 34 | 0.92 | 0.72 | 0.84 | 0.70 |
| FLT3L/p-S6 | TotalPhospho | CCG | 34 | 0.84 | 0.82 | 0.70 | 0.86 |
| G-CSF/p-Stat1 | Fold | CCG | 33 | 0.14 | 0.19 | 0.02 | 0.18 |
| G-CSF/p-Stat1 | TotalPhospho | CCG | 33 | 0.30 | 0.47 | 0.09 | 0.26 |
| G-CSF/p-Stat3 | Fold | CCG | 33 | 0.85 | 0.83 | 0.73 | 1.01 |
| G-CSF/p-Stat3 | TotalPhospho | CCG | 33 | 0.80 | 0.76 | 0.64 | 1.14 |
| G-CSF/p-Stat5 | Fold | CCG | 33 | 0.86 | 0.76 | 0.74 | 0.97 |
| G-CSF/p-Stat5 | TotalPhospho | CCG | 33 | 0.87 | 0.85 | 0.76 | 1.25 |
| IFNα/p-Stat1 | Fold | CCG | 34 | 0.59 | 0.55 | 0.34 | 0.47 |
| IFNα/p-Stat1 | TotalPhospho | CCG | 34 | 0.73 | 0.72 | 0.54 | 0.52 |
| IFNα/p-Stat3 | Fold | CCG | 34 | 0.77 | 0.79 | 0.59 | 0.56 |
| IFNα/p-Stat3 | TotalPhospho | CCG | 34 | 0.73 | 0.71 | 0.53 | 0.74 |
| IFNα/p-Stat5 | Fold | CCG | 34 | 0.75 | 0.78 | 0.57 | 0.85 |
| IFNα/p-Stat5 | TotalPhospho | CCG | 34 | 0.92 | 0.92 | 0.85 | 1.30 |
| IFNγ/p-Stat1 | Fold | CCG | 34 | 0.52 | 0.49 | 0.27 | 0.67 |
| IFNγ/p-Stat1 | TotalPhospho | CCG | 34 | 0.69 | 0.66 | 0.47 | 0.71 |
| IFNγ/p-Stat3 | Fold | CCG | 34 | 0.52 | 0.39 | 0.27 | 0.28 |
| IFNγ/p-Stat3 | TotalPhospho | CCG | 34 | 0.56 | 0.62 | 0.32 | 0.42 |
| IFNγ/p-Stat5 | Fold | CCG | 34 | 0.46 | 0.52 | 0.21 | 0.52 |
| IFNγ/p-Stat5 | TotalPhospho | CCG | 34 | 0.82 | 0.82 | 0.68 | 0.83 |
| IL-27/p-CREB | Fold | CCG | 34 | 0.34 | 0.37 | 0.11 | 0.21 |
| IL-27/p-CREB | TotalPhospho | CCG | 34 | 0.78 | 0.78 | 0.61 | 0.74 |
| IL-27/p-Erk | Fold | CCG | 34 | 0.01 | −0.05 | 0.00 | 0.18 |
| IL-27/p-Erk | TotalPhospho | CCG | 34 | 0.78 | 0.66 | 0.61 | 0.72 |
| IL-27/p-S6 | Fold | CCG | 34 | 0.21 | 0.10 | 0.04 | 0.06 |
| IL-27/p-S6 | TotalPhospho | CCG | 34 | 0.70 | 0.82 | 0.48 | 0.40 |
| none/p-Akt | Basal | CCG | 34 | 0.94 | 0.96 | 0.89 | 0.57 |
| none/p-CREB | Basal | CCG | 34 | 0.81 | 0.73 | 0.66 | 0.72 |
| none/p-Erk (AF647) | Basal | CCG | 34 | 0.93 | 0.90 | 0.86 | 0.67 |
| none/p-Erk (PE) | Basal | CCG | 34 | 0.72 | 0.69 | 0.52 | 0.52 |
| none/p-S6 | Basal | CCG | 34 | 0.83 | 0.79 | 0.68 | 0.36 |
| none/p-Stat1 | Basal | CCG | 34 | 0.42 | 0.53 | 0.17 | 0.21 |
| none/p-Stat3 | Basal | CCG | 34 | 0.49 | 0.53 | 0.24 | 0.37 |
| none/p-Stat5 | Basal | CCG | 34 | 0.88 | 0.88 | 0.77 | 0.82 |
| PMA/p-CREB | Fold | CCG | 34 | 0.85 | 0.85 | 0.73 | 0.92 |
| PMA/p-CREB | TotalPhospho | CCG | 34 | 0.86 | 0.90 | 0.75 | 1.23 |
| PMA/p-Erk | Fold | CCG | 34 | 0.74 | 0.75 | 0.55 | 0.85 |
| PMA/p-Erk | TotalPhospho | CCG | 34 | 0.83 | 0.81 | 0.70 | 1.21 |
| PMA/p-S6 | Fold | CCG | 34 | 0.95 | 0.95 | 0.90 | 0.86 |
| PMA/p-S6 | TotalPhospho | CCG | 34 | 0.92 | 0.94 | 0.85 | 0.82 |

TABLE 20-continued

Reproducibility: Study No. 1

| Node: Modulator/Read-Out | Metric | Biological Category | Num. Pts | Pearson Coefficient | Spearman Coefficient | R2 | SD Value |
|---|---|---|---|---|---|---|---|
| SCF/p-Akt | Fold | CCG | 34 | 0.86 | 0.83 | 0.74 | 0.53 |
| SCF/p-Akt | TotalPhospho | CCG | 34 | 0.93 | 0.91 | 0.87 | 0.71 |
| SCF/p-Erk | Fold | CCG | 34 | 0.39 | 0.39 | 0.15 | 0.18 |
| SCF/p-Erk | TotalPhospho | CCG | 34 | 0.68 | 0.61 | 0.46 | 0.50 |
| SCF/p-S6 | Fold | CCG | 34 | 0.91 | 0.91 | 0.83 | 0.56 |
| SCF/p-S6 | TotalPhospho | CCG | 34 | 0.86 | 0.84 | 0.75 | 0.62 |
| SDF-1α/p-Akt | Fold | CCG | 34 | 0.87 | 0.85 | 0.76 | 0.42 |
| SDF-1α/p-Akt | TotalPhospho | CCG | 34 | 0.91 | 0.90 | 0.83 | 0.70 |
| SDF-1α/p-Erk | Fold | CCG | 34 | 0.38 | 0.49 | 0.15 | 0.22 |
| SDF-1α/p-Erk | TotalPhospho | CCG | 34 | 0.58 | 0.53 | 0.34 | 0.64 |
| SDF-1α/p-S6 | Fold | CCG | 34 | 0.12 | 0.17 | 0.01 | 0.09 |
| SDF-1α/p-S6 | TotalPhospho | CCG | 34 | 0.66 | 0.59 | 0.44 | 0.35 |
| Thapsigargin/p-CREB | Fold | CCG | 34 | 0.89 | 0.91 | 0.80 | 0.70 |
| Thapsigargin/p-CREB | TotalPhospho | CCG | 34 | 0.90 | 0.89 | 0.81 | 0.95 |
| Thapsigargin/p-Erk | Fold | CCG | 34 | 0.94 | 0.56 | 0.88 | 0.43 |
| Thapsigargin/p-Erk | TotalPhospho | CCG | 34 | 0.94 | 0.89 | 0.87 | 0.89 |
| Thapsigargin/p-S6 | Fold | CCG | 34 | 0.91 | 0.79 | 0.82 | 0.40 |
| Thapsigargin/p-S6 | TotalPhospho | CCG | 34 | 0.86 | 0.81 | 0.74 | 0.50 |

Table is sorted alphabetically by node
Node/metrics with a t-test p value or Wilcoxon p value of ≦.05 and an AUC of ≧.66 are shown
Metris are defined in Materials and Methods
Abbreviations are defined in Table 17 c) Univariate Analysis.

In the first study, 147 nodes were assessed for their association with clinical response to standard AML induction therapy. The chosen nodes represented four biologic categories thought to be relevant to AML disease pathophysiology (FIG. 1): a) nodes modulated by myeloid cytokines, chemokines and growth factors; b) nodes modulated by intracellular phosphatases; c) protein expression levels of drug transporters and surface myeloid growth factor receptors; and d) nodes related to apoptosis. Each node was assessed using 2-3 metrics, creating 304 node/metrics. Univariate analysis, unadjusted for multiple testing, was performed on all node/metrics, which were then ranked by AUC of the ROC plots. Fifty-eight node/metrics (Table 21) from all four biological categories had an AUC above 0.66 and a p value≦0.05 (Student t-test or Wilcoxon), a cut off chosen to be higher than the AUC of the ROC plot for age (an accepted prognostic factor for this disease). Sixty-six nodes were not considered candidates for future development and remove prior to the second cohort due to low induced signaling or high correlation with other nodes. As expected, significant heterogeneity was found across most of the nodes measured, highlighting both the diverse biology underlying the disease and the ability of modulated SCNP to quantitatively resolve this heterogeneity at the single cell level. Furthermore, different populations of cells with differing degrees of responsiveness were observed within a patient for a given node/metric combination.

TABLE 21

Univariate Analysis of Node/Metrics for Study No. 1

| Node: Modulator/Read-Out | Metric | Biologic Category | Num. CRs/NRs | t-test P | Wilcoxon P | AUC of ROC | Mean Value of CRs/NRs |
|---|---|---|---|---|---|---|---|
| ABCG2 | PercentPos | Surface Markers | 8/23 | 0.009 | 0.034 | 0.76 | 6.51/8.14 |
| CD40L/p-CREB | TotalPhospho | CCG | 9/25 | 0.004 | 0.003 | 0.83 | 1.55/2.66 |
| CD40L/p-Erk | TotalPhospho | CCG | 9/25 | 0.013 | 0.015 | 0.77 | 1.18/1.64 |
| cKit | Rel. Expression | Surface Markers | 8/23 | 0.012 | 0.018 | 0.78 | 1.63/2.41 |
| cKit | PercentPos | Surface Markers | 8/23 | 0.047 | 0.082 | 0.71 | 41.6/59.6 |
| EPO/p-Stat1 | TotalPhospho | CCG | 9/25 | 0.053 | 0.037 | 0.74 | 0.20/0.42 |
| EPO/p-Stat3 | TotalPhospho | CCG | 9/25 | 0.003 | 0.002 | 0.84 | 0.72/1.23 |
| Etoposide & ZVAD/c-Caspase 3 | TotalPhospho | Apoptosis | 7/20 | 0.084 | 0.048 | 0.76 | 1.48/0.67 |
| Etoposide & ZVAD/p-Chk2−, c-PARP+ | Quad | Apoptosis | 7/22 | 0.019 | 0.010 | 0.83 | 0.22/0.10 |
| Etoposide/p-Chk2−, c-PARP+ | Quad | Apoptosis | 7/22 | 0.010 | 0.015 | 0.81 | 0.49/0.27 |
| FLT3R | TotalPhospho | Surface Markers | 8/23 | 0.014 | 0.026 | 0.77 | 1.81/2.58 |
| FLT3R | Rel. Expression | Surface Markers | 8/23 | 0.004 | 0.006 | 0.82 | 1.32/2.23 |
| FLT3L/p-Akt | Fold | CCG | 9/25 | 0.003 | 0.004 | 0.82 | 0.18/0.64 |
| FLT3L/p-CREB | TotalPhospho | CCG | 9/25 | 0.014 | 0.012 | 0.78 | 1.50/2.12 |
| FLT3L/p-plcγ2 | TotalPhospho | CCG | 9/25 | 0.007 | 0.006 | 0.80 | 1.88/2.80 |
| FLT3L/p-S6 | Fold | CCG | 9/25 | 0.026 | 0.154 | 0.66 | 0.28/0.81 |
| G-CSF/p-Stat3 | TotalPhospho | CCG | 9/25 | 0.056 | 0.050 | 0.72 | 1.66/2.70 |
| G-CSF/p-Stat5 | Fold | CCG | 9/25 | 0.038 | 0.072 | 0.71 | 0.47/1.13 |
| GM-CSF/p-Stat3 | TotalPhospho | CCG | 9/25 | 0.002 | 0.005 | 0.81 | 0.84/1.24 |
| $H_2O_2$ & SCF/p-Erk | TotalPhospho | Phosphatase | 7/22 | 0.047 | 0.122 | 0.70 | 2.16/2.57 |
| $H_2O_2$ & SCF/p-plcγ2 | Fold | Phosphatase | 7/22 | 0.102 | 0.032 | 0.77 | 0.47/−0.14 |
| $H_2O_2$ & SCF/p-SLP 76 | Fold | Phosphatase | 7/22 | 0.026 | 0.042 | 0.76 | 1.37/0.06 |
| $H_2O_2$/p-Lck | Fold | Phosphatase | 7/22 | 0.163 | 0.050 | 0.75 | 0.42/0.12 |
| $H_2O_2$/p-SLP 76 | Fold | Phosphatase | 7/22 | 0.024 | 0.028 | 0.78 | 1.35/0.08 |
| IFNα/p-Stat1 | Fold | CCG | 9/25 | 0.017 | 0.030 | 0.75 | 0.55/0.78 |

TABLE 21-continued

Univariate Analysis of Node/Metrics for Study No. 1

| Node: Modulator/Read-Out | Metric | Biologic Category | Num. CRs/NRs | t-test P | Wilcoxon P | AUC of ROC | Mean Value of CRs/NRs |
|---|---|---|---|---|---|---|---|
| IFNγ/p-Stat1 | Fold | CCG | 9/25 | 0.039 | 0.072 | 0.71 | 0.53/0.90 |
| IFNγ/p-Stat3 | TotalPhospho | CCG | 9/25 | 0.002 | 0.003 | 0.83 | 0.74/1.30 |
| IGF-1/p-CREB | TotalPhospho | CCG | 9/25 | 0.006 | 0.004 | 0.82 | 1.52/2.29 |
| IGF-1/p-Plcγ2 | TotalPhospho | CCG | 9/25 | 0.006 | 0.005 | 0.81 | 1.91/2.76 |
| IL-10/p-Stat1 | TotalPhospho | CCG | 9/25 | 0.035 | 0.037 | 0.74 | 0.20/0.47 |
| IL-10/p-Stat3 | TotalPhospho | CCG | 9/25 | 0.001 | 0.002 | 0.84 | 0.82/1.69 |
| IL-27/p-CREB | TotalPhospho | CCG | 9/25 | 0.003 | 0.002 | 0.84 | 1.40/2.35 |
| IL-27/p-Stat1 | TotalPhospho | CCG | 9/25 | 0.001 | 0.003 | 0.83 | 0.41/0.82 |
| IL-27/p-Stat3 | TotalPhospho | CCG | 9/25 | <0.001 | <0.001 | 0.90 | 1.07/1.86 |
| IL-3/p-CREB | TotalPhospho | CCG | 9/25 | 0.004 | 0.002 | 0.84 | 1.64/2.57 |
| IL-3/p-Stat1 | Fold | CCG | 9/25 | 0.018 | 0.024 | 0.76 | 0.05/−0.01 |
| IL-3/p-Stat3 | Fold | CCG | 9/25 | 0.052 | 0.026 | 0.76 | 0.13/−0.05 |
| IL-3/p-Stat3 | TotalPhospho | CCG | 9/25 | 0.039 | 0.102 | 0.69 | 1.05/1.29 |
| IL-6/p-CREB | TotalPhospho | CCG | 9/25 | 0.020 | 0.019 | 0.76 | 1.70/2.43 |
| IL-6/p-Stat3 | TotalPhospho | CCG | 9/25 | 0.001 | 0.015 | 0.77 | 1.08/1.84 |
| M-CSF/p-Plcγ2 | TotalPhospho | CCG | 9/25 | 0.006 | 0.005 | 0.81 | 1.86/2.81 |
| none/p-CREB | Basal | CCG | 9/25 | 0.001 | 0.001 | 0.87 | 1.58/2.53 |
| none/p-Erk | Basal | CCG | 9/25 | 0.028 | 0.015 | 0.77 | 1.69/2.09 |
| none/p-Plcγ2 | Basal | CCG | 9/25 | 0.008 | 0.009 | 0.79 | 1.73/2.48 |
| none/p-Stat3 | Basal | CCG | 9/25 | 0.005 | 0.005 | 0.81 | 0.89/1.33 |
| none/p-Stat6 | Basal | CCG | 9/25 | 0.008 | 0.019 | 0.76 | 0.62/0.96 |
| SCF/p-Akt | Fold | CCG | 9/25 | 0.018 | 0.007 | 0.81 | 0.12/0.57 |
| SCF/p-CREB | TotalPhospho | CCG | 9/25 | 0.016 | 0.030 | 0.75 | 1.38/1.92 |
| SCF/p-Erk | Fold | CCG | 9/25 | 0.043 | 0.041 | 0.73 | −0.05/0.11 |
| SCF/p-Erk | TotalPhospho | CCG | 9/25 | 0.049 | 0.030 | 0.75 | 1.87/2.28 |
| SCF/p-Plcγ2 | TotalPhospho | CCG | 9/25 | 0.006 | 0.006 | 0.80 | 1.87/2.81 |
| SDF-1α/p-Akt | Fold | CCG | 9/25 | 0.025 | 0.067 | 0.71 | 0.20/0.53 |
| SDF-1α/p-Akt | TotalPhospho | CCG | 9/25 | 0.045 | 0.120 | 0.68 | 0.57/1.04 |
| SDF-1α/p-Erk | TotalPhospho | CCG | 9/25 | 0.056 | 0.041 | 0.73 | 1.80/2.28 |
| Thapsigargin/p-CREB | TotalPhospho | CCG | 9/25 | 0.034 | 0.027 | 0.75 | 1.90/2.76 |
| Thapsigargin/p-S6 | Fold | CCG | 9/25 | 0.021 | 0.076 | 0.70 | 0.04/0.32 |
| Thapsigargin/p-S6 | TotalPhospho | CCG | 9/25 | 0.018 | 0.045 | 0.73 | 0.31/0.68 |
| TNFα/p-Erk | TotalPhospho | CCG | 9/25 | 0.033 | 0.050 | 0.72 | 1.25/1.65 |

Node/metrics with a t-test p value or Wilcoxon p value of ≦.05 and an AUC of ≧.66 are shown
Negative mean CR/NR values represent down regulation as compared to reference/control/normalization
Table is sorted alphabetically by node
Metrics are defined in Materials and Methods
Abbreviations are defined in Supplemental Table 1

Importantly, measurements of basal levels of phosphorylated signaling proteins, such as p-Stat5, p-Akt and p-S6, were not informative in classifying patient samples by clinical response (with AUC of the ROCs values of 0.62, 0.52, and 0.51, respectively (Table 22). However, G-CSF, SCF or Flt3L mediated phosphorylation resulted in significant increases in the Fold metric between patient samples categorized by response and AUC of the ROC values, which increased to 0.71, 0.82, and 0.66 respectively (Table 22), allowing patient stratification into CR or NR categories. The SCF/p-Akt read out is an example shown in FIG. 8A. These data suggest that increased growth factor-mediated signaling occurred in samples derived from NR patients, consistent with the previous findings of Irish et al.[4] Interestingly, the basal expression of cell surface receptors Flt3R and c-Kit also stratified patient samples as CR versus NR with AUC of the ROC plots of 0.82 and 0.78 respectively, confirming a role for these receptors in treatment prediction (Table 21).

TABLE 22

Modulated Readouts are More Predictive than Basal in Study No. 1

| Node: Modulator/Read-Out | Metric | Biologic Category | Num. CRs/NRs | t-test P | Wilcoxon P | AUC of ROC | Mean Value of CRs/NRs |
|---|---|---|---|---|---|---|---|
| none/p-Akt | Basal | CCG | 9/25 | 0.644 | 0.908 | 0.52 | 0.48/0.58 |
| FLT3L/p-Akt | Fold | CCG | 9/25 | 0.003 | 0.004 | 0.82 | 0.18/0.64 |
| SCF/p-Akt | Fold | CCG | 9/25 | 0.018 | 0.007 | 0.81 | 0.12/0.57 |
| none/p-S6 | Basal | CCG | 9/25 | 0.673 | 0.969 | 0.51 | 0.28/0.34 |
| FLT3L/p-S6 | Fold | CCG | 9/25 | 0.026 | 0.154 | 0.66 | 0.28/0.81 |
| none/p-Stat5 | Basal | CCG | 9/25 | 0.304 | 0.298 | 0.62 | 1.77/2.11 |
| G-CSF/p-Stat5 | Fold | CCG | 9/25 | 0.038 | 0.072 | 0.71 | 0.47/1.13 |

Metrics are defined in Materials and Methods
Abbreviations are defined in Table 17

Responses to DNA damage and apoptosis were determined by measuring levels of p-Chk2[43] and cleaved c-PARP respectively, after exposure of samples to etoposide, a topoisomerase II inhibitor. Notably, decreased levels of p-Chk2 and increased levels of c-PARP were seen in CR samples, indicating that the DNA damage response pathway was able to activate apoptosis in these patient samples. In contrast, most NR samples showed accumulated levels of p-Chk2 and low levels of c-PARP suggesting a block in the signals that relay DNA damage to the apoptotic machinery. These data suggest that an efficient relay of signals from the DNA damage response pathway to the apoptotic machinery may be necessary for response to induction therapy.

Because of the high number of variables tested on a relatively small sample set, an assessment of false discovery rate was performed (see Material and Methods). The number of observed node/metrics with a Student t-test $p \leq 0.05$ in our data set was 56, which is higher than expected after random assignment (not shown). Therefore, the estimated probability that the number of nodes found to be significant from the experimental data occurred by chance is less than 0.02.

Sensitivity univariate analysis was performed to test the effect of inclusion of the CRp sample within the NR sample cohort. These analyses resulted in an increase in AUC of the ROC plots for the majority of nodes examined, suggesting that the biology of the blasts contained within the CRp sample was more similar to NR than CR samples (Table 23).

TABLE 23

Sensitivity Analysis for Study No. 1: Univariate Analysis of Node/Metrics with CRp Patient Included in NR Group

| Node | Metric | Biologic Category | t-test P | Wilcoxon P | AUC of ROC | Mean Value of CRs/NRs | Num. CRs/NRs |
|---|---|---|---|---|---|---|---|
| ABCG2 | Rel. Expression | Surface Markers | 0.002 | 0.022 | 0.79 | 0.14/0.33 | 7/24 |
| ABCG2 | PercentPos | Surface Markers | 0.003 | 0.017 | 0.80 | 6.32/8.13 | 7/24 |
| CD40L/p-CREB | Total Phospho | CCG | 0.001 | <.001 | 0.89 | 1.37/2.67 | 8/26 |
| CD40L/p-Erk | Total Phospho | CCG | 0.027 | 0.039 | 0.75 | 1.18/1.62 | 8/26 |
| cKit | Rel. Expression | Surface Markers | 0.007 | 0.012 | 0.81 | 1.53/2.41 | 7/24 |
| cKit | Ppos | CCG | 0.024 | 0.033 | 0.77 | 38.42/59.75 | 7/24 |
| EPO/p-Stat1 | Total Phospho | CCG | 0.050 | 0.025 | 0.76 | 0.17/0.42 | 8/26 |
| EPO/p-Stat3 | Total Phospho | CCG | <.001 | <.001 | 0.90 | 0.64/1.23 | 8/26 |
| Etoposide + ZVAD/Chk2-PARP+ | Quad | Apoptosis | 0.044 | 0.025 | 0.80 | 0.23/0.11 | 6/23 |
| Etoposide 24h/Chk2-PARP+ | Quad | Apoptosis | 0.026 | 0.025 | 0.80 | 0.49/0.28 | 6/23 |
| FLT3L/p-Akt | Fold | CCG | <.001 | <.001 | 0.90 | 0.10/0.65 | 8/26 |
| FLT3L/p-CREB | Fold | CCG | 0.013 | 0.096 | 0.70 | 0.07/0.36 | 8/26 |
| FLT3L/p-CREB | Total Phospho | CCG | 0.004 | 0.003 | 0.84 | 1.39/2.13 | 8/26 |
| FLT3L/p-Erk | Fold | CCG | 0.013 | 0.013 | 0.79 | 0.08/0.33 | 8/26 |
| FLT3L/p-Plcγ2 | Total Phospho | CCG | 0.008 | 0.004 | 0.83 | 1.81/2.78 | 8/26 |
| FLT3L/p-Plcγ2 | Fold | CCG | 0.144 | 0.049 | 0.74 | −0.14/−0.08 | 8/26 |
| FLT3L/p-S6 | Fold | CCG | <.001 | 0.056 | 0.73 | 0.14/0.83 | 8/26 |
| FLT3R | Rel. Expression | Surface Markers | <.001 | 0.001 | 0.89 | 1.16/2.24 | 7/24 |
| FLT3R | PercentPos | Surface Markers | 0.009 | 0.008 | 0.83 | 49.72/76.39 | 7/24 |
| FLT3R | Total Phospho | Surface Markers | 0.037 | 0.061 | 0.74 | 1.84/2.55 | 7/24 |
| G-CSF/p-Stat3 | Fold | CCG | 0.010 | 0.031 | 0.75 | 0.60/1.52 | 8/26 |
| G-CSF/p-Stat3 | Total Phospho | CCG | 0.013 | 0.009 | 0.80 | 1.40/2.74 | 8/26 |
| G-CSF/p-Stat5 | Fold | CCG | 0.006 | 0.022 | 0.77 | 0.33/1.15 | 8/26 |
| GM-CSF/p-Stat3 | Total Phospho | CCG | 0.004 | 0.007 | 0.81 | 0.83/1.23 | 8/26 |
| IFNγ/p-Stat1 | Fold | CCG | 0.006 | 0.015 | 0.78 | 0.45/0.91 | 8/26 |
| IFNα/p-Stat1 | Fold | CCG | 0.004 | 0.009 | 0.80 | 0.50/0.79 | 8/26 |
| IFNγ/p-Stat1 | Total Phospho | CCG | 0.027 | 0.012 | 0.79 | 0.67/1.27 | 8/26 |
| IFNγ/p-Stat3 | Total Phospho | CCG | 0.001 | 0.001 | 0.88 | 0.68/1.3 | 8/26 |
| IFNγ/p-Stat5 | Total Phospho | CCG | 0.058 | 0.043 | 0.74 | 1.62/2.35 | 8/26 |
| IGF-1/p-CREB PE | Total Phospho | CCG | 0.003 | 0.001 | 0.87 | 1.42/2.29 | 8/26 |
| IGF-1/p-CREB Alexa488 | Total Phospho | CCG | 0.097 | 0.053 | 0.73 | 1.11/1.62 | 8/26 |
| IGF-1/p-Plcγ2 | Total Phospho | CCG | 0.004 | 0.003 | 0.84 | 1.82/2.76 | 8/26 |
| Il-3/P-Stat1 | Fold | CCG | 0.042 | 0.062 | 0.73 | 0.05/−0.01 | 8/26 |
| IL-10/p-Stat1 | Total Phospho | CCG | 0.033 | 0.025 | 0.76 | 0.17/0.47 | 8/26 |
| IL-10/p-Stat3 | Total Phospho | CCG | <.001 | <.001 | 0.89 | 0.72/1.69 | 8/26 |
| IL-27/p-CREB | Total Phospho | CCG | <.001 | <.001 | 0.90 | 1.25/2.36 | 8/26 |
| IL-27/p-Stat1 | Total Phospho | CCG | 0.002 | 0.003 | 0.84 | 0.39/0.81 | 8/26 |
| IL-27/p-Stat3 | Total Phospho | CCG | <.001 | <.001 | 0.93 | 1.01/1.85 | 8/26 |
| IL-3/p-CREB | Total Phospho | CCG | 0.001 | 0.001 | 0.88 | 1.51/2.58 | 8/26 |
| IL-3/p-Stat3 | Fold | CCG | 0.062 | 0.042 | 0.75 | 0.15/−0.04 | 8/26 |
| IL-6/p-CREB | Total Phospho | CCG | 0.008 | 0.006 | 0.82 | 1.58/2.44 | 8/26 |
| IL-6/p-Stat3 | Total Phospho | CCG | 0.002 | 0.025 | 0.76 | 1.08/1.81 | 8/26 |
| M-CSF/p-Akt | Fold | CCG | 0.035 | 0.059 | 0.73 | −0.16/0.05 | 8/26 |
| M-CSF/p-CREB | Total Phospho | CCG | 0.067 | 0.039 | 0.75 | 1.26/1.76 | 8/26 |
| M-CSF/p-Plcγ2 | Total Phospho | CCG | 0.007 | 0.006 | 0.82 | 1.79/2.8 | 8/26 |
| none/p-CREB | Basal | CCG | <.001 | <.001 | 0.92 | 1.47/2.53 | 8/26 |
| none/p-Erk | Basal | CCG | 0.051 | 0.035 | 0.75 | 1.69/2.07 | 8/26 |
| none/p-Plcγ2 | Basal | CCG | 0.011 | 0.017 | 0.78 | 1.70/2.46 | 8/26 |
| none/p-Stat3 | Basal | CCG | 0.004 | 0.003 | 0.84 | 0.85/1.32 | 8/26 |
| none/p-Stat6 | Basal | CCG | 0.017 | 0.031 | 0.75 | 0.61/0.95 | 8/26 |
| PMA/p-Erk | Fold | CCG | 0.039 | 0.035 | 0.75 | 1.46/2.03 | 8/26 |
| SCF/p-Akt | Fold | CCG | 0.023 | 0.005 | 0.83 | 0.09/0.56 | 8/26 |
| SCF/p-CREB | Total Phospho | CCG | 0.013 | 0.020 | 0.77 | 1.32/1.92 | 8/26 |
| SCF/p-Erk | Fold | CCG | 0.040 | 0.031 | 0.75 | −0.06/0.11 | 8/26 |
| SCF/p-Plcγ2 | Total Phospho | CCG | 0.007 | 0.006 | 0.82 | 1.80/2.79 | 8/26 |
| SDF-1α/p-Akt | Fold | CCG | 0.008 | 0.024 | 0.77 | 0.15/0.54 | 8/26 |

TABLE 23-continued

Sensitivity Analysis for Study No. 1: Univariate Analysis of Node/Metrics with CRp Patient Included in NR Group

| Node | Metric | Biologic Category | t-test P | Wilcoxon P | AUC of ROC | Mean Value of CRs/NRs | Num. CRs/NRs |
|---|---|---|---|---|---|---|---|
| SDF-1α/p-Akt | Total Phospho | CCG | 0.034 | 0.077 | 0.71 | 0.52/1.04 | 8/26 |
| SDF-1α/p-Erk | Total Phospho | CCG | 0.053 | 0.043 | 0.74 | 1.75/2.27 | 8/26 |
| Thapsigargin/p-CREB | Total Phospho | CCG | 0.025 | 0.015 | 0.78 | 1.79/2.77 | 8/26 |
| Thapsigargin/p-S6 | Fold | CCG | 0.018 | 0.051 | 0.73 | 0.03/0.31 | 8/26 |
| Thapsigargin/p-S6 | Total Phospho | CCG | 0.028 | 0.070 | 0.72 | 0.31/0.67 | 8/26 |

Table is sorted alphabetically by node
Node/metrics with a t-test p value or Wilcoxon p value of ≦.05 and an AUC of ≧.66 are shown
Negative mean CR/NR values represent down regulation as compared to reference/control/normalization
Metrics are defined in Materials and Methods
Abbreviations are defined in Table 17 d) Correlations Between Nodes/Metric Combinations.

Although nodes were analyzed independently in the primary analysis, several of the top-ranking node/metric combinations appeared to be correlated with each other. The correlations between nodes were studied for modulated signaling and surface marker levels. The Pearson correlation coefficients using the fold metrics were computed for all nodes with an AUC of the ROCs>0.66 and p≦0.05 to evaluate correlations of induced signaling. The heat map of the pair wise correlation matrix (not shown) demonstrates that some nodes, often mapping in the same pathway, such as IL3/p-Stat1 and IL3/p-Stat3, and Flt3L/p-Akt and Flt3L/p-S6 were highly correlated. Other nodes such as SCF/p-Akt and IL-3/Stat3 were independent of each other, suggesting that they may be combined to compute a multivariate model with higher predictive value. Notably, comparison of Flt3R and c-KitR expression levels to their ligand-activated pathway readouts demonstrated a poor correlation (i.e. <0.5 correlation coefficient, not shown). These data underscore the additive value of measuring the modulated signaling activity compared to measuring expression level of the surface receptors associated with that specific pathway.

e) Combination of Nodes.

Figure 9:
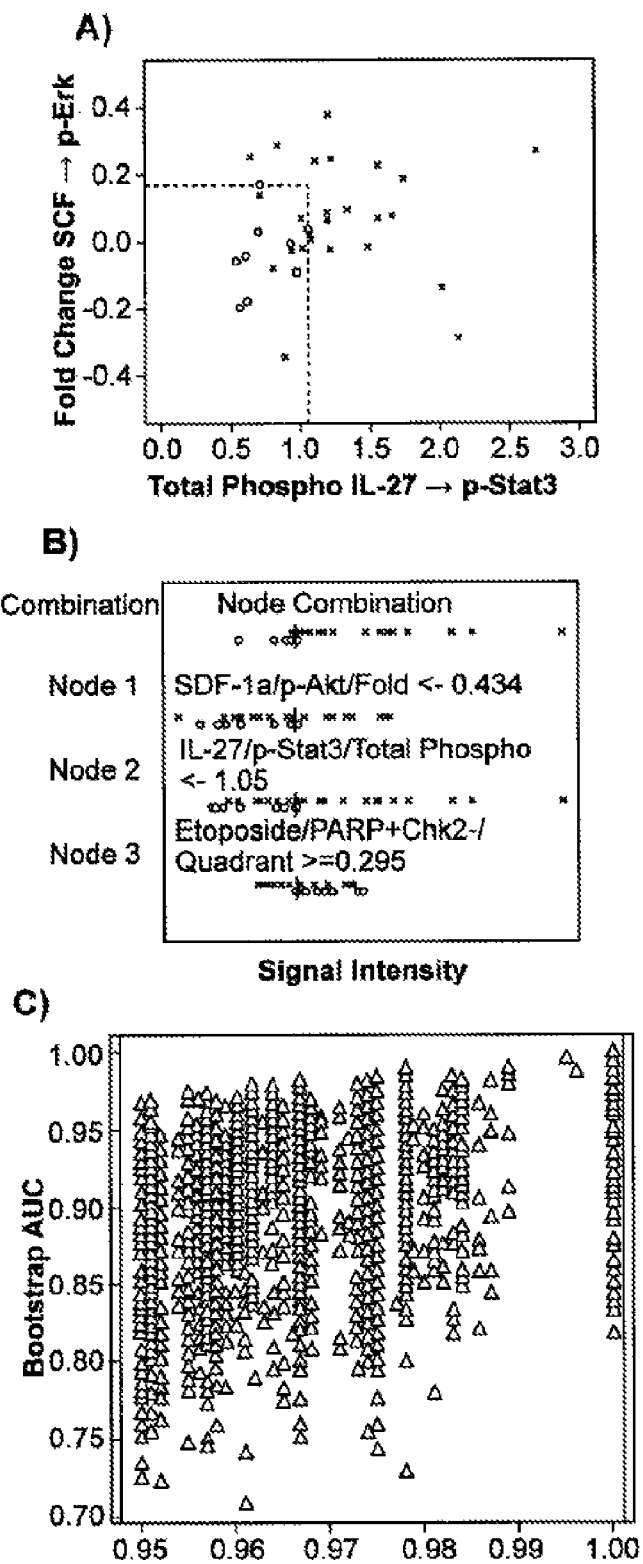
FIG. 9 shows combinations of independent nodes from distinct pathways improve stratification for first study. Examples demonstrate how corners and thresholds for the classifiers are set. (O: CR, X: NR) (A) Doublet combination of nodes i.e. SCF induced p-Erk and IL-27 induced p-Stat3. (B) Triplet combinations of nodes i.e. SDF-α induced p-Akt, IL-27 induced p-Stat3, and Etoposide induced p-CHK2-, c PARP+ cells. C) Comparison of AUCs of ROCs of raw data vs. AUCs of ROCs on bootstrapped data to illustrate robustness of individual combinations. Combinations with AUCs of ROCs above 0.95 on the raw data are shown.

To evaluate nodes that might provide a superior stratification when combined with each other, all node/metrics with an AUC greater than equal to 0.66 were chosen to be part of combination analysis. There were 4465 possible two-node/metric combinations and 138415 possible three-node combinations. Combinations that had a minimum distance AUC greater than the best single node/metric (AUC=0.90) were analyzed further. Table 24 provides as list of nodes that appear most frequent (>3%) among the two or three node/metric combinations. All triplets of nodes with a minimum distance AUC great than 0.95 were also analyzed using the bootstrap procedure described in material and methods. Bootstrapping analysis (FIG. 9C) suggested that some of these combinations might be more robust in distinguishing CRs from the NRs (e.g. SDF1α/p-Akt/Fold with IL-27/p-Stat3/TotalPhospho and etoposide/p-Chk2-,c-PARP+/Quad). While no restrictions were placed on the nodes chosen for each combination, several of the highest ranking combinations contained nodes from multiple biological pathways.

TABLE 24

List of Unique Nodes in Combinations for Study No. 1.

| Node included in any Combination Model | Metric | Biological Category | Frequency of Node in Two-Node Combinations | Best AUC in Two-Node Combination | Frequency of Node in Three-Node Combinations | Best AUC in Three Node Combinations | AUC of Single Node |
|---|---|---|---|---|---|---|---|
| cKit | Rel. Expression | Surface Marker | 17.07 | 0.98 | 17.25 | 1.00 | 0.78 |
| IL-27/p-Stat3 | TotalPhospho | CCG | 25.00 | 0.97 | 15.24 | 1.00 | 0.90 |
| IL-3/p-Creb | TotalPhospho | CCG | 9.15 | 0.96 | 10.05 | 1.00 | 0.84 |
| IGF-1/p-Plcγ2 | TotalPhospho | CCG | 8.54 | 0.95 | 9.28 | 1.00 | 0.81 |
| ABCG2 | Percent Pos. | Surface Marker | 7.93 | 0.97 | 9.26 | 1.00 | 0.76 |
| cKit | Percent Pos. | Surface Marker | 5.49 | 0.94 | 7.97 | 1.00 | 0.71 |
| GM-CSF/p-Stat3 | TotalPhospho | CCG | 5.49 | 0.92 | 7.42 | 1.00 | 0.81 |
| FLT3R | Rel. Expression | Surface Marker | 6.10 | 0.94 | 6.45 | 1.00 | 0.82 |
| IL-6/p-Stat3 | TotalPhospho | CCG | 2.44 | 0.93 | 6.37 | 1.00 | 0.77 |
| IFNγ/p-Stat3 | TotalPhospho | CCG | 7.32 | 0.95 | 5.85 | 1.00 | 0.83 |
| FLT3R | TotalPhospho | Surface Marker | 3.66 | 0.95 | 5.76 | 0.98 | 0.77 |
| Etoposide/p-Chk2-, c-PARP+ | Quad | Apoptosis | 4.88 | 0.95 | 5.71 | 1.00 | 0.81 |
| Etoposide & ZVAD/p-Chk2-, c-PARP+ | Quad | Apoptosis | 4.88 | 0.97 | 5.61 | 1.00 | 0.83 |
| SCF/p-Akt | Fold | CCG | 4.88 | 0.95 | 5.40 | 1.00 | 0.81 |
| SCF/p-Erk | Fold | CCG | 3.05 | 0.92 | 5.06 | 1.00 | 0.73 |
| Etoposide/c-PARP | TotalPhospho | Apoptosis | 2.44 | 0.95 | 4.96 | 1.00 | 0.71 |
| Etoposide/BCL2 | Fold | Apoptosis | 4.27 | 0.93 | 4.87 | 1.00 | 0.70 |
| IL-27/p-Stat5 | TotalPhospho | CCG | 1.83 | 0.93 | 4.82 | 1.00 | 0.66 |
| FLT3L/p-Creb | TotalPhospho | CCG | 4.27 | 0.98 | 4.62 | 1.00 | 0.78 |
| none/p-Stat3 | Basal | CCG | 3.05 | 0.93 | 4.60 | 1.00 | 0.81 |
| IFNα/p-Stat1 | Fold | CCG | 2.44 | 0.96 | 4.38 | 1.00 | 0.75 |
| Etoposide & ZVAD/c-Caspase3 | TotalPhospho | Apoptosis | 3.05 | 0.94 | 4.18 | 1.00 | 0.76 |

TABLE 24-continued

List of Unique Nodes in Combinations for Study No. 1.

| Node included in any Combination Model | Metric | Biological Category | Frequency of Node in Two-Node Combinations | Best AUC in Two-Node Combination | Frequency of Node in Three-Node Combinations | Best AUC in Three Node Combinations | AUC of Single Node |
|---|---|---|---|---|---|---|---|
| Etoposide/p-Chk2 | Fold | Apoptosis | 1.83 | 0.94 | 4.05 | 1.00 | 0.73 |
| none/p-Creb | Basal | CCG | 5.49 | 0.93 | 3.94 | 0.98 | 0.87 |
| EPO/p-Stat3 | TotalPhospho | CCG | 4.88 | 0.95 | 3.91 | 0.98 | 0.84 |
| IL-3/p-Stat3 | TotalPhospho | CCG | 2.44 | 0.92 | 3.83 | 0.99 | 0.69 |
| FLT3L/p-Akt | Fold | CCG | 5.49 | 0.96 | 3.59 | 0.99 | 0.82 |
| Etoposide/p-Chk2+, c-PARP− | Quad | Apoptosis | 1.83 | 0.93 | 3.57 | 1.00 | 0.74 |
| $H_2O_2$/p-Lck | Fold | CCG | 1.83 | 0.93 | 3.56 | 1.00 | 0.75 |
| IGF-1/p-Creb | TotalPhospho | CCG | 2.44 | 0.95 | 3.52 | 1.00 | 0.82 |
| FLT3L/p-Erk | Fold | CCG | 1.22 | 0.92 | 3.44 | 1.00 | 0.72 |
| Thapsigargin/p-Creb | TotalPhospho | CCG | 1.22 | 0.90 | 3.42 | 1.00 | 0.75 |
| IL-10/p-Stat3 | TotalPhospho | CCG | 4.88 | 0.94 | 3.41 | 0.98 | 0.84 |
| CD40L/p-Creb | TotalPhospho | CCG | 1.83 | 0.92 | 3.24 | 0.98 | 0.83 |
| ABCG2 | Rel. Expression | Surface Marker | 1.22 | 0.93 | 3.20 | 1.00 | 0.70 |
| none/p-Chk2−, c-PARP+ | Quad | Apoptosis | 1.22 | 0.93 | 3.19 | 1.00 | 0.69 |

All unique nodes with a minimum frequency of 3% are shown and table is sorted by frequency.
Metrics are defined in Materials and Methods
Abbreviations are defined in Table 17

Second Study:

The second study was performed to assess whether the stratifying signaling profiles developed from the first study could be extrapolated to a fully independent set of AML samples obtained from a different center. In this sample set, 90 nodes were assessed for association with clinical response to standard and high-dose AML induction therapy using the same metrics as the first study. Eighty-seven of the nodes overlapped with the first study (Table 17). Of these, 21 node/metrics were selected for the primary endpoint analysis based on a multistep selection process that considered univariate stratification power, reproducibility (when available), node combination analysis and minimum representation in the four biological categories relevant to AML disease pathophysiology.

a) Patient and Sample Characteristics.

Of the 134 cryopreserved AML BMMC samples in the study, 46 samples were not evaluable due to insufficient viable cells after thawing. In addition, due to the low recovery of viable cells after thawing, the number of cells per sample varied and many samples did not yield enough cells to analyze all planned nodes (Table 17). Both the original 134 and the analyzed sample set in this study (n=88) were representative of the United States AML patient population and response rates, except for an over-representation of female gender and younger age at diagnosis (Table 16 and Table 19)]. As expected, age, cytogenetic groups and secondary malignancies were statistically associated with response to induction therapy (Table 16).

b) Univariate Analysis of Pre-Specified 21 Node/Metric Selected from the First Study (Primary Endpoint).

Univariate analysis, unadjusted for multiple testing, was performed on the 21 pre-specified node/metrics selected for their performance in the first study, and ranked by p-value (Table 25). Based on this analysis, only two node/metric combinations, PMA/p-Erk Fold, and IL-27/p-Stat3 Total-Phoshpo had AUCs of the ROC above 0.66 (0.67 and 0.68, respectively) and a p value≦0.05 (0.047 and 0.048, respectively) in stratifying patients for response to induction therapy. Therefore, no further analysis using these 21 pre-specified node/metrics combinations was performed.

TABLE 25

Extrapolation of Univariate Analysis for 21 Node/Metrics from Study No. 1 to Study No. 2 (Primary Endpoint Analysis No. 2)

| Node: Modulator/ Read-Out | Metric | Biological Category | Num. CRs/NRs 1 | AUC of ROC 1 | t-test P1 | Wilcoxon Test P 1 | Num. CRs/NRs 2 | AUC of ROC 2 | t-test P2 | Wilcoxon Test P 2 |
|---|---|---|---|---|---|---|---|---|---|---|
| PMA/p-ERK | Fold | CCG | 9/25 | 0.70 | 0.063 | 0.079 | 33/9 | 0.67 | 0.047 | 0.135 |
| IL-27/p-Stat3 | TotalPhospho | CCG | 9/25 | 0.90 | <0.001 | <0.001 | 44/13 | 0.68 | 0.073 | 0.048 |
| $H_2O_2$/p-PLCγ2 | Fold | Phosphatase | 7/22 | 0.75 | 0.097 | 0.055 | 48/19 | 0.56 | 0.454 | 0.427 |
| ABCG2 | PercentPos | Surface Marker | 8/23 | 0.76 | 0.009 | 0.034 | 37/11 | 0.55 | 0.516 | 0.646 |
| FLT3R | Rel. Expression | Surface Marker | 8/23 | 0.82 | 0.004 | 0.006 | 40/11 | 0.62 | 0.609 | 0.233 |
| $H_2O_2$/p-SLP 76 | Fold | Phosphatase | 7/22 | 0.78 | 0.024 | 0.028 | 48/18 | 0.59 | 0.287 | 0.238 |
| SCF/p-Akt | Fold | CCG | 9/25 | 0.81 | 0.018 | 0.007 | 51/24 | 0.60 | 0.081 | 0.178 |
| CKit | Rel. Expression | Surface Marker | 8/23 | 0.78 | 0.012 | 0.018 | 40/11 | 0.55 | 0.498 | 0.660 |
| FLT3L/p-Akt | Fold | CCG | 9/25 | 0.82 | 0.003 | 0.004 | 52/26 | 0.50 | 0.555 | 0.962 |
| IFNα/p-Stat1 | Fold | CCG | 9/25 | 0.75 | 0.017 | 0.030 | 35/11 | 0.56 | 0.590 | 0.542 |
| none/p-PLCγ2 | Basal | CCG | 9/25 | 0.79 | 0.008 | 0.009 | 47/16 | 0.55 | 0.666 | 0.526 |
| Etoposide/p-Chk2−, c-PARP+ | Quadrant | Apoptosis | 7/22 | 0.81 | 0.010 | 0.015 | 43/19 | 0.57 | 0.425 | 0.396 |
| none/p-ERK | Basal | CCG | 9/25 | 0.77 | 0.028 | 0.015 | 46/16 | 0.54 | 0.491 | 0.658 |
| none/p-Stat3 | Basal | CCG | 9/25 | 0.81 | 0.005 | 0.005 | 47/16 | 0.53 | 0.738 | 0.722 |
| none/p-CREB | Basal | CCG | 9/25 | 0.87 | 0.001 | 0.001 | 47/16 | 0.51 | 0.929 | 0.882 |
| G CSF/p-Stat3 | Fold | CCG | 9/25 | 0.68 | 0.091 | 0.111 | 47/17 | 0.51 | 0.974 | 0.951 |
| SDF-1α/p-Akt | Fold | CCG | 9/25 | 0.71 | 0.025 | 0.067 | 39/22 | 0.59 | 0.293 | 0.273 |
| G CSF/p-Stat5 | Fold | CCG | 9/25 | 0.71 | 0.038 | 0.072 | 47/17 | 0.53 | 0.868 | 0.721 |

TABLE 25-continued

Extrapolation of Univariate Analysis for 21 Node/Metrics from Study No. 1 to Study No. 2 (Primary Endpoint Analysis No. 2)

| Node: Modulator/Read-Out | Metric | Biological Category | Num. CRs/NRs 1 | AUC of ROC 1 | t-test P1 | Wilcoxon Test P 1 | Num. CRs/NRs 2 | AUC of ROC 2 | t-test P2 | Wilcoxon Test P 2 |
|---|---|---|---|---|---|---|---|---|---|---|
| SCF/p-S6 | Fold | CCG | 9/25 | 0.66 | 0.055 | 0.163 | 50/24 | 0.51 | 0.852 | 0.922 |
| Thapsigargin/p-S6 | Fold | CCG | 9/25 | 0.70 | 0.021 | 0.076 | 32/11 | 0.51 | 0.684 | 0.902 |
| FLT3L/p-S6 | Fold | CCG | 9/25 | 0.66 | 0.026 | 0.154 | 51/26 | 0.51 | 0.889 | 0.842 |

Metrics are defined in Materials and Methods
Abbreviations are defined in Table 17 c) Univariate Analysis of All Nodes/Metric Combinations (Secondary Endpoint).

Univariate analysis, unadjusted for multiple testing, was performed testing all 182 node-metric combinations and ranking them by the resulting AUC of the ROCs. Seventeen node-metrics met the cut-off criteria (i.e. AUC values above 0.66 with a p value≦0.05; Table 26). This number was lower than expected based on the results of the first study but higher than expected by chance.

TABLE 26

Univariate Analysis of Node/Metrics for All Patients in Study No. 2

| Node: Modulator/Read-Out | Metric | Biological Category | Num. CRs/NRs | AUC of ROC | t-test P | Wilcoxon P | Mean Value of CRs/NRs |
|---|---|---|---|---|---|---|---|
| Ara-C & Dauno/c-PARP | Fold | Apoptosis | 35/11 | 0.67 | 0.042 | 0.089 | 1.99/0.82 |
| Etoposide/c-PARP | Fold | Apoptosis | 58/29 | 0.66 | 0.023 | 0.016 | 0.79/0.25 |
| $H_2O_2$/p-Akt | Fold | Phosphatase | 48/19 | 0.66 | 0.065 | 0.044 | 0.68/0.91 |
| IFNγ/p-Stat3 | Fold | CCG | 16/5 | 0.83 | 0.021 | 0.032 | −0.02/0.2 |
| IL-10/p-Stat3 | Fold | CCG | 19/5 | 0.84 | 0.012 | 0.023 | 0.08/0.39 |
| IL-10/p-Stat5 | Fold | CCG | 19/5 | 0.80 | 0.011 | 0.044 | 0.09/0.43 |
| IL-27/p-Stat1 | TotalPhospho | CCG | 44/13 | 0.74 | 0.012 | 0.009 | 1.66/2.63 |
| IL-27/p-Stat3 | Fold | CCG | 44/14 | 0.71 | 0.032 | 0.019 | 0.22/0.58 |
| IL-27/p-Stat3 | TotalPhospho | CCG | 44/13 | 0.68 | 0.073 | 0.048 | 1.88/2.43 |
| IL-3/p-Stat5 | Fold | CCG | 9/5 | 0.78 | 0.022 | 0.112 | 1.99/0.44 |
| IL-6/p-Stat1 | Fold | CCG | 10/5 | 0.94 | 0.034 | 0.005 | −0.01/0.26 |
| IL-6/p-Stat3 | Fold | CCG | 10/5 | 0.86 | 0.069 | 0.032 | 0.12/1.09 |
| IL-6/p-Stat3 | TotalPhospho | CCG | 10/5 | 0.88 | 0.083 | 0.019 | 1.76/2.98 |
| IL-6/p-Stat5 | Fold | CCG | 10/5 | 0.90 | 0.008 | 0.013 | 0.13/0.55 |
| none/p-Erk | Basal | CCG | 33/9 | 0.66 | 0.026 | 0.152 | 1.05/2.14 |
| PMA/p-Erk | Fold | CCG | 33/9 | 0.67 | 0.047 | 0.135 | 2.82/1.74 |
| Thapsigargin/p-Erk | Fold | CCG | 31/9 | 0.68 | 0.014 | 0.112 | 1.22/0.36 |

Table is sorted alphabetically by node
Node/metrics with a t-test p value or Wilcoxon p value of ≦.05 and an AUC of ≧.66 are shown
Negative mean CR/NR values represent down regulation as compared to reference/control/normalization
Metrics are defined in Materials and Methods
Abbreviations are defined in Table 17

TABLE 27

Demographic and Baseline Characteristics for All Patients (Intend To Diagnose) and Non-Evaluable Patients in Study No. 2.

| | Characteristic | All CRs | All NRs | All Pts | P Value All | Non-Evaluable CRs | Non-Evaluable NRs | All Non-Evaluable Pts | P Value Non-Eval |
|---|---|---|---|---|---|---|---|---|---|
| | N | 88 | 46 | 134 | | 31 | 15 | 46 | |
| Age (yr) | Median | 51.8 | 61.7 | 55.5 | | 53.7 | 65 | 56.2 | 0.048 |
| | Range | 27.0-97.0 | 25.0-85.2 | 25.0-85.2 | <.001 | 28.2, 77.8 | 43.4, 85.2 | 28.2, 85.2 | |
| Age Group | <60 yr | 71 (81%) | 22 (48%) | 93 (69%) | <.001 | 20 (65%) | 7 (47%) | 27 (59%) | 0.341 |
| | >=60 yr | 17 (19%) | 24 (52%) | 41 (31%) | | 11 (35%) | 8 (53%) | 19 (41%) | |
| Sex | F | 46 (52%) | 24 (52%) | 70 (52%) | 1 | 14 (45%) | 8 (53%) | 22 (48%) | 0.755 |
| | M | 42 (48%) | 22 (48%) | 64 (48%) | | 17 (55%) | 7 (47%) | 24 (52%) | |

TABLE 27-continued

Demographic and Baseline Characteristics for All Patients (Intend To Diagnose) and Non-Evaluable Patients in Study No. 2.

| Characteristic | | All CRs | All NRs | All Pts | P Value All | Non-Evaluable CRs | Non-Evaluable NRs | All Non-Evaluable Pts | P Value Non-Eval |
|---|---|---|---|---|---|---|---|---|---|
| Cytogentic Group | Favorable | 10 (11%) | 0 (0%) | 10 (7%) | <.001 | 3 (10%) | 0 (0%) | 3 (7%) | 0.005 |
| | Intermediate | 48 (55%) | 12 (26%) | 60 (45%) | | 19 (61%) | 3 (20%) | 22 (48%) | |
| | Unfavorable | 30 (34%) | 34 (74%) | 64 (48%) | | 9 (29%) | 12 (80%) | 21 (46%) | |
| FAB | M0 | 2 (2%) | 1 (2%) | 3 (2%) | 0.697 | 1 (3%) | 0 (0%) | 1 (2%) | 0.621 |
| | M1 | 13 (15%) | 3 (7%) | 16 (12%) | | 5 (16%) | 2 (13%) | 7 (15%) | |
| | M2 | 31 (35%) | 22 (48%) | 53 (40%) | | 9 (29%) | 8 (53%) | 17 (37%) | |
| | M4 | 21 (24%) | 11 (24%) | 32 (24%) | | 7 (23%) | 3 (20%) | 10 (22%) | |
| | M5 | 15 (17%) | 5 (11%) | 20 (15%) | | 7 (23%) | 1 (7%) | 8 (17%) | |
| | M6 | 3 (3%) | 2 (4%) | 5 (4%) | | 1 (3%) | 0 (0%) | 1 (2%) | |
| | Other/Unknown | 3 (3%) | 2 (4%) | 5 (4%) | | 1 (3%) | 1 (7%) | 2 (4%) | |
| Race | White | 30 (34%) | 20 (43%) | 50 (37%) | 0.473 | 15 (48%) | 5 (33%) | 20 (43%) | 0.346 |
| | Other & Unk.* | 58 (66%) | 26 (57%) | 84 (63%) | | 16 (52%) | 10 (66%) | 26 (57%) | |
| FLT3-ITD | Negative | 67 (76%) | 35 (76%) | 102 (76%) | 0.867 | 23 (74%) | 12 (80%) | 35 (76%) | 0.602 |
| | Positive | 17 (19%) | 8 (17%) | 25 (19%) | | 6 (19%) | 3 (20%) | 9 (20%) | |
| | Unknown | 0 (0%) | 0 (0%) | 0 (0%) | | 2 (6%) | 0 (0%) | 2 (4%) | |
| Secondary AML | No | 73 (83%) | 20 (43) | 93 (69%) | <.001 | 26 (84%) | 6 (40%) | 32 (70%) | 0.005 |
| | Yes | 15 (17%) | 26 (57%) | 41 (31%) | | 5 (16%) | 9 (60%) | 14 (30%) | |
| Poor Prognosis† | No | 28 (32%) | 3 (7%) | 31 (23%) | <.001 | 6 (19%) | 0 (0%) | 6 (13%) | 0.068 |
| | Yes | 60 (68%) | 43 (93%) | 103 (77%) | | 25 (81%) | 15 (100%) | 40 (87%) | |
| Induction Therapy | Fludarabine + HDAC | 18 (20%) | 2 (4%) | 20 (15%) | 0.075 | 7 (23%) | 0 (0%) | 7 (15%) | 0.17 |
| | IA + Zarnestra | 20 (23%) | 11 (24%) | 31 (23%) | | 2 (6%) | 2 (13%) | 4 (9%) | |
| | IDA + HDAC | 24 (27%) | 15 (33%) | 39 (29%) | | 7 (23%) | 6 (40%) | 13 (28%) | |
| | Other | 26 (30%) | 18 (39%) | 44 (33%) | | 15 (48%) | 7 (47%) | 22 (48%) | |

*The "Other" values for race are based on Black, Asian, and Hispanic sub groups
†Poor prognosis is defined as having one or of the following high risk features: age >60 years, unfavorable cytogenetics, FLT3 ITD positive or secondary AML We hypothesized that this was a consequence of the higher heterogeneity in demographic and base line characteristic present in this sample set, compared to the first study (Table 16), suggesting the need to examine the data using clinical covariates.

d) Nodes Associated with Disease Response to Induction Chemotherapy in Patient Subsets as Defined by Clinical Covariates.

1. Age: Age, a covariate known to be associated with clinical outcomes in AML, was independently used to test the node/metric combinations for their association with clinical response to induction therapy. Using age as a dichotomous criteria (<60 versus ≧60 years), 28 node/metrics stratified patients for response to induction therapy in the <60 years patient group (Table 28B). Despite the small sample set (n~20), analysis of the older patient cohort samples also revealed unique nodes that distinguished CR from NR samples in this study (Table 28A). These included FLT3L induced increase in p-Erk and p-Akt and $H_2O_2$ induced increase in p-AKT and p-PLCγ2. Since $H_2O_2$ is a tyrosine phosphatase inhibitor[44] increases in p-AKT and p-PLCγ2 following $H_2O_2$ treatment (phosphatase inhibition) in NR samples, suggests altered phosphatase activity may be associated with refractory disease in older patients. Furthermore, incorporation of age as a clinical variable in combination with specific nodes (e.g. IL-27/p-Stat3) increased the predictive value of either age or the node itself, demonstrating the ability of multiparameter flow cytometry to improve on age, an important clinical prognostic indicator for response to induction chemotherapy (not shown).

TABLE 28

Univariate Analysis of Node/Metrics for Study No. 2 within Age Sub-Groups

| Node: Modulator/Read-Out | Metric | Biological Category | Num. CRs/NRs | AUC of ROC | t-test P | Wilcoxon P | Mean Value of CRs/NRs |
|---|---|---|---|---|---|---|---|
| A: Patients age 60 and older | | | | | | | |
| FLT3L/p-Akt | Fold | CCG | 7/14 | 0.85 | 0.011 | 0.010 | 0.00/0.36 |
| FLT3L/p-Erk | Fold | CCG | 6/14 | 0.77 | 0.034 | 0.062 | 0.01/0.21 |
| FLT3L/p-S6 | Fold | CCG | 6/14 | 0.80 | 0.004 | 0.041 | −0.06/0.67 |
| $H_2O_2$/p-Akt | Fold | Phosphatase | 7/9 | 0.78 | 0.029 | 0.071 | 0.45/0.88 |
| $H_2O_2$/p-Akt | TotalPhospho | Phosphatase | 7/9 | 0.79 | 0.026 | 0.055 | 0.84/1.33 |
| $H_2O_2$/p-Plcγ2 | TotalPhospho | Phosphatase | 7/9 | 0.84 | 0.013 | 0.023 | 1.19/1.86 |
| IL-27/p-Stat3 | Fold | CCG | 6/8 | 0.83 | 0.091 | 0.043 | −0.19/0.48 |
| LPS/p-Erk | Fold | CCG | 2/5 | 1.00 | 0.026 | 0.095 | −0.33/−0.16 |
| SCF/p-S6 | Fold | CCG | 6/13 | 0.74 | 0.030 | 0.106 | 0.14/0.70 |
| B: Patients Less than 60 Years old | | | | | | | |
| Ara-C & Dauno/p-Chk2−, c-PARP+ | Quad | Apoptosis | 29/4 | 0.85 | 0.001 | 0.021 | 23.35/7.48 |
| Etoposide/c-PARP | Fold | Apoptosis | 49/14 | 0.74 | 0.115 | 0.007 | 0.89/0.28 |
| Etoposide/p-Chk2−, c-PARP+ | Quad | Apoptosis | 39/7 | 0.72 | 0.010 | 0.071 | 21.17/9.58 |
| GM-CSF/p-Stat3 | TotalPhospho | CCG | 8/2 | 1.00 | 0.069 | 0.044 | 1.51/2.35 |
| IFNα/p-Stat1 | Fold | CCG | 33/4 | 0.75 | 0.050 | 0.114 | 1.72/2.60 |

TABLE 28-continued

Univariate Analysis of Node/Metrics for Study No. 2 within Age Sub-Groups

| Node: Modulator/Read-Out | Metric | Biological Category | Num. CRs/NRs | AUC of ROC | t-test P | Wilcoxon P | Mean Value of CRs/NRs |
|---|---|---|---|---|---|---|---|
| IFNα/p-Stat1 | TotalPhospho | CCG | 33/4 | 0.82 | 0.059 | 0.039 | 2.67/3.84 |
| IFNα/p-Stat3 | TotalPhospho | CCG | 33/4 | 0.79 | 0.014 | 0.065 | 2.62/3.44 |
| IFNγ/p-Stat3 | TotalPhospho | CCG | 14/2 | 1.00 | <0.001 | 0.017 | 1.60/2.71 |
| IFNγ/p-Stat1 | Fold | CCG | 14/2 | 0.96 | 0.036 | 0.033 | 1.35/2.96 |
| IFNγ/p-Stat1 | TotalPhospho | CCG | 14/2 | 0.96 | 0.163 | 0.033 | 2.40/4.13 |
| IFNγ/p-Stat5 | Fold | CCG | 14/2 | 1.00 | 0.009 | 0.017 | 0.68/1.67 |
| IL-10/p-Stat3 | TotalPhospho | CCG | 17/2 | 1.00 | 0.007 | 0.012 | 1.67/2.90 |
| IL-27/p-Stat1 | TotalPhospho | CCG | 38/5 | 0.84 | 0.048 | 0.016 | 1.73/3.12 |
| IL-27/p-Stat3 | Fold | CCG | 38/6 | 0.80 | 0.080 | 0.019 | 0.29/0.72 |
| IL-27/p-Stat3 | TotalPhospho | CCG | 38/5 | 0.83 | 0.047 | 0.014 | 1.97/3.06 |
| IL-6/p-Stat1 | Fold | CCG | 9/2 | 1.00 | 0.202 | 0.036 | −0.02/0.3 |
| IL-6/p-Stat3 | Fold | CCG | 9/2 | 1.00 | 0.271 | 0.036 | 0.13/1.67 |
| IL-6/p-Stat3 | TotalPhospho | CCG | 9/2 | 1.00 | 0.172 | 0.036 | 1.77/4.10 |
| IL-6/p-Stat5 | Fold | CCG | 9/2 | 0.89 | 0.003 | 0.145 | 0.11/0.58 |
| MRP-1 | PercentPos | Surface Markers | 33/4 | 0.70 | 0.018 | 0.222 | 33.19/14.20 |
| none/c-PARP | TotalPhospho | Apoptosis | 14/2 | 0.96 | 0.305 | 0.033 | 1.80/−0.35 |
| none/p-Erk | Basal | CCG | 31/3 | 0.68 | 0.021 | 0.348 | 0.98/1.96 |
| PMA/p-CREB | Fold | CCG | 33/4 | 0.82 | 0.003 | 0.039 | 0.78/1.55 |
| PMA/p-CREB | TotalPhospho | CCG | 33/4 | 0.84 | 0.002 | 0.025 | 3.72/5.00 |
| Staurosporine & ZVAD/Cytochrome-C | TotalPhospho | Apoptosis | 10/2 | 1.00 | 0.107 | 0.030 | 6.40/8.27 |
| Staurosporine/c-PARP | Fold | Apoptosis | 6/2 | 1.00 | 0.036 | 0.071 | 3.47/7.06 |
| Thapsigargin/p-CREB | TotalPhospho | CCG | 30/4 | 0.83 | 0.024 | 0.031 | 2.83/3.71 |
| Thapsigargin/p-Erk | Fold | CCG | 29/3 | 0.67 | 0.019 | 0.365 | 1.28/0.40 |

Node/metrics with a t-test p value or Wilcoxon p value of ≦.05 and an AUC of ≧.66 are shown.
Metrics are defined in Materials and Methods
Abbreviations are defined in Table 17

2. Presence or absence of secondary AML: Due to overlapping baseline disease characteristics of the groups when stratified by age versus presence/absence of secondary AML, the univariate analysis of samples group resulted in similar stratifying nodes (Tables 28 and 29). This suggests that at least in this sample set, age at diagnosis can be considered a surrogate marker for different disease biology. When age was examined as a variable across the secondary AML sample subset no correlation between age and response to therapy was found (FIG. 9), suggesting that the underlying biology of secondary AML is different from that of de novo AML, and age is not prognostic for response in secondary AML.

TABLE 29

Univariate Analysis of Node/Metrics for Study No. 2 within De Novo and Secondary AML Sub-Groups

| Node: Modulator/Read-out | Metric | Biologic Category | Num. CRs/NRs | AUC of ROC | t-test P | Wilcoxon P | Mean Value of CRs/NRs |
|---|---|---|---|---|---|---|---|
| A: Patients with De Novo AML | | | | | | | |
| Etoposide/p-Chk2 | Fold | Apoptosis | 46/14 | 0.67 | 0.033 | 0.058 | 0.59/0.27 |
| FLT3L/p-PLCy2 | TotalPhospho | CCG | 4/3 | 1.00 | 0.023 | 0.057 | 1.26/1.95 |
| GM-CSF/pStat3 | TotalPhospho | CCG | 8/4 | 0.97 | 0.007 | 0.008 | 1.51/2.22 |
| IFNγ/p-Stat3 | Fold | CCG | 14/4 | 0.89 | 0.014 | 0.018 | −0.04/0.24 |
| IFNγ/p-Stat3 | TotalPhospho | CCG | 14/4 | 0.89 | 0.026 | 0.018 | 1.59/2.48 |
| IL-10/p-Stat3 | Fold | CCG | 17/4 | 0.93 | 0.005 | 0.011 | 0.05/0.45 |
| IL-10/p-Stat3 | TotalPhospho | CCG | 17/4 | 0.93 | 0.014 | 0.006 | 1.63/2.68 |
| IL-10/p-Stat5 | Fold | CCG | 17/4 | 0.84 | 0.027 | 0.04 | 0.06/0.43 |
| IL-3/p-Stat1 | TotalPhospho | CCG | 8/4 | 0.88 | 0.040 | 0.048 | 1.03/1.71 |
| IL-3/p-Stat3 | TotalPhospho | CCG | 8/4 | 0.88 | 0.134 | 0.048 | 1.46/2.40 |
| IL-3/p-Stat5 | Fold | CCG | 8/4 | 0.78 | 0.048 | 0.154 | 1.87/0.39 |
| IL-6/p-Stat1 | Fold | CCG | 8/4 | 0.91 | 0.088 | 0.028 | 0.00/0.19 |
| IL-6/p-Stat1 | TotalPhospho | CCG | 8/4 | 0.88 | 0.026 | 0.048 | 1.06/1.67 |
| IL-6/p-Stat3 | TotalPhospho | CCG | 8/4 | 0.91 | 0.092 | 0.028 | 1.77/3.22 |
| IL-6/p-Stat5 | Fold | CCG | 8/4 | 0.88 | 0.023 | 0.048 | 0.12/0.47 |
| none/p-Erk | Basal | CCG | 30/6 | 0.78 | 0.015 | 0.029 | 0.97/2.48 |
| none/p-Stat6 | Basal | CCG | 16/4 | 0.88 | 0.077 | 0.026 | 1.02/1.34 |
| SCF/p-Akt | Fold | CCG | 44/11 | 0.76 | 0.001 | 0.008 | 0.52/−0.20 |
| SCF/p-PLCy2 | TotalPhospho | CCG | 4/3 | 1.00 | 0.037 | 0.057 | 1.29/1.96 |
| SCF/p-S6 | Fold | CCG | 43/11 | 0.67 | 0.013 | 0.098 | 1.05/0.43 |
| SDF-1α/p-CREB | TotalPhospho | CCG | 26/3 | 0.87 | 0.115 | 0.037 | 3.13/1.92 |

TABLE 29-continued

Univariate Analysis of Node/Metrics for Study No. 2 within De Novo and Secondary AML Sub-Groups

| Node: Modulator/Read-out | Metric | Biologic Category | Num. CRs/NRs | AUC of ROC | t-test P | Wilcoxon P | Mean Value of CRs/NRs |
|---|---|---|---|---|---|---|---|
| Stauro & ZVAD/Cytochrome C | TotalPhospho | Apoptosis | 10/4 | 0.90 | 0.092 | 0.024 | 6.40/8.04 |
| Thapsigargin/p-Erk | Fold | CCG | 28/6 | 0.74 | 0.010 | 0.067 | 1.28/0.27 |
| B: Patients with Secondary AML | | | | | | | |
| Etoposide/p-Chk2−, c-PARP+ | Quad | Apoptosis | 8/9 | 0.83 | 0.026 | 0.021 | 32.71/13.24 |
| Etoposide/p-Chk2+, c-PARP− | Quad | Apoptosis | 8/9 | 0.85 | 0.012 | 0.015 | 20.98/55.02 |
| FLT3L/p-Akt | Fold | CCG | 8/13 | 0.77 | 0.025 | 0.045 | 0.19/0.60 |
| FLT3L/p-Erk | Fold | CCG | 8/13 | 0.82 | 0.004 | 0.019 | 0.00/0.32 |
| FLT3L/p-S6 | Fold | CCG | 8/13 | 0.78 | 0.006 | 0.037 | 0.12/1.02 |
| FLT3R | Rel. Expression | Surface Marker | 5/5 | 0.88 | 0.042 | 0.056 | 1.23/1.10 |
| G-CSF/p-Stat1 | Fold | CCG | 6/10 | 0.75 | 0.049 | 0.118 | 0.00/0.36 |
| G-CSF/p-Stat3 | Fold | CCG | 6/10 | 0.78 | 0.024 | 0.073 | 0.06/0.96 |
| G-CSF/p-Stat5 | Fold | CCG | 6/10 | 0.70 | 0.044 | 0.193 | 0.08/1.07 |
| G-CSF/p-Stat5 | TotalPhospho | CCG | 6/9 | 0.78 | 0.047 | 0.088 | 2.58/3.91 |
| IFNα/p-Stat1 | Fold | CCG | 3/5 | 1.00 | 0.020 | 0.036 | 0.91/2.63 |
| IFNα/p-Stat1 | TotalPhospho | CCG | 3/5 | 1.00 | 0.013 | 0.036 | 2.01/3.59 |
| IFNα/p-Stat3 | Fold | CCG | 3/5 | 1.00 | 0.002 | 0.036 | 0.23/1.01 |
| IFNα/p-Stat5 | TotalPhospho | CCG | 3/5 | 1.00 | 0.022 | 0.036 | 3.03/4.60 |
| IL-27/p-Stat1 | Fold | CCG | 6/8 | 0.83 | 0.014 | 0.043 | 0.32/1.90 |
| IL-27/p-Stat1 | TotalPhospho | CCG | 6/7 | 0.88 | 0.013 | 0.022 | 1.50/3.19 |
| IL-27/p-Stat3 | Fold | CCG | 6/8 | 0.98 | 0.001 | 0.001 | −0.01/0.76 |
| IL-27/p-Stat3 | TotalPhospho | CCG | 6/7 | 0.79 | 0.048 | 0.101 | 1.61/2.60 |
| none/p-Chk2−, c-PARP+ | Quad | Apoptosis | 7/11 | 0.81 | 0.062 | 0.035 | 31.05/13.79 |
| PMA/p-CREB | Fold | CCG | 3/5 | 1.00 | 0.010 | 0.036 | 0.04/1.27 |
| SCF/p-S6 | Fold | CCG | 7/13 | 0.84 | 0.001 | 0.014 | 0.21/1.28 |

Node/metrics with a t-test p value or Wilcoxon p value of ≦.05 and an AUC of ≧.66 are shown
Negative mean CR/NR values represent down regulation as compared to reference/control/normalization
Metrics are defined in Materials and Methods
Abbreviations are defined in Table 17

3. Cytogenetics: Since cytogenetic group was a predictive clinical covariate with all patients in the favorable cytogenetic group demonstrating a CR, we evaluated whether nodes could predict response after incorporation of cytogenetic group as a covariate for the patients with intermediate and high-risk cytogenetics. Within the limitations of the small sample set, several nodes, including the IL-27/p-Stat1, p-Stat3 and p-Stat5 nodes, could significantly add to the predictive value of cytogenetic group (Table 30). As expected, FLT3 mutational status was not predictive of response to induction therapy in this data set (Table 16 and Table 31).

TABLE 30

Univariate Analysis of Node/Metrics for Study No. 2 for Patients with Intermediate or High Risk Cytogenetics with Cytogenetic Group as a Covariate.

| Node: Modulator/Read-Out | Metric | Biologic Category | Num. CRs/NRs | AUC model | P value for AUC model | AUC Cyto | P Value for Cyto | AUC of Node | P Value Node |
|---|---|---|---|---|---|---|---|---|---|
| Ara-C & Dauno/p-Chk2−, c-PARP− | Quad | Apoptosis | 29/11 | 0.74 | 0.009 | 0.60 | 0.042 | 0.57 | 0.036 |
| H₂O₂/p-Akt | Fold | Phosphatase | 42/19 | 0.8 | <0.001 | 0.69 | 0.022 | 0.66 | 0.026 |
| H₂O₂/p-Slp 76 | Fold | Phosphatase | 42/18 | 0.78 | <0.001 | 0.72 | 0.007 | 0.59 | 0.071 |
| IFNγ/p-Stat3 | Fold | CCG | 16/5 | 0.84 | 0.01 | 0.54 | 0.532 | 0.83 | 0.056 |
| IL-10/p-Stat3 | Fold | CCG | 19/5 | 0.84 | 0.01 | 0.55 | 0.548 | 0.84 | 0.058 |
| IL-27/p-Stat1 | TotalPhospho | CCG | 39/13 | 0.81 | <0.001 | 0.66 | 0.040 | 0.74 | 0.019 |
| IL-27/p-Stat1 | Fold | CCG | 39/14 | 0.76 | 0.002 | 0.66 | 0.015 | 0.66 | 0.038 |
| IL-27/p-Stat3 | Fold | CCG | 39/14 | 0.81 | <0.001 | 0.66 | 0.009 | 0.71 | 0.010 |
| IL-27/p-Stat3 | TotalPhospho | CCG | 39/13 | 0.76 | 0.002 | 0.66 | 0.024 | 0.68 | 0.072 |
| IL-27/p-Stat5 | Fold | CCG | 39/14 | 0.78 | 0.001 | 0.66 | 0.009 | 0.62 | 0.041 |
| IL-27/p-Stat5 | TotalPhospho | CCG | 38/13 | 0.76 | 0.003 | 0.65 | 0.032 | 0.62 | 0.052 |
| IL-6/p-Stat5 | Fold | CCG | 10/5 | 0.98 | 0.001 | 0.60 | 0.243 | 0.94 | 0.089 |
| SDF-1α/p-CREB | Fold | CCG | 33/22 | 0.74 | 0.001 | 0.67 | 0.090 | 0.69 | 0.033 |
| SDF-1α/p-CREB | TotalPhospho | CCG | 26/9 | 0.84 | 0.001 | 0.75 | 0.023 | 0.66 | 0.090 |

Table is sorted alphabetically by node
Node/metrics with a t-test p value or Wilcoxon p value of ≦.05 and an AUC of ≧.66 are shown
Metrics are defined in Materials and Methods
Abbreviations are defined in Supplemental Table 1

TABLE 31

Demographic and Baseline Characteristics of Intermediate and High Risk Cytogenetic Groups in Study No. 2

| Characteristic | | Int. Risk CRs | Int. Risk NRs | All Int. Risk Pts | Int. Risk P-Value | High Risk CRs | High Risk NRs | All High Risk Pts. | High Risk P-Value |
|---|---|---|---|---|---|---|---|---|---|
| | N | 29 | 9 | 38 | | 21 | 22 | 43 | |
| Age (yr) | Median | 53.6 | 59.3 | 56.1 | 0.071 | 51.2 | 61.7 | 55.8 | 0.143 |
| | Range | 27.0-79.0 | 45.6-68.6 | 27.0-79.0 | | 34.8-77.8 | 25.0-76.3 | 25.0-77.8 | |
| Age Group | <60 yr | 26 (90%) | 5 (56%) | 31 (82%) | 0.041 | 18 (86%) | 10 (45%) | 28 (65%) | 0.01 |
| | >=60 yr | 3 (10%) | 4 (44%) | 7 (18%) | | 3 (14%) | 12 (55%) | 15 (35%) | |
| Sex | F | 17 (59%) | 6 (67%) | 23 (61%) | 1 | 11 (52%) | 10 (45%) | 21 (49%) | 0.763 |
| | M | 12 (41%) | 3 (33%) | 15 (39%) | | 10 (48%) | 12 (55%) | 22 (51%) | |
| FAB | M0 | 0 (0%) | 0 (0%) | 0 (0%) | | 1 (5%) | 1 (5%) | 2 (5%) | 0.831 |
| | M1 | 6 (21%) | 1 (11%) | 7 (18%) | 0.943 | 2 (10%) | 0 (0%) | 2 (5%) | |
| | M2 | 11 (38%) | 4 (44%) | 15 (39%) | | 8 (38%) | 10 (45%) | 18 (42%) | |
| | M4 | 5 (17%) | 2 (22%) | 7 (18%) | | 5 (24%) | 6 (27%) | 11 (26%) | |
| | M5 | 5 (17%) | 2 (22%) | 7 (18%) | | 3 (14%) | 2 (9%) | 5 (12%) | |
| | M6 | 1 (3%) | 0 (0%) | 1 (3%) | | 1 (5%) | 2 (9%) | 3 (7%) | |
| | Other/Unknown | 1 (3%) | 0 (0%) | 1 (3%) | | 1 (5%) | 1 (5%) | 2 (5%) | |
| Race | White | 7 (24%) | 5 (56%) | 12 (32%) | 0.362 | 4 (19%) | 10 (45%) | 14 (33%) | 0.141 |
| | Other & Unknown* | 22 (76%) | 4 (44%) | 26 (68%) | | 17 (81%) | 12 (55%) | 29 (66%) | |
| FLT3-ITD | Negative | 20 (69%) | 6 (67%) | 26 (68%) | 0.821 | 17 (81%) | 17 (77%) | 34 (79%) | 0.555 |
| | Positive | 8 (28%) | 3 (33%) | 11 (29%) | | 3 (14%) | 2 (9%) | 5 (12%) | |
| | Unknown | 1 (3%) | 0 (0%) | 1 (3%) | | 1 (5%) | 3 (14%) | 4 (9%) | |
| Secondary AML | No | 25 (86%) | 5 (56%) | 30 (79%) | 0.071 | 16 (76%) | 9 (41%) | 25 (58%) | 0.031 |
| | Yes | 4 (14%) | 4 (44%) | 8 (21%) | | 5 (24%) | 13 (59%) | 18 (42%) | |
| Poor Prognosis† | No | 16 (55%) | 3 (33%) | 19 (50%) | 0.252 | 0 (0%) | 0 (0%) | 0 (0%) | |
| | Yes | 13 (45%) | 6 (67%) | 19 (50%) | | 21 (100%) | 22 (100%) | 43 (100%) | |
| Induction Therapy | Fludarabine + HDAC | 0 (0%) | 0 (0%) | 0 (0%) | | 4 (19%) | 2 (9%) | 6 (14%) | 0.691 |
| | IA + Zarnestra | 12 (41%) | 3 (33%) | 15 (39%) | 0.492 | 6 (29%) | 6 (27%) | 12 (28%) | |
| | IDA + HDAC | 10 (34%) | 2 (22%) | 12 (32%) | | 7 (33%) | 7 (32%) | 14 (33%) | |
| | Other | 7 (24%) | 4 (44%) | 11 (29%) | | 4 (19%) | 7 (32%) | 11 (26%) | |

The two-sample t test was used to compare mean ages of CR and NR patients. Fisher's Exact test was used to compare CR and NR patients with respect to categorical variables with two levels. The standard Chi-Square test was used to compare CR and NR patients with respect to categorical variables with three or more levels.
*The "Other" values for race are based on Black, Asian, and Hispanic sub groups
†Poor prognosis is defined as having one or more of the following high risk features: age >60 years, unfavorable cytogenetics, FLT3 ITD positive or secondary AML Discussion The two studies reported here show that AML characterization using modulated SCNP can be performed with high technical accuracy and reproducibility to quantitatively characterize the biology of AML in individual patients. Furthermore, this characterization is predictive of disease outcome in response to specific therapeutic interventions and distinct from other known prognostic factors (such as age, secondary AML and cytogenetics). Basal protein expression profiling patterns as measured by RPPA in AML was recently shown to correlate with known morphologic features, cytogenetics and clinical outcomes (Kornblau et al. Blood. 2009; 113:154-164). While these studies show high sensitivity, throughput, and reproducibility for baseline measurements they cannot provide any evaluation of the dynamic response to stimuli of a specific cell population or of single cells in a heterogeneous cell population. Resistance or relapse is thought to arise from rare populations of blasts with different characteristics that enable them to survive induction therapy. We therefore hypothesize that the ability to measure the adaptability of individual cells (or subpopulations) to different modulation and assessing intra-patient clonal heterogeneity, will provide knowledge with greater informative content and relevance with respect to responsiveness and the crucial characteristics that give rise to disease persistence.

The data presented are from two independent, sequentially tested patient sample sets (total n=122) obtained from the leukemic cell banks of two centers, PMH/UHN and MDACC. The sets differ substantially in sample number, source of leukemic cells and patient clinical characteristics. The first, smaller study tested PBMCs, collected from predominately female patients <60 years, whose disease did not respond to standard induction chemotherapy. The second training study included 88 evaluable BMMC AML samples obtained mostly from patients <60 years old, with a more typical rate of responsiveness to cytarabine (plus additional drugs in most) based induction therapy.

The differences in source of leukemic blasts and induction therapy were hypothesized to be unimportant for the interpretation of the study results. It has previously been shown that protein levels in AML cells do not appear to exhibit biologically relevant differences between specimen sources (Kornblau et al. Blood. 2009; 113:154-164) and clinical outcome appears to be independent of cytarabine dose (100 mg/m$^2$-3 g/m$^2$) (Sekeres et al. Blood. 2009; 113:28-36). Both patient cohorts lacked sufficient leukemia samples from older patients responsive to induction chemotherapy limiting the strength of the observations for this subset of patients.

Despite the above limitations, many important observations could be made: First the SCNP assay demonstrates the level of robustness and reproducibility needed for clinical application. The first study began with a large panel of nodes selected for their role in myeloid biology. In particular, pathways known to be altered in multiple malignancies and involved in cell survival, proliferation and DNA damage were probed. Throughout normal myeloid differentiation these pathways are tightly regulated by a variety of cytokines and growth factors used in SCNP assays. For example, SCF and Flt3L are important for maintaining the hematopoietic stem cell pool (Lyman et al. Blood. 1998; 91:1101-1134; Kikushige et al. J Immunol 2008; 180:7358-7367); G-CSF is important for neutrophilic differentiation of hematopoietic progenitor cells (Touw et al. Front Biosci. 2007; 12:800-815); IL-6 family members including IL-6 and IL-27 regulate proliferation, differentiation and functional maturation of cells belonging to multiple hematopoietic lineages (Seita et al. Blood. 2008; 111:1903-1912) and IL-10 modulates the immune response of monocytes and macrophages and was previously shown to play a role in AML blast proliferation (Bruserud et al. Cytokines Cell Mol Ther. 1998; 4:187-198). Consistent with this knowledge, the first training study univariate analysis identified 58/304 statistically significant node/metrics (i.e. AUC of the ROC>0.66 with a p value<0.05), predictive for clinical response to induction therapy. These included G-CSF induced Jak/Stat signaling, previously shown to be potentiated in AML (Irish et al. Cell. 2004; 118:217-228) and new observations of IL-27, IL-10 and IL-6 mediated signaling. Furthermore, transformed cells evade apoptosis by activating survival pathways or by disabling apoptotic DNA damage machinery or signaling. Therefore, Caspase-dependent apoptosis was also used to characterize patient responses after in vitro exposure of AML samples to etoposide and Ara-C/daunorubicin. Importantly both etoposide and Ara-C/daunorubicin activated apoptosis were shown to stratify patients by clinical outcome in both studies.

The external validity of these original observations was then tested in the second training study, which included a larger sample set that was more representative of the general US AML population but more heterogeneous in terms of baseline disease characteristics. The analysis of the data from the two studies suggests that the difference in baseline characteristics of donors in the two studies played a significant role in the differences observed in the stratifying nodes between the two studies. However, similar trends existed for some of the stratifying nodes (such as p-Stat1 and p-Stat3 response to IL-27 and cleaved PARP to etoposide) were observed across the two studies when similar subsets of patients (although small) where compared. Another important observation that emerged from this second study was the ability of SCNP assays to reveal different pathways that correlated with patient outcome within patient subgroups defined by clinical prognostic characteristics such as age, cytogenetics and presence or absence of secondary leukemia. Specifically, in patients younger than 60 years of age, intact communication between DNA damage response and apoptosis after in vitro exposure to chemotherapeutic agents emerged as an important biologic characteristic that identified CR samples. By contrast, for patients over age 60 or with secondary AML lack of response to induction chemotherapy was associated with increased Flt3L induced p-Akt and p-Erk. Importantly, combining age with some predictive nodes (such as IL-27 mediated p-Stat1 or p-Stat3), increased the AUC of the ROCs from 0.65 for age alone to 0.87 and 0.89, respectively, with highly significant p values (not shown). This shows that SCNP assays can distinguish AML disease biology beyond age.

Finally, although univariate analysis of signaling nodes stratified patient samples based on leukemic response to induction therapy, the combination of independently predictive nodes improved predictive value significantly.

In summary, this study demonstrated, in two very diverse patient cohorts, the potential value of using leukemia signaling biology to stratify patient samples into those that likely will or will not respond to ara-c based induction chemotherapy. These results emphasize the value of comprehensive functional assessment of biologically relevant signaling pathways in AML blasts as a basis for the development of highly predictive tests for response to therapy.

Example 9

This example relates to publication "Functional Characterization of FLT3 Receptor Signaling Deregulation in AML by Single Cell Network Profiling (SCNP)". Rosen D B, Minden M D, Kornblau S M, Cohen A, Gayko U, Putta S, Woronicz J, Evensen E, Fantl W J, Cesano A. PLoS ONE. 2010. October; In Press. This publication is incorporated herein by reference it its entirety for all purposes.

This example identifies intracellular signaling pathways associated with FLT3 ITD in two independent cohorts of diagnostic AML samples that serve as an improvement over current clinical tools in the identification of clinically meaningful altered FLT 3 and has implications for cohort selection in the development of FLT3 inhibitors. The two cohorts of data were further analyzed to investigate the differences in signaling between FLT-WT and FLT-ITD samples. The first cohort of data ("study 1") comprised the 34 samples from University Health Network outlined in Table 16 and Table 19. The second cohort of data ("study 2") comprised an 83 sample subset of MD Anderson Cancer Center data outlined in Table 16 (and Table 19). The 83 sample subset was selected based on known FLT3 mutation status. Both cohorts of data were used to investigate differences in FLT3 signaling between leukemic blasts and control data.

FLT3 WT Signaling in Healthy Control and AML Samples

Figure 12:
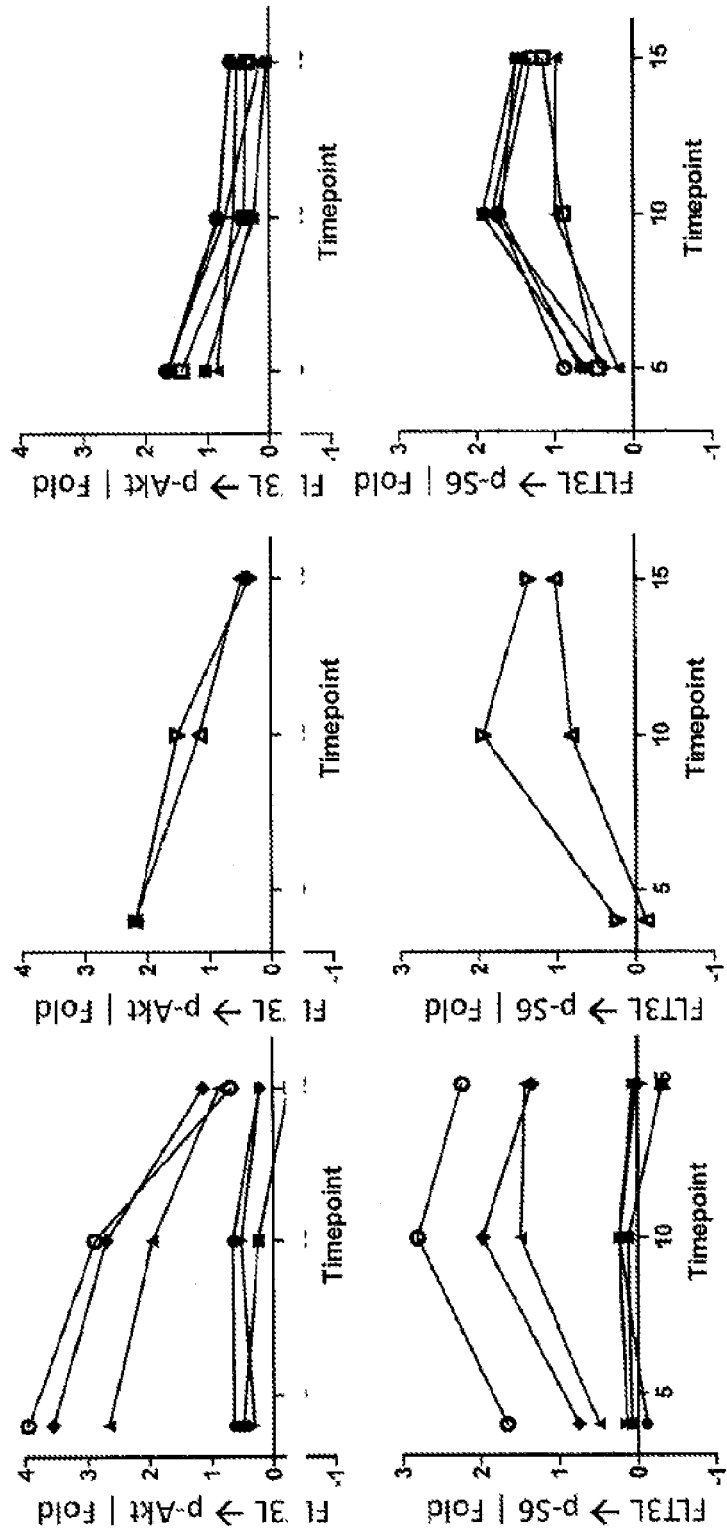
FIG. 12 illustrates FLT3L signaling kinetics in FLT3-WT AML and healthy bone marrow myeloblast (BMMC).

In order to further characterize wild-type FLT receptor signaling in AML, we compared FLT3L-induced signaling in the myeloblast population of control BMMC samples with FLT3L-induced signaling in the leukemic blast population of FLT3-WT AML samples. FLT3L activated the MAPK and PI3K pathways, inducing increased levels of p-Akt and p-S6 in both BMMC and FLT3-WT AML samples at early time points (4 minutes, 10 minutes). However, kinetic differences between the two sets of samples were observed at later time points (FIG. 12). In the BMMC samples, activation of p-Akt and p-S6 was largely diminished by 15 minutes, likely due to regulatory feedback mechanisms. In the FLT3-WT AML samples, sustained p-Erk, p-CREB and p-Akt activation was observed in a number of samples at 15 minutes (FIG. 13). These results demonstrate that kinetic differences in signaling at different time points can be used to distinguish FLT3-WT AML samples from healthy BMMCs.

Variance in intensity of cell signaling may be used to distinguish FLT3-WT and healthy cells. FIGS. 10, 11, 12 and 13 illustrate the ranges of signaling observed in FLT3-WT and BMMC samples. FIG. 1 contains "box and whisker" plots of FLT3 levels and FLT3L-induced S6 signaling for both the FLT3-WT AML and BMMC samples. In BMMC samples, FLT3L induced a narrow range of S6 signaling. In FLT3-WT AML samples, FLT3L induced a wide range of S6 signaling. In agreement, standard deviations from measures of FLT3 signaling were higher in FLT3-WT AML than in healthy BMMb. In addition, the variance in FLT3 receptor signaling was statistically different (p-value=0.003, Levene's test) between the FLT3-WT AML and healthy BMMb samples (FIG. 14) In the BMMC samples, the S6 signaling did not co-occur with increased Stat5 signaling (not shown) however in FLT3-WT AML p-Stat5 was induced by FLT3L in some samples.

Figure 10:
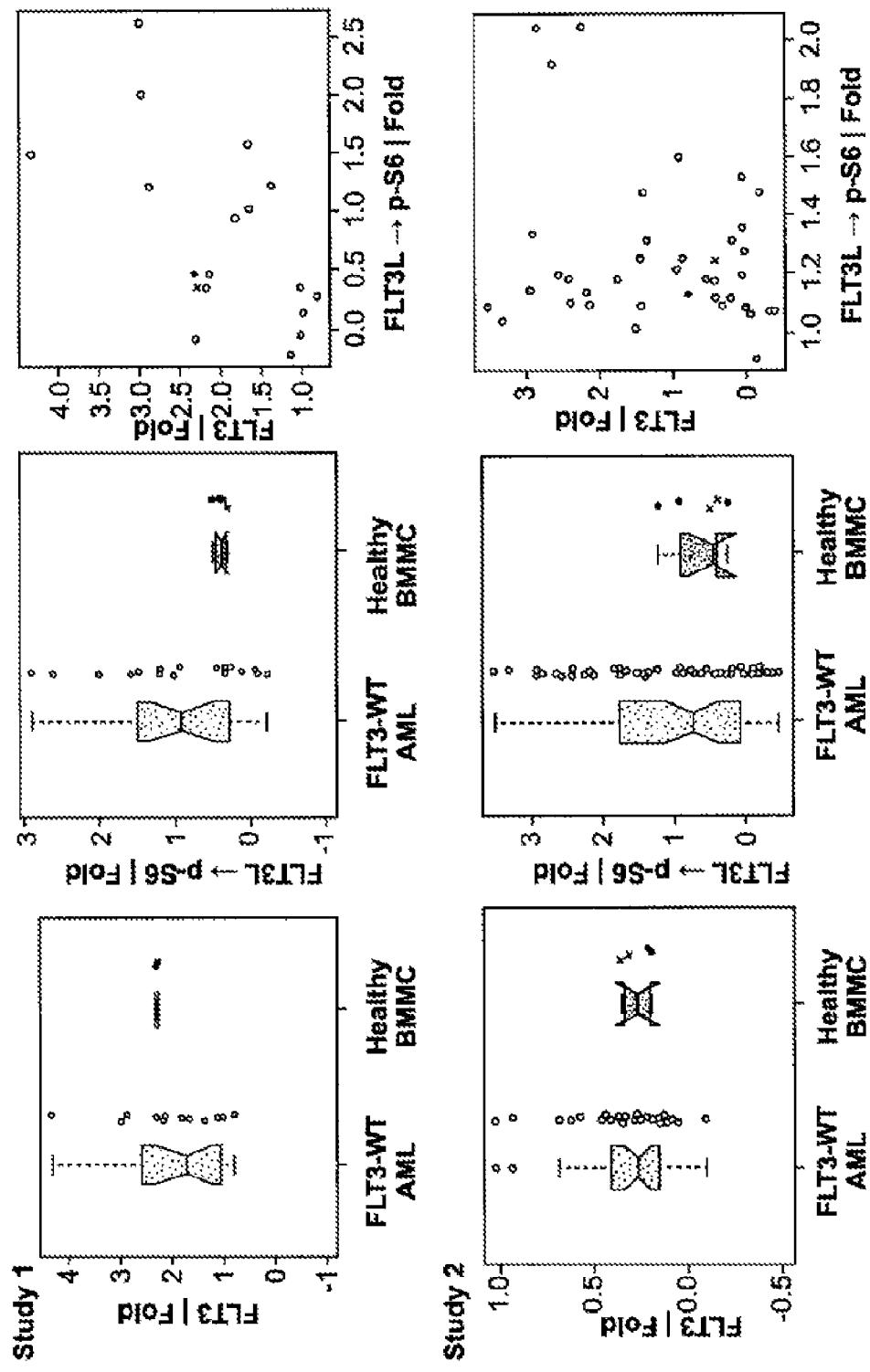
FIG. 10 contains "box and whisker" plots and scatter plots that illustrate the different ranges of signaling observed in FLT3-WT and BMMC cells.

FIG. 10 also contains scatter-plots that compare FLT3L-induced S6 signaling with FLT3 receptor levels. From the scatter-plots, it is shown that the FLT3L-induced S6 signaling is independent of FLT3 receptor levels in both cohorts (i.e. there is no linear correlation between FLT3 expression and S6 signaling), although there may be a threshold level of FLT3 receptor required for S6 signaling.

Figure 11:
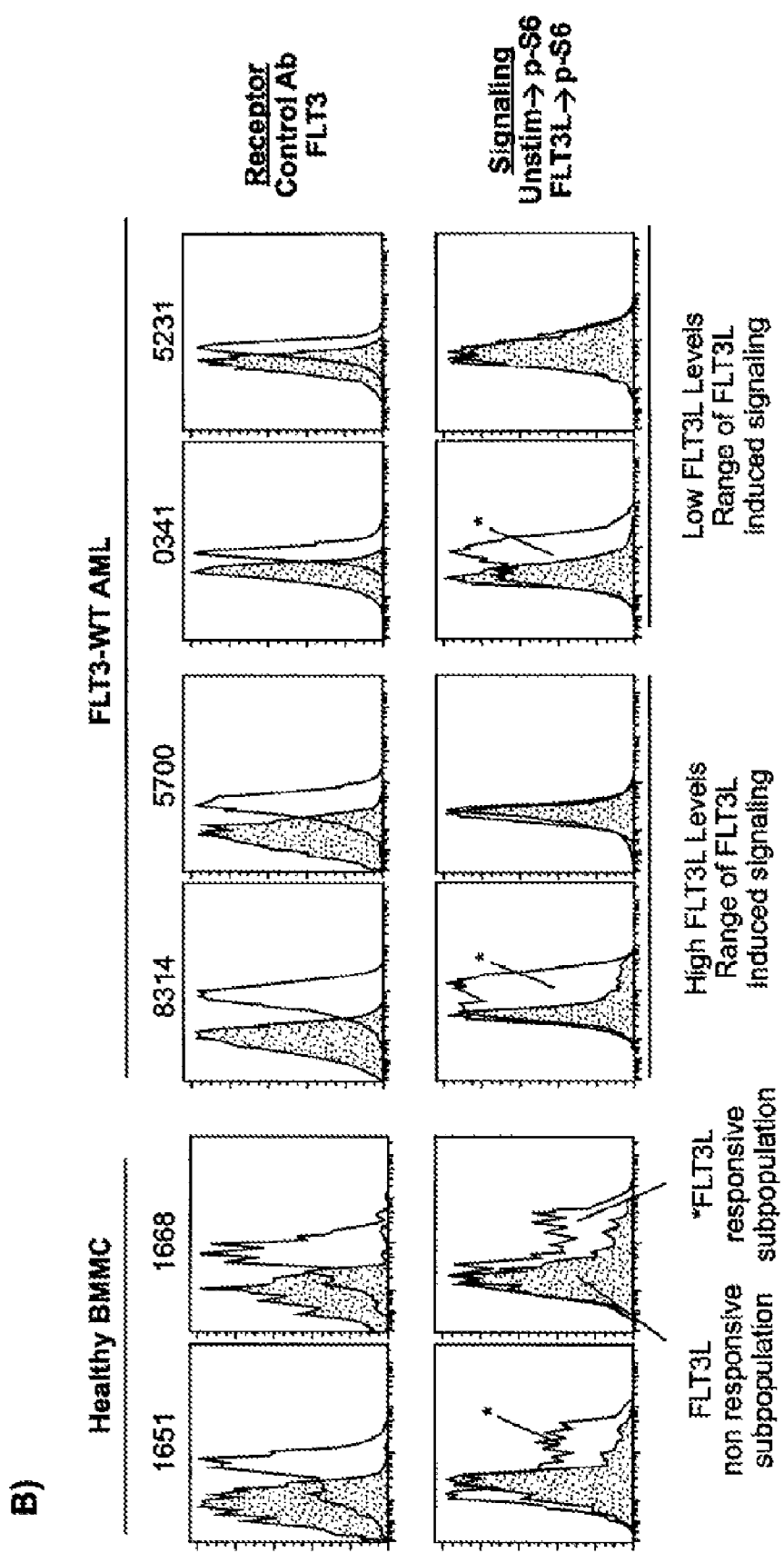
FIG. 11 contains distribution plots that illustrate the different ranges of signaling observed in FLT3-WT and BMMC cells and distinct FLT3L responsive subpopulations in both sets of cells.

Although individual samples displayed uniform FLT3 receptor staining, induction of p-S6 was only observed in a fraction of cells, suggesting the presence of distinct FLT3L responsive and non-responsive subpopulations in healthy and AML samples. FIG. 11 illustrates FLT3L responsive and FLT3L non-responsive subpopulations in BMMC samples. Accordingly, FLT3L-induced p-S6 signaling may be used in gating or other types of analyses in order to select a cell subpopulation with a distinct disease/response phenotype.

Signaling Differences and Classification of FLT3-WT and FLT3-ITD

Univariate analysis, unadjusted for multiple testing, was performed sequentially and independently on the two study cohorts in order to identify signaling nodes that distinguished with FLT3-ITD from FLT3-WT AML patient samples. In study 1, 75 of the 304 node/metrics tested distinguished FLT3-ITD from FLT3-WT AML patient samples with an AUC of ROC>0.7 and p<0.05. Results from study 1 are tabulated in FIG. 22. In study 2, 35 of the 201 node/metrics distinguished FLT3-ITD from FLT3-WT AML patient samples with an AUC of ROC>0.7 and p<0.05. Results from study 2 are tabulated in FIG. 26. Results from both studies include the AUC, Wilcoxon and t-test p-value for each node, and the number/mean value of the samples in the FLT3-ITD and FLT3-WT AML groups with common stratifying nodes summarized in FIG. 23. Although the majority of the discussion herein is directed to nodes that had similar responses within the two cohorts of data, some differences were observed between the two cohorts of data. These differences may have been due to the different clinical characteristics of the two cohorts of data, specifically biases in the data from UHN.

Analysis of the false discovery rate for both studies showed this frequency to be significantly greater than the number of signaling nodes that would be expected to be significantly different between the two groups by chance (t-test p-value=0.0009). Stratifying nodes that distinguished FLT3-ITD from FLT3-WT samples in both studies represented distinct biological networks including Jak/Stat, PI3K and apoptosis pathway readouts (FIG. 22, FIG. 26).

FLT3 Signaling and Receptor Levels in FLT3-WT and FLT3-ITD Samples

Both FLT3-ITD and FLT3-WT samples expressed similar ranges of FLT3 receptor levels. Basal levels of p-Erk, p-Akt, and p-S6 did not differ significantly between FLT3-ITD and FLT3-WT samples. However, we observed distinct FLT3L-induced signaling responses in the two sets of samples. With FLT3L induction, FLT3-ITD samples showed lower levels of induced and total PI3K and MAPK pathway activation compared to FLT3-WT samples.

Figure 15:
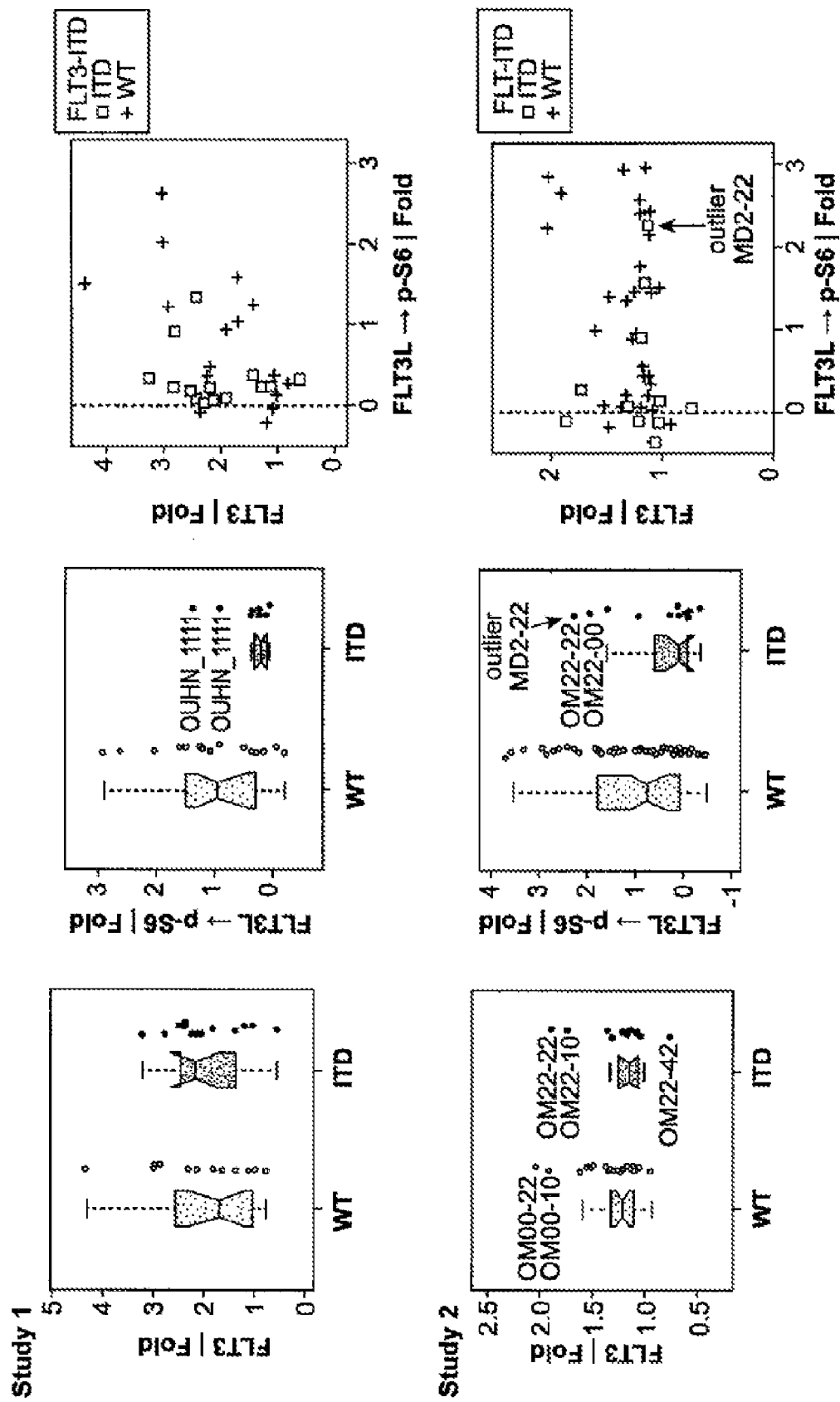
FIG. 15 contains "box and whisker" plots that demonstrate the range of values of both FLT3 receptor levels and FLT3L-induced S6 signaling.

Differences in the PI3K pathway activation were evidenced by FLT3L induction of p-S6 which, in univariate analysis, provided discrimination between FLT3-WT and FLT3-ITD samples in study 1 and study 2 with p-values of 0.038 and 0.036, respectively (Wilcoxon p-values). FIG. 15 contains "bar and whisker" plots that demonstrate the range of values of both FLT3 receptor levels and FLT3L-induced S6 signaling. These plots illustrate that FLT3-ITD exhibits a much narrower range and lower values of S6 signaling as compared to FLT3-WT.

Distinct Jak/Stat Signaling in FLT3-WT and FLT3-ITD Samples

Variance in response to a stimulator may also be used to distinguish samples based on their mutational status. IL-27 induced a wide range of p-Stat responses in the FLT3-WT samples. FLT3-ITD samples displayed minimal responsiveness to IL-27 stimulation.

Figure 16:
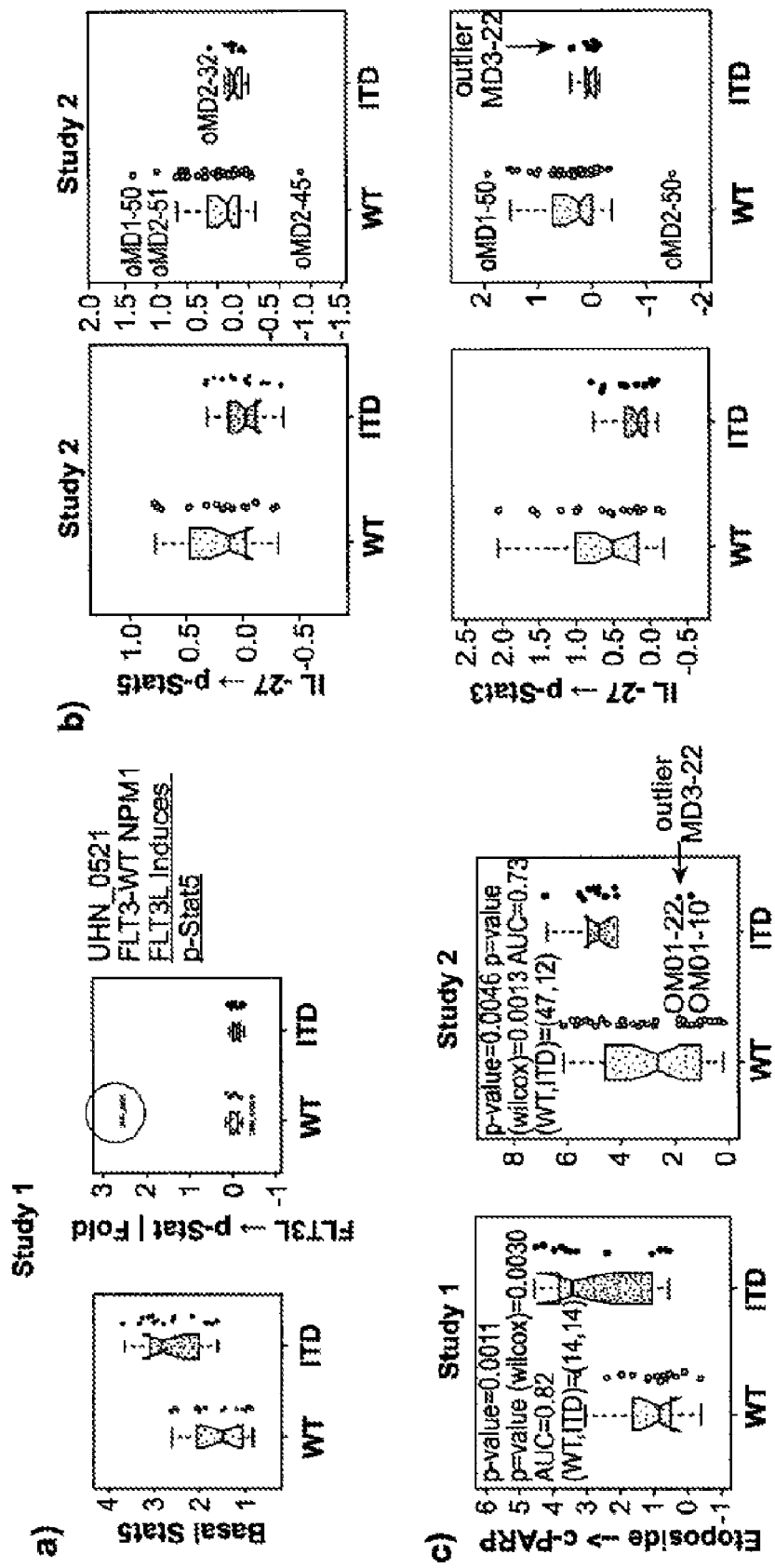
FIG. 16 contains "bar and whisker" plots that demonstrate the observed differences between FLT3-WT and FLT3-ITD samples.

FIG. 16(b) illustrates the differences in IL-27-induced Jak/Stat pathway response between FLT3-WT and FLT3-ITD. IL-27-induced Stat signaling activity was reduced in FLT3-ITD samples with significantly lower induction of p-Stat3 (t-test p-value<0.029) and p-Stat5 (t-test p-value<0.038) in both studies. The fold induction of p-Stat responsive to IL-27 (IL-27→p-Stat 3|Fold) signaling node in univariate analysis distinguished FLT3-WT and FLT3-ITD in both samples (AUC 0.69 in study 1 and AUC 0.73 in study 2, respectively). Notably, FLT3-ITD samples displayed higher basal levels of p-Stat5 and p-Stat1 compared with FLT3-WT samples in Study 1.

Distinct Apoptotic Responses in FLT3-WT and FLT3-ITD Samples

Etoposide-induced DNA damage and apoptosis was measured to identify FLT3-mutation-based differences in DNA Damage response (DDR) and apoptotic machinery. Increased p-Chk2 and cleaved PARP were used to measure the ability of etoposide to induce DNA damage and apoptosis, respectively. FIG. 16(c) illustrates the differences in etoposide-induced DNA damage between FLT3-WT and FLT3-ITD samples. As measured using total cleaved PARP induced by etoposide (etoposide→c-PARP|Total), FLT3-ITD samples were more sensitive to in vitro apoptosis than FLT3-WT samples (AUC 0.82 in study 1 and AUC 0.73 in study 2). Similar results were observed in both study 1 and in study 2 using other mechanistically-distinct apoptosis-inducing agents such as staurosporine, a pan kinase inhibitor, and in study 2, Ara-C/Daunorubicin. Accordingly, a wide range of apoptosis-inducing agents may be used to induce signaling that stratifies FLT3-ITD from FLT3-WT samples.

Figure 17:
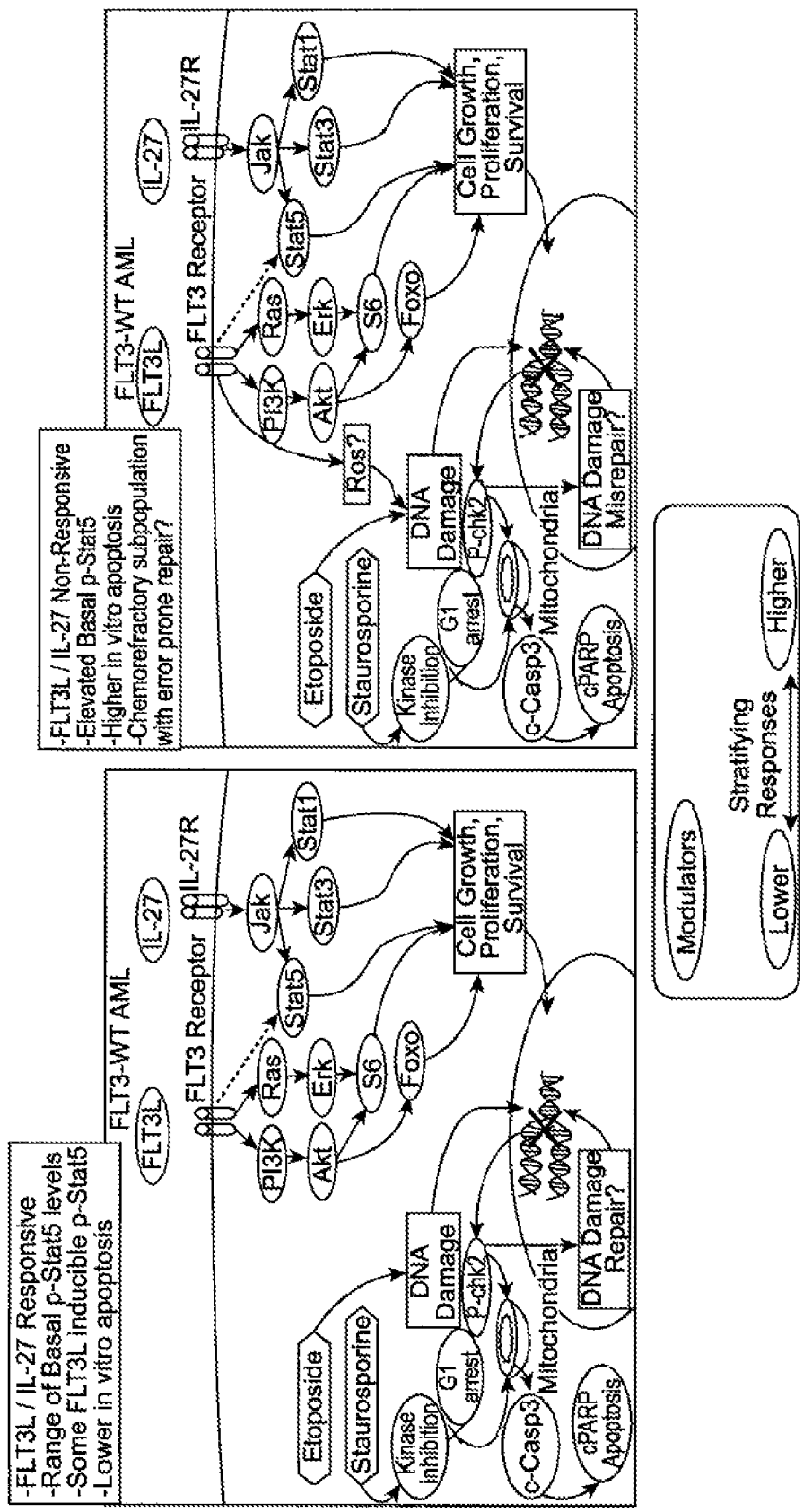
FIG. 17 graphically depicts stratifying nodes that distinguished FLT3-ITD from FLT3-WT samples.

Stratifying nodes that distinguished FLT3-ITD from FLT3-WT samples in both studies represented distinct biological networks including Jak/Stat, PI3K and apoptosis pathway readouts and are summarized graphically in FIG. 17.

FLT3L and IL-27 Induced Signaling in FLT3-ITD, NPM1 Molecular Subgroups

Figure 24:
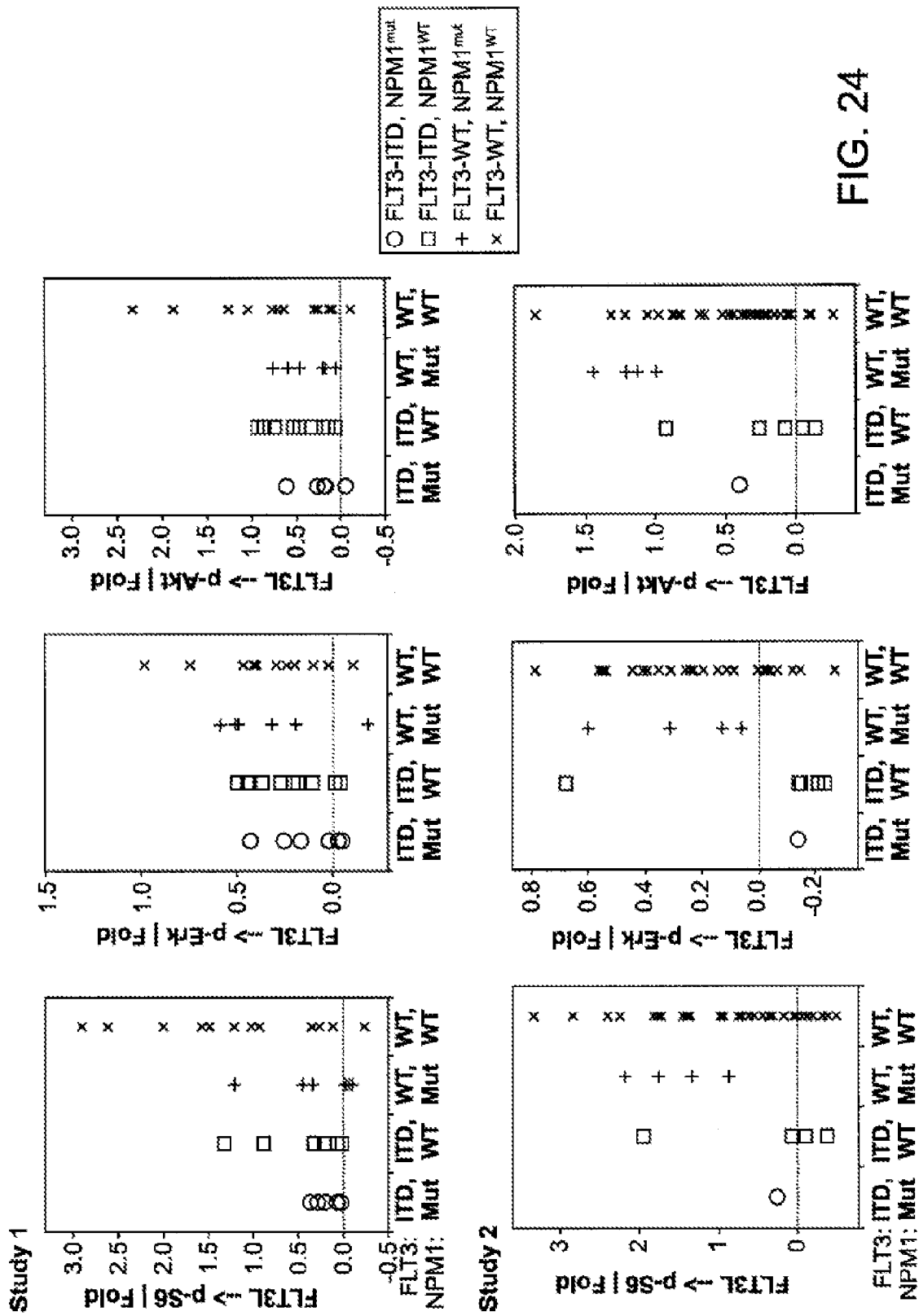
FIG. 24 depicts FLT3L-induced p-S6, p-Erk and p-Akt signaling in different FLT3 subgroups.
Figure 25:
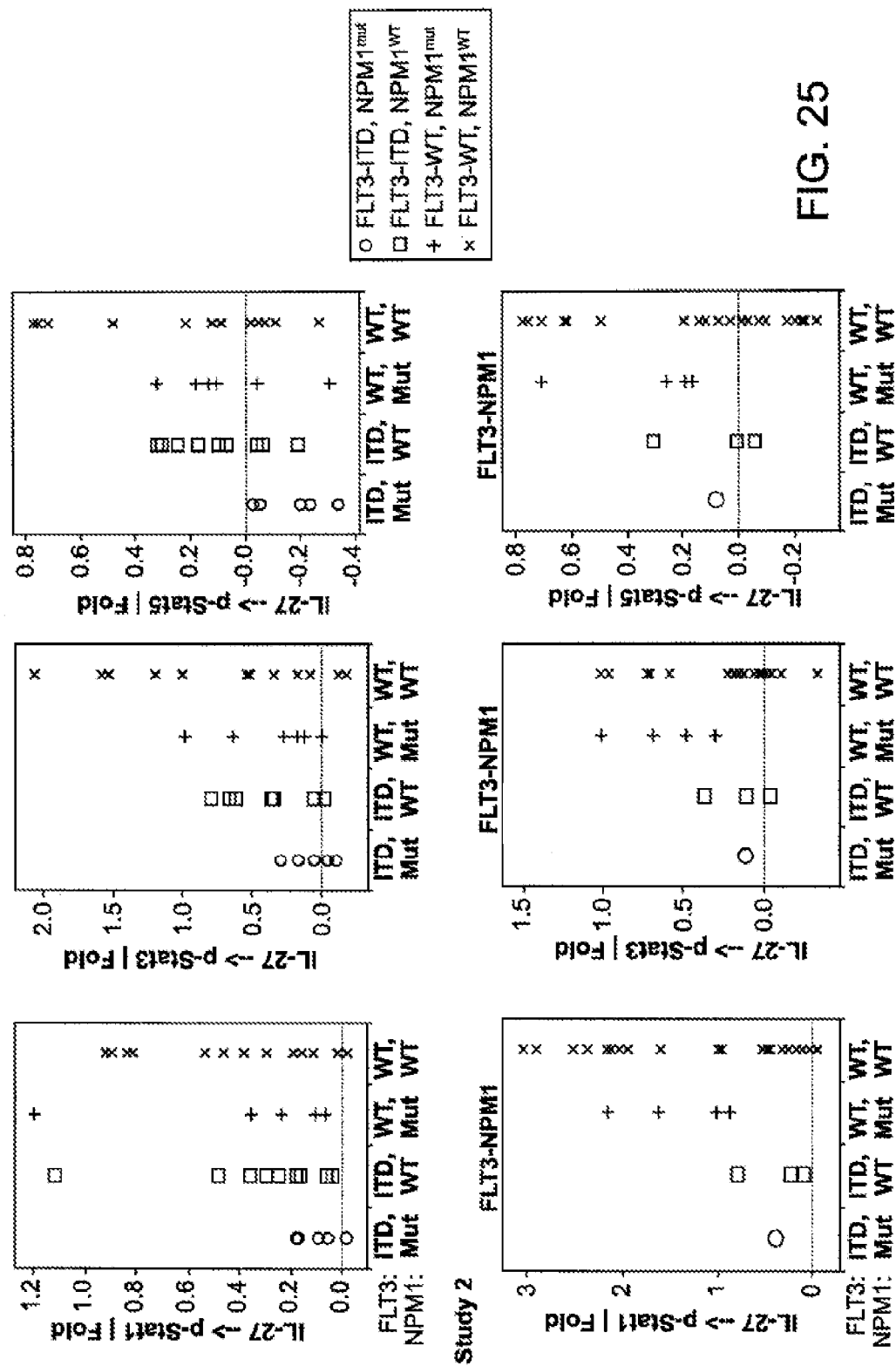
FIG. 25 depicts IL-27-induced p-Stat1, p-Stat3 and p-Stat5 signaling in different FLT3 subgroup.

IL-27 induced Jak/Stat signaling and FLT3L induced PI3K and Raf/Ras/MAPK signaling responses was assessed in FLT3 receptor and NPM1 molecular defined subgroups. For all nodes analyzed, the FLT3-WT/NPM-WT subgroup demonstrated the most variable signaling responses and often contained samples with the most elevated signaling (FIG. 24, 25). In contrast, within FLT3-ITD/NPM1 mutated patients, IL-27-induced and FLT3L-induced signaling appeared more uniform and generally lower compared to FLT3-WT/NPM-WT samples. FLT3-WT/NPM1-WT samples demonstrated the highest variance among FLT3 NPM1 subgroups for IL-27 and FLT3L signaling and demonstrated significantly higher variance compared to both FLT3-ITD subgroups (FIG. 14). Of note, the largest differences in variance were observed between FLT3-WT/NPM-WT and FLT3-ITD/NPM-Mutated samples (FIG. 14).

Correlations Between Nodes

Several of the top-ranking nodes stratifying FLT3-ITD from FLT3-WT samples were analyzed to identify co-variance in FLT3-mutation-dependent signaling. FIG. 18 and FIG. 21 illustrate the correlations between the top ranking nodes. Pearson correlation coefficients were computed for all signaling nodes from study 1 with a t-test p-value≦0.05 demonstrated correlation between nodes belonging to the same pathway. For example, nodes within the Stat pathway (IL-27→p-Stat3|Fold and IL-27→p-Stat5|Fold) exhibited a correlation of R=0.81. The same signaling protein was observed to have similar reactions to different modulators with a correlation of R=0.87 (Thapsigargin→p-CREB|Fold and PMA→p-CREB). Nodes measuring signaling events in different pathways were less correlated (e.g. Thapsigargin→p-CREB Fold and IL-27→p-Stat5|Fold (R=0.04).

The identification of high correlation values between similar nodes affirms the quality of results and allows us to identify FLT3-mutation-stratifying nodes that can be used interchangeably in a classifier such as a bivariate model or a multivariate model. Conversely, identification of FLT3-mutation-stratifying nodes with a poor correlation value allows us to identify pairs of nodes that may complement each other for increased classification accuracy.

Association Between Multiple Signaling Nodes and FLT3 ITD Status—Multivariate Analysis Using Linear Regression FIG. 19 provides a schematic overview of bivariate modeling. Bivariate modeling combines different signaling nodes to generate a model that provides better stratification of FLT3-ITD and FLT3-WT AML samples than the individual nodes. We evaluated all possible pairs of the 75 signaling nodes with AUC of the ROC>0.7 and p-value<0.05 (tabulated in FIG. 22) for their ability to improve stratification of the FLT3 mutational status. This modeling exercise was performed to identify potential combinations within or across pathways that might form the basis of future studies. All combinations of nodes that had an AUC greater than the best single node/metric within the combination were tabulated in FIG. 27. The AUC for the tabulated models ranged from 0.89 to 0.98. As discussed above, the probability of two nodes to complement one another was higher if the nodes participated in different signal transduction pathways: e.g. combining the nodes IL-6→p-Stat5|Total (AUC=0.84) and FLT3L→p-S6|Total (AUC=0.80) yields an improved AUC of 0.98.

Clinical Implications

To better understand the clinical implications of the FLT3-mutation-stratifying nodes, we independently examined the FLT3-mutation-stratifying signaling profiles in samples from two groups of Cytogenetically Normal (CN) AML patients. Each group of patients represented clinically extreme "outliers" based on their mutation status: 1) FLT3-WT AML who experienced disease relapse within 3 months after initial remission (i.e. rapid relapse) and 2) FLT3-ITD AML in complete continuous disease remission for two or more years. In study 2 there were 2 FLT3-WT and 2 FLT3-ITD samples associated with these clinical characteristics.

Figure 20:
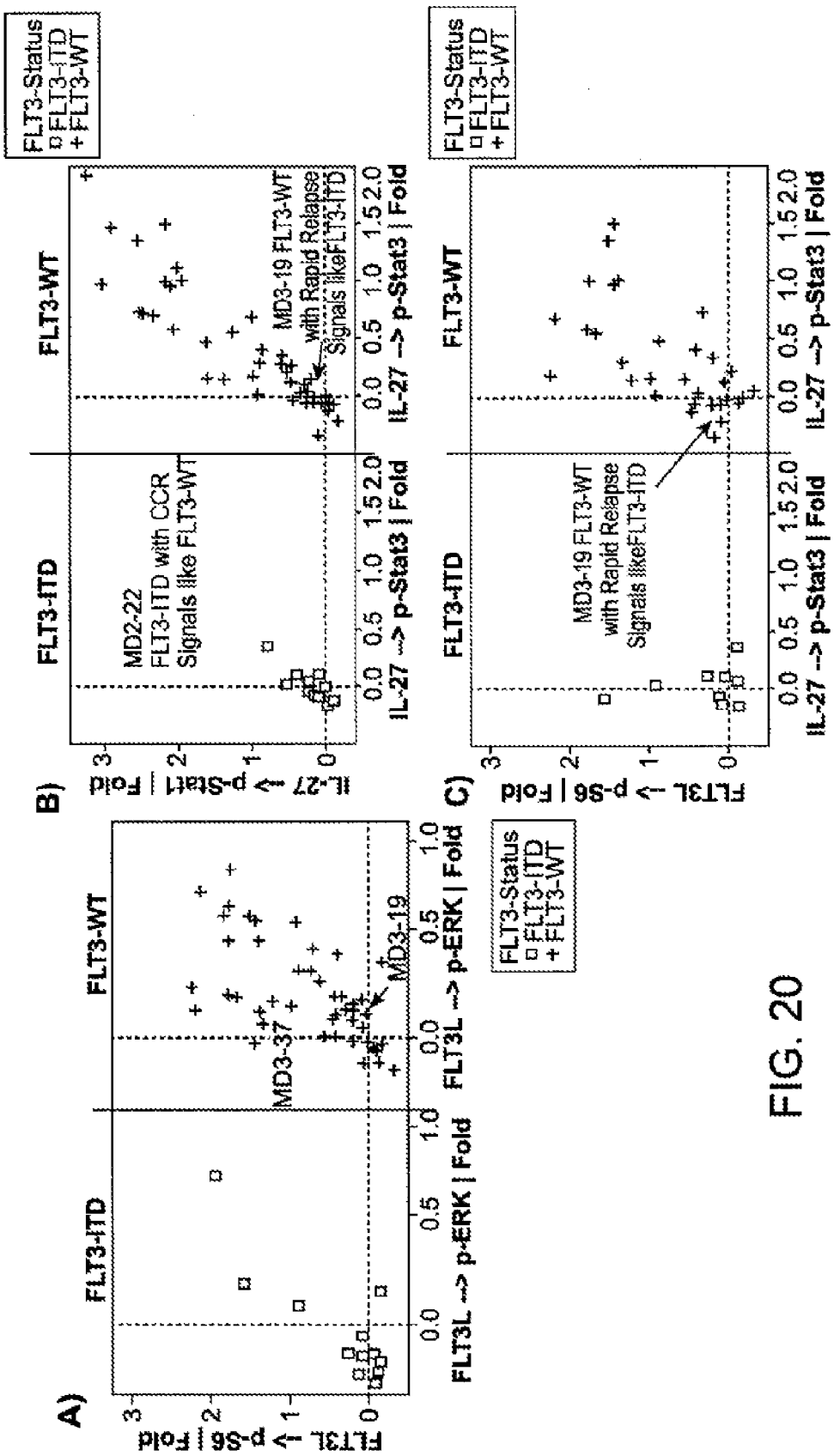
FIG. 20 contains scatter plots that illustrate the signaling profiles of clinical outliers relative to other study samples.

The wide range of signaling responses observed in FLT3-WT AML samples made identification of signaling outliers challenging. FIG. 20(a) provides a scatter-plot of the signaling profiles in the two rapid relapse FLT3-WT samples (MD3-19 and MD3-37) showing attenuated p-S6 and p-Erk in response to FLT3L, similar to the FLT3L-induced signaling observed in FLT3-ITD samples (see FIG. 15, FIG. 16(a) for FLT3-ITD FLT3L-induced signaling). FIGS. 20(b) and 20(c) provide scatter-plots showing minimal IL-27-induced Stat phosphorylation in MD3-19, similar to FLT3-ITD samples (see FIG. 16(b) for FLT3-ITD IL-27-induced Stat signaling), suggesting that these rapid relapse FLT3-WT samples might share similar biology with FLT3-ITD samples in certain pathways.

Identification of FLT3-ITD signaling outliers was aided by the narrow range of signaling responses of this sample set. In the CN FLT3-ITD sample group, two patients remained in complete continuous remission for two or more years. One patient (MD2-22) had been treated with chemotherapy alone and the other (MD3-22) was treated with an allogeneic stem cell transplant (as per NCCN guidelines). Since MD3-22 received high intensity post-remission therapy we focused on signaling associated with sample MD2-22.

MD2-22 obtained from a patient who received high dose Ara-C similar to what is recommended for "low risk" cytogenetic leukemia. We found that the FLT3-ITD MD2-22 sample signaling profile was closer to FLT3-WT as illustrated by the first two principal components of PCA Analysis (not shown). This observation was further reinforced by the number of nodes (16) for which MD2-22 was an outlier among the FLT3-ITD group (i.e. outside of 1.5 times the inter-quartile from the median for FLT3-ITD). These nodes included those from the Jak/Stat pathway (e.g., IFNα→p-Stat1, p-Stat3, p-Stat5; G-CSF→p-Stat3, p-Stat5), the CREB pathway (e.g. PMA→p-CREB); and the PI3K and MAPK pathways (e.g., FLT3L→p-S6, p-Akt; SCF→p-S6, p-Akt). A following molecular analysis of this sample indicated the presence of an NPM1 gene mutation although this information was not available at the time of post-remission treatment.

An analysis within FLT3-WT AML samples, demonstrated that higher measures of induced apoptosis (i.e. Ara-C/Dauno→C-PARP Fold) were associated with CR duration greater than two years (AUCROC: 0.92) These data show the ability of SCNP to provide information, independent from molecular determinations relevant to the clinical decision making of AML.

Discussion

These data suggest that assessing patient samples for the presence of FLT3 receptor deregulation may inform clinical decision making regarding standard treatment as well as serving as a tool for patient stratification in studies attempting to evaluate specific inhibitors of the FLT3 receptor. This functional assessment of biologically relevant signaling pathways in AML blasts shows the spectrum of deregulated signal transduction not previously described in primary AML samples.

The current investigation represents the first analysis comparing pathway activity and inducibility in the absence or presence of modulators known to activate Jak/Stat, PI3-kinase/Akt/S6 and the Ras/Raf/Erk/S6, phosphatase/reactive oxygen species, and DDR/apoptosis pathways in FLT3-WT and FLT3-ITD AML samples. We found that FLT3L induced differential signaling in FLT3-WT AML independently of the presence of FLT3 mutations as compared to the healthy BMMC. These data show that SCNP uncovers important heterogeneity in AML and has potential as a platform for understanding leukemia pathway dependence in the individual patient, information that will be valuable for the selection of therapeutic strategies in the era of personalized medicine.

Although FLT3 receptor levels were similar between the FTL3-WT and FLT3-ITD AML groups in this study, FLT3-ITD samples displayed attenuated responses to FLT3L, as measured by induced levels of p-Erk, p-Akt and p-CREB versus their FLT3-WT counterparts While increased levels of basal p-Erk and p-Akt have been reported in FLT3-ITD expressing cell lines, our data demonstrated comparable levels of basal p-Erk and p-Akt among FLT3-ITD and FLT3-WT primary AML samples. These data suggest the greater dependence of FLT3L inducibility of these signaling networks in FLT3-WT AML and demonstrate FLT3L-independence in FLT3-ITD samples.

Consistent with these studies FLT3-ITD samples expressed increased basal levels of p-Stat1, p-Stat3 and p-Stat5 compared to FLT3-WT samples in Study 1 and in both studies FLT3-ITD AML samples displayed a uniformly limited range in basal p-Stat5 levels compared to FLT3-WT samples. Additionally, in contrast to signaling in healthy myeloid blasts, FLT3L induced p-Stat5 in some FLT3-WT samples, demonstrating deregulated FLT3 receptor signaling even in the absence of FLT3 mutational alterations.

Different signaling responses were also observed between FLT3-WT and FLT3-ITD samples for IL-27 induced Jak/Stat pathway activity. Most studies characterizing the biology of IL-27 have been performed on lymphocytes where this cytokine plays a major role in immune regulation. However, the IL-27 receptor is present on other cell types, including those of the myeloid lineage, where its activation has been shown to enhance proliferation and differentiation of mouse and human hematopoietic stem/progenitor cells. In Study 1, increased levels of basal p-Stat1 and p-Stat5 were observed for FLT3-ITD compared to FLT3-WT samples. Our data suggest these FLT3-ITD samples are less responsive to IL-27 mediated Stat signaling, likely because they already display elevated Stat pathway activity. This growth factor independence could contribute to the poor clinical outcome observed within FLT3-ITD patients.

Analysis of the apoptosis pathways showed that FLT3-ITD samples were more sensitive to in vitro etoposide and other apoptosis inducing agents than FLT3-WT samples. While these results using cryopreserved diagnostic samples may seem somewhat counterintuitive to the clinical findings that FLT3-ITD patients have a worse overall survival and shorter duration of remission, to date the presence of FLT3-ITD has not been associated with response to induction therapy.

The clinical implications of our observations suggest that SCNP analysis could be applied to clinical decision-making as well as to evaluating responsiveness to inhibitors of FLT3 receptor signaling and/or other activated pathways. Despite the limited sample size and the exploratory nature of the analyses some interesting observations emerged. Specifically, we identified FLT3-WT AML samples whose SCNP responses resembled those of FLT3-ITD AML and furthermore behaved clinically like high risk AML. Conversely, we found a case of FLT3-ITD AML that functionally resembled FLT3-WT, and behaved clinically like low-risk AML. These data suggest SCNP has the potential to provide improved prognostic information beyond FLT3 molecular characterization alone. Lastly, multiple therapeutics that target FLT3 receptor (e.g., CEP701, PKC412, AB220) are in development for the treatment of AML. To date, the characterization of AML based on the mutational status of the FLT3 gene has shown not to be very informative in predicting the activity of any of these FLT3 receptor inhibitors and their effects on signaling transduction remains unknown. In this regard, SCNP could be used as a tool to identify AML patients who could benefit from administration of such inhibitors alone or in combinations with other standard agents and/or targeted inhibitors. Further studies in the context of clinical trials are warranted.

Example 10

This example relates to publication "Distinct Patterns of DNA Damage Response and Apoptosis Correlate with Jak/Stat and PI3Kinase Response Profiles in Human Acute Myelogenous Leukemia". Rosen D B, Putta S, Covey T, Huang Y W, Nolan, G P, Cesano, A, Minden M D, Fantl W J. PLoS ONE. 2010 August; 5(8): e12405. This publication is incorporated herein by reference in its entirety for all purposes.

This example further characterizes the data outlined above with regards to Example 6 based on the activities of their intracellular signaling pathways. Analysis of Jak/Stat, PI3K, DNA damage response (DDR) and apoptosis pathway activities demonstrated biologically distinct patient-specific profiles, even within cytogenetically and cell surface uniform patient sub-groups. Thus, while AML is known to be clinically heterogeneous, the biology described in this study shows that the heterogeneity in the disease may be represented by a limited number of intracellular signaling pathways highlighting survival pathways, DDR and their link to apoptosis.

Principle Component Analysis (PCA) was used in addition to our standard metrics for measuring activation levels. PCA is a dimension reduction technique commonly used to represent multi-dimensional data according to the strongest "trends" or associations in the data. Here, we used PCA to represent several nodes in the same pathway according to a trend or direction in the data. PCA was performed for Jak/Stat and PI3K nodes using both "Fold" and "Total" metrics of induced pathway activity along with the corresponding basal nodes.

The application of PCA to multi-dimensional data representing the same pathway is beneficial for several reasons. As discussed above with respect to Example 10, nodes that are part of the same pathway can have a similar response and exhibit covariance over different samples or even cells Accordingly, combining the data into one metric may adequately represent the entire pathway. Also, since PCA identifies the strongest trend in the data, the use of PCA allows for the representation of small variations in a signaling pathway in a single metric. Accordingly, PCA-based metrics may provide the ability to distinguish small variations in signaling pathways associated with disease.

Univariate analysis was also used to identify nodes/metrics that stratified patients based on their disease response to standard induction therapy. Each node/metric combination was evaluated using univariate analyses. Jak/Stat and PI3K nodes that stratified clinical CR and NR patients (Area Under the Curve of the Receiver Operator Characteristic (AUCROC) >0.6 and p-value<0.05) were used for principle component analyses and for selecting examples of the node/metrics that were used to construct the heat-maps.

Results

As described above with regards to Example 6, SCNP analysis of the Jak/Stat and PI3K signaling pathways was carried out in AML blasts after their exposure to a panel of modulators.

Jak/Stat Pathway Activity

To assess the activity and inducibility of the Jak/Stat pathway, samples were treated with G-CSF, IL-6, IL-27, IL-10, IFNα and IFNγ, known to activate the Jak/Stat pathway. AML samples were characterized by the magnitude of their basal Jak/Stat pathway activity as well as by the induced responses (Fold metric) and total level of Jak/Stat pathway activation (Total metric). The latter two metrics used paralleled each other. Low or absent levels of induced phosphorylation of Stat 1, Stat 3 and Stat 5 proteins were associated with gated AML blasts from CR patients exemplified by the 2D flow plots observed for responses of sample UHN_0713 to G-CSF and IL-27 (not shown). In contrast, potentiated Jak/Stat signaling was observed as well as increased pathway activity in cells taken from patients whose leukemia was non-responsive to induction chemotherapy, as observed in a 2D flow plot for myeloid-gated cells for sample UHN_9172 (not shown). In most NR patient samples Jak/Stat signaling was elevated in a cell subpopulation in response to multiple cytokines, whereas cells of most CR patients were largely non-responsive. IL-27 and IL-6-mediated-phosphorylation of Stat3 were closely correlated, as would be expected for two cytokines sharing the gp130 common signal transduction receptor subunit.

PI3K Pathway Activity

A second major survival pathway interrogated in this study was PI3K, known to play a role in most cancers. Converging signals from the PI3K/mTor and Ras/Erk pathways result in phosphorylation of ribosomal protein S6 which correlates with increased protein translation of mRNA transcripts that encode proliferation and survival promoting proteins.

Analogously to activation of the Jak/Stat pathway, application of known activators of the PI3K pathway including FLT3L, SCF and SDF-1α broadly grouped AML samples by the magnitude of their signal transduction responses (Fold metric) and overall pathway activity (Total metric) represented by measurements of p-Akt and p-S6. In the same manner that low levels of modulated Jak/Stat responses and Jak/Stat pathway activity were seen in leukemic cells from CR patients, samples in which p-Akt/p-S6 signaling was low or absent were also associated with clinical responsiveness to chemotherapy. Additionally, in the same manner that high levels of induced Jak/Stat responses and high levels of Jak/Stat pathway activity were seen in leukemic cells from NR patients, elevated PI3K pathway responses were also associated with clinical non-response to chemotherapy as observed by a 2D flow plot for sample UHN_4353 (not shown). Importantly, no associations could be made between cytogenetic risk category and the French American British category (FAB) within these signaling responses.

Figure 28:
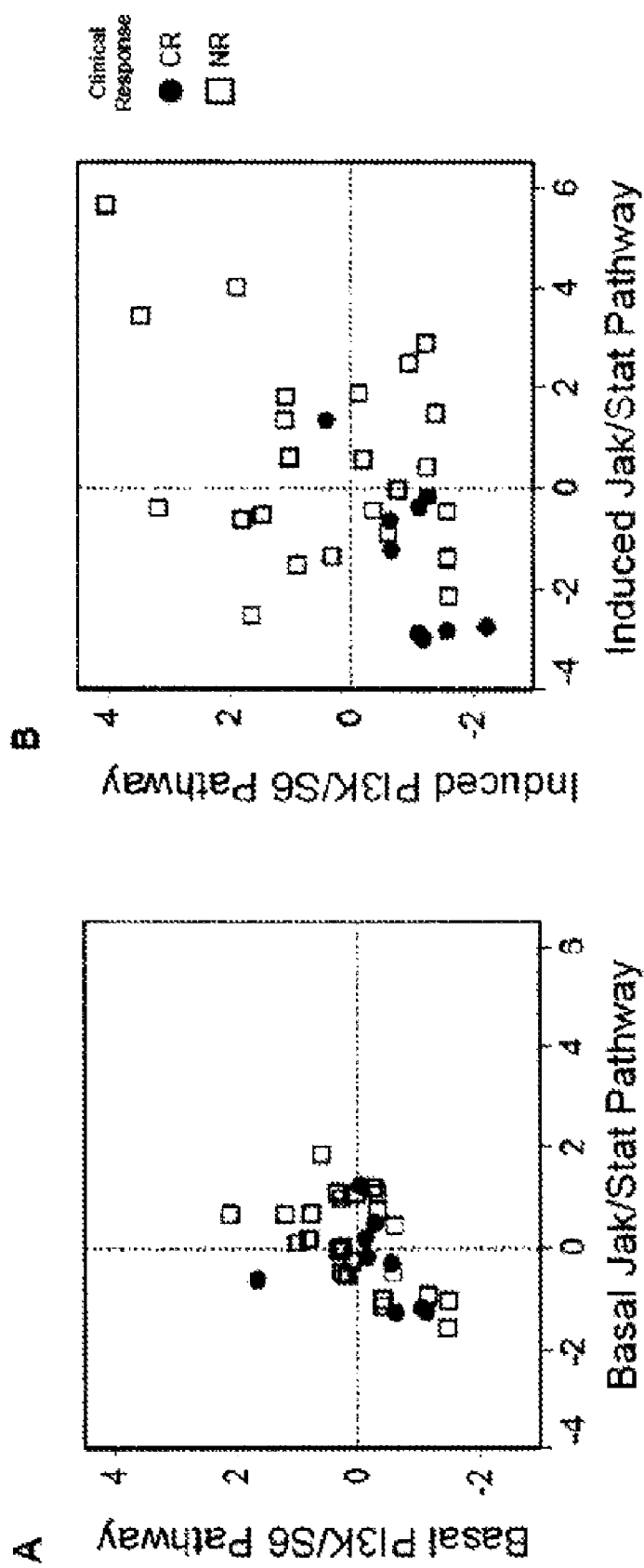
FIG. 28 demonstrates the stratification that PCA achieves when applied to induced nodes in pathways and basal nodes in the same pathways.

Correlated Measures of Induced JAK/STAT and PI3K Signaling Reveals AML Blasts with Distinct Pathway Responses In order to evaluate the effect of modulation on both the Jak/Stat and PI3K pathway activities, PCA was performed for each pathway in its basal state as well as its functionally activated state. The PCA analysis for the activated states of the pathways combined readouts from multiple modulators known to activate the Jak/Stat and PI3K pathways. Induced pathway activity, rather than basal pathway activity, could more readily reveal distinct patient-specific functional response patterns. FIGS. 28(a) and (b) demonstrate the stratification that PCA achieves when applied to induced nodes in pathways is significantly better than for basal nodes. This is to be expected because since PCA identifies the strongest trend in the data. If the pathways don't have a multiplicity of different states due to induction, PCA will not be helpful in segregating the different states.

FIG. 28(b) illustrates the multiple response profiles observed in the modulated AML samples. In the modulated samples, activity was high or low for both pathways or high for one and low for the other pathway. Interestingly, although the number of samples from CR patients (shown in FIG. 28(b) as filled blue circles) is low (n=9), a low signaling capacity in both Jak/Stat and PI3K/S6 pathways was associated with clinical response to chemotherapy. In contrast, augmented signaling responses from one or both the Jak/Stat and PI3K pathways were observed in most samples from chemotherapy refractory patients (i.e. NR patients, shown in FIG. 28(b) as unfilled red squares). A sub-group of the NR AML blast samples low level signaling responses in both Jak/Stat and PI3K pathways (lower-left-hand quadrant) were observed, suggesting that other pathways could be contributing to clinical refractoriness to chemotherapy. These data suggest that activation of the PI3K and Jak/Stat pathways might oppose response to chemotherapy. Further, the stratification between different AML samples achieved using PCA demonstrates that principle component of pathway activity is a useful metric for characterizing heterogeneity in AML samples and stratifying different subtypes of AML cells.

Figure 29:
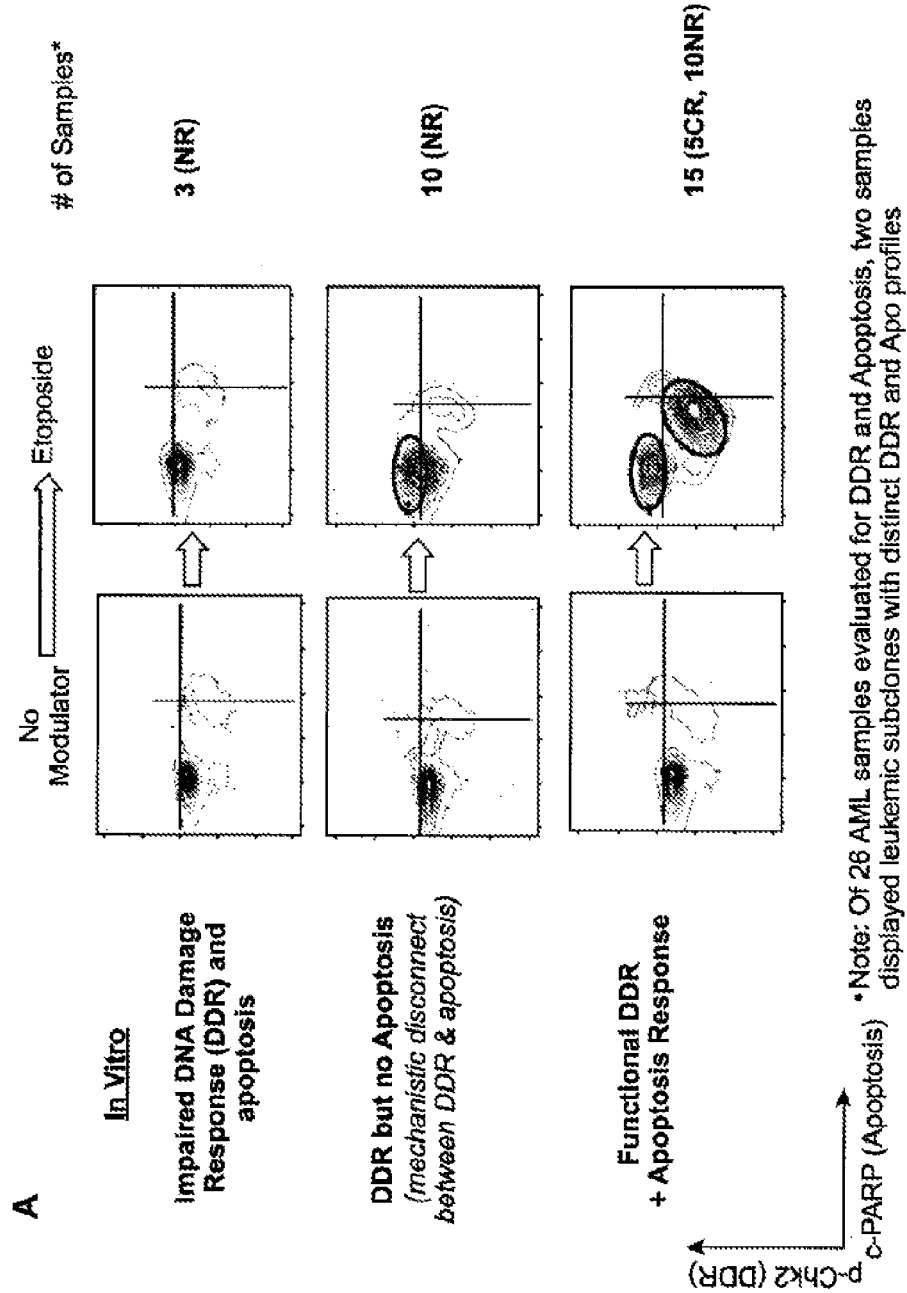
FIG. 29 illustrates three distinct responses to apoptosis and DNA damage repair (DNA) that were observed in AML blasts.

Measurements of DDR and Apoptosis with In Vitro Exposure to Etoposide and Staurosporine As described above with regards to Example 6(a), DDR and apoptosis was measured using Chk2 and cleaved PARP after exposure of AML blasts to etoposide, a topoisomerase II inhibitor that induces double stranded breaks. FIG. 29 illustrates the three distinct responses that were observed: (1) AML blasts with a defective DDR and failure to undergo apoptosis (2) AML blasts with proficient DDR and failure to undergo apoptosis (3) AML blasts with proficient DDR and apoptosis. All CR samples were exemplified by the third profile whereas NR samples were exemplified by all three response profiles.

Figure 30:
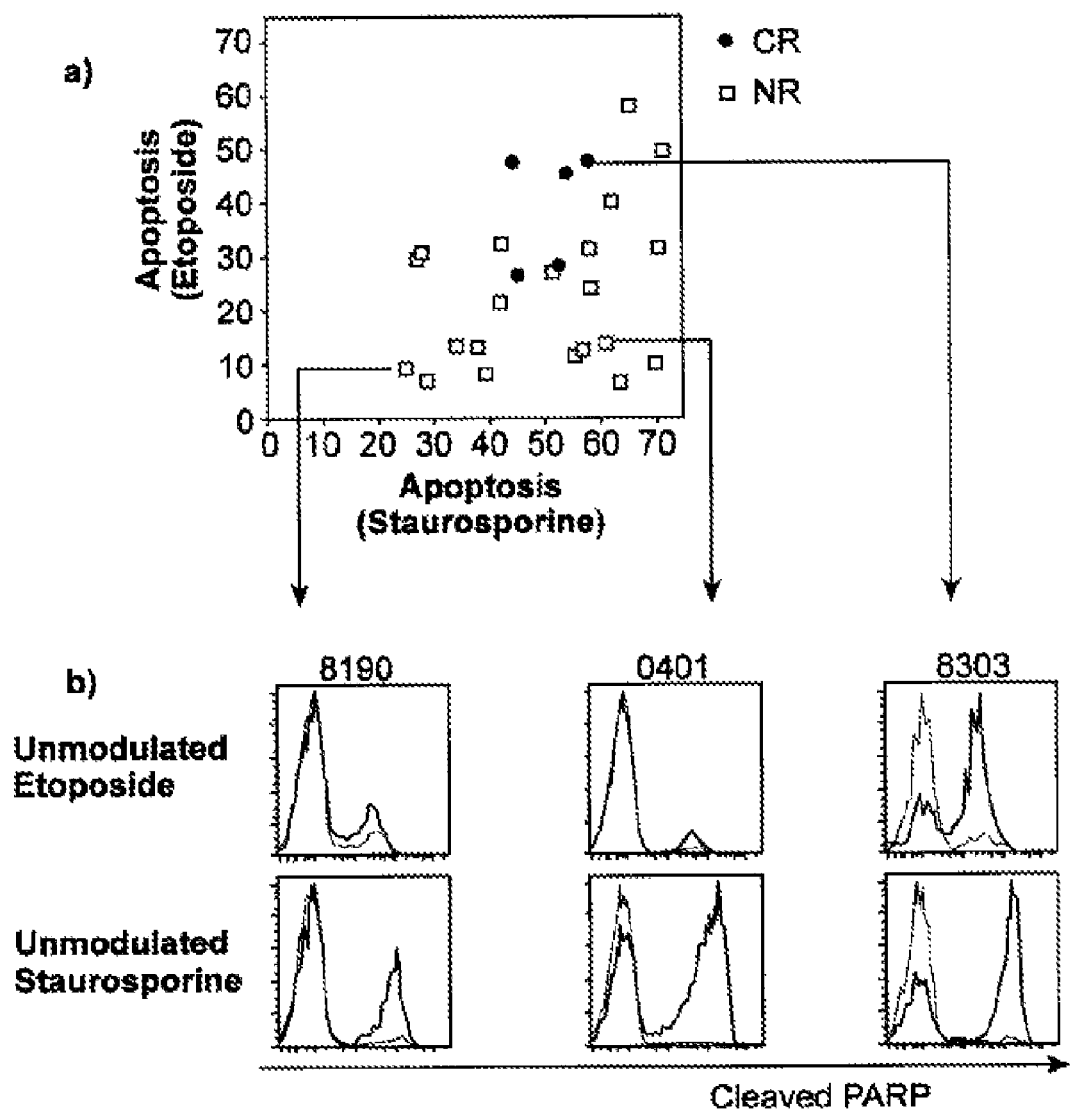
FIG. 30(a) is a scatter plot comparing etoposide versus staurosporine-mediated apoptosis.
FIG. 30(b) contains distribution plots that illustrate sample-specific differences in sensitivity to etoposide and staurosporine-mediated apoptosis.

Staurosporine induced apoptosis responses were evaluable in 26/33 of the AML samples. FIG. 30(a) is a scatter plot comparing etoposide versus staurosporine-mediated apoptosis. FIG. 30(a) shows percentage of cells within an AML sample undergoing apoptosis and for no sample was this value 100% at the time points chosen in this study. All samples with blast subsets refractory to in vitro etoposide exposure, regardless of their staurosporine response, were derived from the NR patient sample subgroup. Apoptosis responses identified all CR patients as apoptosis competent to both agents. However, a negative apoptotic response could not predict all NR patients, underscoring the fact that in vitro responses alone to apoptosis stimulating agents are only part of the equation that describes a clinical outcome.

FIG. 30(b) shows examples of different response profiles for different AML samples (both NR and CR) in response to Etoposide or Staurosporine. Notably some samples were sensitive to staurosporine yet refractory to etoposide (UHN_0401). This implies that the apoptotic machinery per se was intact in these cells and that the resultant refractory response to etoposide could be the result of ineffective communication between the machinery of the DDR with that of apoptosis (exemplified by sample UHN_0401). Other categories of response shown are relative refractoriness to both agents (exemplified by sample UHN_8190) or responsiveness to both agents (exemplified by sample UHN_8303). Treatment with distinct apoptosis inducing agents revealed distinct percentages of apoptotic (c-PARP+) and non-apoptotic (c-PARP−) subpopulations of cells within an individual AML sample. This indicates that within an AML sample there are blast cell subsets with different sensitivities to each agent.

Figure 31:
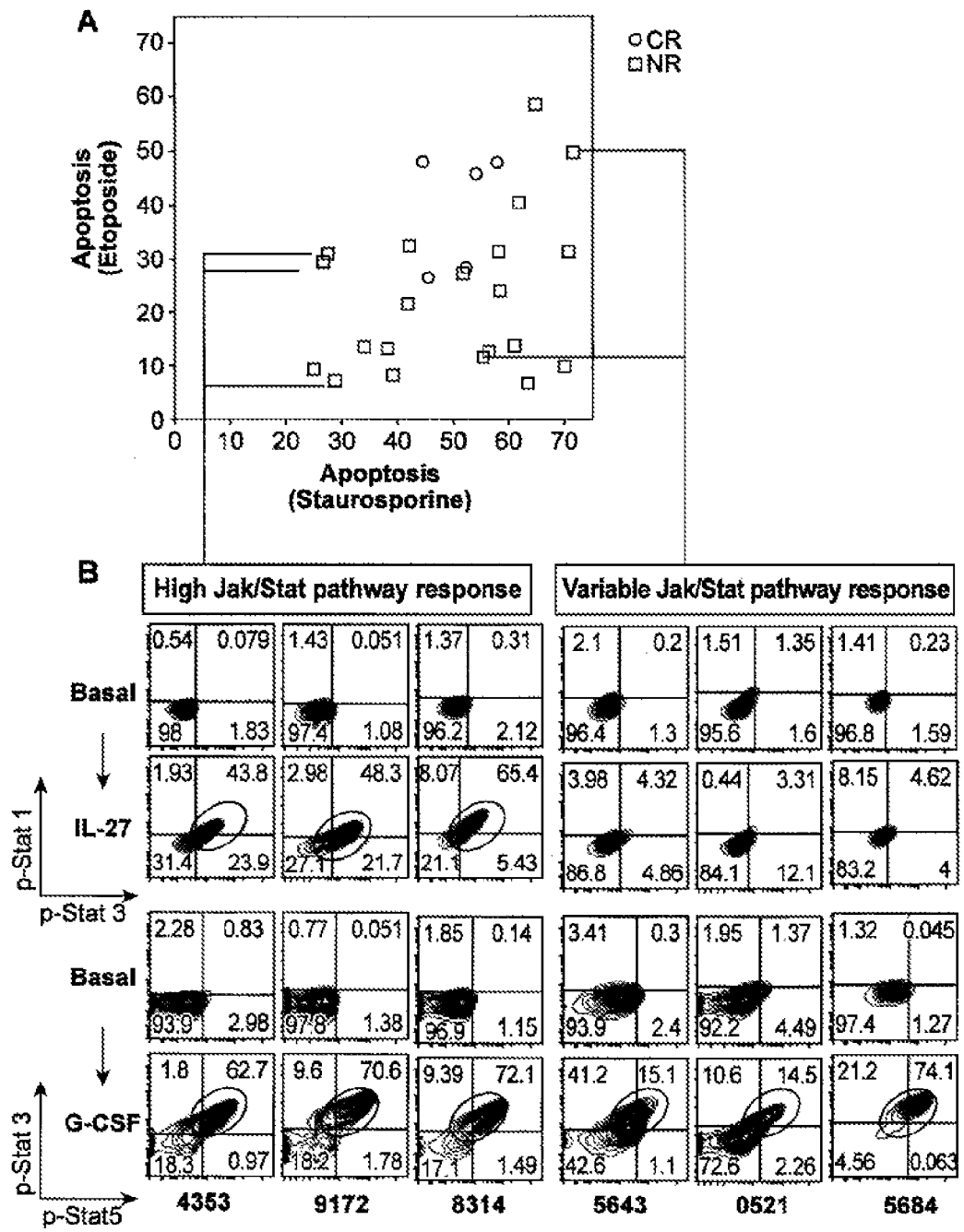
FIG. 31(a) illustrates the selection of staurosporine refractory and responsive cells.
FIG. 31(b) contains scatter plots which illustrate IL-27-induced and G-CSF-induced Stat signaling responses in the staurosporine outliers.
FIG. 31(c) contains scatter plots that compare a principle component representing Stat pathway activity (derived from PCA of the nodes associated Stat pathway).
FIG. 31(d) tabulates the Pearson and Spearman correlations between staurosporine response and individual nodes.
Figure 31:
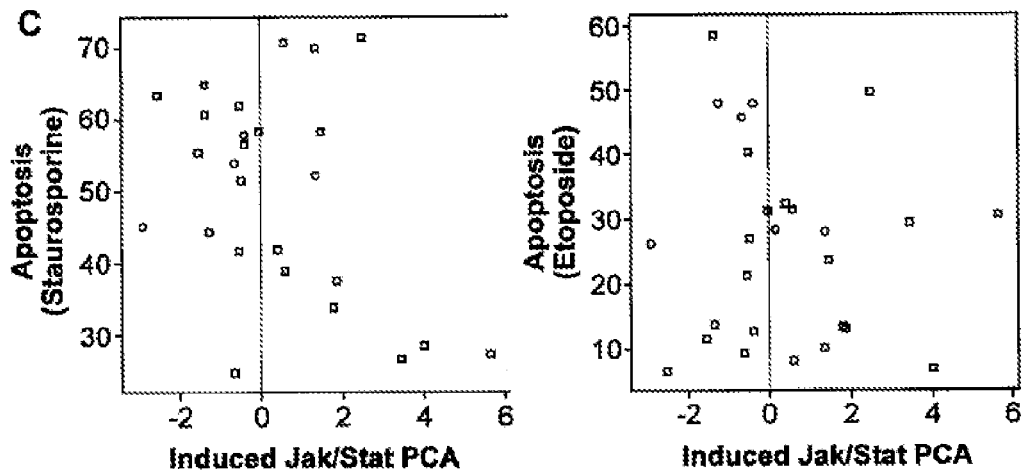

Associations Between In Vitro Apoptosis Profiles and Jak/Stat and PI3K Pathway Activity The Jak/Stat and PI3K pathway activities observed in leukemic samples were further analyzed in the context of the in vitro apoptotic responses illustrated in FIG. 30(a). FIG. 31(a) illustrates the selection of staurosporine refractory and responsive cells. FIG. 31(b) contains scatter plots which illustrate IL-27-induced and G-C SF-induced Stat signaling responses in the staurosporine outliers. FIG. 31(c) contains scatter plots that compare a principle component representing Stat pathway activity (derived from PCA of the nodes associated Stat pathway). FIG. 31(d) tabulates the Pearson and Spearman correlations between staurosporine response and individual nodes.

As shown in FIG. 31(b), Jak/Stat signaling responses were of variable magnitude for samples with relatively low or high responsiveness to etoposide as well as samples that were sensitive to staurosporine (UHN_5643, UHN_0521, UHN_5684 and (C)). In the four samples with the lowest relative response (relative refractoriness) (UHN_4353, UHN_9172, UHN_8314) to staurosporine, Jak/Stat pathway responses were augmented.

The Pearson and Spearman coefficients tabulated in FIG. 31(d) demonstrated a statistically significant negative correlation between staurosporine induced apoptosis and Jak/Stat signaling in this AML sample set, with outliers clearly apparent. Statistical significance was found for the Jak/Stat PCA value with even greater statistical significance observed for individual nodes such as IL-6 or IL-27 induced Stat signaling.

Pearson and Spearman coefficients revealed a lack of correlation for Jak/Stat signaling with etoposide response.

Figure 32:
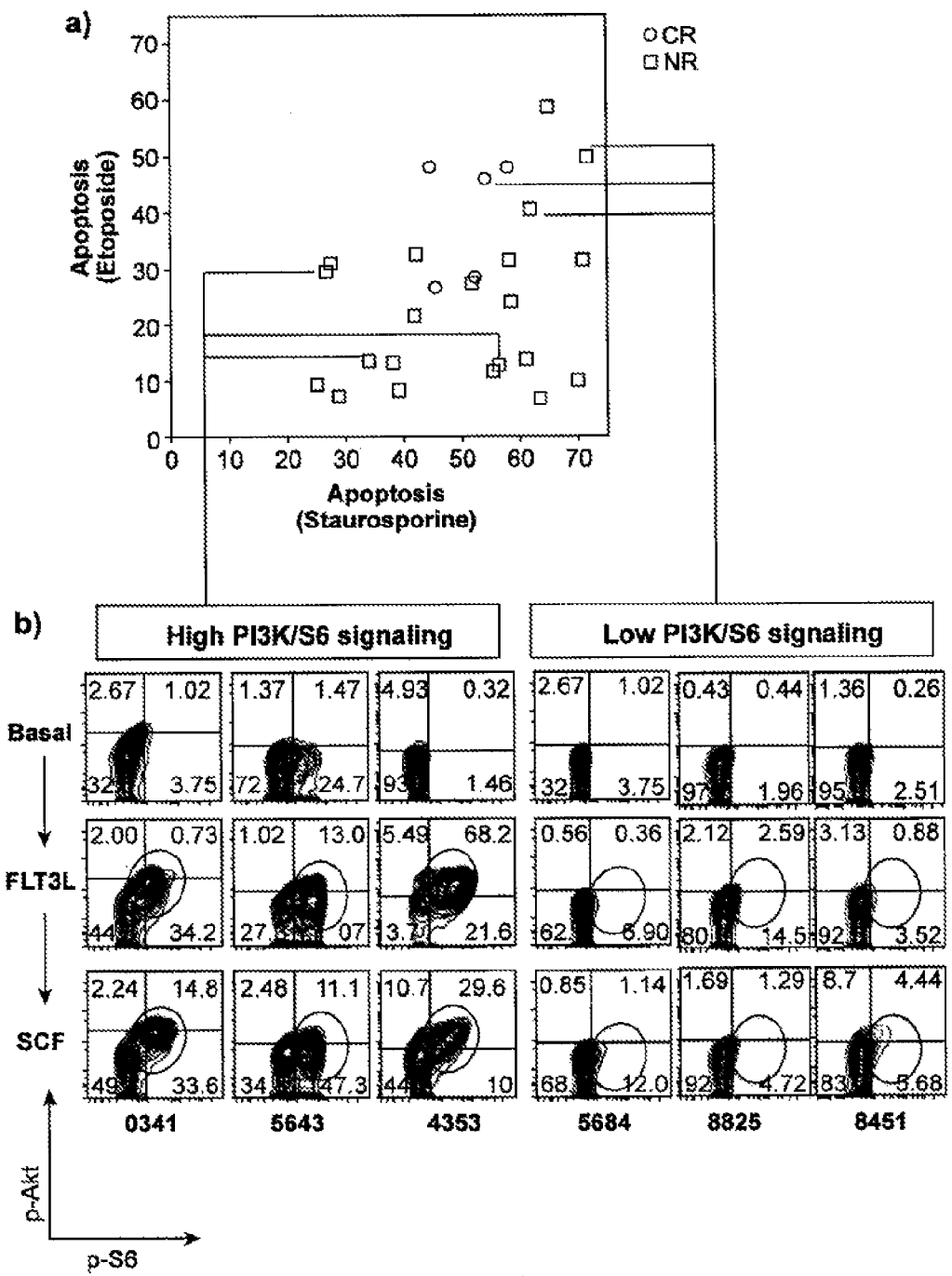
FIG. 32(a) illustrates the selection of etoposide and staurosporine refractory and responsive cells.
FIG. 32(b) contains scatter-plots which illustrate FLT3-induced and SCF-induced PI3K signaling response samples with high or low apoptosis responses to etoposide and staurosporine.
FIG. 32(c) contains scatter-plots that compare a principle component representing PI3K pathway activity (derived from PCA of the nodes associated PI3K pathway).
FIG. 32(d) tabulates the Pearson and Spearman correlations between staurosporine/etoposide response and individual nodes in the PI3K pathway.
Figure 32:
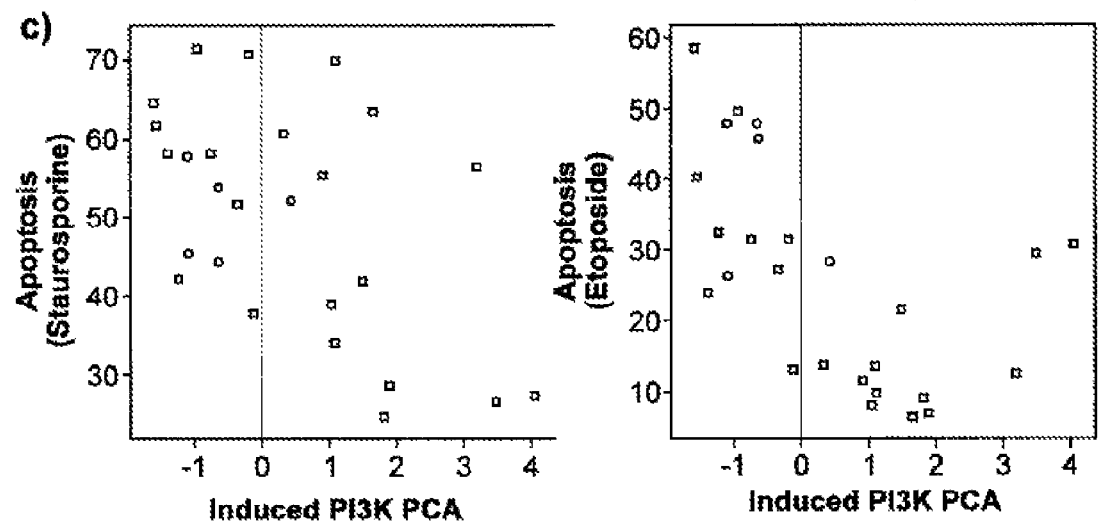

The PI3K pathway activities observed in leukemic samples were further analyzed in the context of the in vitro apoptotic responses illustrated in FIG. 30(a). FIG. 32(a) illustrates the selection of etoposide and staurosporine refractory and responsive cells. FIG. 32(b) contains scatter-plots which illustrate FLT3-induced and SCF-induced PI3K signaling response samples with high or low apoptosis responses to etoposide and staurosporine. FIG. 32(c) contains scatter-plots that compare a principle component representing PI3K pathway activity (derived from PCA of the nodes associated PI3K pathway). FIG. 32(d) tabulates the Pearson and Spearman correlations between staurosporine/etoposide response and individual nodes in the PI3K pathway.

As shown in FIG. 32(b), we observed an inverse correlation between levels of growth factor (SCF and FLT3L) and chemokine (SDF-1α)-mediated-p-Akt and p-S6 signaling and in vitro apoptotic response as characterized through etoposide and staurosporine. The Pearson and Spearman correlation coefficients tabulated in FIG. 32(d) demonstrate that this relationship is statistically significant. FIG. 32(d) demonstrates that the PCA metric for induced PI3K pathway activity has better negative correlation with staurosporine and etoposide response than individual node/metrics. These results confirm that PCA is a valuable tool for capturing signaling heterogeneity that may correlate to, or predict, clinical response.

The scatter-plots in FIG. 32(b) demonstrate that induced PI3K pathway signaling tended to be lower for samples that were apoptosis proficient to both etoposide and staurosporine (UHN_5684, UHN_8825 and UHN_8451). As shown in FIG. 32(b), greater induced p-Akt and p-S6 levels were observed in samples refractory to staurosporine and/or etoposide (UHN_0341, UHN_5643 and UHN_4353).

When taken together, trends for apoptosis, Jak/Stat and PI3K pathway activities (FIGS. 30, 31, and 32) and clinical outcomes suggest that there are limited number of signaling pathway profiles associated with CR patients (i.e. CR patients are homogeneous in signaling), whereas in NR patients many different pathway mechanisms may have evolved for the leukemia to be refractory to chemotherapy (i.e. NR patients are heterogeneous in signaling). All samples from CR patients had blast cell subsets that were sensitive to in vitro staurosporine and etoposide-mediated apoptosis and in general had low Jak/Stat and PI3K pathway responses. Most clinical NR samples that were competent to undergo in vitro apoptosis had an absent or low PI3K response, suggesting that other pathways could be contributing to refraction to therapies that induce apoptosis. All other NR samples were refractory to in vitro etoposide and/or staurosporine exposure with different degrees of elevated Jak/Stat and/or PI3K pathway activation. Since PCA metrics of pathway activation had a clear correlation with apoptotic response, which in turn was predictive of therapeutic response (CR/NR), it can be inferred that PCA metrics of pathway activation provide another valuable metric that can be used to stratify patients as to their clinical response type, but also to further stratify and biologically characterize NR patients according to heterogeneity underlying the disease.

Associations Between In Vitro Apoptosis Profiles and Cell Subpopulations

Analysis of CD33 and CD45 surface expression of all samples within this AML cohort defined three patient samples with two distinguishable leukemic cell subpopulations, referred to as Blast 1 and Blast 2. In all cases, Blast 1 was defined as a cell subset with higher CD33 and CD45 levels, whereas Blast 2 cells had lower levels of these surface proteins. Given the distinct signaling profiles identified for cell subsets within samples harboring only one myeloid blast population as defined by CD33 and CD45 expression, in the preceding data of this study, it seemed likely that samples harboring two myeloid blast populations could harbor distinct signaling profiles.

Figure 33:
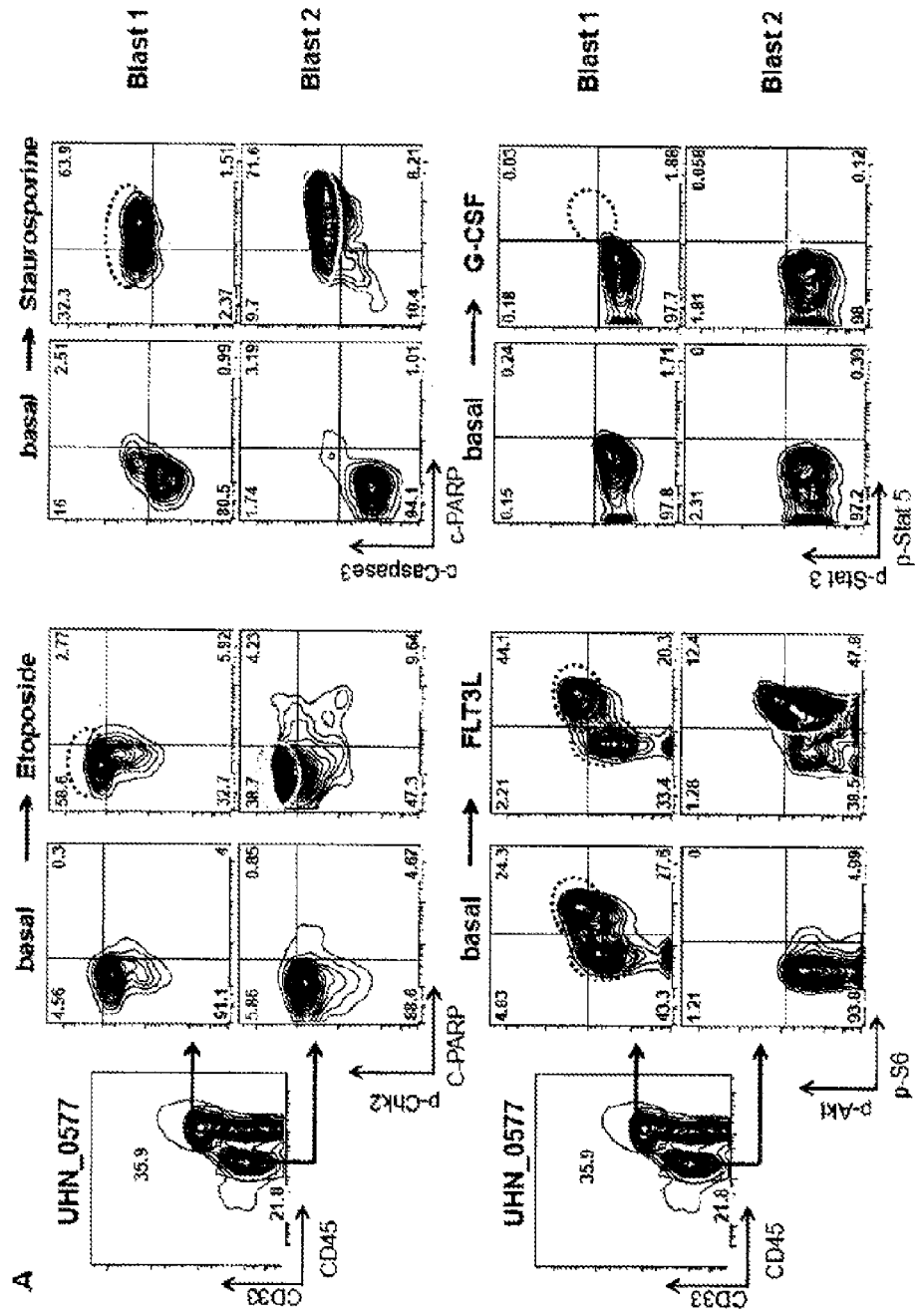
FIG. 33(a) and FIG. 33(b) contain distribution plots that illustrate distinct subpopulations of AML samples and the differences in Etoposide, Staurosporine, FLT3L and G-CSF-induced signaling between the distinct subpopulations of AML.
Figure 33:
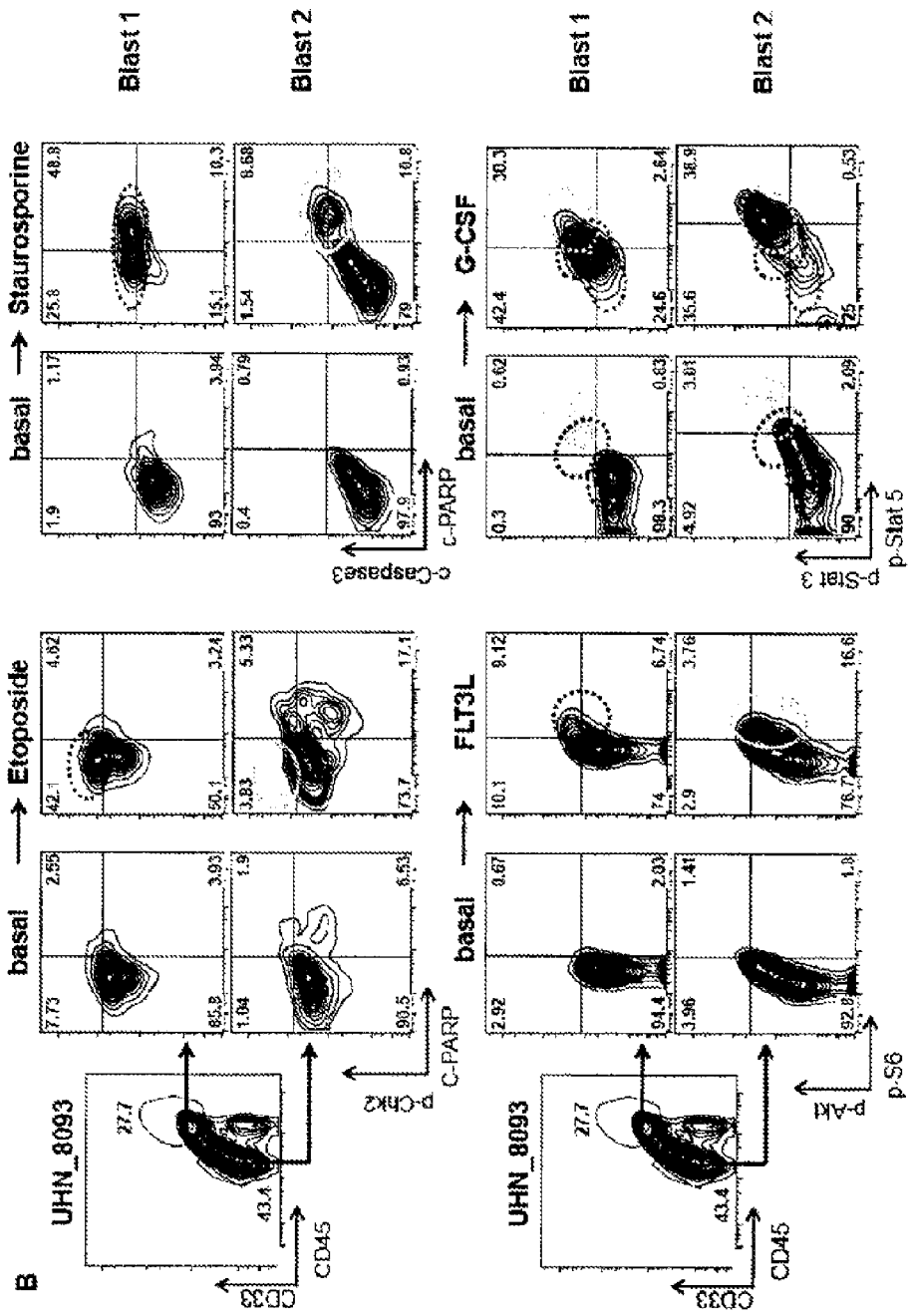

SCNP revealed distinguishable signaling responses within individual cells in each blast population measured simultaneously. FIGS. 33(a) and 33(b) include the data from two of the three samples with available data for signaling and apoptosis nodes, both from NR patients. FIG. 33(a) demonstrates that blast populations 1 and 2 from sample UHN_0577 were refractory to etoposide-mediated apoptosis although both populations exhibited DDR, albeit to different magnitudes as seen by the frequencies of blasts with increased phosphorylation of p-Chk2. Exposure of the samples to staurosporine revealed that the apoptotic machinery was intact in both blast populations suggesting that etoposide refractoriness was the result of disabled communication between DDR and the apoptotic machinery. Comparison of each blast subset for its response to G-CSF revealed minimal increases in p-Stat3 and p-Stat5. However, inspection of the PI3K path-way revealed that Blast 1, but not Blast 2 had two discernible blast cell subsets with different levels of p-Akt and p-S6 in the basal state. Blast 2 had only one "low" level p-Akt and p-S6 blast cell subset. Furthermore, in Blast 1, FLT3L was able to induce both p-Akt and p-S6 signaling in the "low level" basal population. In contrast, for Blast 2 the predominant response to FLT3L was an increase in p-S6 alone. Using the metric of "total" as a measure of overall pathway activity, there was greater overall pathway activity for Blast 1 than for Blast 2 in both the basal and FLT3L-potentiated states reflecting significant contributions of both basal and evoked signaling responses.

As shown in FIG. 33(b), the two blast populations in sample UHN_8093 were both refractory to etoposide possibly through different mechanisms since there was a greater p-Chk2 response in Blast 1 and a reduced DDR in Blast 2. Blast 1 was very responsive to staurosporine which indicated that the apoptotic machinery is intact and that the etoposide refractoriness in Blast 1 could be accounted for by failure of DDR to communicate with the apoptotic machinery. In contrast, Blast 2 was refractory to staurosporine-mediated apoptosis. Notably, in Blast 2 G-CSF mediated greater increases in phosphorylated Stat3 and Stat5 compared to the increases seen in Blast 1. This was reflected by both the "fold" and "total" metrics. Inspection of PI3K pathway activity revealed that only a small blast cell subset responded to FLT3L treatment with the majority of cells remaining unresponsive. These data suggest that the higher activity seen for the Jak/Stat pathway for Blast 2 may account for its refractoriness to in vitro apoptosis and non-response in the clinic consistent with the data in FIG. 31.

Discussion

The current study was designed to determine whether heterogeneity in individual AML samples can be characterized based on in vitro functional performance tests using SCNP to measure survival pathways, DDR and in vitro apoptosis. The major findings were that: (i) an individual sample can be comprised of leukemic blast subsets with distinct Jak/Stat, PI3K, DDR and apoptosis pathway responses, (ii) exposure of samples to modulators allowed these pathway responses to be revealed, (iii) PI3K pathway activity was high in most samples that were refractory to apoptosis-inducing agents in vitro, (iv) Jak/Stat pathway activity was high in samples refractory to staurosporine but only in some samples refractory to etoposide, (v) in vitro DDR and apoptosis profiles were variable in leukemic blasts between different samples and also within the same sample and (vi) SCNP of the pathways chosen reveal a restricted number of profiles for AML blasts from CR patients and multiple profiles for AML blasts from NR patients.

Thus, responders to chemotherapy demonstrated little variation in the signaling potential of the pathways evaluated (that is, cells remained relatively unperturbed by environmental stimuli applied). As such, in the CR samples both the potentiated responses to myeloid activators of the Jak/Stat and PI3K pathways, as well as "basal" pathway activity tended to be low whereas DDR with subsequent apoptosis was robust after in vitro etoposide exposure. By contrast, robust Jak/Stat and PI3K responses were revealed in most NR samples. These data are consistent with, and expand upon previous findings linking functional alterations in Jak/Stat signal transduction with poor response to chemotherapy in AML patients. In addition, all samples with impaired DDR or proficient DDR without subsequent apoptosis were NRs. A subset of NR samples were competent to undergo in vitro apoptosis and had low PI3K and Jak/Stat pathway responses suggesting that in these samples alternative pathways could be contributing to clinical refractoriness to chemotherapy.

This study used 34 diagnostic PBMC samples taken from patients for which clinical out-comes were blinded. However, the sample set was unintentionally biased with samples predominantly from NR, female patients of younger age with intermediate cytogenetics. In spite of these limitations, univariate analysis of this sample set and an independent sample set from a separate institution revealed common nodes for CR and NR stratification suggesting that survival, DDR and apoptosis pathways may be relevant ways to characterize AML disease subtypes.

The data suggest that while DDR, Jak/Stat, and PI3K pathways might serve as useful indicators of the biological underpinnings of therapeutic responses, additional inquiry or pathways might be required to more fully complete the characterization of response. The proliferative and survival properties of the Jak/Stat and PI3K pathways most likely play a central role in AML leukemogenesis as well as in refractoriness and resistance to clinically used DNA damaging agents. For instance, Stat transcription factors are known to play a critical role in normal and leukemic hematopoiesis targeting transcription of genes involved in prolife-ration, survival and differentiation. Receptors that signal through Stat3 and Stat5 are present on AML blasts where they can be activated by a wide variety of growth factors, interleukins and cytokines. Furthermore, in a recent study, the level of Stat5 transcriptional activity was shown to regulate the balance between proliferation and differentiation in hematopoietic stem cells/progenitor cells by activating specific genes associated with these processes. The same group showed that high levels of Stat5 activity disrupted myelopoiesis. In the current study, CR samples showed low or absent Jak/Stat responses and a subset of NR samples showed high magnitudes of Jak/Stat responses while the remaining NRs displayed a continuum of responses. These data suggest that certain levels of Stat activity may be necessary to generate the appropriate transcriptional program necessary for maintaining a particular clonal state of an AML blast cell subset.

In addition, deregulation of the PI3K/mTor signaling pathway has been described in 50-80% of AML cases contributing to the survival and proliferation of AML blast cells. Many causes for pathway deregulation have been cited such as activating mutations in FLT3 and Kit receptors, overexpression of the PI3K class 1A p110δ isoform as well as gain of function mutations in N- and K-Ras. In this study, PI3K pathway activity was determined by measuring levels of p-Akt and p-S6 ribosomal protein as pathway readouts in response to myeloid modulators, FLT3L, SCF and SDF-1α. Consistent with its role in cancer cell survival, potentiated levels of p-Akt and p-S6 were lower in CRs and elevated in clinical NRs, although the two clinical categories were not mutually exclusive since several NR samples had low potentiated PI3K pathway activity.

Moreover, alternative mechanisms of refractoriness could arise from increased DDR, failure to undergo DDR and/or inoperative communication between DDR and apoptosis. For a response to a DNA damaging agent, DNA lesions recruit multi-protein DNA damage sensor complexes that associate with DNA damage transducer proteins such as ataxia telangectasia mutated (ATM), a kinase which upon activation phosphorylates Thr68 (T68) of the checkpoint kinase Chk2. The resultant delay in cell cycle progression provides cells with a chance to repair the DNA damage. If repair fails, cells undergo apoptosis. In this study three DDR/apoptosis profiles distinguished AML samples. In the first, minimal p-Chk2 response was observed and consequently no apoptotic response. In the second profile there seemed to be a failure for DDR to translate into apoptosis and in the third, DDR, apoptosis and their communication was intact. Notably, all clinical responsive patients fell into this latter category. Further sample cohorts are needed to see whether this association between in vitro apoptotic sensitivity and clinical response holds, potentially providing a valuable means for predicting clinical outcomes.

The robust activation of two major survival pathways shown in a subset of AML samples provided a rationale for evaluating apoptotic proficiency in this sample cohort. In vitro exposure of samples to etoposide and staurosporine, two agents that induce apoptosis by different mechanisms, identified distinct blast subsets with different responses to each agent between individual samples and also within the same sample. Samples sensitive to both agents were taken from CR patients. However, this apoptotic proficiency was also observed in some NR patient samples. There are several explanations to account for the unexpected in vitro apoptotic response of NR samples, principally that the in vitro apoptotic responses were not measured with the drugs used clinically (Ara-C/Daunorubicin) by which the NRs were categorized. Further, although Etoposide, Ara-C and Daunorubicin all induce DNA damage they have different mechanisms of action and are substrates for different transporters and thus might not mimic the in vivo responses. It is also possible that the AML biology characterized for these samples is not represented by clinical definitions of NR and CR. Furthermore, in all cases, only a fraction of cells undergo apoptosis and the phenotype of the non-responding cells may account for the apparent disconnect between apoptosis seen in vitro versus the clinical NR.

In order to understand whether there was a link between signaling by survival pathways and in vitro apoptotic responses, correlations were computed. When evaluated for Jak/Stat and PI3K pathway activity, most samples refractory in vitro to either or both etoposide and staurosporine had a cell subset that displayed potentiated PI3K signaling. In contrast, samples refractory to staurosporine displayed elevated Jak/Stat pathway activity whereas there were variable levels of Jak/Stat pathway activity across a range of etoposide induced responses. Given the fine balance between levels of p-Stat 5 that, via a transcriptional program in vivo, regulate blast cell proliferation versus disruption of differentiation, the in vitro experimental conditions utilized here may not have allowed these more subtle changes to be observed between Stat activity and DDR induced apoptosis. It is very likely that these two common survival pathways are playing a major role in conferring refractoriness to chemotherapy, but that alternative, as yet unrevealed, pathways also make a contribution.

Several AML samples within this cohort had two blast cell populations discernible by their surface phenotype suggestive of cell populations representing different stages of differentiation. Of the two samples described in this manuscript, SCNP revealed that each blast cell population had its own distinct signaling and apoptosis profiles. Given the opportunity to apply SCNP assays to samples taken over time from the same patient it may be possible to determine which blast population confers refractoriness to chemotherapy.

Further correlations to defined genetic abnormalities driving these signaling observations could underscore their potential roles in driving AML disease; such as analysis of intracellular signaling pathways in the context of FLT3 mutational status. The output from such studies could be to guide the choice of available investigational and approved agents to provide benefit for AML patients refractory to current chemotherapy regimens.

These data also demonstrate the applicability and utility of using principle component analysis as a metric that can be used to stratify patient data according to signaling pathway response. However, these data also suggest accuracy of stratification can be improved by first identifying distinct sub-populations of AML blasts. For example, the diversity of different signaling pathway responses in NR AML was observed not only within a heterogeneous of samples but also within the same blast from a sample. Likewise, different sub-populations of cells in a single sample demonstrated different sensitivities to apoptosis, as demonstrated in FIG. 30(b). Therefore, these results demonstrate the applicability of sequential analyses such as decision trees or gating analyses, to AML sample data in order to identify and characterize variation in signaling pathway response in distinct sub-populations of heterogeneous AML samples. The identified signaling pathway responses may then be statistically associated with apoptosis profiles that can be used to inform patient treatment.

Samples associated with a multiplicity of sub-populations with different signaling pathway responses can be further characterized according to the relative amounts of each sub-populations (e.g. by a percentage values or ratios). Reports may be generated for physicians that characterize the sub-populations of an AML sample, their relative amounts and the unique biology (e.g. mutational status, signaling mechanisms, etc.) allowing physicians to make informed treatment decisions based on the heterogeneity of the patient's leukemia.

Example 11

SCNP assays were performed on 77 bone marrow samples from pediatric AML patients enrolled in POG trial 9421 of which 67 were evaluable/had sufficient data for analysis and were enriched for non-responders (NR). 80 combinations of modulators and intra-cellular proteins (signaling nodes) were investigated including nodes involved in the phosphoinositide 3-kinase (PI3K), Janus Kinases (JAK), signal transducers and activators of transcription (STAT) and the DNA damage response and apoptosis pathways. Basal and modulated protein levels in leukemic blasts were measured using several metrics (e.g., fold change, total level of phosphorylation, and a rank based method Uu measuring the proportion of cells that shift from baseline), and nodes were examined in univariate and multivariate analyses for their ability to discriminate between AML responsive (CR, n=46) and non-responsive (NR, n=21) to anthracycline/cytarabine-based induction therapy. Furthermore, nodes were examined for their ability to identify patients likely to be in complete continuous remission (CCR, n=23) or relapse (CR-Rel, n=23) within 4 years. Univariate analysis revealed 19 nodes associated with disease response to conventional induction therapy and 9 associated with CR-Rel (i.e., area under the operator/receiver curve (AUC of ROC)>0.65; p<0.05). As in adult studies, nodes involved in the apoptotic response to agents inducing DNA damage (e.g., etoposide→c-PARP AUC 0.83, AraC+Daunorubicin→c-PARP AUC 0.76, AraC+Daunorubicin→p-Chk2 AUC 0.71) showed higher levels of apoptosis in CR samples than in NR samples. Similarly, FLT3 and SCF phosphorylation levels of PI3K pathway members S6 (AUC 0.70) and ERK (AUC 0.65) were also higher in CR samples, while hydrogen peroxide as a modulator (acting either as a reactive oxygen species or as a phosphatase inhibitor) revealed lower p-Akt and p-PLC gamma levels in NR samples (AUC 0.70 for both). In multivariate analysis combination of 2-8 nodes (representing apoptosis, Jak/Stat and PI3K pathways) resulted in classifiers with good performance characteristics (bootstrap adjusted AUC 0.84-0.88) in predicting response to induction therapy. Increased sensitivity to etoposide and anthracycline/cytarabine was also associated with CCR in univariate analysis (AUC 0.77 and 0.68 respectively). Thapsigargin, a modulator known to raise intracellular calcium, induced p-Erk, p-CREB and p-S6 less in CR-Rel than in CCR samples. To predict the response to therapy, multivariate classifiers were better than individual nodes at discriminating between CR-Rel and CCR groups (adjusted AUC>0.8). Additional analyses that evaluate independence and ability to combine clinical or molecular predictors (e.g., cytogenetics, FLT3-ITD) with SCNP data will be presented. Tables 32 and 33 show important nodes for stratifying pediatrics patients into CR vs. NR (Table 32) and relapse (Table 33).

TABLE 32

Important Nodes for stratifyng CR vs. NR

| Node | Importance |
|---|---|
| Etoposide*1440_0_*1*0.1_DMSO*Cleaved PARP_D214_*Blue_E-A*Uа | 1.351 |
| Thapsigargin*15_0_*5*0.05_DMSO*p-ERK 1/2_T202/Y204_*Red_C-A*AdjFoldP1 | 0.633 |
| IL-27*15_0_*3*None*p-Stat3_S727_*Blue_D-A*AdjFoldP1 | 0.539 |
| G-CSF*15_0_*3*None*p-Stat3_S727_*Blue_D-A*AdjFoldP1 | 0.532 |
| Unstim/No Modulator*1440_0_*1*None*Cleaved PARP_D214_*Blue_E-A*Uа | 0.511 |
| Ara-C+Daunorubicin-HCl*1440_0_+1440_0_*1*None*Cleaved PARP_D214_*Blue_E-A*Uа | 0.489 |
| Staurosporine*360_0_*2*0.05_DMSO*Cleaved PARP_D214_*Blue_E-A*Uа | 0.456 |
| Etoposide*1440_0_*1*0.1_DMSO*Cleaved PARP_D214_*Blue_E-A*Uu | 0.449 |
| GM-CSF*15_0_*3*None*p-Stat3_S727_*Blue_D-A*AdjFoldP1 | 0.404 |

TABLE 32-continued

Important Nodes for stratifyng CR vs. NR

| Node | Importance |
|---|---|
| IL-27*15__0__*3*None*p-Stat1__Y701__*Blue__E-A*AdjFoldP1 | 0.373 |
| SCF*15__0__*7*None*p-ERK 1/2__T202/Y204__*Blue__D-A*AdjFoldP1 | 0.369 |
| FLT-3 Ligand*15__0__*7*None*p-S6__S235/236__*Blue__E-A*AdjFoldP1 | 0.364 |
| Hydrogen Peroxide*15__0__*4*None*p-Akt__S473__*Blue__E-A*Ua | 0.353 |
| FLT-3 Ligand*5__0__*7*None*p-S6__S235/236__*Blue__E-A*AdjFoldP1 | 0.349 |
| G-CSF*15__0__*3*None*p-Stat5__Y694__*Red__C-A*AdjFoldP1 | 0.341 |
| Hydrogen Peroxide*15__0__*4*None*p-Akt__S473__*Blue__E-A*AdjFoldP1 | 0.332 |
| Hydrogen Peroxide*15__0__*4*None*p-SLP-76__Y128__*Red__C-A*AdjFoldP1 | 0.305 |
| Ara-C+Daunorubicin-HCl*360__0__+360__0__*1*None*p-Chk2__T68__*Red__C-A*Ua | 0.303 |
| IL-27*15__0__*3*None*p-Stat5__Y694__*Red__C-A*AdjFoldP1 | 0.288 |
| IL-10*15__0__*3*None*p-Stat3__S727__*Blue__D-A*AdjFoldP1 | 0.285 |
| IFN-a-2b*15__0__*3*None*p-Stat3__S727__*Blue__D-A*Ua | 0.261 |
| FLT-3 Ligand*15__0__*6*None*p-Stat3__Y705__*Blue__D-A*AdjFoldP1 | 0.26 |
| G-CSF*15__0__*3*None*p-Stat3__S727__*Blue__D-A*Ua | 0.255 |
| Unstim/No Modulator*360__0__*1*None*p-Chk2__T68__*Red__C-A*Ua | 0.246 |
| Unstim/No Modulator*0*1*0.1__DMSO*Cleaved PARP__D214__*Blue__E-A*Ua | 0.243 |

TABLE 33

Important nodes for stratifying CR-Rel vs. CCR

| Node | Importance |
|---|---|
| G-CSF*15__0__*3*None*p-Stat5__Y694__*Red__C-A*AdjFoldP1 | 0.458 |
| Unstim/No Modulator*360__0__*1*None*Cleaved PARP__D214__*Blue__E-A*Ua | 0.422 |
| Unstim/No Modulator*360__0__*1*0.1__DMSO*Cleaved PARP__D214__*Blue__E-A*Ua | 0.379 |
| Thapsigargin*15__0__*5*0.05__DMSO*p-CREB__S133__*Blue__D-A*AdjFoldP1 | 0.366 |
| Etoposide*360__0__*1*0.1__DMSO*Cleaved PARP__D214__*Blue__E-A*Ua | 0.365 |
| Etoposide*360__0__*1*0.1__DMSO*Cleaved PARP__D214__*Blue__E-A*Uu | 0.356 |
| Thapsigargin*15__0__*5*0.05__DMSO*p-ERK 1/2__T202/Y204__*Red__C-A*AdjFoldP1 | 0.319 |
| IL-3*15__0__*3*None*p-Stat5__Y694__*Red__C-A*Ua | 0.316 |
| Thapsigargin*15__0__*5*0.05__DMSO*p-S6__S235/236__*Blue__E-A*Ua | 0.306 |
| G-CSF*15__0__*3*None*p-Stat1__Y701__*Blue__E-A*AdjFoldP1 | 0.305 |
| IL-3*15__0__*3*None*p-Stat3__S727__*Blue__D-A*AdjFoldP1 | 0.299 |
| Unstim/No Modulator*0+0*9*None*CXCR4*Blue__E-A*RelExpr | 0.298 |
| IL-27*15__0__*3*None*p-Stat5__Y694__*Red__C-A*AdjFoldP1 | 0.292 |
| G-CSF*15__0__*3*None*p-Stat5__Y694__*Red__C-A*Ua | 0.249 |
| Thapsigargin*15__0__*5*0.05__DMSO*p-S6__S235/236__*Blue__E-A*AdjFoldP1 | 0.248 |
| IL-27*15__0__*3*None*p-Stat3__S727__*Blue__D-A*AdjFoldP1 | 0.232 |
| GM-CSF*15__0__*3*None*p-Stat5__Y694__*Red__C-A*Ua | 0.232 |
| Ara-C+Daunorubicin-HCl*360__0__+360__0__*1*None*Cleaved PARP__D214__*Blue__E-A*Ua | 0.224 |
| Staurosporine*360__0__*2*0.05__DMSO*Cleaved PARP__D214__*Blue__E-A*Uu | 0.218 |
| GM-CSF*15__0__*3*None*p-Stat3__S727__*Blue__D-A*AdjFoldP1 | 0.217 |
| SCF*5__0__*7*None*p-S6__S235/236__*Blue__E-A*AdjFoldP1 | 0.216 |
| IL-10*15__0__*3*None*p-Stat5__Y694__*Red__C-A*AdjFoldP1 | 0.213 |
| IL-27*15__0__*3*None*p-Stat1__Y701__*Blue__E-A*AdjFoldP1 | 0.212 |
| IL-27*15__0__*3*None*p-Stat5__Y694__*Red__C-A*Ua | 0.202 |
| GM-CSF*15__0__*3*None*p-Stat1__Y701__*Blue__E-A*AdjFoldP1 | 0.197 |

Conclusion: The training study data show the value of performing quantitative SCNP under modulated conditions as the basis for developing highly predictive tests for response to induction chemotherapy in pediatric patients with newly diagnosed AML. Independent validation studies will follow.

Example 12

Modulated single cell network profiling (SCNP) was used to evaluate the activation state of intracellular signaling molecules (i.e. nodes), including phosphorylated (p)-Akt, p-Erk, p-S6, p-Stat5 and cleaved-PARP, at baseline and after treatment with specific modulators [including cytokines (such as IL-27) growth factors (such as FLT3 ligand) and drugs (such a cytosine arabinoside)] in 7 healthy bone marrow mononuclear blasts (BMMb) and leukemic myeloblasts, characterized for FLT3 receptor mutation status, from 44 AML patients (38 FLT-WT and 6 FLT3-ITD), aged >60 years (ECOG trial E3999). A total of 64 node-metrics were analyzed.

Figure 35:
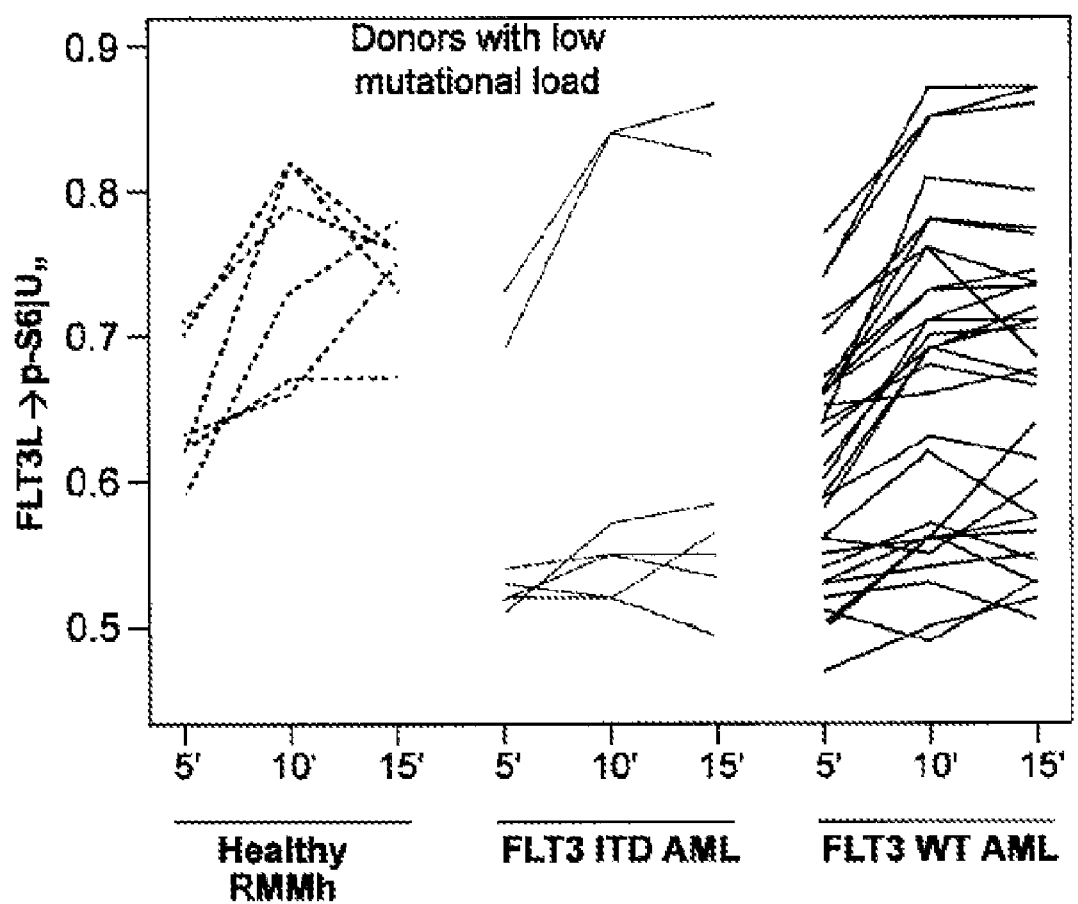
FIG. 35 depicts FLT3 Ligand induced signaling of p-S6 at 5, 10, and 15 min time points in healthy bone marrow myeloblast (BM Mb, and leukemic blast from AML donors with or without FLT3-ITD mutation.

Signaling profiles differed significantly in FLT3-ITD vs. FLT3-WT AML, and in FLT3-WT vs. BMMb (shown in FIG. 35 for a representative node, FLT3 ligand induced p-S6). Specifically, compared to BMMb, FLT3-ITD blasts uniformly showed increased basal p-Stat5 levels, decreased FLT3 ligand-induced activation of PI3K and Raf/Ras/Erk pathways, minimal IL-27 induced activation of the Jak/Stat pathway, and higher apoptotic responses to DNA-damaging agents. Two AMLs harboring a low FLT3-ITD mutant burden, however, exhibited a signaling pattern similar to FLT3-WT AMLs. By contrast, FLT3-WT samples displayed heterogeneous signaling profiles, overlapping both with those of FLT3-ITD and BMMb samples, suggesting that a fraction of FLT3-WT AML exhibit FLT3 receptor pathway deregulation even without FLT3-ITD. Conclusions This study showed that SCNP, which provides a detailed view of intracellular signaling networks at the single-cell level, subclassified patients with AML beyond their molecularly determined FLT3 mutation status. In particular, a fraction of FLT3-WT AML signaled as if containing a FLT3 receptor length mutation while FLT3-ITD with low mutational load signaled like FLT3-WT AMLs. The clinical relevance of this observation, both for disease prognosis and response to kinase inhibitors, will be revealed only if AML patients are accrued to kinase inhibition trials irrespective of FLT3 receptor mutation status. The wide range of signaling responses observed in FLT3-WT AML suggests that disease across FLT3-WT patients is heterogeneous, likely promoted through distinct mutations and alterations, giving rise to distinct signaling profiles in individual patients Our data also provide evidence for the co-existence of differentially signaling blast populations in individual patients. The potential impact of signaling heterogeneity on clinical response needs to be assessed and may require an individualized combination of treatment modalities.

Example 13

We combined signaling pathway analysis and drug response profiling in Acute Myeloid Leukemia (AML) samples using Single Cell Network Profiling (SCNP) assays. This technology allow for the simultaneous measurement of the activation state of multiple signaling proteins at the single cell level.

Cryopreserved peripheral blood mononuclear cell (PBMC) blood samples from patients with AML (N=6) were analyzed in two experimental arms. #1 Signaling Arm: The effect of various kinase inhibitors—tandutinib (Flt3); GDC-0941 (PI3Kinase); CI-1040 (MEK); CP-690550 (JAK3 and JAK2); and rapamycin (mTor)—on multiple signaling proteins in the JAK/STAT, MAPK, PI3K, and mTor pathways was measured in the basal and evoked condition (via 15 minutes growth factors stimulation) with various fluorochrome labeled phospho-specific antibodies in cell subsets defined by the expression of CD34, cKit, CD3, and light scatter properties. #2 Apoptosis/Cytostasis Arm: The leukemic cells were driven into cell cycle using IL-3, stem cell factor, and Flt3 ligand, followed by a 48-hr incubation with a combination of one to five aforementioned kinase inhibitors for a total of 30 treatments per sample. The TKIs impact was measured on distal functional readouts, including apoptosis (cleaved PARP) and cell cycle (CyclinB1-S/G2 phase; p-Histone H3-M phase). All results were compared with results from bone marrow samples from healthy donors (N=6).

Each patient's sample generated a unique signaling profile after short modulation with growth factors (SCF, Flt3L, IL-27, G-CSF) with a broad range of responses (e.g. the percentage of SCF, G-CSF and FLT-3L responsive cells ranged between 6%-49%, 3%-56%, and 3%-22% respectively). The magnitude of signaling (fluorescence change from basal state) was also quantified in multiple cell subsets defined by surface receptor expression. Overall, patient samples could be grouped based on their signaling profile, proliferative potential, and sensitivity to kinase inhibitor treatment. Specifically, two samples with the greatest SCF and G-CSF signaling response also showed the most robust in vitro proliferation and were most sensitive to the JAK inhibitor CP-690,550 (1 µM) (as measured by cytostasis readouts). Whereas, two other samples that displayed only modest SCF and G-CSF signaling, but robust Flt3 signaling expanded slowly in culture and were particularly sensitive to the cytostatic effects of GDC-0941 (1 uM) or tandutinib (1 uM), both as single agent and in combination. Finally, the last two AML samples had weak growth factor signaling and did not proliferate in culture and therefore could not be tested for drug induced cytostasis. Of note, each individual patient sample showed distinct sensitivity (as measured by cytostasis and apoptosis) to different drug combinations. This was in contrast to the bone marrow samples from healthy donors which showed considerable similarity in response across all inhibitor combinations.

This study provides data for the utility of SCNP to dissect the pathophysiologic heterogeneity of hematologic tumors and assess their differential response to single and combination therapies. Ultimately, this functional pathway profiling and drug sensitivity assay could be used in a clinical trial setting to stratify patients.

Example 14

To compare the results of SCNP assays between paired fresh and cryopreserved samples in a multicenter prospective study. 13 fresh BM and PB samples were prospectively collected from pediatric or adult non-M3 AML patients at 3 academic centers and shipped over night. Samples were required to have 2 million viable cells per aliquot for SCNP assays, and underwent ficoll separation and mononuclear cells were divided into 2 aliquots—one processed fresh, and the second cryopreserved for 1 month, and then thawed and processed for the SCNP assay. 70 SCNP node-metrics (i.e. proteomic readouts in the presence or absence of modulator), identified previously as candidate proteomic signatures for several assays in development (including PIK3, Jak/STAT and DNA damage/apoptosis pathways) were investigated. The assay readouts for blast cells from a fresh aliquot were compared to the results from a cryopreserved aliquot by linear regression, Bland-Altman, and Lin's concordance analysis.

The analysis of paired aliquots from 13 patients, with median WBC of 27.9 (3-60) 10e3/ul, showed that cryopreservation did not affect sample quality as measured by percent of cells that were negative for cleaved PARP expression ($R^2$=0.92 cryopreserved vs. fresh). The majority of unmodulated node-metrics (59%) and modulated node-metrics (68%, see Table) had a good correlation between the two preparations as measured by linear regression i.e., $R^2$>0.64. The node-metrics with a lower $R^2$ were using either a dim fluorophore (i.e. Alexa-647) and/or were within the low signal range (e.g., Erk basal); and therefore were not good candidates for future test development. Results using both Bland Altman and Lin's Concordance methods showed good concordance.

These studies highlight the importance of cryopreservation of AML samples at clinical sites and by cooperative groups. These results demonstrate that cryopreservation maintains the activation signaling potential of AML blasts. SCNP assays developed and validated using cryopreserved samples can be applied to fresh samples and integrated prospectively into frontline clinical trials and clinical practice.

TABLE 34

Goodness of fit ($R^2$) values from regressing Cryo against Fresh for modulated node-metrics. Fold and $U_u$ (rank based) metrics measure changes in signaling protein levels due to modulation. A = Alexa

| Modulator | Assay Readout | Color | $R^2$ for Fold | $R^2$ for $U_u$ |
|---|---|---|---|---|
| Cytarabine + Daunorubicin | cPARP | FITC | 0.71 | 0.63 |
| | pChk2 | A. 647 | 0.38 | 0.37 |
| Etoposide | cPARP | FITC | 0.78 | 0.49 |
| | pChk2 | A 647 | 0.52 | 0.37 |
| FLT3L | pAkt | A 647 | 0.13 | 0.09 |
| | pErk ½ | PE | 0.46 | 0.55 |
| | pS6 | A 488 | 0.89 | 0.94 |

TABLE 34-continued

Goodness of fit ($R^2$) values from regressing Cryo against Fresh for modulated node-metrics. Fold and $U_u$ (rank based) metrics measure changes in signaling protein levels due to modulation. A = Alexa

| Modulator | Assay Read-out | Color | $R^2$ for Fold | $R^2$ for $U_u$ |
|---|---|---|---|---|
| G-CSF | pStat1 | A 488 | 0.73 | 0.72 |
|  | pStat3 | PE | 0.88 | 0.94 |
|  | pStat5 | A 647 | 0.89 | 0.85 |
| $H_2O_2$ | pAkt | A 488 | 0.79 | 0.85 |
|  | pPLCy2 | PE | 0.83 | 0.89 |
|  | pSlp76 | A 647 | 0.80 | 0.82 |
| IL-27 | pStat1 | A 488 | 0.92 | 0.93 |
|  | pStat3 | PE | 0.94 | 0.90 |
|  | pStat5 | A 647 | 0.93 | 0.92 |
| PMA | pCreb | PE | 0.92 | 0.93 |
|  | pErk ½ | A 647 | 0.94 | 0.90 |
|  | pS6 | A 488 | 0.93 | 0.92 |
| SCF | pAkt | A 647 | 0.49 | 0.09 |
|  | pErk ½ | PE | 0.15 | 0.18 |
|  | pS6 | A 488 | 0.86 | 0.75 |

Example 15

Objectives: The objective of this study was to compare by SCNP the functional effects of a panel of compounds simultaneously on different signaling pathways (such as the phosphoinositide 3-kinase (PI3K) and the Janus Kinases (Jak) signal transducers and activators of transcription (Stat) pathway) relevant both to the biology of the disease and the development of new therapeutics, in paired, diagnostic, cryopreserved PB mononuclear cells (PBMC) and BMMC samples from 44 AML patients. A paired sample was defined as a BMMC and PBMC specimen collected from the same patient on the same day.

Methods: Modulated SCNP using a multiparametric flow cytometry platform was used to evaluate the activation state of intracellular signaling molecules in leukemic blasts under basal conditions and after treatment with specific modulators (Table 35). The SCNP phosphoflow assay was performed on 88 BMMC/PBMC pairs from ECOG trial, E3999. The relationship between readouts of modulated intracellular proteins ("nodes") between BMMC and PBMC was assessed using linear regression, Bland-Altman method or Lin's concordance correlation coefficient.

Table 35 shows the goodness of fit ($R^2$) values from the linear regression analysis for both the basal levels and the modulated levels of intracellular signaling proteins. Most of the signaling nodes show strong correlations ($R^2$>0.64) with several of the exceptions belonging to nodes with weak response to modulation (e.g. SCF→p-Akt) or antibodies with dim fluorphores (i.e. Alexa 647). The lack of response is however, consistent between the tissue types for the weak response nodes. Using a rank based metric that is less sensitive to the absolute intensity levels seem to perform better for the antibodies with dim fluorophores. Results from other methods; Bland Altman and Lin's Concordance also show good concordance between the tissue types.

The data presented here demonstrate: 1) Specimen source (BM or PB) does not affect proteomic signaling in patients with AML and circulating blasts. 2) PB myeloblasts can be used as a sample source for Nodality SCNP assays to identify functionally distinct leukemic blats cell populations with distinct sensitivities to therapy. 3) The ability to use PB as a sample source will greatly improve the utility of these assays. In particular, our results will facilitate the monitoring of cellular signaling effects following the administration of targeted therapies, e.g., kinase inhibitors, at time-points when BM aspirates are not clinically justifiable.

TABLE 35

Goodness of fit ($R^2$) values from regressing PB against BM. SCNP Nodes with $R^2$ > 0.64 are highlighted Fold and $U_u$ metrics measures increase (or decrease) in signaling protein levels due to modulation. Fold metrics measure the shift intensity, while $U_u$ (rank based) metrics measure the proportion of cells that shift from baseline.

| Modulator | Assay Read-out | Color | R2 for Metric Fold | $U_u$ |
|---|---|---|---|---|
| Ara-C + Daunorubicin | cPARP | FITC | 0.72 | 0.68 |
|  | p-Chk2 | Alexa 647 | 0.73 | 0.81 |
| Etoposide | cPARP | FITC | 0.48 | 0.66 |
|  | p-Chk2 | Alexa 647 | 0.76 | 0.74 |
| FLT-3 Ligand | p-Akt | Alexa 647 | 0.50 | 0.63 |
|  | p-Erk 1/2 | PE | 0.67 | 0.64 |
|  | p-S6 | Alexa 488 | 0.73 | 0.73 |
| G-CSF | p-Stat1 | Alexa 488 | 0.64 | 0.57 |
|  | p-Stat3 | PE | 0.62 | 0.76 |
|  | p-Stat5 | Alexa 647 | 0.63 | 0.78 |
| Hydrogen Peroxide | p-Akt | Alexa 488 | 0.83 | 0.72 |
|  | p-PLCy2 | PE | 0.77 | 0.85 |
|  | p-Slp76 | Alexa 647 | 0.56 | 0.68 |
| IL-27 | p-Stat1 | Alexa 488 | 0.79 | 0.84 |
|  | p-Stat3 | PE | 0.71 | 0.79 |
|  | p-Stat5 | Alexa 647 | 0.72 | 0.72 |
| PMA | p-Creb | PE | 0.71 | 0.82 |
|  | p-Erk 1/2 | Alexa 647 | 0.51 | 0.74 |
|  | p-S6 | Alexa 488 | 0.74 | 0.77 |
| SCF | p-Akt | Alexa 647 | 0.48 | 0.77 |
|  | p-Erk 1/2 | PE | 0.40 | 0.39 |
|  | p-S6 | Alexa 488 | 0.68 | 0.73 |

One method of further improving the concordance between PB and BM specimens could be to adjust the biological measurements by a measure of the presence of sub-populations within the leukemic sample, or by differences in the cell maturity of subpopulations. This could be done for example by measuring the relative presence of CD34+ cells in PB and BM leukemic samples and adjusting the signaling of each tissue based on the % of CD34+ cells in the tissue type. Similarly the signaling or biological measurements of each cell within the sample could be scaled or adjusted according to the relative expression of a specific surface marker on that cell such as CD34 or CD11b or another marker of cell lineage or cell maturity.

Example 16

SCNP assays were performed on paired, bone marrow (BM) and peripheral blood (PB), samples from 44 AML patients (de novo, evolved from an antecedent MDS or MPN or treatment related), >60 years old, enrolled on ECOG trial E3999. Based on two previous training studies, 38 combinations of modulators and intra-cellular proteins (signaling nodes along the phosphoinositide 3-kinase (PI3K), the Janus Kinases (Jak) signal transducers and activators of transcription (Stat) and the DNA damage response and apoptosis pathways) were investigated. Basal and modulated protein levels and the effect of modulation on proteins levels in the leukemic blast cells were expressed using a variety of metrics. A total of 64 node/metric combinations (dimensions) were used to build multi-parametric classifiers (ranging from 2 to 10 nodes/metrics) using different modeling methodologies (including random forest, boosting, lasso and a bootstrapped best subsets logistic modeling approach that shrinks regression coefficients (BBLRS)) able to predict the likelihood of response to induction therapy. The performance characteristics of the classifiers built on the BM samples were then evaluated independently on the paired PB samples.

Figure 34:
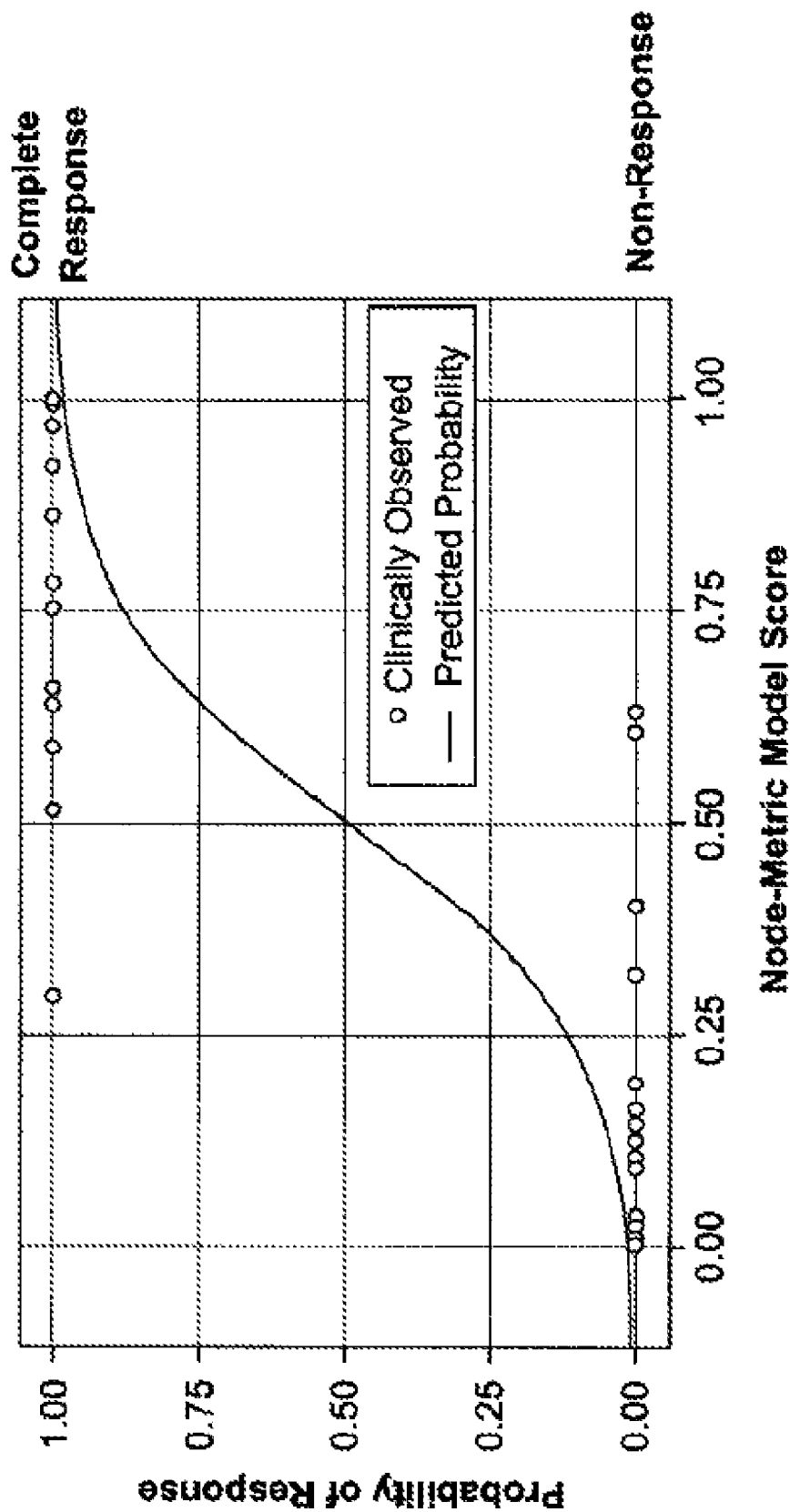
FIG. 34 depicts a model score vs. the predicted probability for the BBLRS model on the training data (unadjusted). Both the true outcome and the predicted probability (along with 95% confidence limits) of Complete Response (CR) are shown on the y-axis.

Several promising models with high area under the operator/receiver curve (AUROC) values (indicating strong agreement between actual clinical responses and responses as predicted by the model) were developed based on SCNP proteomic read outs for BM samples. The observed and predicted values from the current best BBLRS model are shown in FIG. 34. The unadjusted AUROC of this model is 0.98 and the expected AUROC for the model when applied to an independent (validation) sample is 0.84. Five signaling nodes are represented in this model; they include nodes belonging to growth factor-induced survival pathways (PI3K, RAS/MAPK) as well as DNA damage response and apoptosis pathways. When the predictive accuracy of the lead SCNP classifier was compared to that of a model based on traditional clinical/molecular predictors (i.e. the combination of age, therapy-related AML, and karyotype) the adjusted AUROC of the SCNP classifier far surpassed that of the clinical predictors (adjusted AUROC=0.61 for clinical/molecular predictors vs. adjusted AUROC=0.84 for the SCNP classifier). Finally, when the nodes in the best BBLRS model developed on data from BM samples were used to model read outs from the paired PB samples, the adjusted AUROC of the resulting BBLRS model was comparable to that of the model fit to BM samples.

This training set data show the value of performing quantitative SCNP under modulated conditions as the basis for developing highly predictive tests for response to induction chemotherapy. Most importantly, the predictions made by the SCNP classifier are independent of established prognostic factors, such as age and cytogenetics The ability of one set of nodes to accurately predict response in paired BM or PB samples from individual patients suggests that the predictive power of the SCNP assay is independent of sample source, further improving the practicality of the test. Independent validation studies are ongoing.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. A method of drug screening, said method comprising: classifying one or more hematopoietic cells associated with acute leukemia, myelodysplastic syndrome or myeloproliferative neoplasms in an individual by a method comprising:
   a) subjecting a cell population comprising said one or more hematopoietic cells from said individual to a test compound and a plurality of modulators in a plurality of cultures,
   b) characterizing at least three pathways in one or more cells from said plurality of cultures by determining an activation level of at least one activatable element within the at least three pathways, wherein
      i) at least two of the pathways being characterized are an apoptosis and a DNA damage pathway,
      ii) the modulators activate or inhibit one or more of said at least three pathways being characterized, and
   c) classifying said one or more hematopoietic cells into groups comprising response or non-response to therapeutic treatment, or risk of relapse based on said pathways characterization, said classification enabling a decision regarding the test compound and its therapeutic potential for the treatment of acute leukemia, myelodysplastic syndrome or myeloproliferative neoplasms, wherein said decision is based on said classification of said cells.

2. The method of claim 1 wherein said acute leukemia is acute myeloid leukemia.

3. The method of claim 1 wherein the pathways are selected from the group consisting of apoptosis, cell cycle, signaling, and DNA damage pathways.

4. The method of claim 1, wherein the individual has a predefined clinical parameter selected from the group consisting of age, de novo acute myeloid leukemia patient, secondary acute myeloid leukemia patient, and a biochemical/molecular marker.

5. The method of claim 4, wherein said decision is based on said classification of said cells in combination with said predefined clinical parameter.

6. The method of claim 1, wherein said modulators are independently selected from the group consisting of growth factor, mitogen, cytokine, chemokine, adhesion molecule modulator, hormone, small molecule, polynucleotide, antibody, natural compound, lactone, chemotherapeutic agent, immune modulator, carbohydrate, protease, ion, reactive oxygen species, and radiation.

7. The method of claim 1 wherein said modulators are independently selected from the group consisting of FLT3L, GM-CSF, SCF, G-CSF, SDF1a, LPS, PMA, Thapsigargin, IFNg, IFNa, IL-27, IL-3, IL-6, IL-10, ZVAD, $H_2O_2$, Staurosporine, Etoposide, Mylotarg, Daunorubicin, and AraC.

8. The method of claim 1 wherein said activation level is based on an activation state selected from the group consisting of extracellular protease exposure, novel hetero-oligomer formation, glycosylation state, phosphorylation state, acetylation state, methylation state, biotinylation state, glutamylation state, glycylation state, hydroxylation state, isomerization state, prenylation state, myristoylation state, lipoylation state, phosphopantetheinylation state, sulfation state, ISGylation state, nitrosylation state, palmitoylation state, SUMOylation state, ubiquitination state, neddylation state, citrullination state, deamidation state, disulfide bond formation state, proteolytic cleavage state, translocation state, changes in protein turnover, multi-protein complex state, oxidation state, multi-lipid complex, and biochemical changes in cell membrane.

9. The method of claim 8 wherein said activation state is a phosphorylation state.

10. The method of claim 1, wherein said activatable element is selected from the group consisting of proteins, carbohydrates, lipids, nucleic acids and metabolites.

11. The method of claim 10 wherein said activatable element is a protein capable of being phosphorylated and/or dephosphorylated.

12. The method of claim 11 wherein said activatable element is a protein selected from the group consisting of p-Slp-76, p-Plcg2, p-Stat3, p-Stat5, p-Stat1, p-Stat6, p-Creb, cleaved Parp, p-Chk2, p-p65/Rel-A, p-Akt, p-S6, p-ERK, Cleaved Caspase 8, Cleaved Caspase 3, Cytoplasmic Cytochrome C, and p38.

13. The method of claim 1, wherein said method further comprises determining the presence or absence of one or more cell surface markers, intracellular markers, or a combination thereof.

14. The method of claim 13 wherein said one or more cell surface markers and said intracellular markers are independently selected from the group consisting of proteins, carbohydrates, lipids, nucleic acids and metabolites.

15. The method of claim 13 wherein said determining the presence or absence of one or more cell surface markers or intracellular markers comprises determining the presence or absence of an epitope in both activated and non-activated forms of said one or more cell surface markers or said intracellular markers.

16. The method of claim 13, wherein diagnosing, prognosing or determining progression of acute leukemia, myelodysplastic syndrome or myeloproliferative neoplasms in said individual is based on both the activation level of said activatable element and the presence or absence of said one or more cell surface markers, intracellular markers, or combination thereof.

17. The method of claim 1, wherein said activation level is determined by a process comprising binding of a binding element which is specific to a particular activation state of a particular activatable element.

18. The method of claim 17, wherein said binding element comprises an antibody.

19. The method of claim 1, wherein the step of determining the activation level comprises use of flow cytometry, immunofluorescence, confocal microscopy, immunohistochemistry, immunoelectronmicroscopy, nucleic acid amplification, gene array, protein array, mass spectrometry, patch clamp, 2-dimensional gel electrophoresis, differential display gel electrophoresis, microsphere-based multiplex protein assays, ELISA, or label-free cellular assays to determine the activation level of one or more intracellular activatable elements in single cells.

20. The method of claim 1, wherein the at least three pathways are selected from apoptosis, cell cycle, signaling, or DNA damage pathways, further comprising determining whether the apoptosis, cell cycle, signaling, or DNA damage pathways, are functional in said individual based on the activation level of said at least one activatable element, wherein if the apoptosis and DNA damage pathways are functional the individual is predicted to respond to treatment.

21. The method of claim 1, further comprising determining a level of a cytokine receptor, growth factor receptor and/or a drug transporter in said one or more cells.

22. The method of claim 21, wherein said cytokine receptor, growth factor receptor or drug transporter are selected from the group consisting of MDR1, ABCG2, MRP, P-Glycoprotein, CXCR4, FLT3L, and c-kit.

23. The method of claim 21, wherein the level of said cytokine receptor and/or said drug transporter in combination with said cell classification and the clinical parameter are indicative of a diagnosis, prognosis or progression of acute myeloid leukemia, myelodysplastic syndrome or myeloproliferative neoplasms.

24. A method of drug screening, said method comprising: classifying one or more hematopoietic cells associated with acute leukemia, myelodysplastic syndrome or myeloproliferative neoplasms in said individual by a method comprising:
a) subjecting a cell population comprising said one or more hematopoietic cells from said individual to a test compound and a plurality of modulators in separate cultures, wherein:
i) a first modulator is a growth factor or a mitogen,
ii) a second modulator is a cytokine,
iii) a third modulator is a modulator that slows or stops the growth of cells, and/or induces apoptosis of cells, and/or is an inhibitor of a cellular function,
b) determining an activation level of at least one activatable element in one or more cells from each of said separate cultures, wherein the at least one activatable element is within the PI3K/AKT or MAPK pathways and the activation level is measured in response to said growth factor or mitogen, and
c) classifying said one or more hematopoietic cells into groups comprising response or non-response to therapeutic treatment, or risk or relapse, based on said activation level of said at least one activatable element, said classification enabling a decision regarding the test compound and its therapeutic potential to treat acute leukemia, myelodysplastic syndrome or myeloproliferative neoplasms in said individual based on said classification of said one or more hematopoietic cells.

25. The method of claim 24 wherein said acute leukemia is acute myeloid leukemia.

26. The method of claim 24 wherein said activatable element within the PI3K/AKT or MAPK pathway is selected from the group consisting of p-Akt, p-ERK, p38, p-Creb, and pS6 and said growth factor or mitogen is selected from the group consisting of FLT3L, SCF, G-CSF, SDF1a, LPS, PMA, and Thapsigargin.

27. The method of claim 24 wherein said activatable element is within an apoptosis pathway and said activatable element is selected from the group consisting of cleaved Parp, Cleaved Caspase 3, Cleaved Caspase 8, and Cytochrome C, and said modulator that slows or stops the growth of cells and/or induces apoptosis of cells is selected from the group consisting of Staurosporine, Etoposide, Mylotarg, Daunorubicin, and AraC.

28. The method of claim 24 further comprising determining an activation level of an activatable element within a DNA damage pathway or a cell cycle pathway in response to a modulator that slows or stops the growth of cells and/or induces apoptosis of cells.

29. The method of claim 28 wherein said activatable element within a DNA damage pathway is selected from the group consisting of Chk1, Chk2, ATR, ATM, and 14-3-3 and said modulator that slows or stops the growth of cells and/or induces apoptosis of cells is selected from the group consisting of Staurosporine, Etoposide, Mylotarg, Daunorubicin, and AraC.

30. The method of claim 24 further comprising determining a level of a drug transporter, growth factor receptor and/or a cytokine receptor.

31. The method of claim 28 wherein an said at least one activatable element in the PI3K/Akt pathway is Akt and said growth factor is FLT3L.

32. The method of claim 24 wherein said growth factor or mitogen is selected from the group consisting of FLT3L, SCF, G-CSF, SDFla, LPS, PMA, and Thapsigargin.

33. The method of claim 24 wherein said modulator that slows or stops the growth of cells and/or induces apoptosis of cells is selected from the group consisting of Staurosporine, Etoposide, Mylotarg, Daunorubicin, and AraC.

34. The method of claim 24 wherein said activation level is determined by a process comprising binding of a binding element which is specific to a particular activation state of a particular activatable element.

35. The method of claim 34 wherein said binding element comprises an antibody.

36. The method of claim 24 wherein the step of determining the activation level comprises use of flow cytometry, immunofluorescence, confocal microscopy, immunohistochemistry, immunoelectronmicroscopy, nucleic acid amplification, gene array, protein array, mass spectrometry, patch clamp, 2-dimensional gel electrophoresis, differential display gel electrophoresis, microsphere-based multiplex protein assays, ELISA, or label-free cellular assays to determine the activation level of one or more intracellular activatable elements in single cells.

* * * * *